United States Patent [19]

Powell, Jr. et al.

[11] Patent Number: 5,234,900
[45] Date of Patent: Aug. 10, 1993

[54] HERBICIDAL OXABICYCLO ETHERS

[75] Inventors: James E. Powell, Jr., Rising Sun, Md.; Wendy S. Taylor, Wilmington, Del.

[73] Assignee: E. I. Du Pont de Nemours and Company, Wilmington, Del.

[21] Appl. No.: 838,253

[22] PCT Filed: Sep. 5, 1990

[86] PCT No.: PCT/US90/04953
§ 371 Date: Mar. 11, 1992
§ 102(e) Date: Mar. 11, 1992

Related U.S. Application Data

[63] Continuation-in-part of Ser. No. 431,734, Sep. 11, 1989, abandoned.

[51] Int. Cl.$^5$ .................. A01N 43/12; C07D 307/00
[52] U.S. Cl. .................. 504/298; 504/250; 504/292; 544/336; 546/141; 546/153; 546/269; 548/454; 549/23; 549/52; 549/60; 549/399; 549/401; 549/414; 549/463
[58] Field of Search .................. 549/463, 23, 52, 60, 549/414, 399, 401; 544/336; 546/141, 153, 269; 548/454; 504/250, 292, 298

[56] References Cited

U.S. PATENT DOCUMENTS

| | | | |
|---|---|---|---|
| 4,486,219 | 12/1984 | Powell | 71/88 |
| 4,536,586 | 8/1985 | Powell | 549/463 |
| 4,567,283 | 1/1986 | Payne et al. | 549/546 |
| 4,670,041 | 6/1987 | Payne et al. | 71/92 |
| 4,798,621 | 1/1989 | Ackerson et al. | 71/90 |

FOREIGN PATENT DOCUMENTS

| | | |
|---|---|---|
| 81893 | 6/1983 | European Pat. Off. . |
| WO89/02219 | 3/1989 | PCT Int'l Appl. . |
| WO89/11480 | 11/1989 | PCT Int'l Appl. . |
| WO90/09383 | 8/1991 | PCT Int'l Appl. . |
| 2188931 | 8/1990 | United Kingdom . |

*Primary Examiner*—Bernard Dentz

[57] ABSTRACT

The present invention relates to novel oxabicyclo ether derivative compounds, compositions containing these ether derivative compounds, and methods of using these compounds or compositions to control the growth of undesired vegetation. More particularly, the present invention relates to a variety of compounds, compositions, and methods of using them which are herbicidally active on a wide variety of weed species and exhibit safety to rice, cereals or broadleaf crops.

21 Claims, No Drawings

HERBICIDAL OXABICYCLO ETHERS

CROSS-REFERENCE TO RELATED APPLICATION

This application is a continuation-in-part of copending application U.S. Ser. No. 07/431,734 field Sep. 11, 1989, now abandoned, by way of PCT application PCT/US90/04953 filed Sep. 5, 1990.

FIELD OF THE INVENTION

The present invention relates to novel oxabicyclo ether derivative compounds, to compositions containing these ether derivative compounds, and to methods of using these compounds or compositions to control the growth of undesired vegetation. More particularly, the present invention relates to a variety of compounds, compositions, and methods of using them which are herbicidally active on a wide variety of weed species and exhibit safety to rice, cereals and broadleaf crops.

BACKGROUND OF THE INVENTION

Payne et al., U.S. Pat. No. 4,567,283 and Payne et al., U.S. Pat. No. 4,670,041 disclose a variety of herbicidal bicyclic ethers of the Formula

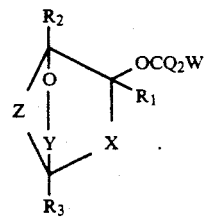

U.S. Pat. No. 4,798,621 and WO 8,902,219 both disclose bicyclic ethers and their method-of-use in rice.

U.S. Pat. No. 4,486,219 discloses bicyclic ethers of the formula:

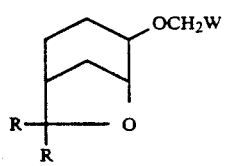

It is an object of the present invention to provide compounds and compositions which exhibit herbicidal activity on a variety of economically important weed species. It is a further object of the present invention to provide compounds and compositions that are herbicidally safe to rice, cereals and broadleaf crops. It is a feature of the present invention to furnish novel oxabicyclo ethers that exhibit useful herbicidal activity. These and other objects, features and advantages will become apparent with respect to the following description of the invention.

SUMMARY OF THE INVENTION

The present invention comprises compounds of the formulas selected from the group consisting of:

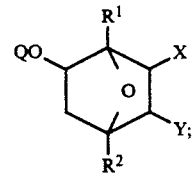   I

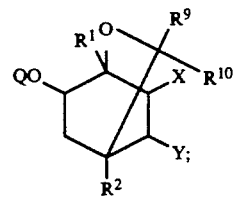   II

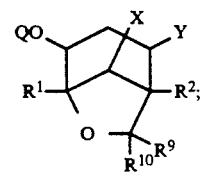   III

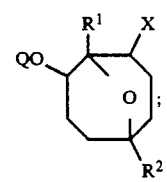   IV

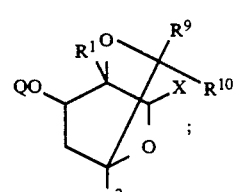   V

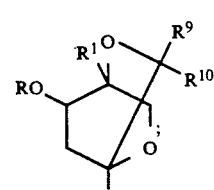   VI

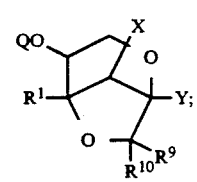   VII

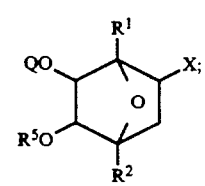   VIII and stereoisomers thereof,
wherein
X and Y are independently H or $C(R^3)(R^4)OR^5$;
Z is $C(R^3)(R^4)OR^5$;
$R^1$ is H or a straight-chain $C_1$–$C_3$ alkyl;

$R^2$ is H, $C_1$-$C_6$ alkyl, $C_2$-$C_4$ alkenyl, $C_2$-$C_4$ alkynyl, phenyl or $C_1$-$C_4$ alkyl substituted by Ph, OH, CN, $OR^8$, $SO_2R^8$, $PhSO_2$, $N_3$, $CO_2R^8$ or $CO_2H$;

$R^3$, $R^4$, $R^9$ and $R^{10}$ are independently H, $C_1$-$C_4$ alkyl, $C_2$-$C_4$ alkenyl, $C_2$-$C_4$ alkynyl or $C_1$-$C_3$ alkyl substituted with $OCH_3$ or $OCH_2CH_3$;

$R^5$ is $C_1$-$C_3$ alkyl, $C_2$-$C_4$ alkenyl, $C_3$-$C_4$ alkynyl, benzyl or $C_1$-$C_4$ alkyl substituted with $OR^8$, $OCF_3$;

$R^8$ is $C_1$-$C_3$ alkyl;

Q is $WCH_2$ or

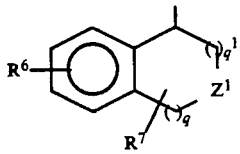

W is phenyl optionally substituted with 1-3 substituents selected from F, Cl, Br, $C_1$-$C_3$ alkyl, $C_1$-$C_3$ alkoxy, OH, CN, $C_1$-$C_3$ haloalkyl, $C_1$—$C_3$ haloalkoxy, $C_1$-$C_3$ alkylthio, $C_2$-$C_4$ alkenyl and $C_2$-$C_4$ alkynyl, or W is a 5 or 6-membered heterocyclic ring containing 0-2 nitrogens, 0-2 oxygens or 0-2 sulfurs, each ring optionally substituted with 1-2 substituents selected from F, Cl, Br, $CH_3$ and $OCH_3$;

$Z^1$ is $CH_2$, $NR_a$, O, S or may be taken to form a double bond with an adjacent carbon;

$R_a$ is H or $C_1$-$C_3$ alkyl;

$R^6$ is H, halogen, $R^8$, $OR^8$, $SR^8$ or CN;

$R^7$ is H, F, Cl, $CH_3$, $OCH_3$, OH or $OR^8$;

$q^1$ is 0, 1 or 2; and q is 0, 1 or 2.

provided that 1) at least one of X and Y is $C(R^3)(R^4)OR^5$;
2) $R^3$, $R^4$, $R^9$ and $R^{10}$ each contains no more than four carbon atoms;
3) in Formula II, if $R^1$ is H then X is $C(R^3)(R^4)OR^5$ and Y is H;
4) the sum of q and $q^1$ is 0, 1 or 2; and
5) if the sum of q and $q^1$ is 0 then $Z^1$ is $CH_2$.

A representative exemplification of the aforementioned heterocycles includes but is not limited to pyrrole, furan, thiophene, tetrahydropyran, tetrahydrofuran, isoxazole, oxazole, pyrazole, imidazole, thiazole, pyridine and pyrazines;

Preferred compounds of the invention for either their biological activity or ease of synthesis are:

1. Compounds of Formulas I, II, III, IV, V, VI, VII, or VIII wherein:

W is phenyl optionally substituted by 1-2 substituents selected from F, Cl, Br, $CH_3$ and $OCH_3$; or W is tetrahydropyran, tetrahydrofuran, thiophene, isoxazole, pyridine or pyrazine, each ring optionally substituted with 1-2 substituents selected from F, Cl, Br, $CH_3$ and $OCH_3$;

Q is

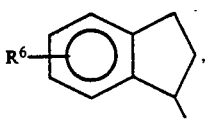 Q-1

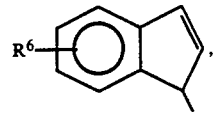 Q-2

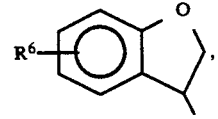 Q-3

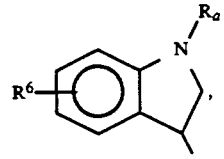 Q-4

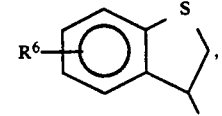 Q-5

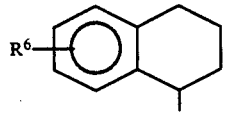 Q-6

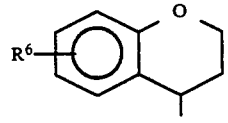 Q-7

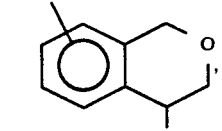 Q-8

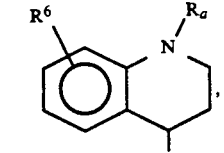 Q-9

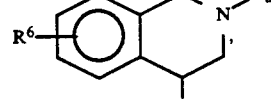 Q-10

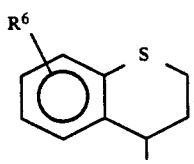 Q-11

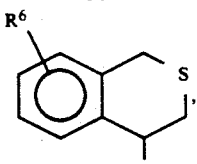 Q-12

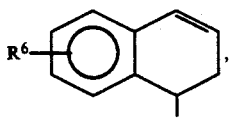 Q-13

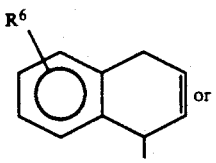 Q-14

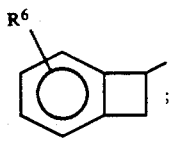 Q-15

$R_a$ is H or $C_1$-$C_3$ alkyl; and
$R^5$ is other than benzyl.

2. Compounds of Preferred 1 wherein $R^2$ is H, $C_1$-$C_3$ alkyl, $C_2$-$C_3$ alkenyl or $C_2$-$C_3$ alkynyl.

3. Compounds of Preferred 2 wherein
$R^3$ is H, $C_1$-$C_3$ alkyl, $C_3$-$C_4$ alkenyl or $C_3$-$C_4$ alkynyl;
$R^4$ is H, $C_1$-$C_3$ alkyl, $C_3$-$C_4$ alkenyl or $C_3$-$C_4$ alkynyl;
$R^5$ is H, $C_1$-$C_3$ alkyl, $C_3$-$C_4$ alkenyl or $C_3$-$C_4$ alkynyl;
$R^9$ is H, $C_1$-$C_3$ alkyl, $C_3$-$C_4$ alkenyl or $C_3$-$C_4$ alkynyl;
$R^{10}$ is H, $C_1$-$C_3$ alkyl, $C_3$-$C_4$ alkenyl or $C_3$-$C_4$ alkynyl;

4. Compounds of Preferred 3 wherein Q is Q-1, Q-3, Q-6, Q-7 or Q-15.

5. Compounds of Preferred 4 wherein the compound is of Formula I.

6. Compounds of Preferred 4 wherein the compound is of Formula II.

7. Compounds of Preferred 4 wherein the compound is of Formula III.

8. Compounds of Preferred 4 wherein the compound is of Formula IV.

9. Compounds of Preferred 4 wherein the compound is of Formula V.

10. Compounds of Preferred 4 wherein the compound is of Formula VI.

11. The Compounds of Preferred 4 wherein the compound is of Formula VII.

12. Compounds of Preferred 4 wherein the compound is of Formula VIII.

Specifically Preferred for its biological activity and/or ease of synthesis is the compound of Preferred 5 which is:

2-(1-ethyl-1-methoxypropyl)-6-(phenylmethoxy)-7-oxabicyclo[2.2.1]heptane, (2-exo, 6-exo); and the compound of Preferred 7 which is:

2-(ethoxymethyl)-5-methyl-4-(phenylmethoxy)-6-oxabicyclo[3.2.1]octane, (2-endo, 4-endo).

All may preferably be selected from the group consisting of pyrrole, furan, thiophene, tetrahydropyran, tetrahydrofuran, isoxazole, oxazole, pyrazole, imidazole, triazole, pyridine, and pyrazine.

Compounds of Formula I–VIII that have the WCH$_2$O group syn with respect to the oxygen-containing bridge are usually more herbicidally active than the anti form. The present invention contemplates all of the herbicidally active forms resulting from synthesis and from deliberately created mixtures.

The compounds of the invention are prepared by treating the appropriately substituted oxabicycloalkanol (Ia-VIIIa) with a compound of the formula WCH$_2$X in which X is a halogen atom or a mesyloxy, tosyloxy group or the like. This reaction is carried out, as shown in Scheme 1, in the present of a strong base, such as an alkali metal hydride, in an inert solvent, such as ethers, aromatic hydrocarbons, dimethylformamide and the like. Suitable temperatures for the reaction are preferably from 20° C. to 100° C. The product ethers are recovered and isolated by conventional techniques.

Compositions suitable for controlling the growth of undersired vegetation are also contemplated as within the scope of this invention. Such compositions comprise an effective amount of any of the compounds disclosed herein and at least one of the following: surfactant, solid, or liquid diluent.

Methods for controlling the growth of undesired vegetation are similarly considered to be within the scope of the invention. These methods comprise applying to the locus to be protected as effective amount of any of the compounds disclosed herein. Of particular importance is the method wherein the locus to be protected is rice.

Scheme 1

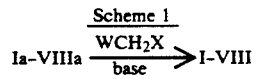

Ia-VIIIa $\xrightarrow{\text{WCH}_2\text{X}}{\text{base}}$ I-VIII

The alkylating agents WCH$_2$X are prepared in the conventional manners known to those skilled in the art from the alcohols WCH$_2$OH.

The alcohols, WCH$_2$OH, are generally known in the art and are most conveniently prepared through metal hydride (e.g., sodium borohydride) reduction of the corresponding bicyclic ketones which can be derived by Friedel-Crafts type cyclization of derivatives of phenylalkylcarboxylic acid, phenoxyalkylcarboxylic acids, phenylthioalkylcarboxylic acids, benzyloxyalkylcarboxylic acids, and benzylthioalkylcarboxylic acids. Details may be found in a) T. Laird in *Comprehensive Organic Chemistry*, D. Barton and W. D. Ollis, ed., Vol. 1, pp. 1165–1168, Pergamon Press, New York (1979); b) M. H. Palmer and N. M. Scollick, *J. Chem. Soc., C.*, (1968), 2833; c) C. E. Dalgliesch and Mann, *J. Chem. Soc.*, (1945), 893; d) C. D. Hurd and S. Hayao, *J. Am. Chem. Soc.*, (1954), 76, 4299 and 5056; and e) R. Lesser, *Chem. Ber.*, (1923), 56, 1642.

Alternatively, the compounds of Formulas I–VIII may be prepared by the coupling procedure described in Scheme 2, which is used in cases where the standard Williamson ether synthesis proves problematic. This procedure uses a Lewis acidic metal oxide wherein the metal can remove the halide ion by forming an insoluble precipitate. For example, Silver (I) oxide can be used and the silver halide is the co-produce. Alternative metal oxides that may be used are HgO, CaO, MgO. N,N-Dimethylformamide and ethereal solvents, such as diethyl ether, tetrahydrofuran, dioxane, or 1,2-dimethoxyethane are the preferred solvents. Other solvents likely to provide good yields include dipolar aprotic solvents like dimethyl sulfoxide, actone and N,N'-dimethylpropyleneures.

Scheme 2

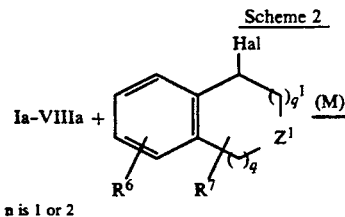

n is 1 or 2

The oxabicycloalkanols (Ia–VIIIa) can be obtained generally by one or more of the following routes: directly by a) epoxidation-cyclization of unsaturated cyclic alcohols, with or without isolation of the epoxy alcohol intermediates; indirectly by b) Diels-Alder reactions of furans with dienophiles; or by c) Diels-Alder reactions of other dienes with dienophiles.

Non-limiting illustrations of the preparation of representative compounds follow.

The compounds of Formula Ia are synthesized through the sequence shown in Scheme 3. Diels-Alder adducts are formed from readily available furans and from dienophiles including acrylate esters, acrolein, acryloyl chloride, and the like (see Murai et al., *J. Chem. Soc., Chem. Comm.* 221 (1981); and Kotsuki et al., *Bull. Chem. Soc. Jpn.*, 57, 3339 (1984); and Laszlo et al., *Tet. Let.*, 25, 4387 (1984); for Diels-Alder methodology). For example, the Diels-Alder adduct (2) is prepared from furan (3) and acryloyl chloride. Treatment of (2) with alcohol and base at 0° C. to ambient temperature produces the corresponding ester. This intermediate is treated with the appropriate Grignard reagent or reducing agent (e.g, lithium aluminum hydride) as shown in Equation 3b. Optionally ,treatment with an alkyl halide or alkyl sulfonate and a base (e.g., sodium hydride) in an inert solvent, such as tetrahydrofuran or N,N-dimethylformamide at ambient temperature to 150° C. produces (4). Alcohol (4a) or ether (4b) is oxidized with a peroxide, such as hydrogen peroxide or m-chloroperbenzoic acid, in a suitable solvent, such as methylene chloride, to yield an epoxide. This intermediate is treated with a reducing agent, such as lithium triethylborohdyride or lithium aluminum hydride, to reductively open the epoxide to produce alcohol Ia, using the method of Krishnamurthy et al., *J. Amer. Chem. Soc.*, 95, 8486 (1973), as shown in Equation 3c.

Scheme 3

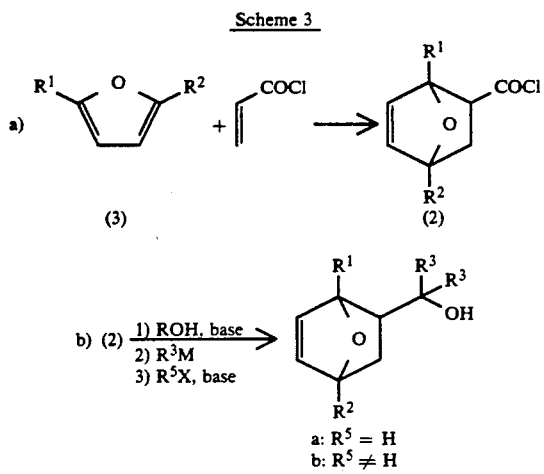

a: $R^5 = H$
b: $R^5 \neq H$

-continued
Scheme 3

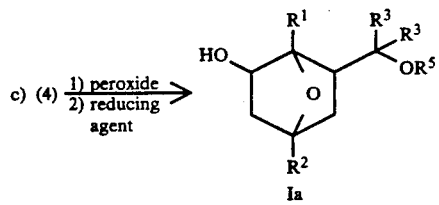

Alternatively, compounds of Formula Ia may be synthesized through the sequence shown in Scheme 4, in which groups $R^3$ and $R^4$ may be varied independently. The Diels-Alder adducts (5) prepared from furan (3) and a vinyl carbonyl (6) are treated with the appropriate Grignard reagent or reducing agent to produce alcohol (7). Alcohol Ia can then be prepared via the routes previously described in Equations 3b and 3c or modifications thereof.

Scheme 4

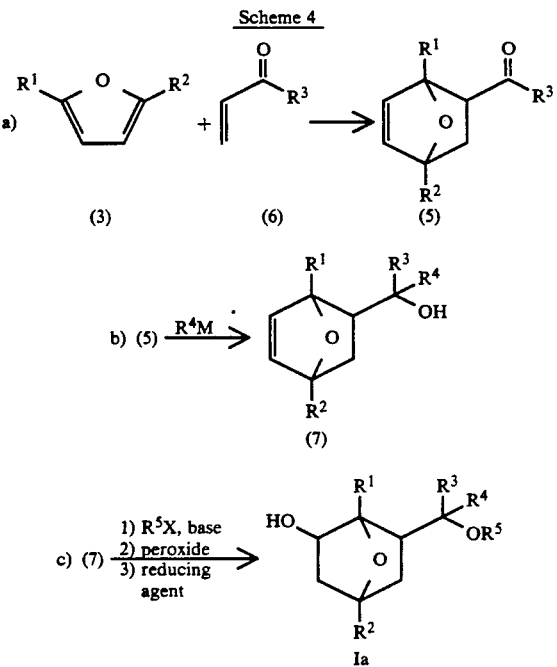

Compounds of Formula Ia, especially where $R^3$ and/or $R^4$ are allylic or vinylic can be prepared through the sequence shown in Scheme 5. The Diels-Alder adducts (8) are treated with a peroxide as described in Equation 3c. This intermediate is treated with the appropriate Grignard reagent such as vinyl magnesium halide or allyl magnesium halide, to produce alcohol (9). Alcohol Ia can be prepared via the routes previously described in Equations 3b and 3c, or modifications thereof.

Scheme 5

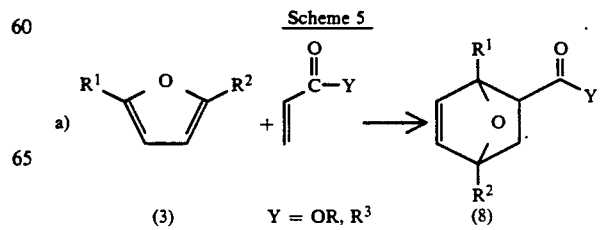

Y = OR, $R^3$

Scheme 5 -continued b) (8) $\xrightarrow{\text{1) peroxide}}_{\text{2) R}^4\text{M}}$ 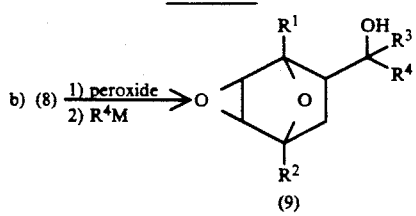
(9)

c) (9) $\xrightarrow{\text{1) R}^5\text{X, base}}_{\substack{\text{2) reducing}\\\text{agent}}}$ 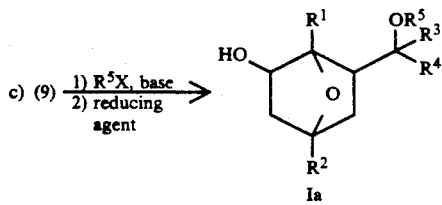
Ia Compounds of Formula Ia can also be synthesize through the sequence shown in Scheme 6. Diels-Alder adducts (10) are formed from furan (3) and a dicarbonyl dienophile, such as maleic anhydride, using the methods of Hanessian et al., *Tet. Lett.*, 27, 5071 (1986) or Woodward et al., *J. Amer. Chem. Soc.*, 70, 1161 (1948). Alcohol Ia can be prepared via the routes shown previously in Equations 4b and 4c or 5b and 5c or modifications thereof.

Scheme 6 a) 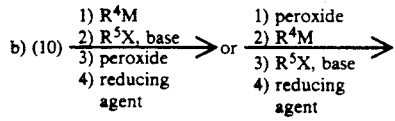 (3) + Y=OR, R³ → (10)

b) (10) $\xrightarrow[\substack{\text{1) R}^4\text{M}\\\text{2) R}^5\text{X, base}\\\text{3) peroxide}\\\text{4) reducing agent}}]{}$ or $\xrightarrow[\substack{\text{1) peroxide}\\\text{2) R}^4\text{M}\\\text{3) R}^5\text{X, base}\\\text{4) reducing agent}}]{}$

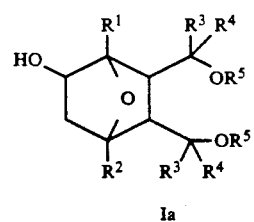
Ia

Compounds of Formula IIa can be prepared by the method described in Scheme 7 or modifications thereof. Cyclohexene (11) can be prepared via a Diels-Alder reaction using the methods of Alder et al., *Chem. Ber.*, 86, 1312 (1953). Treatment of the diester with a Grignard reagent or a reducing agent yields the diol derivative. Monoalkylation, using methods described earlier, yield a mixture of ethers (12). Treatment of (12) with peroxide and acid, as taught in U.S. patent Ser. No. 4,542,244, yields alcohol IIa.

In situations where the endo form is desired, it can be obtained by oxidation of the 2-exo-IIa to the corresponding ketone, followed by reduction of the ketone with a reducing agent, such as sodium borohydride.

Scheme 7 a) 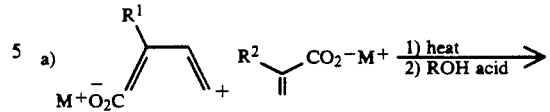 $\xrightarrow{\substack{\text{1) heat}\\\text{2) ROH acid}}}$

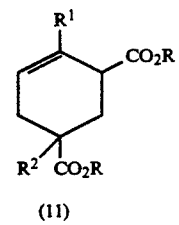
(11)

b) (11) $\xrightarrow{\substack{\text{1) R}^3\text{M}\\\text{2) R}^5\text{X, base}}}$

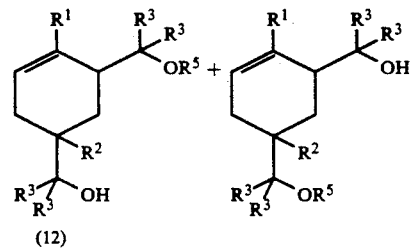
(12)

c) (12) $\xrightarrow{\substack{\text{1) peroxide}\\\text{2) acid}}}$ 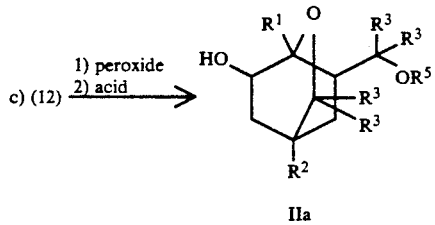
IIa Compounds of Formula IIIa can be prepared by the method described in Scheme 8 or modifications thereof. Cyclohexene (13) can be prepared via a Diels-Alder from readily available dienophiles, such as maleic anhydride, and a diene component, such as isoprene or butadiene, using the methods of Fieser et al., *J. Amer. Chem. Soc.*, 64, 802 (1942). Treatment of (13) with a Grignard reagent or reducing agent yields the diol derivative. Monoalkylation using methods described earlier yields ether (14). Treatment of (14) with peroxide and acid as taught in U.S. patent Ser. No. 4,542,244 yields IIIa.

In situations where the endo form is desired, it can be obtained by oxidation of the 2-exo-IIIa to the corresponding ketone, followed by reduction of the ketone with a reducing agent, such as sodium borohydride.

Scheme 8 a) 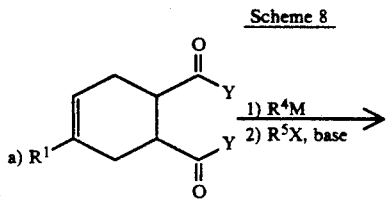 $\xrightarrow{\substack{\text{1) R}^4\text{M}\\\text{2) R}^5\text{X, base}}}$

Y = R³, OR
(13)

-continued
Scheme 8

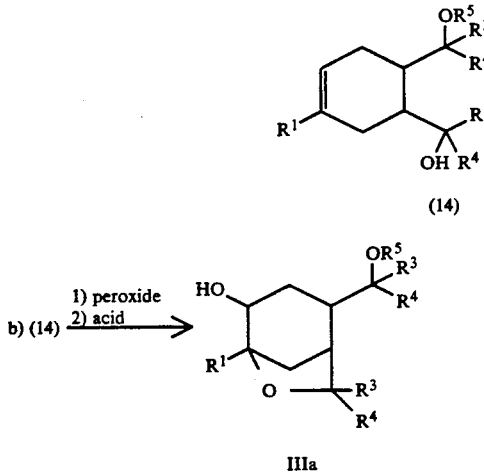

Compounds of Formula IIIa can also be prepared by the method described in Scheme 9 or modifications thereof. cyclohexene (15) can be prepared via a Diels-Alder from diene (16) and a readily available dienophile, such as methylacrylate. Treatment of (15) with a Grignard reagent of reducing agent yields the diol derivative. Monoalkylation using methods described earlier yields ether (17). Treatment of (17) with peroxide and acid, as described earlier, yields IIIa. In situations where the endo form is desired, it can be obtained by oxidation of the 2-exo-IIIa to the corresponding ketone, followed by reduction of the ketone with a reducing agent, such as sodium borohydride.

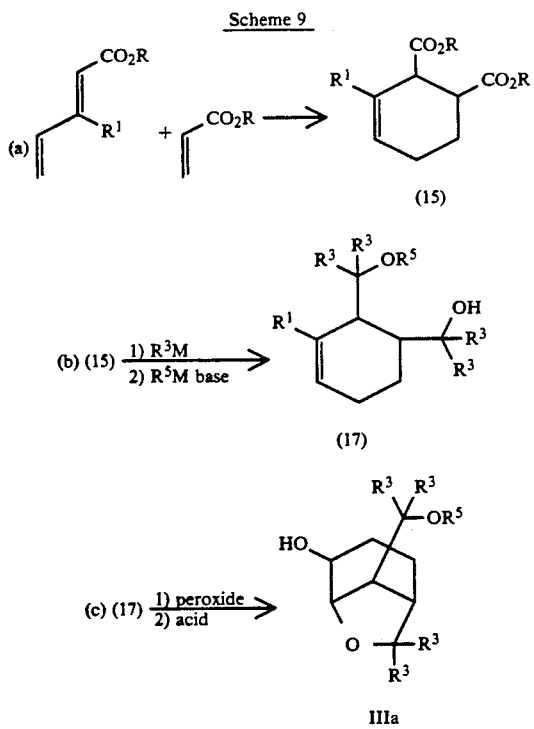

Compounds of Formula IV can be prepared by the method described in Scheme 10. Hydroxylation of 1,5-cyclooctadiene with a catalytic amount of osmium tetroxide and trimethylamine oxide as stoichiometric oxidant, adapted from a literature procedure [Ray et al., Tet. Lett., 21, 449 (1980)], followed by Williamson ether coupling reaction with the appropriate alkylating agent $WCH_2X$, as described previously, yields ether (18). Oxidation of this alcohol using Jones reagent, as described by Heap et al. J. Chem. Soc. B, 164 (1966), yields ketone (19), which is alkylated with an appropriately substituted ketone using an amide base under conditions known in the art. Treatment of the resulting alcohol with an alkyl halide in the presence of a strong base, as described previously, yields (20). Addition of an appropriate Grignard reagent or reducing agent (such as sodium borohydride) to the carbonyl group produces alcohol (21), which is cyclized to yield the desired ether IVa by means of the alkoxymercuratin/demurcuration sequence [Bordwell et al., J. Amer. Chem. Soc., 88, 993 (1966)].

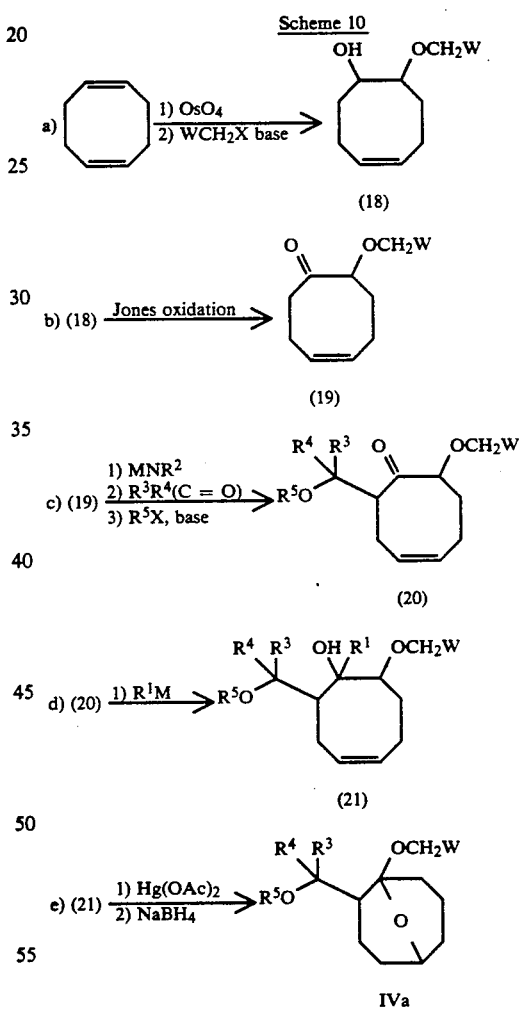

Compounds of Formula VIIa (where X=H) and VIa can be prepared by the method described in Scheme 11 or modifications thereof. Diesters (22) and (23) can be prepared via a Diels-Alder reaction such as described by Ruden et a., (J. Amer. Chem. Soc., 97, 6892 (1975)) using readily available diene components, such as isoprene or butadiene and a dialkylketomalonate. Treatment of the esters with a Grignard reagent or a reducing reagent, as described earlier, yields the diols (24) and (25). Monoalkylation, using methods described earlier, followed by treatment with peroxide and acid, as described earlier, yield alcohols VIIa and VIa. In situations where the endo alcohol is desired, it can be obtained by oxidation of the exo-VIIa or exo-VIa to the corresponding ketone followed by reduction of the ketone with a reducing gent, such as sodium borohydride.

Scheme 11

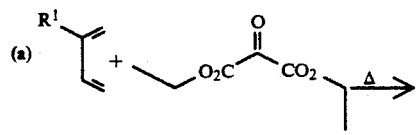

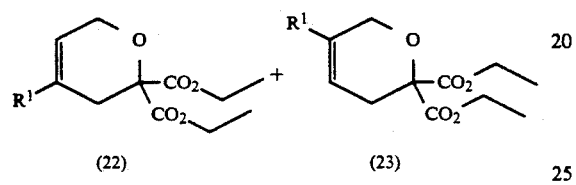

(b) (22) and (23) $\xrightarrow{R^3M}$

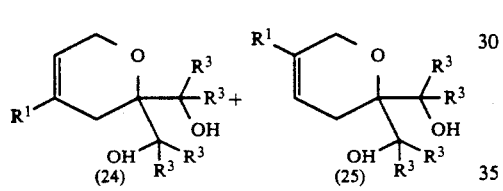

(c) (24) and (25) $\xrightarrow[\substack{1) R^5X, \text{ base} \\ 2) \text{ peroxide} \\ 3) \text{ acid}}]{}$

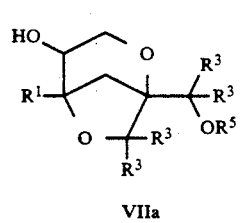 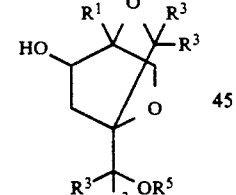

VIIa      VIa

Compounds of Formula VIIa (where Y=H) and of Formula Va can be prepared by the method described in Scheme 12 or modifications thereof. Diene (26) can be prepared from the corresponding diene ester by addition of a Grignard reagent or a reducing agent such as described by Corey et al. (Tet. Let., 30, 2537 (1975), followed by alkylation of the resulting alcohol. Diels-Alder reaction of (26) with glyoxylate using methods similar to Jurczak et al., J. Org. Chem., 44, 3347 (1979) yields (27) and (28). Treatment of (27) and (28) with a Grignard reagent or a reducing agent yields alcohols (29) and (30). Treatment with peroxide and acid as described earlier yields alcohols VIIa and Va. The endo alcohol can be obtained as described in Scheme 11.

Scheme 12

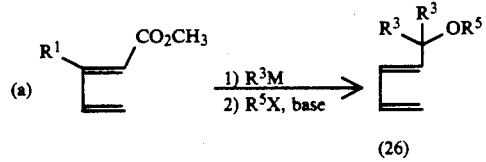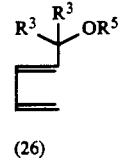

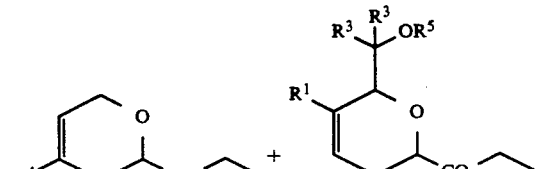

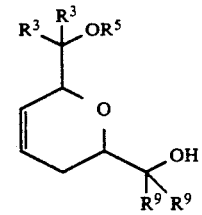

(c) (27) (28) $\xrightarrow{R^3M}$ (d) (29) (30) $\xrightarrow[\substack{1) \text{ peroxide} \\ 2) \text{ acid}}]{}$

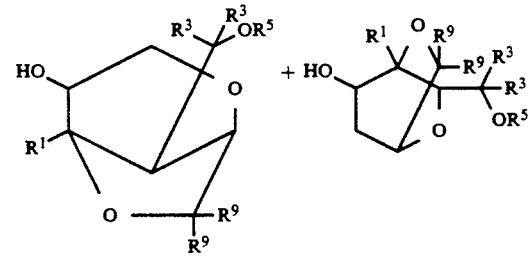

VIIa      Va

Compounds of Formula VIII can be prepared by the method described in Scheme 13. Treatment of compound (4) with a trialkylamine N-oxide and catalytic osmium tetroxide yields triol (31). Alkylation of (31) with a QX (such as benzyl bromide), followed by treatment with $R^5X$ and a strong base, yields VIII.

Scheme 13

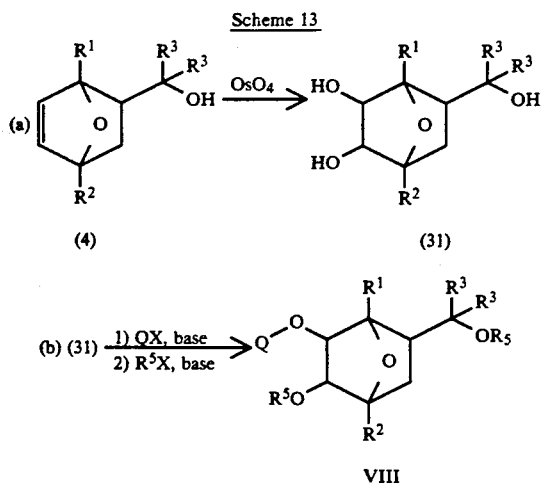

VIII

EXAMPLE 1

Step A: 7-oxabicyclo[2.2.1]hept-5-ene-2-carboxylic acid, 1,4-dimethyl-, methyl ester, (endo and exo, racemic)

Acryloyl chloride (32.8 ml, 0.40 mol) was cooled to 0° C. in an ice-water bath under a nitrogen atmosphere. Aluminum chloride (1.60 g, 0.012 mol) was added in 0.5 g portions with stirring. The mixture was stirred at 5° C. for 10 minutes, then was cooled to −65° C. with an isopropanol-dry ice bath. 2,5-Dimethylfuran (38.4 g, 0.40 mol) was added dropwise at −65° C. to −50° C. over 1.5 hours. After addition was complete, the mixture was stirred for 1 hour. Methylene chloride (250 ml) was added to the mixture. The mixture was then cannulated to a stirring mixture of triethylamine (48.4 g, 0.48 mol) and methanol (160 ml) at −55° C. to −40° C. over 10 minutes. The mixture was stirred at −65° C. for 1.25 hours, then was allowed to warm to ambient temperature. The mixture was poured into 500 ml water. The phases were separated and the aqueous layer was extracted two times with methylene chloride. The combined organic layers were washed with saturated sodium bicarbonate and brine solutions, dried over magnesium sulfate and concentrated in vacuo to leave 35.12 g of a yellow oil. Flash chromatography in 3:1 hexanes:ether on 800 g of silica gel yielded 17.34 g of the endo isomer and 11.82 g of the exo isomer.

NMR (CDCl$_3$) endo isomer: 6.22 (d, 1H), 6.03 (d, 1H), 3.61 (s, 3H), 2.88 (dd, 1H), 1.91 (ddd, 1H), 1.80 (ddd, 1H), 1.70 (s, 3H), 1.56 (2, 3H).

NMR (CDCl$_3$) exo isomer: 6.18 (d, 1H), 6.12 (d, 1H), 3.69 (s, 3H), 2.52 (dd, 1H), 2.0 (dd, 1H), 1.66 (dd, 1H), 1.62 (s, 3H), 1.50 (s, 3H).

Step B: 7-oxabicyclo[2.2.1]hept-5-ene-2-methanol, 1,4-dimethyl-, exo-, (racemic-)

Lithium aluminum hydride (2.3 g, 60.0 mmol) was added under a nitrogen atmosphere to 100 ml dry tetrahydrofuran. The mixture was heated at reflux for 15 minutes, then cooled to 0° C. A solution of 7-oxabicyclo[2.2.1]hept-5-ene-2-carboxylic acid, 1,4-dimethyl-, methyl ester, (exo, racemic) (14.3 g, 78.6 mmol) in 100 ml tetrahydrofuran was added dropwise over 1.5 hours. The mixture was then allowed to warm to ambient temperature and stirred for another 4.0 hours. The mixture was cooled to 5° C. in an ice-water bath and 2.3 ml of water, 2.3 ml of 10% sodium hydroxide, and 2.3 ml of water were added. The solids were removed by suction filtration and washed with 40 ml of cold tetrahydrofuran. The filtrate was concentrated in vacuo to yield 9.5 g of a colorless oil.

NMR (CDCl$_3$): 6.22 (d, 1H), 6.12 (d, 1H), 3.83 (m, 1H), 3.74 (m, 1H), 2.17 (dd, 1H), 1.86 (m, 1H), 1.68 (dd, 1H), 1.59 (s, 3H), 1.58 (s, 3H), 1.51 (dd, 1H).

IR (CH$_2$Cl$_2$): 3620, 3480, 1385, 1330, 1190, 1140, 1120, 1075, 1035, 975, 365 cm$^{-1}$.

MS (CI): 155 (M+1), 137, 109, 107, 96, 95, 93.

Step C: 7-oxabicyclo[2.2.1]hept-2-ene, 1,4-dimethyl-2-[(phenyl methoxy)methyl]-, (exo-, racemic)

Sodium hydride (1.54 g, 3.85 mmol of a 60% oil dispersion) was washed with hexanes, decanted, and suspended in 20 ml of dimethylformamide. A solution of 4.75 g (30.8 mmol) of 7-oxabicyclo[2.2.1]hept-5-ene-2-methanol, 1,4-dimethyl-, exo (racemic) in 40 ml dimethylformamide was added dropwise at 20° over 45 minutes. The mixture was stirred 45 minutes at ambient temperature. Benzyl bromide (6.05 g, 35.4 mmol) was added dropwise in 30 ml dimethylformamide over 30 minutes. The mixture was stirred 20 hours at ambient temperature. The mixture was poured into 350 ml of water and extracted three times with methylene chloride. The combined extracts were washed with brine, dried over magnesium sulfate and concentrated in vacuo to yield 7.83 g of a yellow oil. Flash chromatography in 3:1 hexanes:ether on 400 g of silica gel yielded 3.77 g of a light yellow oil.

NMR (CDCl$_3$): 7.40–7.26 (m, 5H), 6.12 (s, 2H), 4.51 (dq, 2H), 3.60 (dd, 1H), 3.43 (dd, 1H), 1.97 (m, 1H), 1.70 (dd, 1H), 1.56 (s, 3H), 1.53 (s, 3H), 1.18 (dd, 1H).

IR (CH$_2$Cl$_2$): 1595, 1450, 1380, 1360, 1330, 1195, 1140, 1120, 1090, 1035, 1025, 860.

Anal. Calcd. for C$_{16}$H$_{20}$O$_2$: C, 78.69; H, 8.20, Found: C, 78.80; H, 8.37.

Step D: 3.8-dioxatricyclo[3.2.1.0 sup2, sup4]octane, 1,5-dimethyl-6-[(phenylmethoxy)methyl]-, (exo, racemic-)

To a stirring solution of 3.60 g (15.0 mmol) of 7-oxabicyclo[2.2.1]hept-2-ene, 1,4-dimethyl-2-[(phenylmethoxy)methyl]- (exo, racemic) in 50 ml methylene chloride was added 3.56 g (16.5 mmol) of 80% technical m-chloroperbenzoic acid at 0° C. to 10° C. The mixture was stirred at 0° C. to 10° C. for 1 hour, then at ambient temperature. After 20 hours at ambient temperature, the mixture was cooled to 0° C. for 0.5 hour, filtered, and washed with cold methylene chloride. The filtrate was washed with 10% sodium sulfite, sat. sodium bicarbonate, and brine and dried over magnesium sulfate and concentrated in vacuo to yield 4.05 g of a light yellow oil. Flash chromatography in 1:1 hexane:ether on 150 g of silica gel yielded 3.30 g of a colorless liquid.

NMR (CDCl$_3$): 7.40–7.26 (m, 5H), 4.48 (dq, 2H), 3.52 (dd, 1H), 3.26 (dd, 1H), 3.17 (dq, 2H), 2.10–1.98 (m, 1H), 1.85 (dd, 1H), 1.47 (s, 3H), 1.46 (s, 3H), 1.18 (dd, 1H).

IR (CH$_2$Cl$_2$): 1451, 1400, 1380, 1362, 1308, 1216, 1192, 1120, 1090, 1025, 968, 915, 880, 870, 830, 810 cm$^{-1}$.

MS (CI): 261 (M+1), 183, 181, 169, 153, 139, 91.

Step E: 7-oxabicyclo[2.2.1]heptan-2-ol,
1,4-dimethyl-6-[(phenylmethoxy)methyl]-, (exo, racemic), mixed with
-5-[(phenylmethoxy)methyl]regioisomer To a stirring 1M solution of lithium triethylborohydride (25.4 ml) in tetrahydrofuran was added 3.30 g (12.7 mmol) of 3,8-dioxatricyclo[3.2.1.0 sup2, sup4]octane,1,5-dimethyl-6-[(phenylmethoxy)methyl]-, (exo, racemic) in 10 ml tetrahydrofuran at ambient temperature. After 3 hours at reflux, the mixture was cooled to 0° C. and 10.2 g of a 10% sodium hydroxide solution was added dropwise. The mixture was warmed to ambient temperature and 8.64 g of 30% hydrogen peroxide (76.2 mmol) was added dropwise. The mixture was stirred at 40° C. for 30 minutes, then was saturated with potassium carbonate crystals. The mixture was poured into 100 ml ether and the organic layer was separated. The aqueous layer was extracted with ether three times. The combined organic layers were washed with brine, dried over magnesium sulfate and concentrated in vacuo to yield 4.45 g of a light yellow oil. Flash chromatography in 3:1 ether: hexanes on 150 g of silica gel yielded 2.04 g of colorless oil containing a 2:1 mixture of the 5-(phenylmethoxymethyl)isomer: 6-(phenylmethoxy) methyl isomer.

NMR (CDCl$_3$): 7.32 (m, 5H), 4.48 (m, 2H), 3.77 (m, 1H), 3.64 (m, 1H), 3.20 (m, 1H), 2.20 (m, 1H), 1.90 (m, 1H), 1.75 (m, 1H), 1.66 (m, 1H), 1.45, 1.43, 1.41 and 1.38 (s, 6H, total), 1.30 (m, 1H), 1.12 (m, 1H).

IR(CH$_2$Cl$_2$): 3580, 3460 (br), 1452, 1380, 1363, 1203, 1090, 1070, 1027, 860 cm$^{-1}$.

Step F: 7-oxabicyclo[2.2.1]heptane,
1,4-dimethyl-2-(phenylmethoxy)-6-[(phenylmethoxy)-methyl]-, 2:1 with the
-5-[(phenylmethoxy)methyl]isomer, (exo, exo, racemic)

Sodium hydride (0.39 g, 9.73 mmol) was washed with hexanes, decanted, and suspended in 10 ml of dimethylacetamide. To the suspension was added 2.04 g (7.79 mmol) of 7-oxabicyclo[2.2.1]heptan-2-ol, 1,4-dimethyl-6-[(phenylmethoxy)methyl]-(exo, racemic), mixed with -5-[(phenylmethoxy)methyl]regioisomer in 20 ml dimethylacetamide at ambient temperature over 20 minutes. The mixture was stirred at 65° C. for 2 hours, then 1.66 g (9.73 mmol) of benzyl bromide in 10 ml dimethylacetamide was added at 0° C. The mixture was warmed to ambient temperature. After 20 hours, the mixture was poured into 100 ml methylene chloride and 100 ml water. The phases were separated and the aqueous layer was extracted three times with methylene chloride. The combined organic layers were washed with brine, dried, and concentrated in vacuo to yield 4.00 g of a light yellow oil. Flash chromatography in 2:1 hexanes:ether on 150 g of silica gel yielded 1.97 g of a light oil containing a 2:1 mixture of isomers.

NMR (CDCl$_3$): 7.32 (m, 10H), 4.58–4.36 (m, 4H), 3.54 (m, 2H), 3.20 (m, 1H), 2.02 (m, 1H), 1.88 (m, 1H), 1.8–1.6 (m, 1H), 1.47, 1.45 and 1.43 (s, 6H total), 1.2–1.05 (m, 2H).

IR (CH$_2$Cl$_2$): 1605, 1587, 1495, 1452, 1385, 1372, 1360, 1333, 1203, 1185, 1085, 1013, 860 cm$^{-1}$.

MS (CI): 363 (M+1), 335, 261, 246, 245, 244, 215, 181, 155, 137, 119, 91.

EXAMPLE 2

Step A: 7-oxabicyclo[2.2.1]hept-5-ene-2-carboxylic acid, methyl ester (exo and endo, racemic)

To a mixture of 93.0 g (1.37 mmol) of furan and 0.50 g (8.6 mmol) of propylene oxide was added 47.0 g (0.52 mmol) acryloyl chloride at ambient temperature. The mixture was stirred under a nitrogen atmosphere for tree days in the dark. The mixture was then added to a solution of 45.0 ml (0.556 mol) pyridine and 45.0 ml of methanol in 100 ml methylene chloride at 0° C. The mixture was warmed to ambient temperature after the addition was complete. After 1 hour, water was added to the mixture and the layers were separated. The aqueous layer was extracted two times with methylene chloride. The combined organic layers were washed with water, brine and dried over magnesium sulfate and concentrated in vacuo to yield 66.3 g of dark oil containing a 2:1 ratio of exo:endo isomers. Flash chromatography of 4.0 g in 20:1 hexanes:ethyl acetate on 320 g of silica gel separated the endo and exo isomers.

NMR (CDCl$_3$) endo: 6.44 (dd, 1), 6.21 (dd, 1H), 51.7 (dd, 1H), 5.03 (dd, 1H), 3.64 (s, 3H), 3.10 (ddd, 1H), 2.10 (ddd, 1H), 1.58 (dd, 1H).

NMR (CDCl$_3$) exo: 6.37 (dd, 2H), 5.10 (dd, 2H), 3.73 (s, 3H), 2.44 (dd, 1H), 2.18 (dt, 1H), 1.56 (dd, 1H).

Step B: 7-oxabicyclo[2.2.1]hept-5-ene,
2-(1-ethyl-1-methoxypropyl), exo-, (racemic-)

To 20 ml (40 mmol) of 2M ethylmagnesium bromide in tetrahydrofuran at 0° C. was added 3.0 (19.5 mmol) of 7-oxabicyclo[2.2.1]hept-5-ene-2-carboxylic acid, methyl ester (exo, racemic) in 20 ml tetrahydrofuran. The mixture was warmed to reflux. After eight hours, the mixture was cooled to 1° and 20 ml water was added. The mixture was acidified to pH3 with 10% hydrochloric acid, then extracted two times with ether. The combined organic layers were combined, washed with brine, dried over magnesium sulfate and concentrated in vacuo to yield 2.3 g of light yellow oil. This intermediate was dissolved in 50 ml tetrahydrofuran and added to 0.65 g (45.1 mmol) of 60% sodium hydride in oil at 0° C. The solution was warmed to ambient temperature and stirred 10 minutes. Iodomethane (1.3 g, 40.0 mmol) was added and the mixture was refluxed. After 20 hours, the mixture was cooled and poured into 100 ml water. The layers were separated, and the aqueous layer was extracted twice with ether. The organic layers were combined and washed with brine, dried over magnesium sulfate and concentrated in vacuo to yield 1.69 g of yellow oil. Flash chromatography in 6:1 hexanes: ethylacetate yielded 1.27 of a pale yellow oil.

NMR (CDCl$_3$): 6:40 (dd, 1H), 6.28 (dd, 1H), 4.95 (dd, 2H), 3.19 (s, 3H), 1.77 (dd, 1H), 1.60 (m, 4H), 1.47 (dd, 1H), 1.33 (dd, 1H), 0.9 (dt, 6H) .

Step C: 7-oxabicyclo[2.2.1]heptane,
2-(1-ethyl-1-methoxypropyl)-6-(phenylmethoxy)-,
[exo-(2-alpha, 6-alpha)]

Following procedures similar to those described in Steps D, E and F in Example 1, reaction of 1.27 g (6.48 mmol) of 7-oxabicyclo[2.2.1]heptane, 2-(1-ethyl-1-methoxy-propyl)(exo, racemic) with 1.9 g (6.6 mmol) of m-chloroperbenzoic acid gave 0.75 g of a yellow oil. Consequent reaction with 10 ml (10 mmol) of lithium triethylborohydride yielded 0.9 g of a pale yellow oil.

Treatment with benzyl bromide, followed by flash chromatography yielded 0.20 g of a colorless oil.

NMR (CDCl$_3$): 7.33 (m, 5H), 4.55 (m, 4H), 3.64 (dd, 1), 3.16 (s, 3H), 1.85–1.31 (m, 9H), 0.89 and 0.88 (t, t, 6H).

EXAMPLE 3

Step A: cis-7-oxabicyclo[2.2.1]hept-5-ene-2,3-dimethanol, (exo)-

Furan (85.0 ml, 1.17 mol) was added to maleic anhydride (81.0 g, 0.827 mol) in 100 ml ether at ambient temperature. After 20 hours, the precipitated solid was filtered off and washed with ether to give 104 g of white crystalline solid.

Reduction of 34.0 of the Diels-Alder adduct with lithium aluminum hydride, as described previously, yielded 28.0 g oil. The NMR spectrum was the same as that reported in the literature [Das et al.,*J. Med. Chem.*, 31, 930 (1988)].

NMR (CDCl$_3$): 6.40 (s, 2H), 4.70 (s, 2H), 4.00 (br, 2H), 3.80 (m, 4H), 1.95 (m, 2H).

Step B: 7-oxabicyclo[2.2.1]heptane, 2,3-bis(ethoxymethoxy)-5-hydroxy-, [2 exo-(2 alpha, 3 alpha, 5 alpha)]

Alkylation of 14.0 g (0.0897 mol) cis-7-oxabicyclo[2.2.1]-hept-5-ene-2,3-dimethanol using ethyl iodide and sodium hydride was accomplished as described previously to give 15.0 g of the bis-ether. Epoxidation using m-chloroperbenzoic acid, followed by reductive opening with lithium triethylborohydride, as described previously, yielded 4.00 g of oil.

NMR (CDCl$_3$): 4.49 (dd, 1H), 4.23 (s, 1H), 3.96 (brt, 1H), 3.5–3.2 (m, 8H), 2.12 (brd, 1H), 1.95 (m, 3H), 1.55 (ddt, 1H), 1.17 (t, 6H).

MS (CI): 231 (M+1), 259, 185.

Step C: 7-oxabicyclo[2.2.1]heptane, 2,3-bis(ethoxymethoxy)-5-(phenylmethoxy)-, [2 exo-(2 alpha, 3 alpha, 5 alpha)]-

Coupling of 7-oxabicyclo[2.2.1]heptane, 2,3-bis(ethoxymethoxy)-5-(phenylmethoxy)-, [2 exo-(2 alpha, 3 alpha, 5 alpha)] (0.5 g, 2.17 mmol) with benzylbromidine the presence of sodium hydride, as described earlier, yielded 0.40 g of colorless oil.

NMR (CDCl$_3$): 7.33 (m, 5H), 4.52 (m, 4H), 3.75 (dd, 1H), 3.5–3.2 (m, 8H), 2.0–1.7 (m, 4H), 1.21 and 1.20 (t, t, 6H).

EXAMPLE 4

Step A: (±)-4-methyl-4-cyclohexene-1,2-dicarboxylic anhydride

To 50 ml (0.50 mol) of isoprene cooled to 0° C. was added 25 g (0.26 mol) of maleic anhydride portionwise. The reaction mixture was warmed to ambient temperature and stirred for 4 hours. The excess isoprene was removed under vacuum to give 40.5 g of a white solid, m.p. 63°–65° C.

NMR (CDCl$_3$): 5.70 (brs, 1H), 3.45 (m, 2H), 2.50 (m, 4H), 1.81 (s, 3H).

IR (KBr):2900, 1840, 1770, 1445, 1235, 965, 920, 800.

Step B: (±)-cis-4-methyl-4-cyclohexene-1,2-dimethanol

To 300 ml of tetrahydrofuran at 0° C. was added 16.0 g (0.42 mol) lithium aluminum hydride portionwise keeping the reaction temperature between 0° C. and 5° C. A solution of 33.0 g (0.20 mol) of 4-methyl-4-cyclohexene-1,2-dicarboxylic anhydride in 100 ml of tetrahydrofuran was added dropwise over 2 hours keeping the temperature between 0° C. and 10° C. The reaction mixture was warmed to ambient temperature and stirred for 2 hours. The reaction was cooled to 0° C. and 35 ml of ethyl acetate was added dropwise, followed by dropwise addition of 35 ml isopropanol and 35 ml water. The reaction mixture was filtered through celite using acetone, dried with MgSO$_4$ and concentrated to 33.0 g of oil. Flash chromatography in 3:1 hexanes:ethyl acetate, followed by 1:1 hexanes:ethyl acetate and finally ethyl acetate along yielded 18.2 of oil.

NMR (CDCl$_3$): 5.35 (brs, 1H, 3.68 (m, 2H), 3.60 (m, 2H), 3.10 (brs, 2H), 2.05 (brs, 6H), 1.64 (s, 3H).

IR (neat): 3500–3100, 1730W, 1440, 1010.

MS (CI): 157 (M+1), 139, 121.

Step C: 2-endo, 4-exo-(±)-4-hydroxy-5-methyl-6-oxabicyclo[3.2.1]octane-2-methanol To a suspension of 39.0 g (0.124 mol) of 55% m-chloro-perbenzoic acid in 400 ml methylene chloride at 0° C. was added 19.4 g (0.124 mol) of (±)-cis-4-methyl-1,4-cyclohexene-1,2-dimethanol in 100 ml methylene chloride over 15 minutes keeping the temperature less than 8° C. The reaction mixture was warmed to ambient temperature and stirred for 24 hours. The reaction was cooled to 0° C. and 30 ml of a saturated aqueous solution of Na$_2$S$_2$O$_3$ was added dropwise keeping the temperature less than 8° C. The reaction mixture was dried with MgSO$_4$, filtered and concentrated. Flash chromatography in 3:1 hexanes:ethyl acetate, 1:1 hexanes:ethyl acetate, then ethyl acetate alone yielded 6.1 g oily solid.

NMR (CDCl$_3$): 3.80 (brd, 2H), 3.60 (brd, 1H), 3.45 (d, 2H), 2.70 (brs, 2H), 2.42 (brs, 1H), 2.0 (m), 1.5 (m), 1.33 (s, 3H).

IR (neat): 3400–3200, 2900, 1450, 1400, 1380, 1060, 1000, 820.

MS (CI): 173 (M+1), 213, 155.

Step D: (±)-2-endo,4-exo-4-hydroxy-2-(methoxymethyl)-5-methyl-6-oxabicyclo[3.2.1]octane To 1.45 g (0.36 mol) of hexane-washed 60% sodium hydride was added 100 ml tetrahydrofuran. The reaction was cooled to 0° C. and 6.1 g (0.035 mol) of (±)-2-endo,4-exo-4-hydroxy-5-methyl-6-oxabicyclo[3.2.1]octan-2-methanol in 70 ml tetrahydrofuran was added dropwise over 45 minutes keeping the temperature between 0° C. and 5° C. The reaction mixture was warmed to ambient temperature and 2.5 ml (0.04 mol) of methyliodide was added. An additional 1.0 g (0.025 mol) of 60% sodium hydride and 2.0 ml (0.03 mol) of methyliodide was added to the reaction. After 48 hours, the reaction was cooled to 0° C. and 25 ml of water was added dropwise. The reaction mixture was extracted with ether, and then with methylene chloride. The combined organic layers were dried with MgSO$_4$, filtered and concentrated to 7.26 g oil. Flash chromatography in 3:1 hexanes:ethyl acetate yielded 2.0 g of oil.

NMR (CDCl$_3$): 3.80 (m, 2H), 3.60 (brs, 1H), 3.32 (s, 3H), 3.20 (m, 2H), 2.40 (brs, 1H), 2.18 M, 1H), 2.10 (d, 1H), 1.50 (m, 3H), 1.33 (s, 3H).

MS (CI): 187 (M+1), 204, 169, 155.

Step E:
(±)-2-endo-2-(methoxymethyl)-5-methyl-6-oxabicyclo[3.2.1]octan-4-one To 21.0 ml (0.042 mol) of 2M oxalylchloride in methylene chloride at −78° C. was added 4.2 ml (0.06 mol) dimethyl sulfoxide. The reaction mixture was stirred for 15 minutes, then 3.9 g (0.021 mol) of (±)-2-endo,4-exo-4-hydroxy-2-(methoxymethyl)-5-methyl-6-oxabicyclo[3.2.1]octane in 10 ml methylene chloride was added dropwise an the reaction mixture was stirred for 45 minutes. Triethylamine (16.5 ml, 0.12 mol) was added dropwise and the reaction mixture was warmed to ambient temperature. Water was added (50 ml) and the reaction mixture was extracted with methylene chloride, dried over $MgSO_4$, filtered and concentrated. Flash chromatography in 3:1 hexanes:ethyl acetate yielded 0.96 g of oil.

NMR ($CDCl_3$): 4.10 (m, 2H), 3.34 (m, 5H), 2.69 (brs, 1H), 2.5–2.0 (m, 4H), 1.80 (d, 1H), 1.34 (s, 3H).
IR (neat): 2920, 1720s, 1445, 1105, 975.
MS (CI): 185 (M+1), 202, 199, 216.

Step F:
(±)-2-endo,4-endo-4-hydroxy-2-(methoxymethyl)-5-methyl-6-oxabicyclo[3.2.1]octane To 2.2 g (0.012 mol) of (±)-2-endo,4-endo-4-hydroxy-2-(methoxymethyl)-5-methyl-6-oxabicyclo[3.2.1]octan4-one in tetrahydrofuran at −78° C. was added a slight excess of 1 M lithium triethylborohydride in tetrahydrofuran. After 5 minutes 10 ml of water was added and the reaction mixture was warmed to ambient temperature. The reaction mixture was extracted with methylene chloride, dried over $MgSO_4$, filtered and concentrated. Flash chromatography in 1:1 hexanes:ethyl acetate yielded 1.2 g of oil.

NMR ($CDCl_3$): 3.83 (brd, 2H), 3.40 (m, 1H), 3.32 (s, 3H), 3.20 (d, 2H), 2.40 (brs, 1H), 2.05–1.9 (m), 1.52 (d, 1H), 1.34 (s, 3H).

Step G:
2-endo,4-endo-2-(methoxymethyl)-5-methyl-4-(phenylmethoxy)-6-oxabicyclo[3.2.1]octane To 0.12 g (3 mmol) of hexane-washed sodium hydride in tetrahydrofuran was added 0.35 g (1.8 mmol) of (±)-2-endo,4-endo-2-(methoxymethyl)-5-methyl-6-oxabicyclo[3.2.1]octan-4-ol in tetrahydrofuran. The reaction mixture was stirred at 60° C. for 24 hours. Water was added and the reaction mixture was extracted with ether, dried over $MgSO_4$, filtered and concentrated. Flash chromatography in 20:1 hexanes:ethyl acetate yielded an oil.

NMR ($CDCl_3$): 7.32 (m, 5H), 4.62 (d, 1H), 3.82 (d+dd, 2H), 3.32 (s, 3H), 3.2–2.2 (m, 3H), 2.39 (brs, 1H), 2.03 (dt, 1H), 1.8 (m, 2H), 1.49 d, 1H), 1.37 (s, 3H), 1.25 (m, 1H).
IR (neat): 2900, 1460, 1360, 1080, 1000, 960, 850, 730, 690.
MS (CI): 277 (M+1), 294.

EXAMPLE 5

Step A: (±)-diethyl 3,6-dihydro-4-methyl-2H-pyran-2,2-dicarboxylate

To 50 g (0.70 mol) isoprene was added 25 g (0.14 mol) diethylketomalonate and 0.78 g (2.4 mmol) zinc iodide. The reaction mixture was stirred at room temperature for 48 hours. The excess isoprene was removed under vacuum. Flash chromatography in 20:1 hexanes:ethyl acetate yielded 1.2 g of oil.

NMR ($CDCl_3$): 5.40 (brs, 1H), 4.34 (m, 2H), 4.28 (q, 4H), 2.58 (brs, 2H), 1.75 (brs, 3H), 1.29 (t, 6H.
MS (CI): 243 (M+1), 283, 225, 169.

Step B:
(±)-3,6-dihydro-4-methyl-2H-pyran-2,2-dimethanol

To 200 ml tetrahydrofuran at 0° C. was added 4.0 g (0.015 mol) lithium aluminum hydride portionwise. A solution of 12.5 g (0.052 mol) of (±)-diethyl 3,6-dihydro-4-methyl-2H-pyran-2,2-dicarboxylate in 60 ml tetrahydrofuran was added dropwise over 30 minutes. The reaction mixture was warmed to ambient temperature. After 2 hours, the reaction was cooled to 0° C. and successively treated with 30 ml ethyl acetate, 30 ml isopropanol, 30 ml water dropwise keeping the temperature under 10° C. The reaction mixture was filtered through celite with acetone, dried over $MgSO_4$, filtered, and concentrated to an oil. Flash chromatography in 1:1 hexanes:ethyl acetate followed by ethyl acetate alone yielded 5.5 g oil.

NMR ($CDCl_3$); 5.42 (brs, 1H), 4.18 (brs, 2H), 3.71 (d, 2H), 3.65 (d, 2H), 1.84 (brs, 2H), 1.7 (s, 3H).
IR (neat): 3300 broad, 2900, 1435, 1380, 1110, 1020.
MS (CI): 159 (M+1), 173, 141, 127.

Step C:
(±)-exo-4-hydroxy-5-methyl-2,6-dioxabicyclo[3.2.1]octan-1-methanol

To a suspension of 11.0 g (0.035 mol) 55% m-chloroperbenzoic acid in 100 ml methylene chloride at 0° C., was added 5.5 g (0.035 mol) of (±)-3,6-dihydro-4-methyl-2H-pyran-2,2-dimethanol in 100 ml methylene chloride. The reaction mixture was warmed to ambient temperature. After 20 hours, the reaction mixture was cooled to 0° C. and 30 ml of a saturated aqueous solution of $Na_2S_2O_3$ was added dropwise. The reaction mixture was dried over $MgSO_4$, filtered, and concentrated. Flash chromatography in 1:1 hexanes:ethyl acetate followed by ethyl acetate yielded 1.7 of oil.

NMR ($CDCl_3$): 4.13 (dd, 1H), 4.08 (d, 1H), 3.86 (m, 2H), 3.78 (d, 1H), 3.62 (d, 1H), 3.45 (d, 1H), 2.22 (d, 1H), 1.40 (d, 1H), 1.40 (s, 3H).
MS (CI): 175 (M+1), 192, 157.

Step D:
(±)-4-exo-1-(ethoxymethyl)-4-hydroxy-5-methyl-2,6-dioxabicyclo[3.2.1]octane To 0.3 g (0.007 mol) of 60% sodium hydride in tetrahydrofuran was added 1.2 g (0.007 mol) of (±)-exo-4-hydroxy-5-methyl-2,6-dioxabicyclo[3.2.1]octan-1-methanol in tetrahydrofuran followed by 0.6 ml (0.013 mol) ethyliodide. After 24 hours at ambient temperature, water was added and the reaction mixture was extracted with methylene chloride, dried over $MgSO_4$, filtered, and concentrated. Flash chromatography yielded an oil.

NMR ($CDCl_3$): 4.18 (dd, 1H), 4.09 (dd, 1H), 3.95 (d, 1H), 2.81 (m, 2H), 3.65–3.4 (m, 4H), 2.20 (d, 1H), 1.50 (d, 1H), 1.40 (s, 3H), 1.19 (t, 3H).
MS (CI): 203 (M+1), 220, 185.

Step E:
(±)-1-(ethoxymethyl)-5-methyl-2,6-dioxabicyclo[3.2.1]octan-4-one

To 4 ml (0.008 mol) of 2 M oxalylchloride in methylene chloride at −78° C. was added successively 0.7 ml (0.01 mol) dimethylsulfoxide, 1.2 g (0.0058 mol) of (±)-4-exo-1-(ethoxymethyl)-4-hydroxy-5-methyl-2,6-dioxabicyclo[3.2.1]octane and 2.79 ml (0.02 mol) triethylamine. The reaction mixture was warmed to ambient temperature, and water was added. The reaction mixture was extracted with methyl chloride, dried over MgSO₄, filtered and concentrated. Flash chromatography yielded 1.0 g oil.

NMR (CDCl₃): 4.50 (d, 1H), 4.21 (m, 3H), 3.57 (m, 4H), 2.20 (d, 1H), 2.10 (d, 1H), 1.40 (s, 3H), 1.21 (t, 3H).

Step F:
(±)-4-endo-1-(ethoxymethyl)-5-methyl-5-methyl-4-(phenylmethoxy)-2,6-dioxabicyclo[3.2.1]octane To a slight excess of lithium triethylborohydride in tetrahydrofuran at −78° C. was added 1.0 g (0.0049 mol) of (±)-1-(ethoxymethyl)-5-methyl-2,6-dioxabicyclo[3.2.1]octan-4-one. After 5 minutes water was added and the reaction mixture was warmed to ambient temperature. The reaction mixture was extracted with methylene chloride, dried over MgSO₄, filtered, and concentrated to give 0.5 g of oil. To 0.2 g (0.97 mmol) of this oil was added 0.1 g (2.5 mmol) of 60% sodium hydride and 0.25 g (1.5 mmol) of benzylbromide in tetrahydrofuran. After 24 hours at 60° C., water was added and the reaction mixture as extracted with ether, dried over MgSO₄, filtered, and concentrated. Flash chromatography in 20:1 hexanes:ethyl acetate yielded 0.38 g oil.

NMR (CDCl₃): 7.32 (brs, 5H), 4.55 (s, 2H), 4.00 (d+d dd, 3H), 3.68 (t, 1H), 3.40 (m, 4H), 3.38 (dd, 1H), 1.79 (dd, 2H), 1.40 (s, 3H), 1.18 (s, 3H).

EXAMPLE 6

Step A:
(±)-exo,exo,exo-αα-diethyl-5,6-bishydroxy-7-oxabicyclo[2.2.1]heptane-2-methanol To 26.5 g (0.146 mol) of 2-(1-ethyl-1-hydroxypropyl)-7-oxabicyclo[2.2.1]hept-5-ene in 100 ml acetone at 0° C. was added 17.6 g ( 0.15 mol) N-methyl morpholine N-oxide and 10 ml of 4% osmium tetroxide in water. The reaction mixture as warmed to ambient temperature and stirred for 4 days. A saturated aqueous solution of Na₂S₂O₃ was added. The reaction mixture was extracted with ethyl acetate twice and the combined extracts were washed with water and brine, and dried over MgSO₄, filtered, and concentrated. Flash chromatography yielded 12.0 g thick oil.

NMR (CDCl₃): 4.44 (s, 1H), 4.38 (d, 1H), 3.85 (m), 1.8–1.7 (m), 0.84 (t+t, 6H).
MS (CI): 217 (M+1), 234.

Step B:
(±)-exo,exo,exo-α,α-diethyl-6-[(2-fluorophenyl)methoxy]-5-hydroxy-7-oxabicyclo[2.2.1]heptane-2-methanol To 1.2 g (0.03 mol) of 60% sodium hydride in tetrahydrofuran at 0° C. was added 6.0 g (0.028 mol) of (±)-exo,exo,exo-diethyl-5,6-bishydroxy-7-oxabicyclo[2.2.1]heptan-2-methanol in tetrahydrofuran. The reaction mixture was warmed to ambient temperature and 3.4 ml (0.03 mol) of 2-fluorobenzylbromide was added. After 24 hours, water was added and the reaction mixture was extracted with ether, dried over MgSO_r, filtered and concentrated. Flash chromatography yielded 1.3 g oil.

NMR (CDCl₃): 7.5–7.0 (m, 4H), 4.69 (d+d, 2H), 4.50 (s, 1H), 4.40 (d, 1H), 3.92 (dd, 1H), 3.61 (d, 1H), 3.20 (d, 1H), 1.2–2.0 (m), 0.80 (m).
MS (CI): 324 (M+), 342.

Step C:
(±)-exo-exo-exo-5-(1-ethyl-1-methoxypropyl)-3((2-fluorophenyl)methoxy-2-methoxy-7-oxabicyclo[2.2.1-]heptane To 1.3 g (4.0 mmol) of (±)-exo,exo,exo-α,α-diethyl-6-[(2-fluorophenyl)methoxy]-5-hydroxy-7-oxabicyclo[2.2.1]hexane-2-methanol in dimethylformamide was added excess sodium hydride and methyliodide. The reaction mixture was stirred at 70° C. for 12 hours. Following aqueous workup, flash chromatography yielded 0.25 g oil.

NMR (CDCl₃): 7.6–7.0 (m, 4H), 4.71 (brs, 2H), 4.45 (s+d, 2H), 3.66 (d, 1H), 3.52 (d, 1H), 3.52 (d, 1H), 3.42 (s, 3H), 3.15 (s, 3H), 1.8–1.2 (m), 0.80 (m, 6H).
MS (CI): 353 (M+1), 370, 338.

Tables 1–5 present examples of species of the present invention. It is understood that these enumerated examples are merely representative of the range of species contemplated by the present invention. The notation "Ph" connotes a phenyl group. Compounds in Tables 10–15 have the WCH₂O group syn with respect to the oxygen-containing bridge. The endo-exo notation refers to the configuration of the C(R³)(R⁴)OR⁵ group. The indicated ratios (Table 10) refer to cases where the compounds of invention (I) are formed in an inseparable mixture with compounds of Formula (18). The ratio is given in the form (I:(18)).

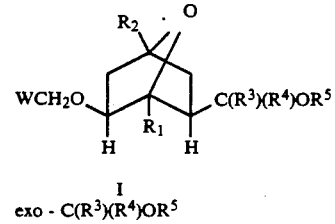

I
exo - C(R³)(R⁴)OR⁵

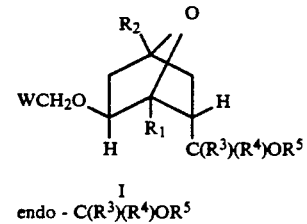

I
endo - C(R³)(R⁴)OR⁵

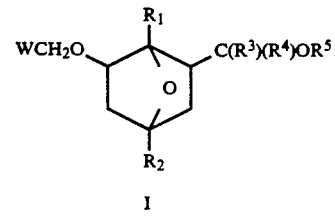

I

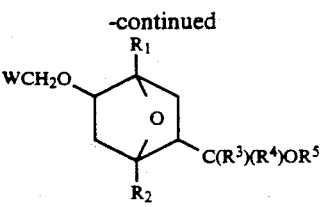

(18)

The species of Tables 1–8 correspond to the Formulas I–VIII of the compounds of the present invention. Thus, the first compound identified in Table 1 (with $R^1$=H; $R^2$=H; $R^3$=CH$_3$CH$_2$; $R^4$=CH$_3$CH$_2$; $R^5$=CH$_3$; and W=2-FPh) is a species of the compound identified as Formula I.

TABLE 1

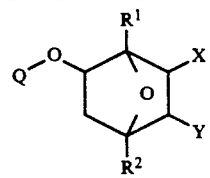

I

X and Y are $C(R^3)(R^4)OR^5$ (unless specified)
$R^1 = R^2 =$ H (unless specified)

| $R^3$ | $R^4$ | $R^5$ | Q | Y |
|---|---|---|---|---|
| CH$_3$CH$_2$ | CH$_3$CH$_2$ | CH$_3$ | CH$_2$(2-FPh) | H |
| CH$_3$CH$_2$ | CH$_3$CH$_2$ | CH$_3$ | CH$_2$(3-FPh) | H |
| CH$_3$CH$_2$ | CH$_3$CH$_2$ | CH$_3$ | CH$_2$(4-FPh) | H |
| CH$_3$CH$_2$ | CH$_3$CH$_2$ | CH$_3$ | CH$_2$(2,3-F$_2$Ph) | H |
| CH$_3$CH$_2$ | CH$_3$CH$_2$ | CH$_3$ | CH$_2$(2,4-F$_2$Ph) | H |
| CH$_3$CH$_2$ | CH$_3$CH$_2$ | CH$_3$ | CH$_2$(2,5-F$_2$Ph) | H |
| CH$_3$CH$_2$ | CH$_3$CH$_2$ | CH$_3$ | CH$_2$(2,6-F$_2$Ph) | H |
| CH$_3$CH$_2$ | CH$_3$CH$_2$ | CH$_3$ | CH$_2$(2-ClPh) | H |
| CH$_3$CH$_2$ | CH$_3$CH$_2$ | CH$_3$ | CH$_2$(3-ClPh) | H |
| CH$_3$CH$_2$ | CH$_3$CH$_2$ | CH$_3$ | CH$_2$(4-ClPh) | H |
| CH$_3$CH$_2$ | CH$_3$CH$_2$ | CH$_3$ | CH$_2$(2,4-Cl$_2$Ph) | H |
| CH$_3$CH$_2$ | CH$_3$CH$_2$ | CH$_3$ | CH$_2$(2,6-Cl$_2$Ph) | H |
| CH$_3$CH$_2$ | CH$_3$CH$_2$ | CH$_3$ | CH$_2$(2-BrPh) | H |
| CH$_3$CH$_2$ | CH$_3$CH$_2$ | CH$_3$ | CH$_2$(3-BrPh) | H |
| CH$_3$CH$_2$ | CH$_3$CH$_2$ | CH$_3$ | CH$_2$(4-BrPh) | H |
| CH$_3$CH$_2$ | CH$_3$CH$_2$ | CH$_3$ | CH$_2$(2,4-Br$_2$Ph) | H |
| CH$_3$CH$_2$ | CH$_3$CH$_2$ | CH$_3$ | CH$_2$(2,6-Br$_2$Ph) | H |
| CH$_3$CH$_2$ | CH$_3$CH$_2$ | CH$_3$ | CH$_2$(2-(OCH$_3$)Ph) | H |
| CH$_3$CH$_2$ | CH$_3$CH$_2$ | CH$_3$ | CH$_2$(3-(OCH$_3$)Ph) | H |
| CH$_3$CH$_2$ | CH$_3$CH$_2$ | CH$_3$ | CH$_2$(4-(OCH$_3$)Ph) | H |
| CH$_3$CH$_2$ | CH$_3$CH$_2$ | CH$_3$ | CH$_2$(2-(CH$_3$)Ph) | H |
| CH$_3$CH$_2$ | CH$_3$CH$_2$ | CH$_3$ | CH$_2$(2,3-(CH$_3$)$_2$Ph) | H |
| CH$_3$CH$_2$ | CH$_3$CH$_2$ | CH$_3$ | CH$_2$(2,4-(CH$_3$)$_2$Ph) | H |
| CH$_3$CH$_2$ | CH$_3$CH$_2$ | CH$_3$ | CH$_2$(2,5-(CH$_3$)$_2$Ph) | H |
| CH$_3$CH$_2$ | CH$_3$CH$_2$ | CH$_3$ | CH$_2$(2,6-(CH$_3$)$_2$Ph) | H |
| CH$_3$CH$_2$ | CH$_3$CH$_2$ | CH$_3$ | CH$_2$(2-(CH$_3$CH$_2$)Ph) | H |
| CH$_3$CH$_2$ | CH$_3$CH$_2$ | CH$_3$ | CH$_2$(4-(CH$_3$CH$_2$)Ph) | H |
| CH$_3$CH$_2$ | CH$_3$CH$_2$ | CH$_3$ | CH$_2$(2-(OH)Ph) | H |
| CH$_3$CH$_2$ | CH$_3$CH$_2$ | CH$_3$ | CH$_2$(2-(CN)Ph) | H |
| CH$_3$CH$_2$ | CH$_3$CH$_2$ | CH$_3$ | CH$_2$(4-(CN)Ph) | H |
| CH$_3$CH$_2$ | CH$_3$CH$_2$ | CH$_3$ | CH$_2$(2-(CF$_3$)Ph) | H |
| CH$_3$CH$_2$ | CH$_3$CH$_2$ | CH$_3$ | CH$_2$(4-(CF$_3$)Ph) | H |
| CH$_3$CH$_2$ | CH$_3$CH$_2$ | CH$_3$ | CH$_2$(2-(OCF$_3$)Ph) | H |
| CH$_3$CH$_2$ | CH$_3$CH$_2$ | CH$_3$ | CH$_2$(4-(OCF$_3$)Ph) | H |
| CH$_3$CH$_2$ | CH$_3$CH$_2$ | CH$_3$ | CH$_2$(2-(SCH$_3$)Ph) | H |
| CH$_3$CH$_2$ | CH$_3$CH$_2$ | CH$_3$ | CH$_2$(4-(SCH$_3$)Ph) | H |
| CH$_3$CH$_2$ | CH$_3$CH$_2$ | CH$_3$ | CH$_2$(2-(CH$_2$CH=CH)Ph) | H |
| CH$_3$CH$_2$ | CH$_3$CH$_2$ | CH$_3$ | CH$_2$(4-(CH$_2$CH=CH)Ph) | H |
| CH$_3$CH$_2$ | CH$_3$CH$_2$ | CH$_3$ | CH$_2$(2-(HC≡C)Ph) | H |
| CH$_3$CH$_2$ | CH$_3$CH$_2$ | CH$_3$ | CH$_2$(4-(HC≡C)Ph) | H |
| CH$_3$CH$_2$ | CH$_3$CH$_2$ | CH$_3$ | CH$_2$(2-pyridyl) | H |
| CH$_3$CH$_2$ | CH$_3$CH$_2$ | CH$_3$ | CH$_2$(3-pyridyl) | H |
| CH$_3$CH$_2$ | CH$_3$CH$_2$ | CH$_3$ | CH$_2$(3-furanyl) | H |
| CH$_3$CH$_2$ | CH$_3$CH$_2$ | CH$_3$ | CH$_2$(2-(3-Cl)pyridyl) | H |
| CH$_3$CH$_2$ | CH$_3$CH$_2$ | CH$_3$ | CH$_2$(3-(2-Cl)pyridyl) | H |
| CH$_3$CH$_2$ | CH$_3$CH$_2$ | CH$_3$ | CH$_2$(2-(3-Br)thiophenyl) | H |
| CH$_3$CH$_2$ | CH$_3$CH$_2$ | CH$_3$ | CH$_2$(3-(2-Br)thiophenyl) | H |
| CH$_3$CH$_2$ | CH$_3$CH$_2$ | CH$_3$ | CH$_2$(2-(5-CH$_3$)furanyl) | H |
| CH$_3$CH$_2$ | CH$_3$CH$_2$ | CH$_3$ | CH$_2$(2-thiophenyl) | H |
| CH$_3$CH$_2$ | CH$_3$CH$_2$ | CH$_3$ | CH$_2$(3-thiophenyl) | H |
| CH$_3$CH$_2$ | CH$_3$CH$_2$ | CH$_3$ | CH$_2$(2-thiazolyl) | H |
| CH$_3$CH$_2$ | CH$_3$CH$_2$ | CH$_3$ | CH$_2$(2-imidazolyl) | H |
| CH$_3$CH$_2$ | CH$_3$CH$_2$ | CH$_3$ | CH$_2$(2-pyrazoyl) | H |
| CH$_3$CH$_2$ | CH$_3$CH$_2$ | CH$_3$ | CH$_2$(2-oxazolyl) | H |
| CH$_3$CH$_2$ | CH$_3$CH$_2$ | CH$_3$ | CH$_2$(2-isoxazolyl) | H |
| CH$_3$CH$_2$ | CH$_3$CH$_2$ | CH$_3$ | CH$_2$(2-pyrrolyl) | H |
| CH$_3$CH$_2$ | CH$_3$CH$_2$ | CH$_3$ | CH$_2$(2-pyrimidinyl) | H |
| CH$_3$CH$_2$ | CH$_3$CH$_2$ | CH$_3$ | CH$_2$(2-pyrazinyl) | H |
| CH$_3$CH$_2$ | CH$_3$CH$_2$ | CH$_3$ | CH$_2$(2-tetrahydropyranyl) | H |

TABLE 1-continued

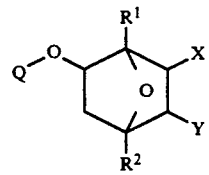

X and Y are C(R³)(R⁴)OR⁵ (unless specified)
R¹ = R² = H (unless specified)

| | | | | |
|---|---|---|---|---|
| CH₃CH₂ | CH₃CH₂ | CH₃ | CH₂(2-tetrahydrofuranyl) | H |
| CH₃CH₂ | CH₃CH₂ | CH₃ | Q-1 | H |
| CH₃CH₂ | CH₃CH₂ | CH₃ | Q-2 | H |
| CH₃CH₂ | CH₃CH₂ | CH₃ | Q-3 | H |
| CH₃CH₂ | CH₃CH₂ | CH₃ | Q-4 | H |
| CH₃CH₂ | CH₃CH₂ | CH₃ | Q-5 | H |
| CH₃CH₂ | CH₃CH₂ | CH₃ | Q-6 | H |
| CH₃CH₂ | CH₃CH₂ | CH₃ | Q-7 | H |
| CH₃CH₂ | CH₃CH₂ | CH₃ | Q-8 | H |
| CH₃CH₂ | CH₃CH₂ | CH₃ | Q-9 | H |
| CH₃CH₂ | CH₃CH₂ | CH₃ | Q-10 | H |
| CH₃CH₂ | CH₃CH₂ | CH₃ | Q-11 | H |
| CH₃CH₂ | CH₃CH₂ | CH₃ | Q-12 | H |
| CH₃CH₂ | CH₃CH₂ | CH₃ | Q-13 | H |
| CH₃CH₂ | CH₃CH₂ | CH₃ | Q-14 | H |
| CH₃CH₂ | CH₃CH₂ | CH₃ | Q-15 | H |
| CH₃CH₂ | CH₃CH₂ | CH₃ | CH₂(Ph) | H |
| CH₃CH₂ | CH₃CH₂ | CH₃CH₂ | CH₂(2-FPh) | H |
| CH₃CH₂ | CH₃CH₂ | CH₃CH₂ | CH₂(2-ClPh) | H |
| CH₃CH₂ | CH₃CH₂ | CH₃CH₂ | CH₂(2-BrPh) | H |
| CH₃CH₂ | CH₃CH₂ | CH₃CH₂ | CH₂(2-(CH₃)Ph) | H |
| CH₃CH₂ | CH₃CH₂ | CH₃CH₂ | CH₂(2-(OCH₃)Ph) | H |
| CH₃CH₂ | CH₃CH₂ | CH₃CH₂ | CH₂(2-(CN)Ph) | H |
| CH₃CH₂ | CH₃CH₂ | CH₃CH₂ | CH₂(2-(CF₃)Ph) | H |
| CH₃CH₂ | CH₃CH₂ | CH₃CH₂ | CH₂(2-(OCF₃)Ph) | H |
| CH₃CH₂ | CH₃CH₂ | CH₃CH₂ | CH₂(2-(SCH₃)Ph) | H |
| CH₃CH₂ | CH₃CH₂ | CH₃CH₂ | CH₂(2-(SCH₃)Ph) | H |
| CH₃CH₂ | CH₃CH₂ | CH₃CH₂ | CH₂(2,6-(F)₂Ph) | H |
| CH₃CH₂ | CH₃CH₂ | CH₃CH₂ | CH₂(2,6-(Cl)₂Ph) | H |
| CH₃CH₂ | CH₃CH₂ | CH₃CH₂ | CH₂(2-pyridyl) | H |
| CH₃CH₂ | CH₃CH₂ | CH₃CH₂ | CH₂(2-furanyl) | H |
| CH₃CH₂ | CH₃CH₂ | CH₃CH₂ | CH₂(2-tetrahydrofuran) | H |
| CH₃CH₂ | CH₃CH₂ | CH₃CH₂ | CH₂(2-tetrahydropyran) | H |
| CH₃CH₂ | CH₃CH₂ | CH₃CH₂ | CH₂(2-thiophenyl) | H |
| CH₃CH₂ | CH₃CH₂ | CH₃CH₂ | CH₂(2-isoxazolyl) | H |
| CH₃CH₂ | CH₃CH₂ | CH₃CH₂ | CH₂(2-pyrazinyl) | H |
| CH₃CH₂ | CH₃CH₂ | CH₃CH₂ | CH₂(Ph) | H |
| CH₃CH₂ | CH₃CH₂ | CH₃CH₂ | Q-1 | H |
| CH₃CH₂ | CH₃CH₂ | CH₃CH₂ | Q-3 | H |
| CH₃CH₂ | CH₃CH₂ | CH₃CH₂ | Q-6 | H |
| CH₃CH₂ | CH₃CH₂ | CH₃CH₂ | Q-7 | H |
| CH₃CH₂ | CH₃CH₂ | CH₃CH₂ | Q-15 | H |
| CH₃CH₂ | CH₃CH₂ | CH₃CH₂CH₂ | CH₂(2-FPh) | H |
| CH₃CH₂ | CH₃CH₂ | CH₃CH₂CH₂ | CH₂(2-ClPh) | H |
| CH₃CH₂ | CH₃CH₂ | CH₃CH₂CH₂ | CH₂(2-BrPh) | H |
| CH₃CH₂ | CH₃CH₂ | CH₃CH₂CH₂ | CH₂(2-(CH₃)Ph) | H |
| CH₃CH₂ | CH₃CH₂ | CH₃CH₂CH₂ | CH₂(2-(OCH₃)Ph) | H |
| CH₃CH₂ | CH₃CH₂ | CH₃CH₂CH₂ | CH₂(2-(CN)Ph) | H |
| CH₃CH₂ | CH₃CH₂ | CH₃CH₂CH₂ | CH₂(2-(CF₃)Ph) | H |
| CH₃CH₂ | CH₃CH₂ | CH₃CH₂CH₂ | CH₂(2-(OCF₃)Ph) | H |
| CH₃CH₂ | CH₃CH₂ | CH₃CH₂CH₂ | CH₂(2-(SCH₃)Ph) | H |
| CH₃CH₂ | CH₃CH₂ | CH₃CH₂CH₂ | CH₂(2,6-(F)₂Ph) | H |
| CH₃CH₂ | CH₃CH₂ | CH₃CH₂CH₂ | CH₂(2,6-(Cl)₂Ph) | H |
| CH₃CH₂ | CH₃CH₂ | CH₃CH₂CH₂ | CH₂(2-pyridyl) | H |
| CH₃CH₂ | CH₃CH₂ | CH₃CH₂CH₂ | CH₂(2-furanyl) | H |
| CH₃CH₂ | CH₃CH₂ | CH₃CH₂CH₂ | CH₂(2-tetrahydrofuran) | H |
| CH₃CH₂ | CH₃CH₂ | CH₃CH₂CH₂ | CH₂(2-tetrahydropyran) | H |
| CH₃CH₂ | CH₃CH₂ | CH₃CH₂CH₂ | CH₂(2-thiophenyl) | H |
| CH₃CH₂ | CH₃CH₂ | CH₃CH₂CH₂ | CH₂(2-isoxazolyl) | H |
| CH₃CH₂ | CH₃CH₂ | CH₃CH₂CH₂ | CH₂(2-pyrazinyl) | H |
| CH₃CH₂ | CH₃CH₂ | CH₃CH₂CH₂ | CH₂(Ph) | H |
| CH₃CH₂ | CH₃CH₂ | CH₃CH₂CH₂ | Q-1 | H |
| CH₃CH₂ | CH₃CH₂ | CH₃CH₂CH₂ | Q-3 | H |
| CH₃CH₂ | CH₃CH₂ | CH₃CH₂CH₂ | Q-6 | H |
| CH₃CH₂ | CH₃CH₂ | CH₃CH₂CH₂ | Q-7 | H |
| CH₃CH₂ | CH₃CH₂ | CH₃CH₂CH₂ | Q-15 | H |
| CH₃CH₂ | CH₃CH₂ | CH₂CH=CH₂ | CH₂(2-FPh) | H |
| CH₃CH₂ | CH₃CH₂ | CH₂CH=CH₂ | CH₂(2-ClPh) | H |
| CH₃CH₂ | CH₃CH₂ | CH₂CH=CH₂ | CH₂(2-BrPh) | H |
| CH₃CH₂ | CH₃CH₂ | CH₂CH=CH₂ | CH₂(2-(CH₃)Ph) | H |
| CH₃CH₂ | CH₃CH₂ | CH₂CH=CH₂ | CH₂(2-(OCH₃)Ph) | H |

TABLE 1-continued

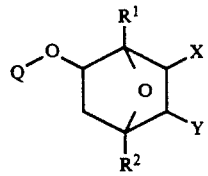

X and Y are C(R³)(R⁴)OR⁵ (unless specified)
R¹ = R² = H (unless specified)

| | | | | |
|---|---|---|---|---|
| CH₃CH₂ | CH₃CH₂ | CH₂CH=CH₂ | CH₂(2-(CN)Ph) | H |
| CH₃CH₂ | CH₃CH₂ | CH₂CH=CH₂ | CH₂(2-(CF₃)Ph) | H |
| CH₃CH₂ | CH₃CH₂ | CH₂CH=CH₂ | CH₂(2-(OCF₃)Ph) | H |
| CH₃CH₂ | CH₃CH₂ | CH₂CH=CH₂ | CH₂(2-(SCH₃)Ph) | H |
| CH₃CH₂ | CH₃CH₂ | CH₂CH=CH₂ | CH₂(2,6-(F)₂Ph) | H |
| CH₃CH₂ | CH₃CH₂ | CH₂CH=CH₂ | CH₂(2,6-(Cl)₂Ph) | H |
| CH₃CH₂ | CH₃CH₂ | CH₂CH=CH₂ | CH₂(2-pyridyl) | H |
| CH₃CH₂ | CH₃CH₂ | CH₂CH=CH₂ | CH₂(2-furanyl) | H |
| CH₃CH₂ | CH₃CH₂ | CH₂CH=CH₂ | CH₂(2-tetrahydrofuran) | H |
| CH₃CH₂ | CH₃CH₂ | CH₂CH=CH₂ | CH₂(2-tetrahydropyran) | H |
| CH₃CH₂ | CH₃CH₂ | CH₂CH=CH₂ | CH₂(2-thiophenyl) | H |
| CH₃CH₂ | CH₃CH₂ | CH₂CH=CH₂ | CH₂(2-isoxazolyl) | H |
| CH₃CH₂ | CH₃CH₂ | CH₂CH=CH₂ | CH₂(2-pyrazinyl) | H |
| CH₃CH₂ | CH₃CH₂ | CH₂CH=CH₂ | CH₂(Ph) | H |
| CH₃CH₂ | CH₃CH₂ | CH₂CH=CH₂ | Q-1 | H |
| CH₃CH₂ | CH₃CH₂ | CH₂CH=CH₂ | Q-3 | H |
| CH₃CH₂ | CH₃CH₂ | CH₂CH=CH₂ | Q-6 | H |
| CH₃CH₂ | CH₃CH₂ | CH₂CH=CH₂ | Q-7 | H |
| CH₃CH₂ | CH₃CH₂ | CH₂CH=CH₂ | Q-15 | H |
| CH₃CH₂ | CH₃CH₂ | CH₂C≡CH | CH₂(2-FPh) | H |
| CH₃CH₂ | CH₃CH₂ | CH₂C≡CH | CH₂(2-ClPh) | H |
| CH₃CH₂ | CH₃CH₂ | CH₂C≡CH | CH₂(2-BrPh) | H |
| CH₃CH₂ | CH₃CH₂ | CH₂C≡CH | CH₂(2-(CH₃)Ph) | H |
| CH₃CH₂ | CH₃CH₂ | CH₂C≡CH | CH₂(2-(OCH₃)Ph) | H |
| CH₃CH₂ | CH₃CH₂ | CH₂C≡CH | CH₂(2-(CN)Ph) | H |
| CH₃CH₂ | CH₃CH₂ | CH₂C≡CH | CH₂(2-(CF₃)Ph) | H |
| CH₃CH₂ | CH₃CH₂ | CH₂C≡CH | CH₂(2-(OCF₃)Ph) | H |
| CH₃CH₂ | CH₃CH₂ | CH₂C≡CH | CH₂(2-(SCH₃)Ph) | H |
| CH₃CH₂ | CH₃CH₂ | CH₂C≡CH | CH₂(2,6-(F)₂Ph) | H |
| CH₃CH₂ | CH₃CH₂ | CH₂C≡CH | CH₂(2,6-(Cl)₂Ph) | H |
| CH₃CH₂ | CH₃CH₂ | CH₂C≡CH | CH₂(2-pyridyl) | H |
| CH₃CH₂ | CH₃CH₂ | CH₂C≡CH | CH₂(2-pyridyl) | H |
| CH₃CH₂ | CH₃CH₂ | CH₂C≡CH | CH₂(2-furanyl) | H |
| CH₃CH₂ | CH₃CH₂ | CH₂C≡CH | CH₂(2-tetrahydrofuran) | H |
| CH₃CH₂ | CH₃CH₂ | CH₂C≡CH | CH₂(2-tetrahydropyran) | H |
| CH₃CH₂ | CH₃CH₂ | CH₂C≡CH | CH₂(2-thiophenyl) | H |
| CH₃CH₂ | CH₃CH₂ | CH₂C≡CH | CH₂(2-isoxazolyl) | H |
| CH₃CH₂ | CH₃CH₂ | CH₂C≡CH | CH₂(2-pyrazinyl) | H |
| CH₃CH₂ | CH₃CH₂ | CH₂C≡CH | CH₂(Ph) | H |
| CH₃CH₂ | CH₃CH₂ | CH₂C≡CH | Q-1 | H |
| CH₃CH₂ | CH₃CH₂ | CH₂C≡CH | Q-3 | H |
| CH₃CH₂ | CH₃CH₂ | CH₂C≡CH | Q-6 | H |
| CH₃CH₂ | CH₃CH₂ | CH₂C≡CH | Q-7 | H |
| CH₃CH₂ | CH₃CH₂ | CH₂C≡CH | Q-15 | H |
| CH₃CH₂ | CH₃CH₂ | CH₂Ph | CH₂(2-FPh) | H |
| CH₃CH₂ | CH₃CH₂ | CH₂Ph | CH₂(2-ClPh) | H |
| CH₃CH₂ | CH₃CH₂ | CH₂Ph | CH₂(2-BrPh) | H |
| CH₃CH₂ | CH₃CH₂ | CH₂Ph | CH₂(2-(CH₃)Ph) | H |
| CH₃CH₂ | CH₃CH₂ | CH₂Ph | CH₂(2-(OCH₃)Ph) | H |
| CH₃CH₂ | CH₃CH₂ | CH₂Ph | CH₂(2-(CN)Ph) | H |
| CH₃CH₂ | CH₃CH₂ | CH₂Ph | CH₂(2-(CF₃)Ph) | H |
| CH₃CH₂ | CH₃CH₂ | CH₂Ph | CH₂(2-(OCF₃)Ph) | H |
| CH₃CH₂ | CH₃CH₂ | CH₂Ph | CH₂(2-(SCH₃)Ph) | H |
| CH₃CH₂ | CH₃CH₂ | CH₂Ph | CH₂(2,6-(F)₂Ph) | H |
| CH₃CH₂ | CH₃CH₂ | CH₂Ph | CH₂(2,6-(Cl)₂Ph) | H |
| CH₃CH₂ | CH₃CH₂ | CH₂Ph | CH₂(2-pyridyl) | H |
| CH₃CH₂ | CH₃CH₂ | CH₂Ph | CH₂(2-furanyl) | H |
| CH₃CH₂ | CH₃CH₂ | CH₂Ph | CH₂(2-tetrahydrofuran) | H |
| CH₃CH₂ | CH₃CH₂ | CH₂Ph | CH₂(2-tetrahydropyran) | H |
| CH₃CH₂ | CH₃CH₂ | CH₂Ph | CH₂(2-thiophenyl) | H |
| CH₃CH₂ | CH₃CH₂ | CH₂Ph | CH₂(2-isoxazolyl) | H |
| CH₃CH₂ | CH₃CH₂ | CH₂Ph | CH₂(2-pyrazinyl) | H |
| CH₃CH₂ | CH₃CH₂ | CH₂Ph | CH₂(Ph) | H |
| CH₃CH₂ | CH₃CH₂ | CH₂Ph | Q-1 | H |
| CH₃CH₂ | CH₃CH₂ | CH₂Ph | Q-3 | H |
| CH₃CH₂ | CH₃CH₂ | CH₂Ph | Q-6 | H |
| CH₃CH₂ | CH₃CH₂ | CH₂Ph | Q-7 | H |
| CH₃CH₂ | CH₃CH₂ | CH₂Ph | Q-15 | H |
| CH₂CH₂ | CH₃CH₂ | CH₂OCH₃ | CH₂(2-FPh) | H |
| CH₂CH₂ | CH₃CH₂ | CH₂OCH₃ | CH₂(2-ClPh) | H |
| CH₂CH₂ | CH₃CH₂ | CH₂OCH₃ | CH₂(2-BrPh) | H |

TABLE 1-continued

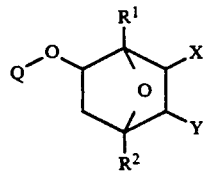

X and Y are C(R³)(R⁴)OR⁵ (unless specified)
R¹ = R² = H (unless specified)

| | | | | |
|---|---|---|---|---|
| CH₂CH₂ | CH₃CH₂ | CH₂OCH₃ | CH₂(2-(CH₃)Ph) | H |
| CH₂CH₂ | CH₃CH₂ | CH₂OCH₃ | CH₂(2-(OCH₃)Ph) | H |
| CH₂CH₂ | CH₃CH₂ | CH₂OCH₃ | CH₂(2-(CN)Ph) | H |
| CH₂CH₂ | CH₃CH₂ | CH₂OCH₃ | CH₂(2-(CF₃)Ph) | H |
| CH₂CH₂ | CH₃CH₂ | CH₂OCH₃ | CH₂(2-(OCF₃)Ph) | H |
| CH₂CH₂ | CH₃CH₂ | CH₂OCH₃ | CH₂(2-(SCH₃)Ph) | H |
| CH₂CH₂ | CH₃CH₂ | CH₂OCH₃ | CH₂(2,6-(F)₂Ph) | H |
| CH₂CH₂ | CH₃CH₂ | CH₂OCH₃ | CH₂(2,6-(Cl)₂Ph) | H |
| CH₂CH₂ | CH₃CH₂ | CH₂OCH₃ | CH₂(2-pyridyl) | H |
| CH₂CH₂ | CH₃CH₂ | CH₂OCH₃ | CH₂(2-furanyl) | H |
| CH₂CH₂ | CH₃CH₂ | CH₂OCH₃ | CH₂(2-tetrahydrofuran) | H |
| CH₂CH₂ | CH₃CH₂ | CH₂OCH₃ | CH₂(2-tetrahydropyran) | H |
| CH₂CH₂ | CH₃CH₂ | CH₂OCH₃ | CH₂(2-thiophenyl) | H |
| CH₂CH₂ | CH₃CH₂ | CH₂OCH₃ | CH₂(2-isoxazolyl) | H |
| CH₂CH₂ | CH₃CH₂ | CH₂OCH₃ | CH₂(2-pyrazinyl) | H |
| CH₂CH₂ | CH₃CH₂ | CH₂OCH₃ | CH₂(Ph) | H |
| CH₂CH₂ | CH₃CH₂ | CH₂OCH₃ | Q-1 | H |
| CH₂CH₂ | CH₃CH₂ | CH₂OCH₃ | Q-3 | H |
| CH₂CH₂ | CH₃CH₂ | CH₂OCH₃ | Q-6 | H |
| CH₂CH₂ | CH₃CH₂ | CH₂OCH₃ | Q-7 | H |
| CH₂CH₂ | CH₃CH₂ | CH₂OCH₃ | Q-15 | H |
| CH₃CH₂CH₂ | CH₃CH₂CH₂ | CH₃ | CH₂(2-FPh) | H |
| CH₃CH₂CH₂ | CH₃CH₂CH₂ | CH₃ | CH₂(2-ClPh) | H |
| CH₃CH₂CH₂ | CH₃CH₂CH₂ | CH₃ | CH₂(2-BrPh) | H |
| CH₃CH₂CH₂ | CH₃CH₂CH₂ | CH₃ | CH₂(2-(CH₃)Ph) | H |
| CH₃CH₂CH₂ | CH₃CH₂CH₂ | CH₃ | CH₂(2-(OCH₃)Ph) | H |
| CH₃CH₂CH₂ | CH₃CH₂CH₂ | CH₃ | CH₂(2-(CN)Ph) | H |
| CH₃CH₂CH₂ | CH₃CH₂CH₂ | CH₃ | CH₂(2-(CF₃)Ph) | H |
| CH₃CH₂CH₂ | CH₃CH₂CH₂ | CH₃ | CH₂(2-(OCF₃)Ph) | H |
| CH₃CH₂CH₂ | CH₃CH₂CH₂ | CH₃ | CH₂(2-(SCH₃)Ph) | H |
| CH₃CH₂CH₂ | CH₃CH₂CH₂ | CH₃ | CH₂(2,6-(F)₂Ph) | H |
| CH₃CH₂CH₂ | CH₃CH₂CH₂ | CH₃ | CH₂(2,6-(Cl)₂Ph) | H |
| CH₃CH₂CH₂ | CH₃CH₂CH₂ | CH₃ | CH₂(2-pyridyl) | H |
| CH₃CH₂CH₂ | CH₃CH₂CH₂ | CH₃ | CH₂(2-furanyl) | H |
| CH₃CH₂CH₂ | CH₃CH₂CH₂ | CH₃ | CH₂(2-tetrahydrofuran) | H |
| CH₃CH₂CH₂ | CH₃CH₂CH₂ | CH₃ | CH₂(2-tetrahydropyran) | H |
| CH₃CH₂CH₂ | CH₃CH₂CH₂ | CH₃ | CH₂(2-thiophenyl) | H |
| CH₃CH₂CH₂ | CH₃CH₂CH₂ | CH₃ | CH₂(2-isoxazolyl) | H |
| CH₃CH₂CH₂ | CH₃CH₂CH₂ | CH₃ | CH₂(2-pyrazinyl) | H |
| CH₃CH₂CH₂ | CH₃CH₂CH₂ | CH₃ | CH₂(Ph) | H |
| CH₃CH₂CH₂ | CH₃CH₂CH₂ | CH₃ | Q-1 | H |
| CH₃CH₂CH₂ | CH₃CH₂CH₂ | CH₃ | Q-3 | H |
| CH₃CH₂CH₂ | CH₃CH₂CH₂ | CH₃ | Q-6 | H |
| CH₃CH₂CH₂ | CH₃CH₂CH₂ | CH₃ | Q-7 | H |
| CH₃CH₂CH₂ | CH₃CH₂CH₂ | CH₃ | Q-15 | H |
| CH₃CH₂CH₂ | CH₃CH₂CH₂ | CH₃CH₂ | CH₂(Ph) | H |
| CH₃CH₂CH₂ | CH₃CH₂CH₂ | CH₃CH₂ | CH₂(Ph) | H |
| CH₃CH₂CH₂ | CH₃CH₂CH₂ | CH₂Ph | CH₂(Ph) | H |
| CH₃CH₂CH₂CH₂ | CH₃CH₂CH₂CH₂ | CH₃ | CH₂(2-FPh) | H |
| CH₃CH₂CH₂CH₂ | CH₃CH₂CH₂CH₂ | CH₃ | CH₂(2-ClPh) | H |
| CH₃CH₂CH₂CH₂ | CH₃CH₂CH₂CH₂ | CH₃ | CH₂(2-BrPh) | H |
| CH₃CH₂CH₂CH₂ | CH₃CH₂CH₂CH₂ | CH₃ | CH₂(2-(CH₃)Ph) | H |
| CH₃CH₂CH₂CH₂ | CH₃CH₂CH₂CH₂ | CH₃ | CH₂(2-(OCH₃)Ph) | H |
| CH₃CH₂CH₂CH₂ | CH₃CH₂CH₂CH₂ | CH₃ | CH₂(2-(CN)Ph) | H |
| CH₃CH₂CH₂CH₂ | CH₃CH₂CH₂CH₂ | CH₃ | CH₂(2-(CF₃)Ph) | H |
| CH₃CH₂CH₂CH₂ | CH₃CH₂CH₂CH₂ | CH₃ | CH₂(2-(OCF₃)Ph) | H |
| CH₃CH₂CH₂CH₂ | CH₃CH₂CH₂CH₂ | CH₃ | CH₂(2-(SCH₃)Ph) | H |
| CH₃CH₂CH₂CH₂ | CH₃CH₂CH₂CH₂ | CH₃ | CH₂(2,6-(F)₂Ph) | H |
| CH₃CH₂CH₂CH₂ | CH₃CH₂CH₂CH₂ | CH₃ | CH₂(2,6-(Cl)₂Ph) | H |
| CH₃CH₂CH₂CH₂ | CH₃CH₂CH₂CH₂ | CH₃ | CH₂(2-pyridyl) | H |
| CH₃CH₂CH₂CH₂ | CH₃CH₂CH₂CH₂ | CH₃ | CH₂(2-furanyl) | H |
| CH₃CH₂CH₂CH₂ | CH₃CH₂CH₂CH₂ | CH₃ | CH₂(2-tetrahydrofuran) | H |
| CH₃CH₂CH₂CH₂ | CH₃CH₂CH₂CH₂ | CH₃ | CH₂(2-tetrahydropyran) | H |
| CH₃CH₂CH₂CH₂ | CH₃CH₂CH₂CH₂ | CH₃ | CH₂(2-thiophenyl) | H |
| CH₃CH₂CH₂CH₂ | CH₃CH₂CH₂CH₂ | CH₃ | CH₂(2-isoxazolyl) | H |
| CH₃CH₂CH₂CH₂ | CH₃CH₂CH₂CH₂ | CH₃ | CH₂(2-pyrazinyl) | H |
| CH₃CH₂CH₂CH₂ | CH₃CH₂CH₂CH₂ | CH₃ | CH₂(Ph) | H |
| CH₃CH₂CH₂CH₂ | CH₃CH₂CH₂CH₂ | CH₃ | Q-1 | H |
| CH₃CH₂CH₂CH₂ | CH₃CH₂CH₂CH₂ | CH₃ | Q-3 | H |
| CH₃CH₂CH₂CH₂ | CH₃CH₂CH₂CH₂ | CH₃ | Q-6 | H |
| CH₃CH₂CH₂CH₂ | CH₃CH₂CH₂CH₂ | CH₃ | Q-7 | H |

TABLE 1-continued

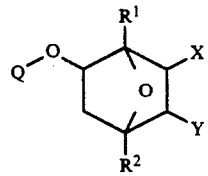

X and Y are C(R³)(R⁴)OR⁵ (unless specified)
$R^1 = R^2 = H$ (unless specified)

| | | | | |
|---|---|---|---|---|
| CH₃CH₂CH₂CH₂ | CH₃CH₂CH₂CH₂ | CH₃ | Q-15 | H |
| CH₃CH₂CH₂CH₂ | CH₃CH₂CH₂CH₂ | CH₃CH₂ | CH₂(Ph) | H |
| CH₃ | CH₃CH₂ | CH₃ | CH₂(2-FPh) | H |
| CH₃ | CH₃CH₂ | CH₃ | CH₂(2-ClPh) | H |
| CH₃ | CH₃CH₂ | CH₃ | CH₂(2-(CH₃)Ph) | H |
| CH₃ | CH₃CH₂ | CH₃ | CH₂(2,6-Cl₂Ph) | H |
| CH₃ | CH₃CH₂ | CH₃ | CH₂(2-CF₃Ph) | H |
| CH₃ | CH₃CH₂ | CH₃ | CH₂(2-tetrahydropyran) | H |
| CH₃ | CH₃CH₂ | CH₃ | CH₂(2-pyridyl) | H |
| CH₃ | CH₃CH₂ | CH₃ | CH₂(Ph) | H |
| CH₃ | CH₃CH₂ | CH₃ | Q-1 | H |
| CH₃ | CH₃CH₂ | CH₃ | Q-3 | H |
| CH₃ | CH₃CH₂ | CH₃ | Q-6 | H |
| CH₃ | CH₃CH₂ | CH₃ | Q-7 | H |
| CH₃ | CH₃CH₂ | CH₃ | Q-15 | H |
| CH₂CH=CH₂ | CH₂CH=CH₂ | CH₃ | CH₂(2-FPh) | H |
| CH₂CH=CH₂ | CH₂CH=CH₂ | CH₃ | CH₂(2-ClPh) | H |
| CH₂CH=CH₂ | CH₂CH=CH₂ | CH₃ | CH₂(2-(CH₃)Ph) | H |
| CH₂CH=CH₂ | CH₂CH=CH₂ | CH₃ | CH₂(2,6-Cl₂Ph) | H |
| CH₂CH=CH₂ | CH₂CH=CH₂ | CH₃ | CH₂(2-CF₃Ph) | H |
| CH₂CH=CH₂ | CH₂CH=CH₂ | CH₃ | CH₂(2-tetrahydropyran) | H |
| CH₂CH=CH₂ | CH₂CH=CH₂ | CH₃ | CH₂(2-pyridyl) | H |
| CH₂CH=CH₂ | CH₂CH=CH₂ | CH₃ | CH₂(Ph) | H |
| CH₂CH=CH₂ | CH₂CH=CH₂ | CH₃ | Q-1 | H |
| CH₂CH=CH₂ | CH₂CH=CH₂ | CH₃ | Q-3 | H |
| CH₂CH=CH₂ | CH₂CH=CH₂ | CH₃ | Q-6 | H |
| CH₂CH=CH₂ | CH₂CH=CH₂ | CH₃ | Q-7 | H |
| CH₂CH=CH₂ | CH₂CH=CH₂ | CH₃ | Q-15 | H |
| CH=CH₂ | CH=CH₂ | CH₃ | CH₂(2-FPh) | H |
| CH=CH₂ | CH=CH₂ | CH₃ | CH₂(2-ClPh) | H |
| CH=CH₂ | CH=CH₂ | CH₃ | CH₂(2-(CH₃)Ph) | H |
| CH=CH₂ | CH=CH₂ | CH₃ | CH₂(2,6-Cl₂Ph) | H |
| CH=CH₂ | CH=CH₂ | CH₃ | CH₂(2-CF₃Ph) | H |
| CH=CH₂ | CH=CH₂ | CH₃ | CH₂(2-tetrahydropyran) | H |
| CH=CH₂ | CH=CH₂ | CH₃ | CH₂(2-pyridyl) | H |
| CH=CH₂ | CH=CH₂ | CH₃ | CH₂(Ph) | H |
| CH=CH₂ | CH=CH₂ | CH₃ | Q-1 | H |
| CH=CH₂ | CH=CH₂ | CH₃ | Q-3 | H |
| CH=CH₂ | CH=CH₂ | CH₃ | Q-6 | H |
| CH=CH₂ | CH=CH₂ | CH₃ | Q-7 | H |
| CH=CH₂ | CH=CH₂ | CH₃ | Q-15 | H |
| CH₂C≡CH | CH₂C≡CH | CH₃ | CH₂(2-FPh) | H |
| CH₂C≡CH | CH₂C≡CH | CH₃ | CH₂(2-ClPh) | H |
| CH₂C≡CH | CH₂C≡CH | CH₃ | CH₂(2-(CH₃)Ph) | H |
| CH₂C≡CH | CH₂C≡CH | CH₃ | CH₂(2,6-Cl₂Ph) | H |
| CH₂C≡CH | CH₂C≡CH | CH₃ | CH₂(2-CF₃Ph) | H |
| CH₂C≡CH | CH₂C≡CH | CH₃ | CH₂(2-tetrahydropyran) | H |
| CH₂C≡CH | CH₂C≡CH | CH₃ | CH₂(2-pyridyl) | H |
| CH₂C≡CH | CH₂C≡CH | CH₃ | CH₂(Ph) | H |
| CH₂C≡CH | CH₂C≡CH | CH₃ | Q-1 | H |
| CH₂C≡CH | CH₂C≡CH | CH₃ | Q-3 | H |
| CH₂C≡CH | CH₂C≡CH | CH₃ | Q-6 | H |
| CH₂C≡CH | CH₂C≡CH | CH₃ | Q-7 | H |
| CH₂C≡CH | CH₂C≡CH | CH₃ | Q-15 | H |
| CH₂OCH₃ | CH₂OCH₃ | CH₃ | CH₂(2-FPh) | H |
| CH₂OCH₃ | CH₂OCH₃ | CH₃ | CH₂(2-ClPh) | H |
| CH₂OCH₃ | CH₂OCH₃ | CH₃ | CH₂(2-(CH₃)Ph) | H |
| CH₂OCH₃ | CH₂OCH₃ | CH₃ | CH₂(2,6-Cl₂Ph) | H |
| CH₂OCH₃ | CH₂OCH₃ | CH₃ | CH₂(2-CF₃Ph) | H |
| CH₂OCH₃ | CH₂OCH₃ | CH₃ | CH₂(2-tetrahydropyran) | H |
| CH₂OCH₃ | CH₂OCH₃ | CH₃ | CH₂(2-pyridyl) | H |
| CH₂OCH₃ | CH₂OCH₃ | CH₃ | CH₂(Ph) | H |
| CH₂OCH₃ | CH₂OCH₃ | CH₃ | Q-1 | H |
| CH₂OCH₃ | CH₂OCH₃ | CH₃ | Q-3 | H |
| CH₂OCH₃ | CH₂OCH₃ | CH₃ | Q-6 | H |
| CH₂OCH₃ | CH₂OCH₃ | CH₃ | Q-7 | H |
| CH₂OCH₃ | CH₂OCH₃ | CH₃ | Q-15 | H |
| CH₃CH₂ | H | CH₃ | CH₂(2-FPh) | H |
| CH₃CH₂ | H | CH₃ | CH₂(2-ClPh) | H |
| CH₃CH₂ | H | CH₃ | CH₂(2-(CH₃)Ph) | H |
| CH₃CH₂ | H | CH₃ | CH₂(2,6-Cl₂Ph) | H |

TABLE 1-continued

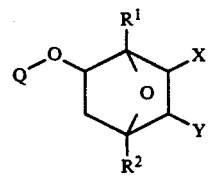

X and Y are C(R$^3$)(R$^4$)OR$^5$ (unless specified)
R$^1$ = R$^2$ = H (unless specified)

| | | | | |
|---|---|---|---|---|
| CH$_3$CH$_2$ | H | CH$_3$ | CH$_2$(2-CF$_3$Ph) | H |
| CH$_3$CH$_2$ | H | CH$_3$ | CH$_2$(2-tetrahydropyran) | H |
| CH$_3$CH$_2$ | H | CH$_3$ | CH$_2$(2-pyridyl) | H |
| CH$_3$CH$_2$ | H | CH$_3$ | CH$_2$(Ph) | H |
| CH$_3$CH$_2$ | H | CH$_3$ | Q-1 | H |
| CH$_3$CH$_2$ | H | CH$_3$ | Q-3 | H |
| CH$_3$CH$_2$ | H | CH$_3$ | Q-6 | H |
| CH$_3$CH$_2$ | H | CH$_3$ | Q-7 | H |
| CH$_3$CH$_2$ | H | CH$_3$ | Q-15 | H |
| CH$_2$CH$_2$CH$_3$ | H | CH$_3$ | CH$_2$(2-FPh) | H |
| CH$_2$CH$_2$CH$_3$ | H | CH$_3$ | CH$_2$(2-ClPh) | H |
| CH$_2$CH$_2$CH$_3$ | H | CH$_3$ | CH$_2$(2-(CH$_3$)Ph) | H |
| CH$_2$CH$_2$CH$_3$ | H | CH$_3$ | CH$_2$(2,6-Cl$_2$Ph) | H |
| CH$_2$CH$_2$CH$_3$ | H | CH$_3$ | CH$_2$(2-CF$_3$Ph) | H |
| CH$_2$CH$_2$CH$_3$ | H | CH$_3$ | CH$_2$(2-tetrahydropyran) | H |
| CH$_2$CH$_2$CH$_3$ | H | CH$_3$ | CH$_2$(2-pyridyl) | H |
| CH$_2$CH$_2$CH$_3$ | H | CH$_3$ | CH$_2$(Ph) | H |
| CH$_2$CH$_2$CH$_3$ | H | CH$_3$ | Q-1 | H |
| CH$_2$CH$_2$CH$_3$ | H | CH$_3$ | Q-3 | H |
| CH$_2$CH$_2$CH$_3$ | H | CH$_3$ | Q-6 | H |
| CH$_2$CH$_2$CH$_3$ | H | CH$_3$ | Q-7 | H |
| CH$_2$CH$_2$CH$_3$ | H | CH$_3$ | Q-15 | H |
| CH$_3$CH$_2$CH$_2$CH$_2$ | H | CH$_3$ | CH$_2$(2-FPh) | H |
| CH$_3$CH$_2$CH$_2$CH$_2$ | H | CH$_3$ | CH$_2$(2-ClPh) | H |
| CH$_3$CH$_2$CH$_2$CH$_2$ | H | CH$_3$ | CH$_2$(2-(CH$_3$)Ph) | H |
| CH$_3$CH$_2$CH$_2$CH$_2$ | H | CH$_3$ | CH$_2$(2,6-Cl$_2$Ph) | H |
| CH$_3$CH$_2$CH$_2$CH$_2$ | H | CH$_3$ | CH$_2$(2-CF$_3$Ph) | H |
| CH$_3$CH$_2$CH$_2$CH$_2$ | H | CH$_3$ | CH$_2$(2-tetrahydropyran) | H |
| CH$_3$CH$_2$CH$_2$CH$_2$ | H | CH$_3$ | CH$_2$(2-pyridyl) | H |
| CH$_3$CH$_2$CH$_2$CH$_2$ | H | CH$_3$ | CH$_2$(Ph) | H |
| CH$_3$CH$_2$CH$_2$CH$_2$ | H | CH$_3$ | Q-1 | H |
| CH$_3$CH$_2$CH$_2$CH$_2$ | H | CH$_3$ | Q-3 | H |
| CH$_3$CH$_2$CH$_2$CH$_2$ | H | CH$_3$ | Q-6 | H |
| CH$_3$CH$_2$CH$_2$CH$_2$ | H | CH$_3$ | Q-7 | H |
| CH$_3$CH$_2$CH$_2$CH$_2$ | H | CH$_3$ | Q-15 | H |
| CH$_3$ | CH$_3$ | CH$_3$ | CH$_2$(2-FPh) | H |
| CH$_3$ | CH$_3$ | CH$_3$ | CH$_2$(2-ClPh) | H |
| CH$_3$ | CH$_3$ | CH$_3$ | CH$_2$(2-(CH$_3$)Ph) | H |
| CH$_3$ | CH$_3$ | CH$_3$ | CH$_2$(2,6-Cl$_2$Ph) | H |
| CH$_3$ | CH$_3$ | CH$_3$ | CH$_2$(2-CF$_3$Ph) | H |
| CH$_3$ | CH$_3$ | CH$_3$ | CH$_2$(2-tetrahydropyran) | H |
| CH$_3$ | CH$_3$ | CH$_3$ | CH$_2$(2-pyridyl) | H |
| CH$_3$ | CH$_3$ | CH$_3$ | CH$_2$(Ph) | H |
| CH$_3$ | CH$_3$ | CH$_3$ | Q-1 | H |
| CH$_3$ | CH$_3$ | CH$_3$ | Q-3 | H |
| CH$_3$ | CH$_3$ | CH$_3$ | Q-6 | H |
| CH$_3$ | CH$_3$ | CH$_3$ | Q-7 | H |
| CH$_3$ | CH$_3$ | CH$_3$ | Q-15 | H |

| R$^1$ | R$^2$ | R$^3$ | R$^4$ | R$^5$ | Q | Y |
|---|---|---|---|---|---|---|
| CH$_3$ | CH$_3$ | H | H | CH$_3$ | CH$_2$(2-FPh) | H |
| CH$_3$ | CH$_3$ | H | H | CH$_3$ | CH$_2$(2-ClPh) | H |
| CH$_3$ | CH$_3$ | H | H | CH$_3$ | CH$_2$(2-BrPh) | H |
| CH$_3$ | CH$_3$ | H | H | CH$_3$ | CH$_2$(2-(CH$_3$)Ph) | H |
| CH$_3$ | CH$_3$ | H | H | CH$_3$ | CH$_2$(2-(OCH$_3$)Ph) | H |
| CH$_3$ | CH$_3$ | H | H | CH$_3$ | CH$_2$(2-(CN)Ph) | H |
| CH$_3$ | CH$_3$ | H | H | CH$_3$ | CH$_2$(2-(CF$_3$)Ph) | H |
| CH$_3$ | CH$_3$ | H | H | CH$_3$ | CH$_2$(2-(OCF$_3$)Ph) | H |
| CH$_3$ | CH$_3$ | H | H | CH$_3$ | CH$_2$(2-(SCH$_3$)Ph) | H |
| CH$_3$ | CH$_3$ | H | H | CH$_3$ | CH$_2$(2,6-(F)$_2$Ph) | H |
| CH$_3$ | CH$_3$ | H | H | CH$_3$ | CH$_2$(2,6-(Cl)$_2$Ph) | H |
| CH$_3$ | CH$_3$ | H | H | CH$_3$ | CH$_2$(2-pyridyl) | H |
| CH$_3$ | CH$_3$ | H | H | CH$_3$ | CH$_2$(2-furanyl) | H |
| CH$_3$ | CH$_3$ | H | H | CH$_3$ | CH$_2$(2-tetrahydrofuran) | H |
| CH$_3$ | CH$_3$ | H | H | CH$_3$ | CH$_2$(2-tetrahydropyran) | H |
| CH$_3$ | CH$_3$ | H | H | CH$_3$ | CH$_2$(2-thiophenyl) | H |
| CH$_3$ | CH$_3$ | H | H | CH$_3$ | CH$_2$(2-isoxazolyl) | H |
| CH$_3$ | CH$_3$ | H | H | CH$_3$ | CH$_2$(2-pyrazinyl) | H |
| CH$_3$ | CH$_3$ | H | H | CH$_3$ | CH$_2$(Ph) | H |
| CH$_3$ | CH$_3$ | H | H | CH$_3$ | Q-1 | H |
| CH$_3$ | CH$_3$ | H | H | CH$_3$ | Q-3 | H |

TABLE 1-continued

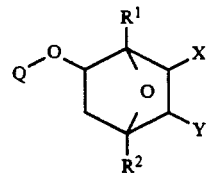

I

X and Y are C(R³)(R⁴)OR⁵ (unless specified)
R¹ = R² = H (unless specified)

| | | | | | | |
|---|---|---|---|---|---|---|
| CH₃ | CH₃ | H | H | CH₃ | Q-6 | H |
| CH₃ | CH₃ | H | H | CH₃ | Q-7 | H |
| CH₃ | CH₃ | H | H | CH₃ | Q-15 | H |
| CH₃ | CH₃ | H | H | CH₃CH₂ | CH₂(2-FPh) | H |
| CH₃ | CH₃ | H | H | CH₃CH₂ | CH₂(2-ClPh) | H |
| CH₃ | CH₃ | H | H | CH₃CH₂ | CH₂(2-(CH₃)Ph) | H |
| CH₃ | CH₃ | H | H | CH₃CH₂ | CH₂(2,6-F₂Ph) | H |
| CH₃ | CH₃ | H | H | CH₃CH₂ | CH₂(2-BrPh) | H |
| CH₃ | CH₃ | H | H | CH₃CH₂ | CH₂(2,6-Cl₂Ph) | H |
| CH₃ | CH₃ | H | H | CH₃CH₂ | CH₂(2-pyridyl) | H |
| CH₃ | CH₃ | H | H | CH₃CH₂ | CH₂(Ph) | H |
| CH₃ | CH₃ | H | H | CH₃CH₂ | Q-1 | H |
| CH₃ | CH₃ | H | H | CH₃CH₂ | Q-3 | H |
| CH₃ | CH₃ | H | H | CH₃CH₂ | Q-6 | H |
| CH₃ | CH₃ | H | H | CH₃CH₂ | Q-7 | H |
| CH₃ | CH₃ | H | H | CH₃CH₂ | Q-15 | H |
| CH₃ | CH₃ | H | H | CH₂CH=CH₂ | CH₂(2-FPh) | H |
| CH₃ | CH₃ | H | H | CH₂CH=CH₂ | CH₂(2-ClPh) | H |
| CH₃ | CH₃ | H | H | CH₂CH=CH₂ | CH₂(2-(CH₃)Ph) | H |
| CH₃ | CH₃ | H | H | CH₂CH=CH₂ | CH₂(2,6-Cl₂Ph) | H |
| CH₃ | CH₃ | H | H | CH₂CH=CH₂ | CH₂(2-CF₃Ph) | H |
| CH₃ | CH₃ | H | H | CH₂CH=CH₂ | CH₂(2-tetrahydropyran) | H |
| CH₃ | CH₃ | H | H | CH₂CH=CH₂ | CH₂(2-pyridyl) | H |
| CH₃ | CH₃ | H | H | CH₂CH=CH₂ | CH₂(Ph) | H |
| CH₃ | CH₃ | H | H | CH₂CH=CH₂ | Q-1 | H |
| CH₃ | CH₃ | H | H | CH₂CH=CH₂ | Q-3 | H |
| CH₃ | CH₃ | H | H | CH₂CH=CH₂ | Q-6 | H |
| CH₃ | CH₃ | H | H | CH₂CH=CH₂ | Q-7 | H |
| CH₃ | CH₃ | H | H | CH₂CH=CH₂ | Q-15 | H |
| CH₃ | CH₃ | H | H | CH₂Ph | CH₂(Ph) | H |
| CH₃ | CH₃ | H | H | CH₂Ph | CH₂(2-FPh) | H |
| CH₃ | CH₃ | H | H | CH₂Ph | CH₂(2-(CH₃)Ph) | H |
| CH₃ | CH₃ | H | H | CH₂Ph | CH₂(2,6-Cl₂Ph) | H |
| CH₃ | CH₃ | H | H | CH₂Ph | Q-3 | H |
| CH₃ | CH₃ | H | H | CH₂CH=CH(CH₃) | CH₂(Ph) | H |
| CH₃ | CH₃ | H | H | CH₂CH=CH(CH₃) | CH₂(2-FPh) | H |
| CH₃ | CH₃ | H | H | CH₂CH=CH(CH₃) | CH₂(2-(CH₃)Ph) | H |
| CH₃ | CH₃ | H | H | CH₂CH=CH(CH₃) | CH₂(2,6-Cl₂Ph) | H |
| CH₃ | CH₃ | H | H | CH₂CH=CH(CH₃) | Q-3 | H |
| CH₃ | CH₃ | H | H | CH₂OCH₃ | CH₂(Ph) | H |
| CH₃ | CH₃ | H | H | CH₂OCH₃ | CH₂(2-FPh) | H |
| CH₃ | CH₃ | H | H | CH₂OCH₃ | CH₂(2-(CH₃)Ph) | H |
| CH₃ | CH₃ | H | H | CH₂OCH₃ | CH₂(2,6-Cl₂Ph) | H |
| CH₃ | CH₃ | H | H | CH₂OCH₃ | Q-3 | H |
| CH₃ | CH₃ | CH₃ | CH₃ | CH₃ | CH₂(Ph) | H |
| CH₃ | CH₃ | CH₃ | CH₃ | CH₃ | CH₂(2-FPh) | H |
| CH₃ | CH₃ | CH₃ | CH₃ | CH₃ | CH₂(2-(CH₃)Ph) | H |
| CH₃ | CH₃ | CH₃ | CH₃ | CH₃ | CH₂(2,6-Cl₂Ph) | H |
| CH₃ | CH₃ | CH₃ | CH₃ | CH₃ | Q-3 | H |
| CH₃ | CH₃ | CH₃ | CH₃ | CH₂CH₃ | CH₂(Ph) | H |
| CH₃ | CH₃ | CH₃ | CH₃ | CH₂CH₃ | CH₂(2-FPh) | H |
| CH₃ | CH₃ | CH₃ | CH₃ | CH₂CH₃ | CH₂(2-(CH₃)Ph) | H |
| CH₃ | CH₃ | CH₃ | CH₃ | CH₂CH₃ | CH₂(2,6-Cl₂Ph) | H |
| CH₃ | CH₃ | CH₃ | CH₃ | CH₂CH₃ | Q-3 | H |
| CH₃ | CH₃ | CH₂CH₂CH₃ | CH₃ | CH₃ | CH₂(Ph) | H |
| CH₃ | CH₃ | CH₂CH₂CH₃ | CH₃ | CH₃ | CH₂(2-FPh) | H |
| CH₃ | CH₃ | CH₂CH₂CH₃ | CH₃ | CH₃ | CH₂(2-(CH₃)Ph) | H |
| CH₃ | CH₃ | CH₂CH₂CH₃ | CH₃ | CH₃ | CH₂(2,6-Cl₂Ph) | H |
| CH₃ | CH₃ | CH₂CH₂CH₃ | CH₃ | CH₃ | Q-3 | H |
| CH₂CH₃ | CH₂CH₃ | H | H | CH₃ | CH₂(Ph) | H |
| CH₂CH₃ | CH₂CH₃ | H | H | CH₃ | CH₂(2-FPh) | H |
| CH₂CH₃ | CH₂CH₃ | H | H | CH₃ | CH₂(2-(CH₃)Ph) | H |
| CH₂CH₃ | CH₂CH₃ | H | H | CH₃ | CH₂(2,6-Cl₂Ph) | H |
| CH₂CH₃ | CH₂CH₃ | H | H | CH₃ | Q-3 | H |
| CH₂CH₃ | CH₂CH₃ | H | H | CH₂CH₃ | CH₂(Ph) | H |
| CH₂CH₃ | CH₂CH₃ | H | H | CH₂CH₃ | CH₂(2-FPh) | H |
| CH₂CH₃ | CH₂CH₃ | H | H | CH₂CH₃ | CH₂(2-(CH₃)Ph) | H |
| CH₂CH₃ | CH₂CH₃ | H | H | CH₂CH₃ | CH₂(2,6-Cl₂Ph) | H |
| CH₂CH₃ | CH₂CH₃ | H | H | CH₂CH₃ | Q-3 | H |
| CH₂CH₃ | CH₂CH₃ | H | H | CH₂CH=CH₂ | CH₂(Ph) | H |
| CH₂CH₃ | CH₂CH₃ | H | H | CH₂CH=CH₂ | CH₂(2-FPh) | H |

TABLE 1-continued

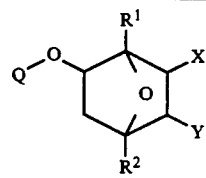

X and Y are $C(R^3)(R^4)OR^5$ (unless specified)
$R^1 = R^2 = H$ (unless specified)

| | | | | | | |
|---|---|---|---|---|---|---|
| CH$_2$CH$_3$ | CH$_2$CH$_3$ | H | H | CH$_2$CH=CH$_2$ | CH$_2$(2-(CH$_3$)Ph) | H |
| CH$_2$CH$_3$ | CH$_2$CH$_3$ | H | H | CH$_2$CH=CH$_2$ | CH$_2$(2,6-Cl$_2$Ph) | H |
| CH$_2$CH$_3$ | CH$_2$CH$_3$ | H | H | CH$_2$CH=CH$_2$ | Q-3 | H |
| CH$_2$CH$_3$ | CH$_2$CH$_3$ | CH$_3$ | CH$_3$ | CH$_3$ | CH$_2$(Ph) | H |
| CH$_2$CH$_3$ | CH$_2$CH$_3$ | CH$_3$ | CH$_3$ | CH$_3$ | CH$_2$(2-FPh) | H |
| CH$_2$CH$_3$ | CH$_2$CH$_3$ | CH$_3$ | CH$_3$ | CH$_3$ | CH$_2$(2-(CH$_3$)Ph) | H |
| CH$_2$CH$_3$ | CH$_2$CH$_3$ | CH$_3$ | CH$_3$ | CH$_3$ | CH$_2$(2,6-Cl$_2$Ph) | H |
| CH$_2$CH$_3$ | CH$_2$CH$_3$ | CH$_3$ | CH$_3$ | CH$_3$ | Q-3 | H |
| CH$_2$CH$_3$ | CH$_2$CH$_3$ | CH$_2$CH$_2$CH$_3$ | CH$_2$CH$_2$CH$_3$ | CH$_3$ | CH$_2$(Ph) | H |
| CH$_2$CH$_3$ | CH$_2$CH$_3$ | CH$_2$CH$_2$CH$_3$ | CH$_2$CH$_2$CH$_3$ | CH$_3$ | CH$_2$(2-FPh) | H |
| CH$_2$CH$_3$ | CH$_2$CH$_3$ | CH$_2$CH$_2$CH$_3$ | CH$_2$CH$_2$CH$_3$ | CH$_3$ | CH$_2$(2-(CH$_3$)Ph) | H |
| CH$_2$CH$_3$ | CH$_2$CH$_3$ | CH$_2$CH$_2$CH$_3$ | CH$_2$CH$_2$CH$_3$ | CH$_3$ | CH$_2$(2,6-Cl$_2$Ph) | H |
| CH$_2$CH$_3$ | CH$_2$CH$_3$ | CH$_2$CH$_2$CH$_3$ | CH$_2$CH$_2$CH$_3$ | CH$_3$ | Q-3 | H |
| H | CH=CH$_2$ | CH$_2$CH$_3$ | CH$_2$CH$_3$ | CH$_3$ | CH$_2$(Ph) | H |
| H | CH=CH$_2$ | CH$_2$CH$_3$ | CH$_2$CH$_3$ | CH$_3$ | CH$_2$(2-FPh) | H |
| H | CH=CH$_2$ | CH$_2$CH$_3$ | CH$_2$CH$_3$ | CH$_3$ | CH$_2$(2-(CH$_3$)Ph) | H |
| H | CH=CH$_2$ | CH$_2$CH$_3$ | CH$_2$CH$_3$ | CH$_3$ | CH$_2$(2,6-Cl$_2$Ph) | H |
| H | CH=CH$_2$ | CH$_2$CH$_3$ | CH$_2$CH$_3$ | CH$_3$ | Q-3 | H |
| H | C≡CH | CH$_2$CH$_3$ | CH$_2$CH$_3$ | CH$_3$ | CH$_2$(Ph) | H |
| H | C≡CH | CH$_2$CH$_3$ | CH$_2$CH$_3$ | CH$_3$ | CH$_2$(2-FPh) | H |
| H | C≡CH | CH$_2$CH$_3$ | CH$_2$CH$_3$ | CH$_3$ | CH$_2$(2-(CH$_3$)Ph) | H |
| H | C≡CH | CH$_2$CH$_3$ | CH$_2$CH$_3$ | CH$_3$ | CH$_2$(2,6-Cl$_2$Ph) | H |
| H | C≡CH | CH$_2$CH$_3$ | CH$_2$CH$_3$ | CH$_3$ | Q-3 | H |
| H | Ph | CH$_2$CH$_3$ | CH$_2$CH$_3$ | CH$_3$ | CH$_2$(Ph) | H |
| H | Ph | CH$_2$CH$_3$ | CH$_2$CH$_3$ | CH$_3$ | CH$_2$(2-FPh) | H |
| H | Ph | CH$_2$CH$_3$ | CH$_2$CH$_3$ | CH$_3$ | CH$_2$(2-(CH$_3$)Ph) | H |
| H | Ph | CH$_2$CH$_3$ | CH$_2$CH$_3$ | CH$_3$ | CH$_2$(2,6-Cl$_2$Ph) | H |
| H | Ph | CH$_2$OCH$_3$ | CH$_2$CH$_3$ | CH$_3$ | Q-3 | H |
| H | CH$_2$OCH$_3$ | CH$_2$CH$_3$ | CH$_2$CH$_3$ | CH$_3$ | CH$_2$(Ph) | H |
| H | CH$_2$OCH$_3$ | CH$_2$CH$_3$ | CH$_2$CH$_3$ | CH$_3$ | CH$_2$(2-FPh) | H |
| H | CH$_2$OCH$_3$ | CH$_2$CH$_3$ | CH$_2$CH$_3$ | CH$_3$ | CH$_2$(2-(CH$_3$)Ph) | H |
| H | CH$_2$OCH$_3$ | CH$_2$CH$_3$ | CH$_2$CH$_3$ | CH$_3$ | CH$_2$(2,6-Cl$_2$Ph) | H |
| H | CH$_2$OCH$_3$ | CH$_2$CH$_3$ | CH$_2$CH$_3$ | CH$_3$ | Q-3 | H |
| H | H | CH$_2$CH$_2$CH$_3$ | CH$_2$CH$_2$CH$_3$ | CH$_2$(2(CH$_3$)Ph | CH$_2$(2-(CH$_3$)Ph) | H |
| H | H | CH$_2$CH$_2$CH$_3$ | CH$_2$CH$_2$CH$_3$ | (2-FPh) | CH$_2$(2-FPh) | H |
| CH$_3$ | CH$_3$ | H | H | CH$_3$ | CH$_2$(2-FPh) | H |
| CH$_3$ | CH$_3$ | H | H | CH$_3$ | CH$_2$(2-ClPh) | H |
| CH$_3$ | CH$_3$ | H | H | CH$_3$ | CH$_2$(2-BrPh) | H |
| CH$_3$ | CH$_3$ | H | H | CH$_3$ | CH$_2$(2-(CH$_3$)Ph) | H |
| CH$_3$ | CH$_3$ | H | H | CH$_3$ | CH$_2$(2-(OCH$_3$)Ph) | H |
| CH$_3$ | CH$_3$ | H | H | CH$_3$ | CH$_2$(2-(CN)Ph) | H |
| CH$_3$ | CH$_3$ | H | H | CH$_3$ | CH$_2$(2-(CF$_3$)Ph) | H |
| CH$_3$ | CH$_3$ | H | H | CH$_3$ | CH$_2$(2-(OCF$_3$)Ph) | H |
| CH$_3$ | CH$_3$ | H | H | CH$_3$ | CH$_2$(2-(SCH$_3$)Ph) | H |
| CH$_3$ | CH$_3$ | H | H | CH$_3$ | CH$_2$(2,6-(F)$_2$Ph) | H |
| CH$_3$ | CH$_3$ | H | H | CH$_3$ | CH$_2$(2,6-(Cl)$_2$Ph) | H |
| CH$_3$ | CH$_3$ | H | H | CH$_3$ | CH$_2$(2-pyridyl) | H |
| CH$_3$ | CH$_3$ | H | H | CH$_3$ | CH$_2$(2-furanyl) | H |
| CH$_3$ | CH$_3$ | H | H | CH$_3$ | CH$_2$(2-tetrahydrofuran) | H |
| CH$_3$ | CH$_3$ | H | H | CH$_3$ | CH$_2$(2-tetrahydropyran) | H |
| CH$_3$ | CH$_3$ | H | H | CH$_3$ | CH$_2$(2-thiophenyl) | H |
| CH$_3$ | CH$_3$ | H | H | CH$_3$ | CH$_2$(2-isoxazolyl) | H |
| CH$_3$ | CH$_3$ | H | H | CH$_3$ | CH$_2$(2-pyrazinyl) | H |
| CH$_3$ | CH$_3$ | H | H | CH$_3$ | CH$_2$(Ph) | H |
| CH$_3$ | CH$_3$ | H | H | CH$_3$ | Q-1 | H |
| CH$_3$ | CH$_3$ | H | H | CH$_3$ | Q-3 | H |
| CH$_3$ | CH$_3$ | H | H | CH$_3$ | Q-6 | H |
| CH$_3$ | CH$_3$ | H | H | CH$_3$ | Q-7 | H |
| CH$_3$ | CH$_3$ | H | H | CH$_3$ | Q-15 | H |
| CH$_3$ | CH$_3$ | H | H | CH$_3$CH$_2$ | CH$_2$(2-FPh) | H |
| CH$_3$ | CH$_3$ | H | H | CH$_3$CH$_2$ | CH$_2$(2-ClPh) | H |
| CH$_3$ | CH$_3$ | H | H | CH$_3$CH$_2$ | CH$_2$(2-(CH$_3$)Ph) | H |
| CH$_3$ | CH$_3$ | H | H | CH$_3$CH$_2$ | CH$_2$(2,6-F$_2$Ph) | H |
| CH$_3$ | CH$_3$ | H | H | CH$_3$CH$_2$ | CH$_2$(2-BrPh) | H |
| CH$_3$ | CH$_3$ | H | H | CH$_3$CH$_2$ | CH$_2$(2,6-Cl$_2$Ph) | H |
| CH$_3$ | CH$_3$ | H | H | CH$_3$CH$_2$ | CH$_2$(2-pyridyl) | H |
| CH$_3$ | CH$_3$ | H | H | CH$_3$CH$_2$ | CH$_2$(Ph) | H |
| CH$_3$ | CH$_3$ | H | H | CH$_3$CH$_2$ | Q-1 | H |
| CH$_3$ | CH$_3$ | H | H | CH$_3$CH$_2$ | Q-3 | H |
| CH$_3$ | CH$_3$ | H | H | CH$_3$CH$_2$ | Q-6 | H |
| CH$_3$ | CH$_3$ | H | H | CH$_3$CH$_2$ | Q-7 | H |

TABLE 1-continued

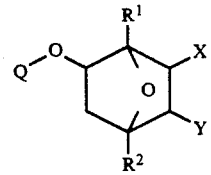

X and Y are C(R³)(R⁴)OR⁵ (unless specified)
R¹ = R² = H (unless specified)

| | | | | | | |
|---|---|---|---|---|---|---|
| CH₃ | CH₃ | H | H | CH₃CH₂ | Q-15 | H |
| CH₃ | CH₃ | H | H | CH₂CH=CH₂ | CH₂(2-FPh) | H |
| CH₃ | CH₃ | H | H | CH₂CH=CH₂ | CH₂(2-ClPh) | H |
| CH₃ | CH₃ | H | H | CH₂CH=CH₂ | CH₂(2-(CH₃)Ph) | H |
| CH₃ | CH₃ | H | H | CH₂CH=CH₂ | CH₂(2,6-Cl₂Ph) | H |
| CH₃ | CH₃ | H | H | CH₂CH=CH₂ | CH₂(2-CF₃Ph) | H |
| CH₃ | CH₃ | H | H | CH₂CH=CH₂ | CH₂(2-tetrahydropyran) | H |
| CH₃ | CH₃ | H | H | CH₂CH=CH₂ | CH₂(2-pyridyl) | H |
| CH₃ | CH₃ | H | H | CH₂CH=CH₂ | CH₂(Ph) | H |
| CH₃ | CH₃ | H | H | CH₂CH=CH₂ | Q-1 | H |
| CH₃ | CH₃ | H | H | CH₂CH=CH₂ | Q-3 | H |
| CH₃ | CH₃ | H | H | CH₂CH=CH₂ | Q-6 | H |
| CH₃ | CH₃ | H | H | CH₂CH=CH₂ | Q-7 | H |
| CH₃ | CH₃ | H | H | CH₂CH=CH₂ | Q-15 | H |
| CH₃ | CH₃ | H | H | CH₂Ph | CH₂(Ph) | H |
| CH₃ | CH₃ | H | H | CH₂Ph | CH₂(2-FPh) | H |
| CH₃ | CH₃ | H | H | CH₂Ph | CH₂(2-(CH₃)Ph) | H |
| CH₃ | CH₃ | H | H | CH₂Ph | CH₂(2,6-Cl₂Ph) | H |
| CH₃ | CH₃ | H | H | CH₂Ph | Q-3 | H |
| CH₃ | CH₃ | H | H | CH₂CH=CH(CH₃) | CH₂(Ph) | H |
| CH₃ | CH₃ | H | H | CH₂CH=CH(CH₃) | CH₂(2-FPh) | H |
| CH₃ | CH₃ | H | H | CH₂CH=CH(CH₃) | CH₂(2-(CH₃)Ph) | H |
| CH₃ | CH₃ | H | H | CH₂CH=CH(CH₃) | CH₂(2,6-Cl₂Ph) | H |
| CH₃ | CH₃ | H | H | CH₂CH=CH(CH₃) | Q-3 | H |
| CH₃ | CH₃ | H | H | CH₂OCH₃ | CH₂(Ph) | H |
| CH₃ | CH₃ | H | H | CH₂OCH₃ | CH₂(2-FPh) | H |
| CH₃ | CH₃ | H | H | CH₂OCH₃ | CH₂(2-(CH₃)Ph) | H |
| CH₃ | CH₃ | H | H | CH₂OCH₃ | CH₂(2,6-Cl₂Ph) | H |

| R¹ | R² | R³ | R⁴ | R⁵ | W | X |
|---|---|---|---|---|---|---|
| CH₃ | CH₃ | H | H | CH₂OCH₃ | Q-3 | H |
| CH₃ | CH₃ | CH₃ | CH₃ | CH₃ | CH₂(Ph) | H |
| CH₃ | CH₃ | CH₃ | CH₃ | CH₃ | CH₂(2-FPh) | H |
| CH₃ | CH₃ | CH₃ | CH₃ | CH₃ | CH₂(2-(CH₃)Ph) | H |
| CH₃ | CH₃ | CH₃ | CH₃ | CH₃ | CH₂(2,6-Cl₂Ph) | H |
| CH₃ | CH₃ | CH₃ | CH₃ | CH₃ | Q-3 | H |
| CH₃ | CH₃ | CH₃ | CH₃ | CH₂CH₃ | CH₂(Ph) | H |
| CH₃ | CH₃ | CH₃ | CH₃ | CH₂CH₃ | CH₂(2-FPh) | H |
| CH₃ | CH₃ | CH₃ | CH₃ | CH₂CH₃ | CH₂(2-(CH₃)Ph) | H |
| CH₃ | CH₃ | CH₃ | CH₃ | CH₂CH₃ | CH₂(2,6-Cl₂Ph) | H |
| CH₃ | CH₃ | CH₃ | CH₃ | CH₂CH₃ | Q-3 | H |
| CH₃ | CH₃ | CH₂CH₂CH₃ | CH₃ | CH₃ | CH₂(Ph) | H |
| CH₃ | CH₃ | CH₂CH₂CH₃ | CH₃ | CH₃ | CH₂(2-FPh) | H |
| CH₃ | CH₃ | CH₂CH₂CH₃ | CH₃ | CH₃ | CH₂(2-(CH₃)Ph) | H |
| CH₃ | CH₃ | CH₂CH₂CH₃ | CH₃ | CH₃ | CH₂(2,6-Cl₂Ph) | H |
| CH₃ | CH₃ | CH₂CH₂CH₃ | CH₃ | CH₃ | Q-3 | H |
| CH₂CH₃ | CH₂CH₃ | H | H | CH₃ | CH₂(Ph) | H |
| CH₂CH₃ | CH₂CH₃ | H | H | CH₃ | CH₂(2-FPh) | H |
| CH₂CH₃ | CH₂CH₃ | H | H | CH₃ | CH₂(2-(CH₃)Ph) | H |
| CH₂CH₃ | CH₂CH₃ | H | H | CH₃ | CH₂(2,6-Cl₂Ph) | H |
| CH₂CH₃ | CH₂CH₃ | H | H | CH₃ | Q-3 | H |
| CH₂CH₃ | CH₂CH₃ | H | H | CH₂CH₃ | CH₂(Ph) | H |
| CH₂CH₃ | CH₂CH₃ | H | H | CH₂CH₃ | CH₂(2-FPh) | H |
| CH₂CH₃ | CH₂CH₃ | H | H | CH₂CH₃ | CH₂(2-(CH₃)Ph) | H |
| CH₂CH₃ | CH₂CH₃ | H | H | CH₂CH₃ | CH₂(2,6-Cl₂Ph) | H |
| CH₂CH₃ | CH₂CH₃ | H | H | CH₂CH₃ | Q-3 | H |
| CH₂CH₃ | CH₂CH₃ | H | H | CH₂CH=CH₂ | CH₂(Ph) | H |
| CH₂CH₃ | CH₂CH₃ | H | H | CH₂CH=CH₂ | CH₂(2-FPh) | H |
| CH₂CH₃ | CH₂CH₃ | H | H | CH₂CH=CH₂ | CH₂(2-(CH₃)Ph) | H |
| CH₂CH₃ | CH₂CH₃ | H | H | CH₂CH=CH₂ | CH₂(2,6-Cl₂Ph) | H |
| CH₂CH₃ | CH₂CH₃ | H | H | CH₂CH=CH₂ | Q-3 | H |
| CH₂CH₃ | CH₂CH₃ | CH₃ | CH₃ | CH₃ | CH₂(Ph) | H |
| CH₂CH₃ | CH₂CH₃ | CH₃ | CH₃ | CH₃ | CH₂(2-FPh) | H |
| CH₂CH₃ | CH₂CH₃ | CH₃ | CH₃ | CH₃ | CH₂(2-(CH₃)Ph) | H |
| CH₂CH₃ | CH₂CH₃ | CH₃ | CH₃ | CH₃ | CH₂(2,6-Cl₂Ph) | H |
| CH₂CH₃ | CH₂CH₃ | CH₃ | CH₃ | CH₃ | Q-3 | H |
| CH₂CH₃ | CH₂CH₃ | CH₂CH₂CH₃ | CH₂CH₂CH₃ | CH₃ | CH₂(Ph) | H |
| CH₂CH₃ | CH₂CH₃ | CH₂CH₂CH₃ | CH₂CH₂CH₃ | CH₃ | CH₂(2-FPh) | H |
| CH₂CH₃ | CH₂CH₃ | CH₂CH₂CH₃ | CH₂CH₂CH₃ | CH₃ | CH₂(2-(CH₃)Ph) | H |
| CH₂CH₃ | CH₂CH₃ | CH₂CH₂CH₃ | CH₂CH₂CH₃ | CH₃ | CH₂(2,6-Cl₂Ph) | H |
| CH₂CH₃ | CH₂CH₃ | CH₂CH₂CH₃ | CH₂CH₂CH₃ | CH₃ | Q-3 | H |

TABLE 1-continued

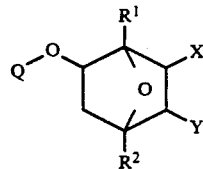

X and Y are $C(R^3)(R^4)OR^5$ (unless specified)
$R^1 = R^2 = H$ (unless specified)

| | | | | | | |
|---|---|---|---|---|---|---|
| H | CH=CH$_2$ | CH$_2$CH$_3$ | CH$_2$CH$_3$ | CH$_3$ | CH$_2$(Ph) | H |
| H | CH=CH$_2$ | CH$_2$CH$_3$ | CH$_2$CH$_3$ | CH$_3$ | CH$_2$(2-FPh) | H |
| H | CH=CH$_2$ | CH$_2$CH$_3$ | CH$_2$CH$_3$ | CH$_3$ | CH$_2$(2-(CH$_3$)Ph) | H |
| H | CH=CH$_2$ | CH$_2$CH$_3$ | CH$_2$CH$_3$ | CH$_3$ | CH$_2$(2,6-Cl$_2$Ph) | H |
| H | CH=CH$_2$ | CH$_2$CH$_3$ | CH$_2$CH$_3$ | CH$_3$ | Q-3 | H |
| H | C≡CH | CH$_2$CH$_3$ | CH$_2$CH$_3$ | CH$_3$ | CH$_2$(Ph) | H |
| H | C≡CH | CH$_2$CH$_3$ | CH$_2$CH$_3$ | CH$_3$ | CH$_2$(2-FPh) | H |
| H | C≡CH | CH$_2$CH$_3$ | CH$_2$CH$_3$ | CH$_3$ | CH$_2$(2-(CH$_3$)Ph) | H |
| H | C≡CH | CH$_2$CH$_3$ | CH$_2$CH$_3$ | CH$_3$ | CH$_2$(2,6-Cl$_2$Ph) | H |
| H | C≡CH | CH$_2$CH$_3$ | CH$_2$CH$_3$ | CH$_3$ | Q-3 | H |
| H | Ph | CH$_2$CH$_3$ | CH$_2$CH$_3$ | CH$_3$ | CH$_2$(Ph) | H |
| H | Ph | CH$_2$CH$_3$ | CH$_2$CH$_3$ | CH$_3$ | CH$_2$(2-FPh) | H |
| H | Ph | CH$_2$CH$_3$ | CH$_2$CH$_3$ | CH$_3$ | CH$_2$(2-(CH$_3$)Ph) | H |
| H | Ph | CH$_2$CH$_3$ | CH$_2$CH$_3$ | CH$_3$ | CH$_2$(2,6-Cl$_2$Ph) | H |
| H | Ph | CH$_2$CH$_3$ | CH$_2$CH$_3$ | CH$_3$ | Q-3 | H |
| H | CH$_2$OCH$_3$ | CH$_2$CH$_3$ | CH$_2$CH$_3$ | CH$_3$ | CH$_2$(Ph) | H |
| H | CH$_2$OCH$_3$ | CH$_2$CH$_3$ | CH$_2$CH$_3$ | CH$_3$ | CH$_2$(2-FPh) | H |
| H | CH$_2$OCH$_3$ | CH$_2$CH$_3$ | CH$_2$CH$_3$ | CH$_3$ | CH$_2$(2-(CH$_3$)Ph) | H |
| H | CH$_2$OCH$_3$ | CH$_2$CH$_3$ | CH$_2$CH$_3$ | CH$_3$ | CH$_2$(2,6-Cl$_2$Ph) | H |
| H | CH$_2$OCH$_3$ | CH$_2$CH$_3$ | CH$_2$CH$_3$ | CH$_3$ | Q-3 | H |
| H | H | CH$_2$CH$_2$CH$_3$ | CH$_2$CH$_2$CH$_3$ | CH$_2$(2(CH$_3$)Ph) | CH$_2$(2-(CH$_3$)Ph) | H |
| H | H | CH$_2$CH$_2$CH$_3$ | CH$_2$CH$_2$CH$_3$ | (2-FPh) | CH$_2$(2-FPh) | H |
| H | H | CH$_2$CH$_3$ | CH$_2$CH$_3$ | CH$_3$ | CH$_2$(2-FPh) | H |
| H | H | CH$_2$CH$_3$ | CH$_2$CH$_3$ | CH$_3$ | CH$_2$(2-ClPh) | H |
| H | H | CH$_2$CH$_3$ | CH$_2$CH$_3$ | CH$_3$ | CH$_2$(2-BrPh) | H |
| H | H | CH$_2$CH$_3$ | CH$_2$CH$_3$ | CH$_3$ | CH$_2$(2-(CH$_3$)Ph) | H |
| H | H | CH$_2$CH$_3$ | CH$_2$CH$_3$ | CH$_3$ | CH$_2$(2-(OCH$_3$)Ph) | H |
| H | H | CH$_2$CH$_3$ | CH$_2$CH$_3$ | CH$_3$ | CH$_2$(2-(CN)Ph) | H |
| H | H | CH$_2$CH$_3$ | CH$_2$CH$_3$ | CH$_3$ | CH$_2$(2-(CF$_3$)Ph) | H |
| H | H | CH$_2$CH$_3$ | CH$_2$CH$_3$ | CH$_3$ | CH$_2$(2-(OCF$_3$)Ph) | H |
| H | H | CH$_2$CH$_3$ | CH$_2$CH$_3$ | CH$_3$ | CH$_2$(2-(SCH$_3$)Ph) | H |
| H | H | CH$_2$CH$_3$ | CH$_2$CH$_3$ | CH$_3$ | CH$_2$(2,6-(F)$_2$Ph) | H |
| H | H | CH$_2$CH$_3$ | CH$_2$CH$_3$ | CH$_3$ | CH$_2$(2,6-(Cl)$_2$Ph) | H |
| H | H | CH$_2$CH$_3$ | CH$_2$CH$_3$ | CH$_3$ | CH$_2$(2-pyridyl) | H |
| H | H | CH$_2$CH$_3$ | CH$_2$CH$_3$ | CH$_3$ | CH$_2$(2-furanyl) | H |
| H | H | CH$_2$CH$_3$ | CH$_2$CH$_3$ | CH$_3$ | CH$_2$(2-tetrahydrofuran) | H |
| H | H | CH$_2$CH$_3$ | CH$_2$CH$_3$ | CH$_3$ | CH$_2$(2-tetrahydropyran) | H |
| H | H | CH$_2$CH$_3$ | CH$_2$CH$_3$ | CH$_3$ | CH$_2$(2-thiophenyl) | H |
| H | H | CH$_2$CH$_3$ | CH$_2$CH$_3$ | CH$_3$ | CH$_2$(2-isoxazolyl) | H |
| H | H | CH$_2$CH$_3$ | CH$_2$CH$_3$ | CH$_3$ | CH$_2$(2-pyrazinyl) | H |
| H | H | CH$_2$CH$_3$ | CH$_2$CH$_3$ | CH$_3$ | CH$_2$(Ph) | H |
| H | H | CH$_2$CH$_3$ | CH$_2$CH$_3$ | CH$_3$ | Q-1 | H |
| H | H | CH$_2$CH$_3$ | CH$_2$CH$_3$ | CH$_3$ | Q-3 | H |
| H | H | CH$_2$CH$_3$ | CH$_2$CH$_3$ | CH$_3$ | Q-6 | H |
| H | H | CH$_2$CH$_3$ | CH$_2$CH$_3$ | CH$_3$ | Q-7 | H |
| H | H | CH$_2$CH$_3$ | CH$_2$CH$_3$ | CH$_3$ | Q-15 | H |
| H | H | CH$_2$CH$_3$ | CH$_2$CH$_3$ | CH$_2$CH$_3$ | CH$_2$(2-FPh) | H |
| H | H | CH$_2$CH$_3$ | CH$_2$CH$_3$ | CH$_2$CH$_3$ | CH$_2$(2-ClPh) | H |
| H | H | CH$_2$CH$_3$ | CH$_2$CH$_3$ | CH$_2$CH$_3$ | CH$_2$(2-(CH$_3$)Ph) | H |
| H | H | CH$_2$CH$_3$ | CH$_2$CH$_3$ | CH$_2$CH$_3$ | CH$_2$(2,6-Cl$_2$Ph) | H |
| H | H | CH$_2$CH$_3$ | CH$_2$CH$_3$ | CH$_2$CH$_3$ | CH$_2$(2-CF$_3$Ph) | H |
| H | H | CH$_2$CH$_3$ | CH$_2$CH$_3$ | CH$_2$CH$_3$ | CH$_2$(2-tetrahydropyran) | H |
| H | H | CH$_2$CH$_3$ | CH$_2$CH$_3$ | CH$_2$CH$_3$ | CH$_2$(2-pyridyl) | H |
| H | H | CH$_2$CH$_3$ | CH$_2$CH$_3$ | CH$_2$CH$_3$ | CH$_2$(Ph) | H |
| H | H | CH$_2$CH$_3$ | CH$_2$CH$_3$ | CH$_2$CH$_3$ | Q-1 | H |
| H | H | CH$_2$CH$_3$ | CH$_2$CH$_3$ | CH$_2$CH$_3$ | Q-3 | H |
| H | H | CH$_2$CH$_3$ | CH$_2$CH$_3$ | CH$_2$CH$_3$ | Q-6 | H |
| H | H | CH$_2$CH$_3$ | CH$_2$CH$_3$ | CH$_2$CH$_3$ | Q-7 | H |
| H | H | CH$_2$CH$_3$ | CH$_2$CH$_3$ | CH$_2$CH$_3$ | Q-15 | H |
| H | H | CH$_2$CH$_3$ | CH$_2$CH$_3$ | CH$_2$CH=CH$_2$ | CH$_2$(2-FPh) | H |
| H | H | CH$_2$CH$_3$ | CH$_2$CH$_3$ | CH$_2$CH=CH$_2$ | CH$_2$(2-ClPh) | H |
| H | H | CH$_2$CH$_3$ | CH$_2$CH$_3$ | CH$_2$CH=CH$_2$ | CH$_2$(2-(CH$_3$)Ph) | H |
| H | H | CH$_2$CH$_3$ | CH$_2$CH$_3$ | CH$_2$CH=CH$_2$ | CH$_2$(2,6-Cl$_2$Ph) | H |
| H | H | CH$_2$CH$_3$ | CH$_2$CH$_3$ | CH$_2$CH=CH$_2$ | CH$_2$(2-CF$_3$Ph) | H |
| H | H | CH$_2$CH$_3$ | CH$_2$CH$_3$ | CH$_2$CH=CH$_2$ | CH$_2$(2-tetrahydropyran) | H |
| H | H | CH$_2$CH$_3$ | CH$_2$CH$_3$ | CH$_2$CH=CH$_2$ | CH$_2$(2-pyridyl) | H |
| H | H | CH$_2$CH$_3$ | CH$_2$CH$_3$ | CH$_2$CH=CH$_2$ | CH$_2$(Ph) | H |
| H | H | CH$_2$CH$_3$ | CH$_2$CH$_3$ | CH$_2$CH=CH$_2$ | Q-1 | H |
| H | H | CH$_2$CH$_3$ | CH$_2$CH$_3$ | CH$_2$CH=CH$_2$ | Q-3 | H |
| H | H | CH$_2$CH$_3$ | CH$_2$CH$_3$ | CH$_2$CH=CH$_2$ | Q-6 | H |
| H | H | CH$_2$CH$_3$ | CH$_2$CH$_3$ | CH$_2$CH=CH$_2$ | Q-7 | H |

TABLE 1-continued

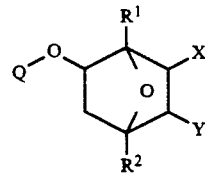

X and Y are C(R³)(R⁴)OR⁵ (unless specified)
R¹ = R² = H (unless specified)

| | | | | | | |
|---|---|---|---|---|---|---|
| H | H | CH₂CH₃ | CH₂CH₃ | CH₂CH=CH₂ | Q-15 | H |
| H | H | H | H | CH₃ | CH₂(2-FPh) | H |
| H | H | H | H | CH₃ | CH₂(2-ClPh) | H |
| H | H | H | H | CH₃ | CH₂(2-(CH₃)Ph) | H |
| H | H | H | H | CH₃ | CH₂(2,6-Cl₂Ph) | H |
| H | H | H | H | CH₃ | CH₂(2-CF₃Ph) | H |
| H | H | H | H | CH₃ | CH₂(2-tetrahydropyran) | H |
| H | H | H | H | CH₃ | CH₂(2-pyridyl) | H |
| H | H | H | H | CH₃ | CH₂(Ph) | H |
| H | H | H | H | CH₃ | Q-1 | H |
| H | H | H | H | CH₃ | Q-3 | H |
| H | H | H | H | CH₃ | Q-6 | H |
| H | H | H | H | CH₃ | Q-7 | H |
| H | H | H | H | CH₃ | Q-15 | H |
| H | H | H | H | CH₂CH₃ | CH₂(2-FPh) | H |
| H | H | H | H | CH₂CH₃ | CH₂(2-ClPh) | H |
| H | H | H | H | CH₂CH₃ | CH₂(2-(CH₃)Ph) | H |
| H | H | H | H | CH₂CH₃ | CH₂(2,6-Cl₂Ph) | H |
| H | H | H | H | CH₂CH₃ | CH₂(2-CF₃Ph) | H |
| H | H | H | H | CH₂CH₃ | CH₂(2-tetrahydropyran) | H |
| H | H | H | H | CH₂CH₃ | CH₂(2-pyridyl) | H |
| H | H | H | H | CH₂CH₃ | CH₂(Ph) | H |
| H | H | H | H | CH₂CH₃ | Q-1 | H |
| H | H | H | H | CH₂CH₃ | Q-3 | H |
| H | H | H | H | CH₂CH₃ | Q-6 | H |
| H | H | H | H | CH₂CH₃ | Q-7 | H |
| H | H | H | H | CH₂CH₃ | Q-15 | H |
| H | H | CH₃ | CH₃ | CH₃ | CH₂(2-FPh) | H |
| H | H | CH₃ | CH₃ | CH₃ | CH₂(2-ClPh) | H |
| H | H | CH₃ | CH₃ | CH₃ | CH₂(2-(CH₃)Ph) | H |
| H | H | CH₃ | CH₃ | CH₃ | CH₂(2,6-Cl₂Ph) | H |
| H | H | CH₃ | CH₃ | CH₃ | CH₂(2-CF₃Ph) | H |
| H | H | CH₃ | CH₃ | CH₃ | CH₂(2-tetrahydropyran) | H |
| H | H | CH₃ | CH₃ | CH₃ | CH₂(2-pyridyl) | H |
| H | H | CH₃ | CH₃ | CH₃ | CH₂(Ph) | H |
| H | H | CH₃ | CH₃ | CH₃ | Q-1 | H |
| H | H | CH₃ | CH₃ | CH₃ | Q-3 | H |
| H | H | CH₃ | CH₃ | CH₃ | Q-6 | H |
| H | H | CH₃ | CH₃ | CH₃ | Q-7 | H |
| H | H | CH₃ | CH₃ | CH₃ | Q-15 | H |
| CH₃ | CH₃ | CH₂CH₃ | CH₂CH₃ | CH₃ | CH₂(2-FPh) | H |
| CH₃ | CH₃ | CH₂CH₃ | CH₂CH₃ | CH₃ | CH₂(2-ClPh) | H |
| CH₃ | CH₃ | CH₂CH₃ | CH₂CH₃ | CH₃ | CH₂(2-(CH₃)Ph) | H |
| CH₃ | CH₃ | CH₂CH₃ | CH₂CH₃ | CH₃ | CH₂(2,6-Cl₂Ph) | H |
| CH₃ | CH₃ | CH₂CH₃ | CH₂CH₃ | CH₃ | CH₂(2-CF₃Ph) | H |
| CH₃ | CH₃ | CH₂CH₃ | CH₂CH₃ | CH₃ | CH₂(2-tetrahydropyran) | H |
| CH₃ | CH₃ | CH₂CH₃ | CH₂CH₃ | CH₃ | CH₂(2-pyridyl) | H |
| CH₃ | CH₃ | CH₂CH₃ | CH₂CH₃ | CH₃ | CH₂(Ph) | H |
| CH₃ | CH₃ | CH₂CH₃ | CH₂CH₃ | CH₃ | Q-1 | H |
| CH₃ | CH₃ | CH₂CH₃ | CH₂CH₃ | CH₃ | Q-3 | H |
| CH₃ | CH₃ | CH₂CH₃ | CH₂CH₃ | CH₃ | Q-6 | H |
| CH₃ | CH₃ | CH₂CH₃ | CH₂CH₃ | CH₃ | Q-7 | H |
| CH₃ | CH₃ | CH₂CH₃ | CH₂CH₃ | CH₃ | Q-15 | H |
| CH₃ | CH₃ | CH₃ | CH₃ | CH₃ | CH₂(2-FPh) | H |
| CH₃ | CH₃ | CH₃ | CH₃ | CH₃ | CH₂(2-ClPh) | H |
| CH₃ | CH₃ | CH₃ | CH₃ | CH₃ | CH₂(2-(CH₃)Ph) | H |
| CH₃ | CH₃ | CH₃ | CH₃ | CH₃ | CH₂(2,6-Cl₂Ph) | H |
| CH₃ | CH₃ | CH₃ | CH₃ | CH₃ | CH₂(2-CF₃Ph) | H |
| CH₃ | CH₃ | CH₃ | CH₃ | CH₃ | CH₂(2-tetrahydropyran) | H |
| CH₃ | CH₃ | CH₃ | CH₃ | CH₃ | CH₂(2-pyridyl) | H |
| CH₃ | CH₃ | CH₃ | CH₃ | CH₃ | CH₂(Ph) | H |
| CH₃ | CH₃ | CH₃ | CH₃ | CH₃ | Q-1 | H |
| CH₃ | CH₃ | CH₃ | CH₃ | CH₃ | Q-3 | H |
| CH₃ | CH₃ | CH₃ | CH₃ | CH₃ | Q-6 | H |
| CH₃ | CH₃ | CH₃ | CH₃ | CH₃ | Q-7 | H |
| CH₃ | CH₃ | CH₃ | CH₃ | CH₃ | Q-15 | H |
| CH₂CH₃ | CH₂CH₃ | CH₂CH₃ | CH₂CH₃ | CH₃ | CH₂(2-FPh) | H |
| CH₂CH₃ | CH₂CH₃ | CH₂CH₃ | CH₂CH₃ | CH₃ | CH₂(2-ClPh) | H |
| CH₂CH₃ | CH₂CH₃ | CH₂CH₃ | CH₂CH₃ | CH₃ | CH₂(2-(CH₃)Ph) | H |
| CH₂CH₃ | CH₂CH₃ | CH₂CH₃ | CH₂CH₃ | CH₃ | CH₂(2,6-Cl₂Ph) | H |
| CH₂CH₃ | CH₂CH₃ | CH₂CH₃ | CH₂CH₃ | CH₃ | CH₂(2-CF₃Ph) | H |

TABLE 1-continued

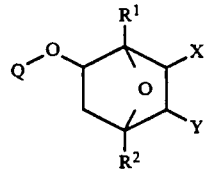

X and Y are C(R³)(R⁴)OR⁵ (unless specified)
R¹ = R² = H (unless specified)

| | | | | | | |
|---|---|---|---|---|---|---|
| CH₂CH₃ | CH₂CH₃ | CH₂CH₃ | CH₂CH₃ | CH₃ | CH₂(2-tetrahydropyran) | H |
| CH₂CH₃ | CH₂CH₃ | CH₂CH₃ | CH₂CH₃ | CH₃ | CH₂(2-pyridyl) | H |
| CH₂CH₃ | CH₂CH₃ | CH₂CH₃ | CH₂CH₃ | CH₃ | CH₂(Ph) | H |
| CH₂CH₃ | CH₂CH₃ | CH₂CH₃ | CH₂CH₃ | CH₃ | Q-1 | H |
| CH₂CH₃ | CH₂CH₃ | CH₂CH₃ | CH₂CH₃ | CH₃ | Q-3 | H |
| CH₂CH₃ | CH₂CH₃ | CH₂CH₃ | CH₂CH₃ | CH₃ | Q-6 | H |
| CH₂CH₃ | CH₂CH₃ | CH₂CH₃ | CH₂CH₃ | CH₃ | Q-7 | H |
| CH₂CH₃ | CH₂CH₃ | CH₂CH₃ | CH₂CH₃ | CH₃ | Q-15 | H |
| CH₃ | CH₃ | H | H | CH₃ | CH₂(Ph) | H |
| CH₃ | CH₃ | H | H | CH₃ | CH₂(2-FPh) | H |
| CH₃ | CH₃ | H | H | CH₃ | CH₂(2-(CH₃)Ph) | H |
| CH₃ | CH₃ | H | H | CH₃ | CH₂(2,6-Cl₂Ph) | H |
| CH₃ | CH₃ | H | H | CH₃ | Q-3 | H |
| CH₃ | CH₃ | CH₃ | CH₃ | CH₃ | CH₂(Ph) | H |
| CH₃ | CH₃ | CH₃ | CH₃ | CH₃ | CH₂(2-FPh) | H |
| CH₃ | CH₃ | CH₃ | CH₃ | CH₃ | CH₂(2-(CH₃)Ph) | H |
| CH₃ | CH₃ | CH₃ | CH₃ | CH₃ | CH₂(2,6-Cl₂Ph) | H |
| CH₃ | CH₃ | CH₃ | CH₃ | CH₃ | Q-3 | H |
| CH₂CH₃ | CH₂CH₃ | H | H | CH₃ | CH₂(Ph) | H |
| CH₂CH₃ | CH₂CH₃ | H | H | CH₃ | CH₂(2-FPh) | H |
| CH₂CH₃ | CH₂CH₃ | H | H | CH₃ | CH₂(2-(CH₃)Ph) | H |
| CH₂CH₃ | CH₂CH₃ | H | H | CH₃ | CH₂(2,6-Cl₂Ph) | H |
| CH₂CH₃ | CH₂CH₃ | H | H | CH₃ | Q-3 | H |
| CH₂CH₃ | CH₂CH₃ | CH₃ | CH₃ | CH₃ | CH₂(Ph) | H |
| CH₂CH₃ | CH₂CH₃ | CH₃ | CH₃ | CH₃ | CH₂(2-FPh) | H |
| CH₂CH₃ | CH₂CH₃ | CH₃ | CH₃ | CH₃ | CH₂(2-(CH₃)Ph) | H |
| CH₂CH₃ | CH₂CH₃ | CH₃ | CH₃ | CH₃ | CH₂(2,6-Cl₂Ph) | H |
| CH₂CH₃ | CH₂CH₃ | CH₃ | CH₃ | CH₃ | Q-3 | H |
| H | CH₃ | CH₂CH₃ | CH₂CH₃ | CH₃ | CH₂(Ph) | H |
| H | CH₃ | CH₂CH₃ | CH₂CH₃ | CH₃ | CH₂(2-FPh) | H |
| H | CH₃ | CH₂CH₃ | CH₂CH₃ | CH₃ | CH₂(2-(CH₃)Ph) | H |
| H | CH₃ | CH₂CH₃ | CH₂CH₃ | CH₃ | CH₂(2,6-Cl₂Ph) | H |
| H | CH₃ | CH₂CH₃ | CH₂CH₃ | CH₃ | Q-3 | H |
| H | H | CH₂CH₂CH₃ | CH₂CH₂CH₃ | CH₃ | CH₂(2,5-(F)₂Ph) | H |
| H | H | CH₂CH₂CH₃ | CH₂CH₂CH₃ | CH₃ | CH₂(2,4-(F)₂Ph) | H |
| H | H | CH₂CH₂CH₃ | CH₂CH₂CH₃ | CH₃ | CH₂(4-FPh) | H |
| H | H | CH₂CH₂CH₃ | CH₂CH₂CH₃ | CH₃ | CH₂(3-FPh) | H |
| H | H | CH₂CH₂CH₃ | CH₂CH₂CH₃ | CH₃ | CH₂(3-ClPh) | H |
| H | H | CH₂CH(CH₃)₂ | CH₂CH(CH₃)₂ | CH₃ | CH₂(2,5-(F)₂Ph) | H |
| H | H | CH₂CH(CH₃)₂ | CH₂CH(CH₃)₂ | CH₃ | CH₂(2,4-(F)₂Ph) | H |
| H | H | CH₂CH(CH₃)₂ | CH₂CH(CH₃)₂ | CH₃ | CH₂(4-FPh) | H |
| H | H | CH₂CH(CH₃)₂ | CH₂CH(CH₃)₂ | CH₃ | CH₂(3-FPh) | H |
| H | H | CH₂CH(CH₃)₂ | CH₂CH(CH₃)₂ | CH₃ | CH₂(3-ClPh) | H |
| H | H | CH₂CH₃ | CH₂CH₃ | CH₃ | CH₂(2,5-(F)₂Ph) | H |
| H | H | CH₂CH₃ | CH₂CH₃ | CH₃ | CH₂(2,4-(F)₂Ph) | H |
| H | H | CH₂CH₃ | CH₂CH₃ | CH₃ | CH₂(4-FPh) | H |
| H | H | CH₂CH₃ | CH₂CH₃ | CH₃ | CH₂(3-FPh) | H |
| H | H | CH₂CH₃ | CH₂CH₃ | CH₃ | CH₂(3-ClPh) | H |
| H | H | CH=CH₂ | CH=CH₂ | CH₃ | CH₂(2,5-(F)₂Ph) | H |
| H | H | CH=CH₂ | CH=CH₂ | CH₃ | CH₂(2,4-(F)₂Ph) | H |
| H | H | CH=CH₂ | CH=CH₂ | CH₃ | CH₂(4-FPh) | H |
| H | H | CH=CH₂ | CH=CH₂ | CH₃ | CH₂(3-FPh) | H |
| H | H | CH=CH₂ | CH=CH₂ | CH₃ | CH₂(3-ClPh) | H |
| H | H | CH₃ | CH₂CH₂CH₃ | CH₃ | CH₂(2,5-(F)₂Ph) | H |
| H | H | CH₃ | CH₂CH₂CH₃ | CH₃ | CH₂(2,4-(F)₂Ph) | H |
| H | H | CH₃ | CH₂CH₂CH₃ | CH₃ | CH₂(4-FPh) | H |
| H | H | CH₃ | CH₂CH₂CH₃ | CH₃ | CH₂(3-FPh) | H |
| H | H | CH₃ | CH₂CH₂CH₃ | CH₃ | CH₂(3-ClPh) | H |
| H | H | CH₃ | CH₂CH₂CH₂CH₃ | CH₃ | CH₂(2,5-(F)₂Ph) | H |
| H | H | CH₃ | CH₂CH₂CH₂CH₃ | CH₃ | CH₂(2,4-(F)₂Ph) | H |
| H | H | CH₃ | CH₂CH₂CH₂CH₃ | CH₃ | CH₂(4-FPh) | H |
| H | H | CH₃ | CH₂CH₂CH₂CH₃ | CH₃ | CH₂(3-FPh) | H |
| H | H | CH₃ | CH₂CH₂CH₂CH₃ | CH₃ | CH₂(3-ClPh) | H |
| H | H | CH₃ | CH₂CH₃ | CH₃ | CH₂(2,5-(F)₂Ph) | H |
| H | H | CH₃ | CH₂CH₃ | CH₃ | CH₂(2,4-(F)₂Ph) | H |
| H | H | CH₃ | CH₂CH₃ | CH₃ | CH₂(4-FPh) | H |
| H | H | CH₃ | CH₂CH₃ | CH₃ | CH₂(3-FPh) | H |
| H | H | CH₃ | CH₂CH₃ | CH₃ | CH₂(3-ClPh) | H |

TABLE 2

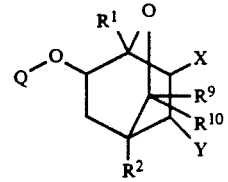

II

X and Y are C(R³)(R⁴)OR⁵ (unless specified)

| R¹ | R² | R³ = R⁴ | R⁹ = R¹⁰ | R⁵ | Q | Y |
|---|---|---|---|---|---|---|
| H | H | $CH_2CH_3$ | $CH_2CH_3$ | $CH_3$ | $CH_2$(2-FPh) | H |
| H | H | $CH_2CH_3$ | $CH_2CH_3$ | $CH_3$ | $CH_2$(2-ClPh) | H |
| H | H | $CH_2CH_3$ | $CH_2CH_3$ | $CH_3$ | $CH_2$(2-BrPh) | H |
| H | H | $CH_2CH_3$ | $CH_2CH_3$ | $CH_3$ | $CH_2$(2-($CH_3$)Ph) | H |
| H | H | $CH_2CH_3$ | $CH_2CH_3$ | $CH_3$ | $CH_2$(2-($OCH_3$)Ph) | H |
| H | H | $CH_2CH_3$ | $CH_2CH_3$ | $CH_3$ | $CH_2$(2-(CN)Ph) | H |
| H | H | $CH_2CH_3$ | $CH_2CH_3$ | $CH_3$ | $CH_2$(2-($CF_3$)Ph) | H |
| H | H | $CH_2CH_3$ | $CH_2CH_3$ | $CH_3$ | $CH_2$(2-($OCF_3$)Ph) | H |
| H | H | $CH_2CH_3$ | $CH_2CH_3$ | $CH_3$ | $CH_2$(2-($SCH_3$)Ph) | H |
| H | H | $CH_2CH_3$ | $CH_2CH_3$ | $CH_3$ | $CH_2$(2,6-$(F)_2$Ph) | H |
| H | H | $CH_2CH_3$ | $CH_2CH_3$ | $CH_3$ | $CH_2$(2,6-$(Cl)_2$Ph) | H |
| H | H | $CH_2CH_3$ | $CH_2CH_3$ | $CH_3$ | $CH_2$(2-pyridyl) | H |
| H | H | $CH_2CH_3$ | $CH_2CH_3$ | $CH_3$ | $CH_2$(2-furanyl) | H |
| H | H | $CH_2CH_3$ | $CH_2CH_3$ | $CH_3$ | $CH_2$(2-tetrahydrofuran) | H |
| H | H | $CH_2CH_3$ | $CH_2CH_3$ | $CH_3$ | $CH_2$(2-tetrahydropyran) | H |
| H | H | $CH_2CH_3$ | $CH_2CH_3$ | $CH_3$ | $CH_2$(2-thiophenyl) | H |
| H | H | $CH_2CH_3$ | $CH_2CH_3$ | $CH_3$ | $CH_2$(2-isoxazolyl) | H |
| H | H | $CH_2CH_3$ | $CH_2CH_3$ | $CH_3$ | $CH_2$(2-pyrazinyl) | H |
| H | H | $CH_2CH_3$ | $CH_2CH_3$ | $CH_3$ | $CH_2$(Ph) | H |
| H | H | $CH_2CH_3$ | $CH_2CH_3$ | $CH_3$ | Q-1 | H |
| H | H | $CH_2CH_3$ | $CH_2CH_3$ | $CH_3$ | Q-3 | H |
| H | H | $CH_2CH_3$ | $CH_2CH_3$ | $CH_3$ | Q-6 | H |
| H | H | $CH_2CH_3$ | $CH_2CH_3$ | $CH_3$ | Q-7 | H |
| H | H | $CH_2CH_3$ | $CH_2CH_3$ | $CH_3$ | Q-15 | H |
| H | H | $CH_2CH_3$ | $CH_2CH_3$ | $CH_2CH_3$ | $CH_2$(2-FPh) | H |
| H | H | $CH_2CH_3$ | $CH_2CH_3$ | $CH_2CH_3$ | $CH_2$(2-ClPh) | H |
| H | H | $CH_2CH_3$ | $CH_2CH_3$ | $CH_2CH_3$ | $CH_2$(2-($CH_3$)Ph) | H |
| H | H | $CH_2CH_3$ | $CH_2CH_3$ | $CH_2CH_3$ | $CH_2$(2,6-$Cl_2$Ph) | H |
| H | H | $CH_2CH_3$ | $CH_2CH_3$ | $CH_2CH_3$ | $CH_2$(2-$CF_3$Ph) | H |
| H | H | $CH_2CH_3$ | $CH_2CH_3$ | $CH_2CH_3$ | $CH_2$(2-tetrahydropyran) | H |
| H | H | $CH_2CH_3$ | $CH_2CH_3$ | $CH_2CH_3$ | $CH_2$(2-pyridyl) | H |
| H | H | $CH_2CH_3$ | $CH_2CH_3$ | $CH_2CH_3$ | $CH_2$(Ph) | H |
| H | H | $CH_2CH_3$ | $CH_2CH_3$ | $CH_2CH_3$ | Q-1 | H |
| H | H | $CH_2CH_3$ | $CH_2CH_3$ | $CH_2CH_3$ | Q-3 | H |
| H | H | $CH_2CH_3$ | $CH_2CH_3$ | $CH_2CH_3$ | Q-6 | H |
| H | H | $CH_2CH_3$ | $CH_2CH_3$ | $CH_2CH_3$ | Q-7 | H |
| H | H | $CH_2CH_3$ | $CH_2CH_3$ | $CH_2CH_3$ | Q-15 | H |
| H | H | $CH_2CH_3$ | $CH_2CH_3$ | $CH_2CH=CH_2$ | $CH_2$(2-FPh) | H |
| H | H | $CH_2CH_3$ | $CH_2CH_3$ | $CH_2CH=CH_2$ | $CH_2$(2-ClPh) | H |
| H | H | $CH_2CH_3$ | $CH_2CH_3$ | $CH_2CH=CH_2$ | $CH_2$(2-($CH_3$)Ph) | H |
| H | H | $CH_2CH_3$ | $CH_2CH_3$ | $CH_2CH=CH_2$ | $CH_2$(2,6-$Cl_2$Ph) | H |
| H | H | $CH_2CH_3$ | $CH_2CH_3$ | $CH_2CH=CH_2$ | $CH_2$(2-$CF_3$Ph) | H |
| H | H | $CH_2CH_3$ | $CH_2CH_3$ | $CH_2CH=CH_2$ | $CH_2$(2-tetrahydropyran) | H |
| H | H | $CH_2CH_3$ | $CH_2CH_3$ | $CH_2CH=CH_2$ | $CH_2$(2-pyridyl) | H |
| H | H | $CH_2CH_3$ | $CH_2CH_3$ | $CH_2CH=CH_2$ | $CH_2$(Ph) | H |
| H | H | $CH_2CH_3$ | $CH_2CH_3$ | $CH_2CH=CH_2$ | Q-1 | H |
| H | H | $CH_2CH_3$ | $CH_2CH_3$ | $CH_2CH=CH_2$ | Q-3 | H |
| H | H | $CH_2CH_3$ | $CH_2CH_3$ | $CH_2CH=CH_2$ | Q-6 | H |
| H | H | $CH_2CH_3$ | $CH_2CH_3$ | $CH_2CH=CH_2$ | Q-7 | H |
| H | H | $CH_2CH_3$ | $CH_2CH_3$ | $CH_2CH=CH_2$ | Q-15 | H |
| H | H | H | H | $CH_3$ | $CH_2$(2-FPh) | H |
| H | H | H | H | $CH_3$ | $CH_2$(2-ClPh) | H |
| H | H | H | H | $CH_3$ | $CH_2$(2-($CH_3$)Ph) | H |
| H | H | H | H | $CH_3$ | $CH_2$(2,6-$Cl_2$Ph) | H |
| H | H | H | H | $CH_3$ | $CH_2$(2-$CF_3$Ph) | H |
| H | H | H | H | $CH_3$ | $CH_2$(2-tetrahydropyran) | H |
| H | H | H | H | $CH_3$ | $CH_2$(2-pyridyl) | H |
| H | H | H | H | $CH_3$ | $CH_2$(Ph) | H |
| H | H | H | H | $CH_3$ | Q-1 | H |
| H | H | H | H | $CH_3$ | Q-3 | H |
| H | H | H | H | $CH_3$ | Q-6 | H |
| H | H | H | H | $CH_3$ | Q-7 | H |
| H | H | H | H | $CH_3$ | Q-15 | H |
| H | H | $CH_3$ | $CH_3$ | $CH_3$ | $CH_2$(2-FPh) | H |
| H | H | $CH_3$ | $CH_3$ | $CH_3$ | $CH_2$(2-ClPh) | H |
| H | H | $CH_3$ | $CH_3$ | $CH_3$ | $CH_2$(2-($CH_3$)Ph) | H |
| H | H | $CH_3$ | $CH_3$ | $CH_3$ | $CH_2$(2,6-$Cl_2$Ph) | H |
| H | H | $CH_3$ | $CH_3$ | $CH_3$ | $CH_2$(2-$CF_3$Ph) | H |
| H | H | $CH_3$ | $CH_3$ | $CH_3$ | $CH_2$(2-tetrahydropyran) | H |
| H | H | $CH_3$ | $CH_3$ | $CH_3$ | $CH_2$(2-pyridyl) | H |

TABLE 2-continued

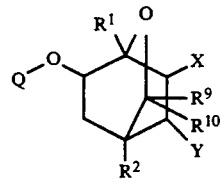

X and Y are $C(R^3)(R^4)OR^5$ (unless specified)

| | | | | | | |
|---|---|---|---|---|---|---|
| H | H | $CH_3$ | $CH_3$ | $CH_3$ | $CH_2(Ph)$ | H |
| H | H | $CH_3$ | $CH_3$ | $CH_3$ | Q-1 | H |
| H | H | $CH_3$ | $CH_3$ | $CH_3$ | Q-3 | H |
| H | H | $CH_3$ | $CH_3$ | $CH_3$ | Q-6 | H |
| H | H | $CH_3$ | $CH_3$ | $CH_3$ | Q-7 | H |
| H | H | $CH_3$ | $CH_3$ | $CH_3$ | Q-15 | H |
| $CH_3$ | H | $CH_2CH_3$ | $CH_2CH_3$ | $CH_3$ | $CH_2(2\text{-FPh})$ | H |
| $CH_3$ | H | $CH_2CH_3$ | $CH_2CH_3$ | $CH_3$ | $CH_2(2\text{-ClPh})$ | H |
| $CH_3$ | H | $CH_2CH_3$ | $CH_2CH_3$ | $CH_3$ | $CH_2(2\text{-}(CH_3)Ph)$ | H |
| $CH_3$ | H | $CH_2CH_3$ | $CH_2CH_3$ | $CH_3$ | $CH_2(2,6\text{-}Cl_2Ph)$ | H |
| $CH_3$ | H | $CH_2CH_3$ | $CH_2CH_3$ | $CH_3$ | $CH_2(2\text{-}CF_3Ph)$ | H |
| $CH_3$ | H | $CH_2CH_3$ | $CH_2CH_3$ | $CH_3$ | $CH_2(2\text{-tetrahydropyran})$ | H |
| $CH_3$ | H | $CH_2CH_3$ | $CH_2CH_3$ | $CH_3$ | $CH_2(2\text{-pyridyl})$ | H |
| $CH_3$ | H | $CH_2CH_3$ | $CH_2CH_3$ | $CH_3$ | $CH_2(Ph)$ | H |
| $CH_3$ | H | $CH_2CH_3$ | $CH_2CH_3$ | $CH_3$ | Q-1 | H |
| $CH_3$ | H | $CH_2CH_3$ | $CH_2CH_3$ | $CH_3$ | Q-3 | H |
| $CH_3$ | H | $CH_2CH_3$ | $CH_2CH_3$ | $CH_3$ | Q-6 | H |
| $CH_3$ | H | $CH_2CH_3$ | $CH_2CH_3$ | $CH_3$ | Q-7 | H |
| $CH_3$ | H | $CH_2CH_3$ | $CH_2CH_3$ | $CH_3$ | Q-15 | H |
| $CH_2CH_3$ | H | $CH_3$ | $CH_3$ | $CH_3$ | $CH_2(2\text{-FPh})$ | H |
| $CH_2CH_3$ | H | $CH_3$ | $CH_3$ | $CH_3$ | $CH_2(2\text{-ClPh})$ | H |
| $CH_2CH_3$ | H | $CH_3$ | $CH_3$ | $CH_3$ | $CH_2(2\text{-}(CH_3)Ph)$ | H |
| $CH_2CH_3$ | H | $CH_3$ | $CH_3$ | $CH_3$ | $CH_2(2,6\text{-}Cl_2Ph)$ | H |
| $CH_2CH_3$ | H | $CH_3$ | $CH_3$ | $CH_3$ | $CH_2(2\text{-}CF_3Ph)$ | H |
| $CH_2CH_3$ | H | $CH_3$ | $CH_3$ | $CH_3$ | $CH_2(2\text{-tetrahydropyran})$ | H |
| $CH_2CH_3$ | H | $CH_3$ | $CH_3$ | $CH_3$ | $CH_2(2\text{-pyridyl})$ | H |
| $CH_2CH_3$ | H | $CH_3$ | $CH_3$ | $CH_3$ | $CH_2(Ph)$ | H |
| $CH_2CH_3$ | H | $CH_3$ | $CH_3$ | $CH_3$ | Q-1 | H |
| $CH_2CH_3$ | H | $CH_3$ | $CH_3$ | $CH_3$ | Q-3 | H |
| $CH_2CH_3$ | H | $CH_3$ | $CH_3$ | $CH_3$ | Q-6 | H |
| $CH_2CH_3$ | H | $CH_3$ | $CH_3$ | $CH_3$ | Q-7 | H |
| $CH_2CH_3$ | H | $CH_3$ | $CH_3$ | $CH_3$ | Q-15 | H |
| $CH_3$ | H | H | H | $CH_3$ | Q-1 | H |
| $CH_3$ | H | H | H | $CH_3$ | Q-3 | H |
| $CH_3$ | H | H | H | $CH_3$ | Q-6 | H |
| $CH_3$ | H | H | H | $CH_3$ | Q-7 | H |
| $CH_3$ | H | H | H | $CH_3$ | Q-15 | H |
| $CH_3$ | H | H | H | $CH_3$ | $CH_2(2\text{-FPh})$ | H |
| $CH_3$ | H | H | H | $CH_3$ | $CH_2(2\text{-ClPh})$ | H |
| $CH_3$ | H | H | H | $CH_3$ | $CH_2(2\text{-}(CH_3)Ph)$ | H |
| $CH_3$ | H | H | H | $CH_3$ | $CH_2(2,6\text{-}Cl_2Ph)$ | H |
| $CH_3$ | H | H | H | $CH_3$ | $CH_2(2\text{-}CF_3Ph)$ | H |
| $CH_3$ | H | H | H | $CH_3$ | $CH_2(2\text{-tetrahydropyran})$ | H |
| $CH_3$ | H | H | H | $CH_3$ | $CH_2(2\text{-pyridyl})$ | H |
| $CH_3$ | H | H | H | $CH_3$ | $CH_2(Ph)$ | H |
| $CH_3$ | H | $CH_3$ | $CH_3$ | $CH_3$ | Q-1 | H |
| $CH_3$ | H | $CH_3$ | $CH_3$ | $CH_3$ | Q-3 | H |
| $CH_3$ | H | $CH_3$ | $CH_3$ | $CH_3$ | Q-6 | H |
| $CH_3$ | H | $CH_3$ | $CH_3$ | $CH_3$ | Q-7 | H |
| $CH_3$ | H | $CH_3$ | $CH_3$ | $CH_3$ | Q-15 | H |
| $CH_3$ | H | $CH_3$ | $CH_3$ | $CH_3$ | $CH_2(2\text{-FPh})$ | H |
| $CH_3$ | H | $CH_3$ | $CH_3$ | $CH_3$ | $CH_2(2\text{-ClPh})$ | H |
| $CH_3$ | H | $CH_3$ | $CH_3$ | $CH_3$ | $CH_2(2\text{-}(CH_3)Ph)$ | H |
| $CH_3$ | H | $CH_3$ | $CH_3$ | $CH_3$ | $CH_2(2,6\text{-}Cl_2Ph)$ | H |
| $CH_3$ | H | $CH_3$ | $CH_3$ | $CH_3$ | $CH_2(2\text{-}CF_3Ph)$ | H |
| $CH_3$ | H | $CH_3$ | $CH_3$ | $CH_3$ | $CH_2(2\text{-tetrahydropyran})$ | H |
| $CH_3$ | H | $CH_3$ | $CH_3$ | $CH_3$ | $CH_2(2\text{-pyridyl})$ | H |
| $CH_3$ | H | $CH_3$ | $CH_3$ | $CH_3$ | $CH_2(Ph)$ | H |
| $CH_3$ | $CH_3$ | $CH_3$ | $CH_3$ | $CH_3$ | Q-1 | H |
| $CH_3$ | $CH_3$ | $CH_3$ | $CH_3$ | $CH_3$ | Q-3 | H |
| $CH_3$ | $CH_3$ | $CH_3$ | $CH_3$ | $CH_3$ | Q-6 | H |
| $CH_3$ | $CH_3$ | $CH_3$ | $CH_3$ | $CH_3$ | Q-7 | H |
| $CH_3$ | $CH_3$ | $CH_3$ | $CH_3$ | $CH_3$ | Q-15 | H |
| $CH_3$ | $CH_3$ | $CH_3$ | $CH_3$ | $CH_3$ | $CH_2(2\text{-FPh})$ | H |
| $CH_3$ | $CH_3$ | $CH_3$ | $CH_3$ | $CH_3$ | $CH_2(2\text{-ClPh})$ | H |
| $CH_3$ | $CH_3$ | $CH_3$ | $CH_3$ | $CH_3$ | $CH_2(2\text{-}(CH_3)Ph)$ | H |
| $CH_3$ | $CH_3$ | $CH_3$ | $CH_3$ | $CH_3$ | $CH_2(2,6\text{-}Cl_2Ph)$ | H |
| $CH_3$ | $CH_3$ | $CH_3$ | $CH_3$ | $CH_3$ | $CH_2(2\text{-}CF_3Ph)$ | H |
| $CH_3$ | $CH_3$ | $CH_3$ | $CH_3$ | $CH_3$ | $CH_2(2\text{-tetrahydropyran})$ | H |
| $CH_3$ | $CH_3$ | $CH_3$ | $CH_3$ | $CH_3$ | $CH_2(2\text{-pyridyl})$ | H |
| $CH_3$ | $CH_3$ | $CH_3$ | $CH_3$ | $CH_3$ | $CH_2(Ph)$ | H |
| $CH_3$ | H | H | $CH_3$ | $CH_3$ | Q-1 | H |

TABLE 2-continued

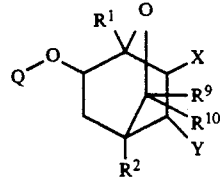

X and Y are C(R³)(R⁴)OR⁵ (unless specified)

| R¹ | R² | R³ | R⁴ | R⁵ | Q | X/Y |
|---|---|---|---|---|---|---|
| CH₃ | H | H | CH₃ | CH₃ | Q-3 | H |
| CH₃ | H | H | CH₃ | CH₃ | Q-6 | H |
| CH₃ | H | H | CH₃ | CH₃ | Q-7 | H |
| CH₃ | H | H | CH₃ | CH₃ | Q-15 | H |
| CH₃ | H | H | CH₃ | CH₃ | CH₂(2-FPh) | H |
| CH₃ | H | H | CH₃ | CH₃ | CH₂(2-ClPh) | H |
| CH₃ | H | H | CH₃ | CH₃ | CH₂(2-(CH₃)Ph) | H |
| CH₃ | H | H | CH₃ | CH₃ | CH₂(2,6-Cl₂Ph) | H |
| CH₃ | H | H | CH₃ | CH₃ | CH₂(2-CF₃Ph) | H |
| CH₃ | H | H | CH₃ | CH₃ | CH₂(2-tetrahydropyran) | H |
| CH₃ | H | H | CH₃ | CH₃ | CH₂(2-pyridyl) | H |
| CH₃ | H | H | CH₃ | CH₃ | CH₂(Ph) | H |
| CH₃ | H | H | CH₂CH₃ | CH₃ | Q-1 | H |
| CH₃ | H | H | CH₂CH₃ | CH₃ | Q-3 | H |
| CH₃ | H | H | CH₂CH₃ | CH₃ | Q-6 | H |
| CH₃ | H | H | CH₂CH₃ | CH₃ | Q-7 | H |
| CH₃ | H | H | CH₂CH₃ | CH₃ | Q-15 | H |
| CH₃ | H | H | CH₂CH₃ | CH₃ | CH₂(2-FPh) | H |
| CH₃ | H | H | CH₂CH₃ | CH₃ | CH₂(2-ClPh) | H |
| CH₃ | H | H | CH₂CH₃ | CH₃ | CH₂(2-(CH₃)Ph) | H |
| CH₃ | H | H | CH₂CH₃ | CH₃ | CH₂(2,6-Cl₂Ph) | H |
| CH₃ | H | H | CH₂CH₃ | CH₃ | CH₂(2-CF₃Ph) | H |
| CH₃ | H | H | CH₂CH₃ | CH₃ | CH₂(2-tetrahydropyran) | H |
| CH₃ | H | H | CH₂CH₃ | CH₃ | CH₂(2-pyridyl) | H |
| CH₃ | H | H | CH₂CH₃ | CH₃ | CH₂(Ph) | H |
| CH₃ | H | CH₃ | H | CH₃ | Q-1 | H |
| CH₃ | H | CH₃ | H | CH₃ | Q-3 | H |
| CH₃ | H | CH₃ | H | CH₃ | Q-6 | H |
| CH₃ | H | CH₃ | H | CH₃ | Q-7 | H |
| CH₃ | H | CH₃ | H | CH₃ | Q-15 | H |
| CH₃ | H | CH₃ | H | CH₃ | CH₂(2-FPh) | H |
| CH₃ | H | CH₃ | H | CH₃ | CH₂(2-ClPh) | H |
| CH₃ | H | CH₃ | H | CH₃ | CH₂(2-(CH₃)Ph) | H |
| CH₃ | H | CH₃ | H | CH₃ | CH₂(2,6-Cl₂Ph) | H |
| CH₃ | H | CH₃ | H | CH₃ | CH₂(2-CF₃Ph) | H |
| CH₃ | H | CH₃ | H | CH₃ | CH₂(2-tetrahydropyran) | H |
| CH₃ | H | CH₃ | H | CH₃ | CH₂(2-pyridyl) | H |
| CH₃ | H | CH₃ | H | CH₃ | CH₂(Ph) | H |
| R¹ | R² | R³ = R⁴ | R⁹ = R¹⁰ | R⁵ | Q | X |
| CH₃ | H | CH₂CH₃ | H | CH₂CH₃ | CH₂(2-FPh) | H |
| CH₃ | H | CH₂CH₃ | H | CH₂CH₃ | CH₂(2-ClPh) | H |
| CH₃ | H | CH₂CH₃ | H | CH₂CH₃ | CH₂(2-(CH₃)Ph) | H |
| CH₃ | H | CH₂CH₃ | H | CH₂CH₃ | CH₂(2,6-Cl₂Ph) | H |
| CH₃ | H | CH₂CH₃ | H | CH₂CH₃ | CH₂(2-CF₃Ph) | H |
| CH₃ | H | CH₂CH₃ | CH₂CH₃ | CH₃ | CH₂(2-tetrahydropyran) | H |
| CH₃ | H | CH₂CH₃ | CH₂CH₃ | CH₃ | CH₂(2-pyridyl) | H |
| CH₃ | H | CH₂CH₃ | CH₂CH₃ | CH₃ | CH₂(Ph) | H |
| CH₃ | H | CH₂CH₃ | CH₂CH₃ | CH₃ | Q-1 | H |
| CH₃ | H | CH₂CH₃ | CH₂CH₃ | CH₃ | Q-3 | H |
| CH₃ | H | CH₂CH₃ | CH₂CH₃ | CH₃ | Q-6 | H |
| CH₃ | H | CH₂CH₃ | CH₂CH₃ | CH₃ | Q-7 | H |
| CH₃ | H | CH₂CH₃ | CH₂CH₃ | CH₃ | Q-15 | H |
| CH₂CH₃ | H | CH₃ | CH₃ | CH₃ | CH₂(2-FPh) | H |
| CH₂CH₃ | H | CH₃ | CH₃ | CH₃ | CH₂(2-ClPh) | H |
| CH₂CH₃ | H | CH₃ | CH₃ | CH₃ | CH₂(2-(CH₃)Ph) | H |
| CH₂CH₃ | H | CH₃ | CH₃ | CH₃ | CH₂(2,6-Cl₂Ph) | H |
| CH₂CH₃ | H | CH₃ | CH₃ | CH₃ | CH₂(2-CF₃Ph) | H |
| CH₂CH₃ | H | CH₃ | CH₃ | CH₃ | CH₂(2-tetrahydropyran) | H |
| CH₂CH₃ | H | CH₃ | CH₃ | CH₃ | CH₂(2-pyridyl) | H |
| CH₂CH₃ | H | CH₃ | CH₃ | CH₃ | CH₂(Ph) | H |
| CH₂CH₃ | H | CH₃ | CH₃ | CH₃ | Q-1 | H |
| CH₂CH₃ | H | CH₃ | CH₃ | CH₃ | Q-3 | H |
| CH₂CH₃ | H | CH₃ | CH₃ | CH₃ | Q-6 | H |
| CH₂CH₃ | H | CH₃ | CH₃ | CH₃ | Q-7 | H |
| CH₂CH₃ | H | CH₃ | CH₃ | CH₃ | Q-15 | H |
| CH₃ | H | H | H | CH₃ | Q-1 | H |
| CH₃ | H | H | H | CH₃ | Q-3 | H |
| CH₃ | H | H | H | CH₃ | Q-6 | H |
| CH₃ | H | H | H | CH₃ | Q-7 | H |
| CH₃ | H | H | H | CH₃ | Q-15 | H |
| CH₃ | H | H | H | CH₃ | CH₂(2-FPh) | H |

TABLE 2-continued

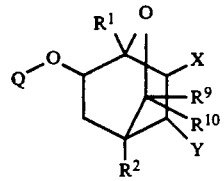

X and Y are C(R³)(R⁴)OR⁵ (unless specified)

| | | | | | | |
|---|---|---|---|---|---|---|
| $CH_3$ | H | H | H | $CH_3$ | $CH_2$(2-ClPh) | H |
| $CH_3$ | H | H | H | $CH_3$ | $CH_2$(2-($CH_3$)Ph) | H |
| $CH_3$ | H | H | H | $CH_3$ | $CH_2$(2,6-$Cl_2$Ph) | H |
| $CH_3$ | H | H | H | $CH_3$ | $CH_2$(2-$CF_3$Ph) | H |
| $CH_3$ | H | H | H | $CH_3$ | $CH_2$(2-tetrahydropyran) | H |
| $CH_3$ | H | H | H | $CH_3$ | $CH_2$(2-pyridyl) | H |
| $CH_3$ | H | H | H | $CH_3$ | $CH_2$(Ph) | H |
| $CH_3$ | H | $CH_3$ | $CH_3$ | $CH_3$ | Q-1 | H |
| $CH_3$ | H | $CH_3$ | $CH_3$ | $CH_3$ | Q-3 | H |
| $CH_3$ | H | $CH_3$ | $CH_3$ | $CH_3$ | Q-6 | H |
| $CH_3$ | H | $CH_3$ | $CH_3$ | $CH_3$ | Q-7 | H |
| $CH_3$ | H | $CH_3$ | $CH_3$ | $CH_3$ | Q-15 | H |
| $CH_3$ | H | $CH_3$ | $CH_3$ | $CH_3$ | $CH_2$(2-FPh) | H |
| $CH_3$ | H | $CH_3$ | $CH_3$ | $CH_3$ | $CH_2$(2-ClPh) | H |
| $CH_3$ | H | $CH_3$ | $CH_3$ | $CH_3$ | $CH_2$(2-($CH_3$)Ph) | H |
| $CH_3$ | H | $CH_3$ | $CH_3$ | $CH_3$ | $CH_2$(2,6-$Cl_2$Ph) | H |
| $CH_3$ | H | $CH_3$ | $CH_3$ | $CH_3$ | $CH_2$(2-$CF_3$Ph) | H |
| $CH_3$ | H | $CH_3$ | $CH_3$ | $CH_3$ | $CH_2$(2-tetrahydropyran) | H |
| $CH_3$ | H | $CH_3$ | $CH_3$ | $CH_3$ | $CH_2$(2-pyridyl) | H |
| $CH_3$ | H | $CH_3$ | $CH_3$ | $CH_3$ | $CH_2$(Ph) | H |
| $CH_3$ | $CH_3$ | $CH_3$ | $CH_3$ | $CH_3$ | Q-1 | H |
| $CH_3$ | $CH_3$ | $CH_3$ | $CH_3$ | $CH_3$ | Q-3 | H |
| $CH_3$ | $CH_3$ | $CH_3$ | $CH_3$ | $CH_3$ | Q-6 | H |
| $CH_3$ | $CH_3$ | $CH_3$ | $CH_3$ | $CH_3$ | Q-7 | H |
| $CH_3$ | $CH_3$ | $CH_3$ | $CH_3$ | $CH_3$ | Q-15 | H |
| $CH_3$ | $CH_3$ | $CH_3$ | $CH_3$ | $CH_3$ | $CH_2$(2-FPh) | H |
| $CH_3$ | $CH_3$ | $CH_3$ | $CH_3$ | $CH_3$ | $CH_2$(2-ClPh) | H |
| $CH_3$ | $CH_3$ | $CH_3$ | $CH_3$ | $CH_3$ | $CH_2$(2-($CH_3$)Ph) | H |
| $CH_3$ | $CH_3$ | $CH_3$ | $CH_3$ | $CH_3$ | $CH_2$(2,6-$Cl_2$Ph) | H |
| $CH_3$ | $CH_3$ | $CH_3$ | $CH_3$ | $CH_3$ | $CH_2$(2-$CF_3$Ph) | H |
| $CH_3$ | $CH_3$ | $CH_3$ | $CH_3$ | $CH_3$ | $CH_2$(2-tetrahydropyran) | H |
| $CH_3$ | $CH_3$ | $CH_3$ | $CH_3$ | $CH_3$ | $CH_2$(2-pyridyl) | H |
| $CH_3$ | $CH_3$ | $CH_3$ | $CH_3$ | $CH_3$ | $CH_2$(Ph) | H |
| $CH_3$ | H | H | $CH_3$ | $CH_3$ | Q-1 | H |
| $CH_3$ | H | H | $CH_3$ | $CH_3$ | Q-3 | H |
| $CH_3$ | H | H | $CH_3$ | $CH_3$ | Q-6 | H |
| $CH_3$ | H | H | $CH_3$ | $CH_3$ | Q-7 | H |
| $CH_3$ | H | H | $CH_3$ | $CH_3$ | Q-15 | H |
| $CH_3$ | H | H | $CH_3$ | $CH_3$ | $CH_2$(2-FPh) | H |
| $CH_3$ | H | H | $CH_3$ | $CH_3$ | $CH_2$(2-ClPh) | H |
| $CH_3$ | H | H | $CH_3$ | $CH_3$ | $CH_2$(2-($CH_3$)Ph) | H |
| $CH_3$ | H | H | $CH_3$ | $CH_3$ | $CH_2$(2,6-$Cl_2$Ph) | H |
| $CH_3$ | H | H | $CH_3$ | $CH_3$ | $CH_2$(2-$CF_3$Ph) | H |
| $CH_3$ | H | H | $CH_3$ | $CH_3$ | $CH_2$(2-tetrahydropyran) | H |
| $CH_3$ | H | H | $CH_3$ | $CH_3$ | $CH_2$(2-pyridyl) | H |
| $CH_3$ | H | H | $CH_3$ | $CH_3$ | $CH_2$(Ph) | H |
| $CH_3$ | H | H | $CH_2CH_3$ | $CH_3$ | Q-1 | H |
| $CH_3$ | H | H | $CH_2CH_3$ | $CH_3$ | Q-3 | H |
| $CH_3$ | H | H | $CH_2CH_3$ | $CH_3$ | Q-6 | H |
| $CH_3$ | H | H | $CH_2CH_3$ | $CH_3$ | Q-7 | H |
| $CH_3$ | H | H | $CH_2CH_3$ | $CH_3$ | Q-15 | H |
| $CH_3$ | H | H | $CH_2CH_3$ | $CH_3$ | $CH_2$(2-FPh) | H |
| $CH_3$ | H | H | $CH_2CH_3$ | $CH_3$ | $CH_2$(2-ClPh) | H |
| $CH_3$ | H | H | $CH_2CH_3$ | $CH_3$ | $CH_2$(2-($CH_3$)Ph) | H |
| $CH_3$ | H | H | $CH_2CH_3$ | $CH_3$ | $CH_2$(2,6-$Cl_2$Ph) | H |
| $CH_3$ | H | H | $CH_2CH_3$ | $CH_3$ | $CH_2$(2-$CF_3$Ph) | H |
| $CH_3$ | H | H | $CH_2CH_3$ | $CH_3$ | $CH_2$(2-tetrahydropyran) | H |
| $CH_3$ | H | H | $CH_2CH_3$ | $CH_3$ | $CH_2$(2-pyridyl) | H |
| $CH_3$ | H | H | $CH_2CH_3$ | $CH_3$ | $CH_2$(Ph) | H |
| $CH_3$ | H | $CH_3$ | H | $CH_3$ | Q-1 | H |
| $CH_3$ | H | $CH_3$ | H | $CH_3$ | Q-3 | H |
| $CH_3$ | H | $CH_3$ | H | $CH_3$ | Q-6 | H |
| $CH_3$ | H | $CH_3$ | H | $CH_3$ | Q-7 | H |
| $CH_3$ | H | $CH_3$ | H | $CH_3$ | Q-15 | H |
| $CH_3$ | H | $CH_3$ | H | $CH_3$ | $CH_2$(2-FPh) | H |
| $CH_3$ | H | $CH_3$ | H | $CH_3$ | $CH_2$(2-ClPh) | H |
| $CH_3$ | H | $CH_3$ | H | $CH_3$ | $CH_2$(2-($CH_3$)Ph) | H |
| $CH_3$ | H | $CH_3$ | H | $CH_3$ | $CH_2$(2,6-$Cl_2$Ph) | H |
| $CH_3$ | H | $CH_3$ | H | $CH_3$ | $CH_2$(2-$CF_3$Ph) | H |
| $CH_3$ | H | $CH_3$ | H | $CH_3$ | $CH_2$(2-tetrahydropyran) | H |
| $CH_3$ | H | $CH_3$ | H | $CH_3$ | $CH_2$(2-pyridyl) | H |

TABLE 2-continued

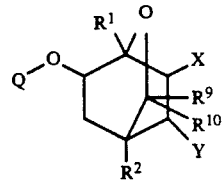

II

X and Y are C(R³)(R⁴)OR⁵ (unless specified)

| CH₃ | H | CH₃ | H | CH₃ | CH₂(Ph) | H |
|---|---|---|---|---|---|---|

TABLE 3

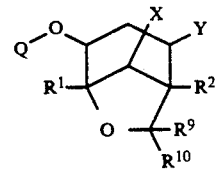

III

X and Y are C(R³)(R⁴)OR⁵ (unless specified)

| R¹ | R² | R³ = R⁴ | R⁹ = R¹⁰ | R⁵ | Q | Y |
|---|---|---|---|---|---|---|
| H | H | CH₂CH₃ | CH₂CH₃ | CH₃ | CH₂(2-FPh) | H |
| H | H | CH₂CH₃ | CH₂CH₃ | CH₃ | CH₂(2-ClPh) | H |
| H | H | CH₂CH₃ | CH₂CH₃ | CH₃ | CH₂(2-BrPh) | H |
| H | H | CH₂CH₃ | CH₂CH₃ | CH₃ | CH₂(2-(CH₃)Ph) | H |
| H | H | CH₂CH₃ | CH₂CH₃ | CH₃ | CH₂(2-(OCH₃)Ph) | H |
| H | H | CH₂CH₃ | CH₂CH₃ | CH₃ | CH₂(2-(CN)Ph) | H |
| H | H | CH₂CH₃ | CH₂CH₃ | CH₃ | CH₂(2-(CF₃)pH) | H |
| H | H | CH₂CH₃ | CH₂CH₃ | CH₃ | CH₂(2-(OCF₃)Ph) | H |
| H | H | CH₂CH₃ | CH₂CH₃ | CH₃ | CH₂(2-(SCH₃)Ph) | H |
| H | H | CH₂CH₃ | CH₂CH₃ | CH₃ | CH₂(2,6-(F)₂Ph) | H |
| H | H | CH₂CH₃ | CH₂CH₃ | CH₃ | CH₂(2,6-Cl)₂Ph) | H |
| H | H | CH₂CH₃ | CH₂CH₃ | CH₃ | CH₂(2-pyridyl) | H |
| H | H | CH₂CH₃ | CH₂CH₃ | CH₃ | CH₂(2-furanyl) | H |
| H | H | CH₂CH₃ | CH₂CH₃ | CH₃ | CH₂(2-tetrahydrofuran) | H |
| H | H | CH₂CH₃ | CH₂CH₃ | CH₃ | CH₂(2-tetrahydropyran) | H |
| H | H | CH₂CH₃ | CH₂CH₃ | CH₃ | CH₂(2-thiophenyl) | H |
| H | H | CH₂CH₃ | CH₂CH₃ | CH₃ | CH₂(2-isoxazolyl) | H |
| H | H | CH₂CH₃ | CH₂CH₃ | CH₃ | CH₂(2-pyrazinyl) | H |
| H | H | CH₂CH₃ | CH₂CH₃ | CH₃ | CH₂(Ph) | H |
| H | H | CH₂CH₃ | CH₂CH₃ | CH₃ | Q-1 | H |
| H | H | CH₂CH₃ | CH₂CH₃ | CH₃ | Q-3 | H |
| H | H | CH₂CH₃ | CH₂CH₃ | CH₃ | Q-6 | H |
| H | H | CH₂CH₃ | CH₂CH₃ | CH₃ | Q-7 | H |
| H | H | CH₂CH₃ | CH₂CH₃ | CH₃ | Q-15 | H |
| H | H | CH₂CH₃ | CH₂CH₃ | CH₂CH₃ | CH₂(2-FPh) | H |
| H | H | CH₂CH₃ | CH₂CH₃ | CH₂CH₃ | CH₂(2-ClPh) | H |
| H | H | CH₂CH₃ | CH₂CH₃ | CH₂CH₃ | CH₂(2-(CH₃)Ph) | H |
| H | H | CH₂CH₃ | CH₂CH₃ | CH₂CH₃ | CH₂(2,6-Cl₂Ph) | H |
| H | H | CH₂CH₃ | CH₂CH₃ | CH₂CH₃ | CH₂(2-CF₃Ph) | H |
| H | H | CH₂CH₃ | CH₂CH₃ | CH₂CH₃ | CH₂(2-tetrahydropyran) | H |
| H | H | CH₂CH₃ | CH₂CH₃ | CH₂CH₃ | CH₂(2-pyridyl) | H |
| H | H | CH₂CH₃ | CH₂CH₃ | CH₂CH₃ | CH₂(Ph) | H |
| H | H | CH₂CH₃ | CH₂CH₃ | CH₂CH₃ | Q-1 | H |
| H | H | CH₂CH₃ | CH₂CH₃ | CH₂CH₃ | Q-3 | H |
| H | H | CH₂CH₃ | CH₂CH₃ | CH₂CH₃ | Q-6 | H |
| H | H | CH₂CH₃ | CH₂CH₃ | CH₂CH₃ | Q-7 | H |
| H | H | CH₂CH₃ | CH₂CH₃ | CH₂CH₃ | Q-15 | H |
| H | H | CH₂CH₃ | CH₂CH₃ | CH₂CH=CH₂ | CH₂(2-FPh) | H |
| H | H | CH₂CH₃ | CH₂CH₃ | CH₂CH=CH₂ | CH₂(2-ClPh) | H |
| H | H | CH₂CH₃ | CH₂CH₃ | CH₂CH=CH₂ | CH₂(2-(CH₃)Ph) | H |
| H | H | CH₂CH₃ | CH₂CH₃ | CH₂CH=CH₂ | CH₂(2,6-Cl₂Ph) | H |
| H | H | CH₂CH₃ | CH₂CH₃ | CH₂CH=CH₂ | CH₂(2-CF₃Ph) | H |
| H | H | CH₂CH₃ | CH₂CH₃ | CH₂CH=CH₂ | CH₂(2-tetrahydropyran) | H |
| H | H | CH₂CH₃ | CH₂CH₃ | CH₂CH=CH₂ | CH₂(2-pyridyl) | H |
| H | H | CH₂CH₃ | CH₂CH₃ | CH₂CH=CH₂ | CH₂(Ph) | H |
| H | H | CH₂CH₃ | CH₂CH₃ | CH₂CH=CH₂ | Q-1 | H |
| H | H | CH₂CH₃ | CH₂CH₃ | CH₂CH=CH₂ | Q-3 | H |
| H | H | CH₂CH₃ | CH₂CH₃ | CH₂CH=CH₂ | Q-6 | H |
| H | H | CH₂CH₃ | CH₂CH₃ | CH₂CH=CH₂ | Q-7 | H |
| H | H | CH₂CH₃ | CH₂CH₃ | CH₂CH=CH₂ | Q-15 | H |
| H | H | H | H | CH₃ | CH₂(2-FPh) | H |

TABLE 3-continued

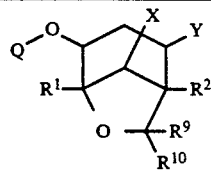

III

X and Y are C(R³)(R⁴)OR⁵ (unless specified)

| $R^1$ | $R^2$ | $R^3 = R^4$ | $R^9 = R^{10}$ | $R^5$ | Q | |
|---|---|---|---|---|---|---|
| H | H | H | H | $CH_3$ | $CH_2$(2-ClPh) | H |
| H | H | H | H | $CH_3$ | $CH_2$(2-($CH_3$)Ph) | H |
| H | H | H | H | $CH_3$ | $CH_2$(2,6-$Cl_2$Ph) | H |
| H | H | H | H | $CH_3$ | $CH_2$(2-$CF_3$Ph) | H |
| H | H | H | H | $CH_3$ | $CH_2$(2-tetrahydropyran) | H |
| H | H | H | H | $CH_3$ | $CH_2$(2-pyridyl) | H |
| H | H | H | H | $CH_3$ | $CH_2$(Ph) | H |
| H | H | H | H | $CH_3$ | Q-1 | H |
| H | H | H | H | $CH_3$ | Q-3 | H |
| H | H | H | H | $CH_3$ | Q-6 | H |
| H | H | H | H | $CH_3$ | Q-7 | H |
| H | H | H | H | $CH_3$ | Q-15 | H |
| H | H | $CH_3$ | $CH_3$ | $CH_3$ | $CH_2$(2-FPh) | H |
| H | H | $CH_3$ | $CH_3$ | $CH_3$ | $CH_2$(2-ClPh) | H |
| H | H | $CH_3$ | $CH_3$ | $CH_3$ | $CH_2$(2-($CH_3$)Ph) | H |
| H | H | $CH_3$ | $CH_3$ | $CH_3$ | $CH_2$(2,6-$Cl_2$Ph) | H |
| H | H | $CH_3$ | $CH_3$ | $CH_3$ | $CH_2$(2-$CF_3$Ph) | H |
| H | H | $CH_3$ | $CH_3$ | $CH_3$ | $CH_2$(2-tetrahydropyran) | H |
| H | H | $CH_3$ | $CH_3$ | $CH_3$ | $CH_2$(2-pyridyl) | H |
| H | H | $CH_3$ | $CH_3$ | $CH_3$ | $CH_2$(Ph) | H |
| H | H | $CH_3$ | $CH_3$ | $CH_3$ | Q-1 | H |
| H | H | $CH_3$ | $CH_3$ | $CH_3$ | Q-3 | H |
| H | H | $CH_3$ | $CH_3$ | $CH_3$ | Q-6 | H |
| H | H | $CH_3$ | $CH_3$ | $CH_3$ | Q-7 | H |
| $CH_3$ | H | $CH_3$ | $CH_3$ | $CH_3$ | Q-15 | H |
| $CH_3$ | H | $CH_2CH_3$ | $CH_2CH_3$ | $CH_3$ | $CH_2$(2-FPh) | H |
| $CH_3$ | H | $CH_2CH_3$ | $CH_2CH_3$ | $CH_3$ | $CH_2$(2-ClPh) | H |
| $CH_3$ | H | $CH_2CH_3$ | $CH_2CH_3$ | $CH_3$ | $CH_2$(2-($CH_3$)Ph) | H |
| $CH_3$ | H | $CH_2CH_3$ | $CH_2CH_3$ | $CH_3$ | $CH_2$(2,6-$Cl_2$Ph) | H |
| $CH_3$ | H | $CH_2CH_3$ | $CH_2CH_3$ | $CH_3$ | $CH_2$(2-$CF_3$Ph) | H |
| $CH_3$ | H | $CH_2CH_3$ | $CH_2CH_3$ | $CH_3$ | $CH_2$(2-tetrahydropyran) | H |
| $CH_3$ | H | $CH_2CH_3$ | $CH_2CH_3$ | $CH_3$ | $CH_2$(2-pyridyl) | H |
| $CH_3$ | H | $CH_2CH_3$ | $CH_2CH_3$ | $CH_3$ | $CH_2$(Ph) | H |
| $CH_3$ | H | $CH_2CH_3$ | $CH_2CH_3$ | $CH_3$ | Q-1 | H |
| $CH_3$ | H | $CH_2CH_3$ | $CH_2CH_3$ | $CH_3$ | Q-3 | H |
| $CH_3$ | H | $CH_2CH_3$ | $CH_2CH_3$ | $CH_3$ | Q-6 | H |
| $CH_3$ | H | $CH_2CH_3$ | $CH_2CH_3$ | $CH_3$ | Q-7 | H |
| $CH_3$ | H | $CH_2CH_3$ | $CH_2CH_3$ | $CH_3$ | Q-15 | H |
| $CH_2CH_3$ | H | $CH_2CH_3$ | $CH_2CH_3$ | $CH_3$ | $CH_2$(2-FPh) | H |
| $CH_2CH_3$ | H | $CH_2CH_3$ | $CH_2CH_3$ | $CH_3$ | $CH_2$(2-ClPh) | H |
| $CH_2CH_3$ | H | $CH_2CH_3$ | $CH_2CH_3$ | $CH_3$ | $CH_2$(2-($CH_3$)Ph) | H |
| $CH_2CH_3$ | H | $CH_2CH_3$ | $CH_2CH_3$ | $CH_3$ | $CH_2$(2,6-$Cl_2$Ph) | H |
| $CH_2CH_3$ | H | $CH_2CH_3$ | $CH_2CH_3$ | $CH_3$ | $CH_2$(2-$CF_3$Ph) | H |
| $CH_2CH_3$ | H | $CH_2CH_3$ | $CH_2CH_3$ | $CH_3$ | $CH_2$(2-tetrahydropyran) | H |
| $CH_2CH_3$ | H | $CH_2CH_3$ | $CH_2CH_3$ | $CH_3$ | $CH_2$(2-pyridyl) | H |
| $CH_2CH_3$ | H | $CH_2CH_3$ | $CH_2CH_3$ | $CH_3$ | $CH_2$(Ph) | H |
| $CH_2CH_3$ | H | $CH_2CH_3$ | $CH_2CH_3$ | $CH_3$ | Q-1 | H |
| $CH_2CH_3$ | H | $CH_2CH_3$ | $CH_2CH_3$ | $CH_3$ | Q-3 | H |
| $CH_2CH_3$ | H | $CH_2CH_3$ | $CH_2CH_3$ | $CH_3$ | Q-6 | H |
| $CH_2CH_3$ | H | $CH_2CH_3$ | $CH_2CH_3$ | $CH_3$ | Q-7 | H |
| $CH_2CH_3$ | H | $CH_2CH_3$ | $CH_2CH_3$ | $CH_3$ | Q-15 | H |
| H | $CH_3$ | $CH_2CH_3$ | $CH_2CH_3$ | $CH_3$ | $CH_2$(2-FPh) | H |
| H | $CH_3$ | $CH_2CH_3$ | $CH_2CH_3$ | $CH_3$ | $CH_2$(2-ClPh) | H |
| H | $CH_3$ | $CH_2CH_3$ | $CH_2CH_3$ | $CH_3$ | $CH_2$(2-($CH_3$)Ph) | H |
| H | $CH_3$ | $CH_2CH_3$ | $CH_2CH_3$ | $CH_3$ | $CH_2$(2,6-$Cl_2$Ph) | H |
| H | $CH_3$ | $CH_2CH_3$ | $CH_2CH_3$ | $CH_3$ | $CH_2$(2-$CF_3$Ph) | H |
| H | $CH_3$ | $CH_2CH_3$ | $CH_2CH_3$ | $CH_3$ | $CH_2$(2-tetrahydropyran) | H |
| H | $CH_3$ | $CH_2CH_3$ | $CH_2CH_3$ | $CH_3$ | $CH_2$(2-pyridyl) | H |
| H | $CH_3$ | $CH_2CH_3$ | $CH_2CH_3$ | $CH_3$ | $CH_2$(Ph) | H |
| H | $CH_3$ | $CH_2CH_3$ | $CH_2CH_3$ | $CH_3$ | Q-1 | H |
| H | $CH_3$ | $CH_2CH_3$ | $CH_2CH_3$ | $CH_3$ | Q-3 | H |
| H | $CH_3$ | $CH_2CH_3$ | $CH_2CH_3$ | $CH_3$ | Q-6 | H |
| H | $CH_3$ | $CH_2CH_3$ | $CH_2CH_3$ | $CH_3$ | Q-7 | H |
| H | $CH_3$ | $CH_2CH_3$ | $CH_2CH_3$ | $CH_3$ | Q-15 | H |
| H | H | $CH_3$ | H | $CH_3$ | $CH_2$(2-FPh) | H |
| H | H | $CH_3$ | H | $CH_3$ | $CH_2$(2-ClPh) | H |
| H | H | $CH_3$ | H | $CH_3$ | $CH_2$(2-($CH_3$)Ph) | H |
| H | H | $CH_3$ | H | $CH_3$ | $CH_2$(2,6-$Cl_2$Ph) | H |

TABLE 3-continued

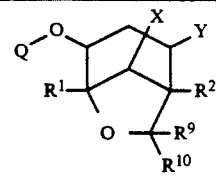

III

X and Y are C(R³)(R⁴)OR⁵ (unless specified)

| R¹ | R² | R³ = R⁴ | R⁹ = R¹⁰ | R⁵ | Q | |
|---|---|---|---|---|---|---|
| H | H | CH₃ | H | CH₃ | CH₂(2-CF₃Ph) | H |
| H | H | CH₃ | H | CH₃ | CH₂(2-tetrahydropyran) | H |
| H | H | CH₃ | H | CH₃ | CH₂(2-pyridyl) | H |
| H | H | CH₃ | H | CH₃ | CH₂(Ph) | H |
| H | H | CH₃ | H | CH₃ | Q-1 | H |
| H | H | CH₃ | H | CH₃ | Q-3 | H |
| H | H | CH₃ | H | CH₃ | Q-6 | H |
| H | H | CH₃ | H | CH₃ | Q-7 | H |
| H | H | CH₃ | H | CH₃ | Q-15 | H |
| CH₃ | H | H | CH₃ | CH₃ | CH₂(2-FPh) | H |
| CH₃ | H | H | CH₃ | CH₃ | CH₂(2-ClPh) | H |
| CH₃ | H | H | CH₃ | CH₃ | CH₂(2-(CH₃)Ph) | H |
| CH₃ | H | H | CH₃ | CH₃ | CH₂(2,6-Cl₂Ph) | H |
| CH₃ | H | H | CH₃ | CH₃ | CH₂(2-CF₃Ph) | H |
| CH₃ | H | H | CH₃ | CH₃ | CH₂(2-tetrahydropyran) | H |
| CH₃ | H | H | CH₃ | CH₃ | CH₂(2-pyridyl) | H |
| CH₃ | H | H | CH₃ | CH₃ | CH₂(Ph) | H |
| CH₃ | H | H | CH₃ | CH₃ | Q-1 | H |
| CH₃ | H | H | CH₃ | CH₃ | Q-3 | H |
| CH₃ | H | H | CH₃ | CH₃ | Q-6 | H |
| CH₃ | H | H | CH₃ | CH₃ | Q-7 | H |
| CH₃ | H | H | CH₃ | CH₃ | Q-15 | H |
| CH₃ | H | H | H | CH₃ | CH₂(2-FPh) | H |
| CH₃ | H | H | H | CH₃ | CH₂(2-ClPh) | H |
| CH₃ | H | H | H | CH₃ | CH₂(2-(CH₃)Ph) | H |
| CH₃ | H | H | H | CH₃ | CH₂(2,6-Cl₂Ph) | H |
| CH₃ | H | H | H | CH₃ | CH₂(2-CF₃Ph) | H |
| CH₃ | H | H | H | CH₃ | CH₂(2-tetrahydropyran) | H |
| CH₃ | H | H | H | CH₃ | CH₂(2-pyridyl) | H |
| CH₃ | H | H | H | CH₃ | CH₂(Ph) | H |
| CH₃ | H | H | H | CH₃ | Q-1 | H |
| CH₃ | H | H | H | CH₃ | Q-3 | H |
| CH₃ | H | H | H | CH₃ | Q-6 | H |
| CH₃ | H | H | H | CH₃ | Q-7 | H |
| CH₃ | H | H | H | CH₃ | Q-15 | H |
| CH₃ | H | CH₃ | CH₃ | CH₃ | CH₂(2-FPh) | H |
| CH₃ | H | CH₃ | CH₃ | CH₃ | CH₂(2-ClPh) | H |
| CH₃ | H | CH₃ | CH₃ | CH₃ | CH₂(2-(CH₃)Ph) | H |
| CH₃ | H | CH₃ | CH₃ | CH₃ | CH₂(2,6-Cl₂Ph) | H |
| CH₃ | H | CH₃ | CH₃ | CH₃ | CH₂(2-CF₃Ph) | H |
| CH₃ | H | CH₃ | CH₃ | CH₃ | CH₂(2-tetrahydropyran) | H |
| CH₃ | H | CH₃ | CH₃ | CH₃ | CH₂(2-pyridyl) | H |
| CH₃ | H | CH₃ | CH₃ | CH₃ | CH₂(Ph) | H |
| CH₃ | H | CH₃ | CH₃ | CH₃ | Q-1 | H |
| CH₃ | H | CH₃ | CH₃ | CH₃ | Q-3 | H |
| CH₃ | H | CH₃ | CH₃ | CH₃ | Q-6 | H |
| CH₃ | H | CH₃ | CH₃ | CH₃ | Q-7 | H |
| CH₃ | H | CH₃ | CH₃ | CH₃ | Q-15 | H |
| | | | | | | X |
| H | H | CH₂CH₃ | CH₂CH₃ | CH₃ | CH₂(2-FPh) | H |
| H | H | CH₂CH₃ | CH₂CH₃ | CH₃ | CH₂(2-ClPh) | H |
| H | H | CH₂CH₃ | CH₂CH₃ | CH₃ | CH₂(2-BrPh) | H |
| H | H | CH₂CH₃ | CH₂CH₃ | CH₃ | CH₂(2-(CH₃)Ph) | H |
| H | H | CH₂CH₃ | CH₂CH₃ | CH₃ | CH₂(2-(OCH₃)Ph) | H |
| H | H | CH₂CH₃ | CH₂CH₃ | CH₃ | CH₂(2-(CN)Ph) | H |
| H | H | CH₂CH₃ | CH₂CH₃ | CH₃ | CH₂(2-(CF₃)pH) | H |
| H | H | CH₂CH₃ | CH₂CH₃ | CH₃ | CH₂(2-(OCF₃)Ph) | H |
| H | H | CH₂CH₃ | CH₂CH₃ | CH₃ | CH₂(2-(SCH₃)Ph) | H |
| H | H | CH₂CH₃ | CH₂CH₃ | CH₃ | CH₂(2,6-(F)₂Ph) | H |
| H | H | CH₂CH₃ | CH₂CH₃ | CH₃ | CH₂(2,6-(Cl)₂Ph) | H |
| H | H | CH₂CH₃ | CH₂CH₃ | CH₃ | CH₂(2-pyridyl) | H |
| H | H | CH₂CH₃ | CH₂CH₃ | CH₃ | CH₂(2-furanyl) | H |
| H | H | CH₂CH₃ | CH₂CH₃ | CH₃ | CH₂(2-tetrahydrofuran) | H |
| H | H | CH₂CH₃ | CH₂CH₃ | CH₃ | CH₂(2-tetrahydropyran) | H |
| H | H | CH₂CH₃ | CH₂CH₃ | CH₃ | CH₂(2-thiophenyl) | H |
| H | H | CH₂CH₃ | CH₂CH₃ | CH₃ | CH₂(2-isoxazolyl) | H |
| H | H | CH₂CH₃ | CH₂CH₃ | CH₃ | CH₂(2-pyrazinyl) | H |
| H | H | CH₂CH₃ | CH₂CH₃ | CH₃ | CH₂(Ph) | H |

TABLE 3-continued

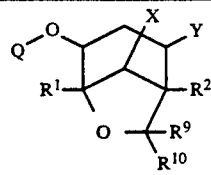

III

X and Y are C(R³)(R⁴)OR⁵ (unless specified)

| R¹ | R² | R³ = R⁴ | R⁹ = R¹⁰ | R⁵ | Q | |
|---|---|---|---|---|---|---|
| H | H | CH₂CH₃ | CH₂CH₃ | CH₃ | Q-1 | H |
| H | H | CH₂CH₃ | CH₂CH₃ | CH₃ | Q-3 | H |
| H | H | CH₂CH₃ | CH₂CH₃ | CH₃ | Q-6 | H |
| H | H | CH₂CH₃ | CH₂CH₃ | CH₃ | Q-7 | H |
| H | H | CH₂CH₃ | CH₂CH₃ | CH₃ | Q-15 | H |
| H | H | CH₂CH₃ | CH₂CH₃ | CH₂CH₃ | CH₂(2-FPh) | H |
| H | H | CH₂CH₃ | CH₂CH₃ | CH₂CH₃ | CH₂(2-ClPh) | H |
| H | H | CH₂CH₃ | CH₂CH₃ | CH₂CH₃ | CH₂(2-(CH₃)Ph) | H |
| H | H | CH₂CH₃ | CH₂CH₃ | CH₂CH₃ | CH₂(2,6-Cl₂Ph) | H |
| H | H | CH₂CH₃ | CH₂CH₃ | CH₂CH₃ | CH₂(2-CF₃Ph) | H |
| H | H | CH₂CH₃ | CH₂CH₃ | CH₂CH₃ | CH₂(2-tetrahydropyran) | H |
| H | H | CH₂CH₃ | CH₂CH₃ | CH₂CH₃ | CH₂(2-pyridyl) | H |
| H | H | CH₂CH₃ | CH₂CH₃ | CH₂CH₃ | CH₂(Ph) | H |
| H | H | CH₂CH₃ | CH₂CH₃ | CH₂CH₃ | Q-1 | H |
| H | H | CH₂CH₃ | CH₂CH₃ | CH₂CH₃ | Q-3 | H |
| H | H | CH₂CH₃ | CH₂CH₃ | CH₂CH₃ | Q-6 | H |
| H | H | CH₂CH₃ | CH₂CH₃ | CH₂CH₃ | Q-7 | H |
| H | H | CH₂CH₃ | CH₂CH₃ | CH₂CH₃ | Q-15 | H |
| H | H | CH₂CH₃ | CH₂CH₃ | CH₂CH=CH₂ | CH₂(2-FPh) | H |
| H | H | CH₂CH₃ | CH₂CH₃ | CH₂CH=CH₂ | CH₂(2-ClPh) | H |
| H | H | CH₂CH₃ | CH₂CH₃ | CH₂CH=CH₂ | CH₂(2-(CH₃)Ph) | H |
| H | H | CH₂CH₃ | CH₂CH₃ | CH₂CH=CH₂ | CH₂(2,6-Cl₂Ph) | H |
| H | H | CH₂CH₃ | CH₂CH₃ | CH₂CH=CH₂ | CH₂(2-CF₃Ph) | H |
| H | H | CH₂CH₃ | CH₂CH₃ | CH₂CH=CH₂ | CH₂(2-tetrahydropyran) | H |
| H | H | CH₂CH₃ | CH₂CH₃ | CH₂CH=CH₂ | CH₂(2-pyridyl) | H |
| H | H | CH₂CH₃ | CH₂CH₃ | CH₂CH=CH₂ | CH₂(Ph) | H |
| H | H | CH₂CH₃ | CH₂CH₃ | CH₂CH=CH₂ | Q-1 | H |
| H | H | CH₂CH₃ | CH₂CH₃ | CH₂CH=CH₂ | Q-3 | H |
| H | H | CH₂CH₃ | CH₂CH₃ | CH₂CH=CH₂ | Q-6 | H |
| H | H | CH₂CH₃ | CH₂CH₃ | CH₂CH=CH₂ | Q-7 | H |
| H | H | CH₂CH₃ | CH₂CH₃ | CH₂CH=CH₂ | Q-15 | H |
| H | H | H | H | CH₃ | CH₂(2-FPh) | H |
| H | H | H | H | CH₃ | CH₂(2-ClPh) | H |
| H | H | H | H | CH₃ | CH₂(2-(CH₃)Ph) | H |
| H | H | H | H | CH₃ | CH₂(2,6-Cl₂Ph) | |
| H | H | H | H | CH₃ | CH₂(2-CF₃Ph) | H |
| H | H | H | H | CH₃ | CH₂(2-tetrahydropyran) | H |
| H | H | H | H | CH₃ | CH₂(2-pyridyl) | H |
| H | H | H | H | CH₃ | CH₂(Ph) | H |
| H | H | H | H | CH₃ | Q-1 | H |
| H | H | H | H | CH₃ | Q-3 | H |
| H | H | H | H | CH₃ | Q-6 | H |
| H | H | H | H | CH₃ | Q-7 | H |
| H | H | H | H | CH₃ | Q-15 | H |
| H | H | CH₃ | CH₃ | CH₃ | CH₂(2-FPh) | H |
| H | H | CH₃ | CH₃ | CH₃ | CH₂(2-ClPh) | H |
| H | H | CH₃ | CH₃ | CH₃ | CH₂(2-(CH₃)Ph) | H |
| H | H | CH₃ | CH₃ | CH₃ | CH₂(2,6-Cl₂Ph) | H |
| H | H | CH₃ | CH₃ | CH₃ | CH₂(2-CF₃Ph) | H |
| H | H | CH₃ | CH₃ | CH₃ | CH₂(2-tetrahydropyran) | H |
| H | H | CH₃ | CH₃ | CH₃ | CH₂(2-pyridyl) | H |
| H | H | CH₃ | CH₃ | CH₃ | CH₂(Ph) | H |
| H | H | CH₃ | CH₃ | CH₃ | Q-1 | H |
| H | H | CH₃ | CH₃ | CH₃ | Q-3 | H |
| H | H | CH₃ | CH₃ | CH₃ | Q-6 | H |
| H | H | CH₃ | CH₃ | CH₃ | Q-7 | H |
| H | H | CH₃ | CH₃ | CH₃ | Q-15 | H |
| H | H | CH₃ | CH₃ | CH₃ | CH₂(2,4-FPh) | H |
| H | H | CH₃ | CH₃ | CH₃ | CH₂(2,5-(F)₂Ph) | H |
| H | H | CH₃ | CH₃ | CH₃ | CH₂(2,6-(F)₂Ph) | H |
| H | H | CH₃ | CH₃ | CH₃ | CH₂(2-BrPh) | H |
| CH₃ | H | H | H | CH₃ | CH₂(2-FPh) | H |
| CH₃ | H | H | H | CH₃ | CH₂(2-ClPh) | H |
| CH₃ | H | H | H | CH₃ | CH₂(2-BrPh) | H |
| CH₃ | H | H | H | CH₃ | CH₂(2-(CH₃)Ph) | H |
| CH₃ | H | H | H | CH₃ | CH₂(2-(OCH₃)Ph) | H |
| CH₃ | H | H | H | CH₃ | CH₂(2-(CN)Ph) | H |
| CH₃ | H | H | H | CH₃ | CH₂(2-(CF₃)Ph) | H |

TABLE 3-continued

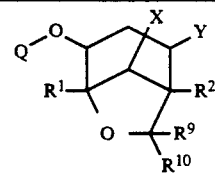

III

X and Y are C(R³)(R⁴)OR⁵ (unless specified)

| R¹ | R² | R³ = R⁴ | R⁹ = R¹⁰ | R⁵ | Q | |
|---|---|---|---|---|---|---|
| CH₃ | H | H | H | CH₃ | CH₂(2-(OCF₃)Ph) | H |
| CH₃ | H | H | H | CH₃ | CH₂(2-(SCH₃)Ph) | H |
| CH₃ | H | H | H | CH₃ | CH₂(2,6-(F)₂Ph) | H |
| CH₃ | H | H | H | CH₃ | CH₂(2,6-(Cl)₂Ph) | H |
| CH₃ | H | H | H | CH₃ | CH₂(2-pyridyl) | H |
| CH₃ | H | H | H | CH₃ | CH₂(2-furanyl) | H |
| CH₃ | H | H | H | CH₃ | CH₂(2-tetrahydrofuran) | H |
| CH₃ | H | H | H | CH₃ | CH₂(2-tetrahydropyran) | H |
| CH₃ | H | H | H | CH₃ | CH₂(2-thiophenyl) | H |
| CH₃ | H | H | H | CH₃ | CH₂(2-isoxazolyl) | H |
| CH₃ | H | H | H | CH₃ | CH₂(2-pyrazinyl) | H |
| CH₃ | H | H | H | CH₃ | CH₂(Ph) | H |
| CH₃ | H | H | H | CH₃ | Q-1 | H |
| CH₃ | H | H | H | CH₃ | Q-3 | H |
| CH₃ | H | H | H | CH₃ | Q-6 | H |
| CH₃ | H | H | H | CH₃ | Q-7 | H |
| CH₃ | H | H | H | CH₃ | Q-15 | H |
| CH₃ | H | H | H | CH₃ | CH₂(2,4-(F)₂Ph) | H |
| CH₃ | H | H | H | CH₃ | CH₂(2,5-(F)₂Ph) | H |
| CH₃ | H | H | H | CH₃ | CH₂(2-F,6-ClPh) | H |
| CH₃ | H | H | H | CH₂CH₃ | CH₂(2-FPh) | H |
| CH₃ | H | H | H | CH₂CH₃ | CH₂(2-ClPh) | H |
| CH₃ | H | H | H | CH₂CH₃ | CH₂(2-(CH₃)Ph) | H |
| CH₃ | H | H | H | CH₂CH₃ | CH₂(2,6-Cl₂Ph) | H |
| CH₃ | H | H | H | CH₂CH₃ | CH₂(2-CF₃Ph) | H |
| CH₃ | H | H | H | CH₂CH₃ | CH₂(2-tetrahydropyran) | H |
| CH₃ | H | H | H | CH₂CH₃ | CH₂(2-pyridyl) | H |
| CH₃ | H | H | H | CH₂CH₃ | CH₂(Ph) | H |
| CH₃ | H | H | H | CH₂CH₃ | Q-1 | H |
| CH₃ | H | H | H | CH₂CH₃ | Q-3 | H |
| CH₃ | H | H | H | CH₂CH₃ | Q-6 | H |
| CH₃ | H | H | H | CH₂CH₃ | Q-7 | H |
| CH₃ | H | H | H | CH₂CH₃ | Q-15 | H |
| CH₃ | H | H | H | CH₂CH₃ | CH₂(2,6-(F)₂Ph) | H |
| CH₃ | H | H | H | CH₂CH=CH₂ | CH₂(2-FPh) | H |
| CH₃ | H | H | H | CH₂CH=CH₂ | CH₂(2-ClPh) | H |
| CH₃ | H | H | H | CH₂CH=CH₂ | CH₂(2-(CH₃)Ph) | H |
| CH₃ | H | H | H | CH₂CH=CH₂ | CH₂(2,6-Cl₂Ph) | H |
| CH₃ | H | H | H | CH₂CH=CH₂ | CH₂(2-CF₃Ph) | H |
| CH₃ | H | H | H | CH₂CH=CH₂ | CH₂(2-tetrahydropyran) | H |
| CH₃ | H | H | H | CH₂CH=CH₂ | CH₂(2-pyridyl) | H |
| CH₃ | H | H | H | CH₂CH=CH₂ | CH₂(Ph) | H |
| CH₃ | H | H | H | CH₂CH=CH₂ | Q-1 | H |
| CH₃ | H | H | H | CH₂CH=CH₂ | Q-3 | H |
| CH₃ | H | H | H | CH₂CH=CH₂ | Q-6 | H |
| CH₃ | H | H | H | CH₂CH=CH₂ | Q-7 | H |
| CH₃ | H | H | H | CH₂CH=CH₂ | Q-15 | H |
| CH₃CH₂ | H | H | H | CH₃ | CH₂(2-FPh) | H |
| CH₃CH₂ | H | H | H | CH₃ | CH₂(2-ClPh) | H |
| CH₃CH₂ | H | H | H | CH₃ | CH₂(2-(CH₃)Ph) | H |
| CH₃CH₂ | H | H | H | CH₃ | CH₂(2,6-Cl₂Ph) | H |
| CH₃CH₂ | H | H | H | CH₃ | CH₂(2-CF₃Ph) | H |
| CH₃CH₂ | H | H | H | CH₃ | CH₂(2-tetrahydropyran) | H |
| CH₃CH₂ | H | H | H | CH₃ | CH₂(2-pyridyl) | H |
| CH₃CH₂ | H | H | H | CH₃ | CH₂(Ph) | H |
| CH₃CH₂ | H | H | H | CH₃ | Q-1 | H |
| CH₃CH₂ | H | H | H | CH₃ | Q-3 | H |
| CH₃CH₂ | H | H | H | CH₃ | Q-6 | H |
| CH₃CH₂ | H | H | H | CH₃ | Q-7 | H |
| CH₃CH₂ | H | H | H | CH₃ | Q-15 | H |
| CH₃CH₂ | H | H | H | CH₃ | CH₂(2,6-(F)₂Ph) | H |
| CH₃ | H | CH₃ | CH₃ | CH₃ | CH₂(2-FPh) | H |
| CH₃ | H | CH₃ | CH₃ | CH₃ | CH₂(2-ClPh) | H |
| CH₃ | H | CH₃ | CH₃ | CH₃ | CH₂(2-(CH₃)Ph) | H |
| CH₃ | H | CH₃ | CH₃ | CH₃ | CH₂(2,6-Cl₂Ph) | H |
| CH₃ | H | CH₃ | CH₃ | CH₃ | CH₂(2-CF₃Ph) | H |
| CH₃ | H | CH₃ | CH₃ | CH₃ | CH₂(2-tetrahydropyran) | H |
| CH₃ | H | CH₃ | CH₃ | CH₃ | CH₂(2-pyridyl) | H |

TABLE 3-continued

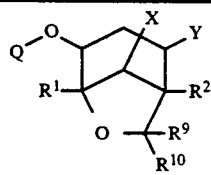

III

| | | | X and Y are C(R³)(R⁴)OR⁵ (unless specified) | | | |
|---|---|---|---|---|---|---|
| R¹ | R² | R³ = R⁴ | R⁹ = R¹⁰ | R⁵ | Q | |
| CH₃ | H | CH₃ | CH₃ | CH₃ | CH₂(Ph) | H |
| CH₃ | H | CH₃ | CH₃ | CH₃ | Q-1 | H |
| CH₃ | H | CH₃ | CH₃ | CH₃ | Q-3 | H |
| CH₃ | H | CH₃ | CH₃ | CH₃ | Q-6 | H |
| CH₃ | H | CH₃ | CH₃ | CH₃ | Q-7 | H |
| CH₃ | H | CH₃ | CH₃ | CH₃ | Q-15 | H |
| CH₃ | H | CH₂CH₃ | CH₂CH₃ | CH₃ | CH₂(2-FPh) | H |
| CH₃ | H | CH₂CH₃ | CH₂CH₃ | CH₃ | CH₂(2-ClPh) | H |
| CH₃ | H | CH₂CH₃ | CH₂CH₃ | CH₃ | CH₂(2-(CH₃)Ph) | H |
| CH₃ | H | CH₂CH₃ | CH₂CH₃ | CH₃ | CH₂(2,6-Cl₂Ph) | H |
| CH₃ | H | CH₃ | CH₃ | CH₃ | CH₂(2,6-(F)₂Ph) | H |
| CH₃ | H | CH₃ | CH₃ | CH₃ | CH₂(2,4-(F)₂Ph) | H |
| CH₃ | H | CH₂CH₃ | CH₂CH₃ | CH₃ | CH₂(2-tetrahydropyran) | H |
| CH₃ | H | CH₂CH₃ | CH₂CH₃ | CH₃ | CH₂(2-pyridyl) | H |
| CH₃ | H | CH₂CH₃ | CH₂CH₃ | CH₃ | CH₂(Ph) | H |
| CH₃ | H | CH₂CH₃ | CH₂CH₃ | CH₃ | Q-1 | H |
| CH₃ | H | CH₂CH₃ | CH₂CH₃ | CH₃ | Q-3 | H |
| CH₃ | H | CH₂CH₃ | CH₂CH₃ | CH₃ | Q-6 | H |
| CH₃ | H | CH₂CH₃ | CH₂CH₃ | CH₃ | Q-7 | H |
| CH₃ | H | CH₂CH₃ | CH₂CH₃ | CH₃ | Q-15 | H |
| CH₃ | H | CH₂CH₃ | CH₂CH₃ | CH₃ | CH₂(2,6-(F)₂Ph) | H |
| CH₂CH₃ | H | CH₂CH₃ | CH₂CH₃ | CH₃ | CH₂(2-FPh) | H |
| CH₂CH₃ | H | CH₂CH₃ | CH₂CH₃ | CH₃ | CH₂(2-ClPh) | H |
| CH₂CH₃ | H | CH₂CH₃ | CH₂CH₃ | CH₃ | CH₂(2-(CH₃)Ph) | H |
| CH₂CH₃ | H | CH₂CH₃ | CH₂CH₃ | CH₃ | CH₂(2,6-Cl₂Ph) | H |
| CH₂CH₃ | H | CH₂CH₃ | CH₂CH₃ | CH₃ | CH₂(2-CF₃Ph) | H |
| CH₂CH₃ | H | CH₂CH₃ | CH₂CH₃ | CH₃ | CH₂(2-tetrahydropyran) | H |
| CH₂CH₃ | H | CH₂CH₃ | CH₂CH₃ | CH₃ | CH₂(2-pyridyl) | H |
| CH₂CH₃ | H | CH₂CH₃ | CH₂CH₃ | CH₃ | CH₂(Ph) | H |
| CH₂CH₃ | H | CH₂CH₃ | CH₂CH₃ | CH₃ | Q-1 | H |
| CH₂CH₃ | H | CH₂CH₃ | CH₂CH₃ | CH₃ | Q-3 | H |
| CH₂CH₃ | H | CH₂CH₃ | CH₂CH₃ | CH₃ | Q-6 | H |
| CH₂CH₃ | H | CH₂CH₃ | CH₂CH₃ | CH₃ | Q-7 | H |
| CH₂CH₃ | H | CH₂CH₃ | CH₂CH₃ | CH₃ | Q-15 | H |
| CH₃ | CH₃ | CH₂CH₃ | CH₂CH₃ | CH₃ | CH₂(2-FPh) | H |
| CH₃ | CH₃ | CH₂CH₃ | CH₂CH₃ | CH₃ | CH₂(2-ClPh) | H |
| CH₃ | CH₃ | CH₂CH₃ | CH₂CH₃ | CH₃ | CH₂(2-(CH₃)Ph) | H |
| CH₃ | CH₃ | CH₂CH₃ | CH₂CH₃ | CH₃ | CH₂(2,6-Cl₂Ph) | H |
| CH₃ | CH₃ | CH₂CH₃ | CH₂CH₃ | CH₃ | CH₂(2-CF₃Ph) | H |
| CH₃ | CH₃ | CH₂CH₃ | CH₂CH₃ | CH₃ | CH₂(2-tetrahydropyran) | H |
| CH₃ | CH₃ | CH₂CH₃ | CH₂CH₃ | CH₃ | CH₂(2-pyridyl) | H |
| CH₃ | CH₃ | CH₂CH₃ | CH₂CH₃ | CH₃ | CH₂(Ph) | H |
| CH₃ | CH₃ | CH₂CH₃ | CH₂CH₃ | CH₃ | Q-1 | H |
| H | CH₃ | CH₂CH₃ | CH₂CH₃ | CH₃ | Q-3 | H |
| H | CH₃ | CH₂CH₃ | CH₂CH₃ | CH₃ | Q-6 | H |
| H | CH₃ | CH₂CH₃ | CH₂CH₃ | CH₃ | Q-7 | H |
| H | CH₃ | CH₂CH₃ | CH₂CH₃ | CH₃ | Q-15 | H |
| CH₃ | H | CH₃ | H | CH₃ | CH₂(2-FPh) | H |
| CH₃ | H | CH₃ | H | CH₃ | CH₂(2-ClPh) | H |
| CH₃ | H | CH₃ | H | CH₃ | CH₂(2-(CH₃)Ph) | H |
| CH₃ | H | CH₃ | H | CH₃ | CH₂(2,6-Cl₂Ph) | H |
| CH₃ | H | CH₃ | H | CH₃ | CH₂(2-CF₃Ph) | H |
| CH₃ | H | CH₃ | H | CH₃ | CH₂(2-tetrahydropyran) | H |
| CH₃ | H | CH₃ | H | CH₃ | CH₂(2-pyridyl) | H |
| CH₃ | H | CH₃ | H | CH₃ | CH₂(Ph) | H |
| CH₃ | H | CH₃ | H | CH₃ | Q-1 | H |
| CH₃ | H | CH₃ | H | CH₃ | Q-3 | H |
| CH₃ | H | CH₃ | H | CH₃ | Q-6 | H |
| CH₃ | H | CH₃ | H | CH₃ | Q-7 | H |
| CH₃ | H | CH₃ | H | CH₃ | Q-15 | H |
| CH₃ | H | CH₃ | H | CH₃ | CH₂(2,6-(F)₂Ph) | H |
| CH₃ | H | H | CH₃ | CH₃ | Q-1 | H |
| CH₃ | H | H | CH₃ | CH₃ | Q-3 | H |
| CH₃ | H | H | CH₃ | CH₃ | Q-6 | H |
| CH₃ | H | H | CH₃ | CH₃ | Q-7 | H |
| CH₃ | H | H | CH₃ | CH₃ | Q-15 | H |
| CH₃ | H | H | CH₃ | CH₃ | CH₂(2-FPh) | H |
| CH₃ | H | H | CH₃ | CH₃ | CH₂(2-ClPh) | H |

TABLE 3-continued

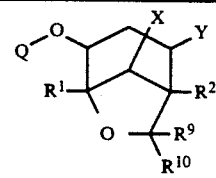

III

X and Y are C(R³)(R⁴)OR⁵ (unless specified)

| R¹ | R² | R³ = R⁴ | R⁹ = R¹⁰ | R⁵ | Q | |
|---|---|---|---|---|---|---|
| CH₃ | H | H | CH₃ | CH₃ | CH₂(2-(CH₃)Ph) | H |
| CH₃ | H | H | CH₃ | CH₃ | CH₂(2,6-Cl₂Ph) | H |
| CH₃ | H | H | CH₃ | CH₃ | CH₂(2-CF₃Ph) | H |
| CH₃ | H | H | CH₃ | CH₃ | CH₂(2-tetrahydropyran) | H |
| CH₃ | H | H | CH₃ | CH₃ | CH₂(2-pyridyl) | H |
| CH₃ | H | H | CH₃ | CH₃ | CH₂(Ph) | H |
| CH₃ | H | H | CH₃ | CH₃ | Q-1 | H |
| CH₃ | H | H | CH₃ | CH₃ | Q-3 | H |
| CH₃ | H | H | CH₃ | CH₃ | Q-6 | H |
| CH₃ | H | H | CH₃ | CH₃ | Q-7 | H |
| CH₃ | H | H | CH₃ | CH₃ | Q-15 | H |
| CH₃ | H | H | CH₂CH₃ | CH₃ | CH₂(2,6-(F)₂Ph) | H |
| CH₃ | H | H | CH₂CH₃ | CH₃ | CH₂(2-FPh) | H |
| CH₃ | H | H | CH₂CH₃ | CH₃ | CH₂(2-ClPh) | H |
| CH₃ | H | H | CH₂CH₃ | CH₃ | CH₂(2-(CH₃)Ph) | H |
| CH₃ | H | H | CH₂CH₃ | CH₃ | CH₂(2,6-Cl₂Ph) | H |
| CH₃ | H | H | CH₂CH₃ | CH₃ | CH₂(2-CF₃Ph) | H |
| CH₃ | H | H | CH₂CH₃ | CH₃ | CH₂(2-tetrahydropyran) | H |
| CH₃ | H | H | CH₂CH₃ | CH₃ | CH₂(2-pyridyl) | H |
| CH₃ | H | H | CH₂CH₃ | CH₃ | CH₂(Ph) | H |
| CH₃ | H | H | CH₂CH₃ | CH₃ | Q-1 | H |
| CH₃ | H | H | CH₂CH₃ | CH₃ | Q-3 | H |
| CH₃ | H | H | CH₂CH₃ | CH₃ | Q-6 | H |
| CH₃ | H | H | CH₂CH₃ | CH₃ | Q-7 | H |
| CH₃ | H | H | CH₂CH₃ | CH₃ | Q-15 | H |
| CH₂CH₃ | H | CH₃ | CH₃ | CH₃ | CH₂(2-FPh) | H |
| CH₂CH₃ | H | CH₃ | CH₃ | CH₃ | CH₂(2-ClPh) | H |
| CH₂CH₃ | H | CH₃ | CH₃ | CH₃ | CH₂(2-(CH₃)Ph) | H |
| CH₂CH₃ | H | CH₃ | CH₃ | CH₃ | CH₂(2,6-Cl₂Ph) | H |
| CH₂CH₃ | H | CH₃ | CH₃ | CH₃ | CH₂(2-CF₃Ph) | H |
| CH₂CH₃ | H | CH₃ | CH₃ | CH₃ | CH₂(2-tetrahydropyran) | H |
| CH₂CH₃ | H | CH₃ | CH₃ | CH₃ | CH₂(2-pyridyl) | H |
| CH₂CH₃ | H | CH₃ | CH₃ | CH₃ | CH₂(Ph) | H |
| CH₂CH₃ | H | CH₃ | CH₃ | CH₃ | Q-1 | H |
| CH₂CH₃ | H | CH₃ | CH₃ | CH₃ | Q-3 | H |
| CH₂CH₃ | H | CH₃ | CH₃ | CH₃ | Q-6 | H |
| CH₂CH₃ | H | CH₃ | CH₃ | CH₃ | Q-7 | H |
| CH₂CH₃ | H | CH₃ | CH₃ | CH₃ | Q-15 | H |

TABLE 4

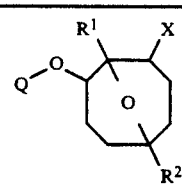

IV

X = C(R³)(R⁴)OR⁵

| R¹ | R² | R³ | R⁴ | R⁵ | Q |
|---|---|---|---|---|---|
| H | H | CH₃CH₂ | CH₃CH₂ | CH₃ | CH₂(2-FPh) |
| H | H | CH₃CH₂ | CH₃CH₂ | CH₃ | CH₂(2-ClPh) |
| H | H | CH₃CH₂ | CH₃CH₂ | CH₃ | CH₂(2-BrPh) |
| H | H | CH₃CH₂ | CH₃CH₂ | CH₃ | CH₂(2-(CH₃)Ph) |
| H | H | CH₃CH₂ | CH₃CH₂ | CH₃ | CH₂(22-(OCH₃)Ph) |
| H | H | CH₃CH₂ | CH₃CH₂ | CH₃ | CH₂(2-(CN)Ph) |
| H | H | CH₃CH₂ | CH₃CH₂ | CH₃ | CH₂(2-(CF₃)Ph) |
| H | H | CH₃CH₂ | CH₃CH₂ | CH₃ | CH₂(2-(OCF₃)Ph) |
| H | H | CH₃CH₂ | CH₃CH₂ | CH₃ | CH₂(2-(SCH₃)Ph) |
| H | H | CH₃CH₂ | CH₃CH₂ | CH₃ | CH₂(2,6-(F)₂Ph) |
| H | H | CH₃CH₂ | CH₃CH₂ | CH₃ | CH₂(2,6-(Cl)₂Ph) |
| H | H | CH₃CH₂ | CH₃CH₂ | CH₃ | CH₂(2-pyridyl) |

TABLE 4-continued

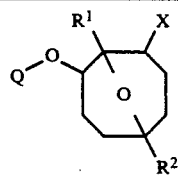

IV

X = C(R³)(R⁴)OR⁵

| R¹ | R² | R³ | R⁴ | R⁵ | Q |
|---|---|---|---|---|---|
| H | H | CH₃CH₂ | CH₃CH₂ | CH₃ | CH₂(2-furanyl) |
| H | H | CH₃CH₂ | CH₃CH₂ | CH₃ | CH₂(2-tetrahydrofuran) |
| H | H | CH₃CH₂ | CH₃CH₂ | CH₃ | CH₂(2-tetrahydropyran) |
| H | H | CH₃CH₂ | CH₃CH₂ | CH₃ | CH₂(2-thiophenyl) |
| H | H | CH₃CH₂ | CH₃CH₂ | CH₃ | CH₂(2-isoxazolyl) |
| H | H | CH₃CH₂ | CH₃CH₂ | CH₃ | CH₂(2-pyrazinyl) |
| H | H | CH₃CH₂ | CH₃CH₂ | CH₃ | CH₂(Ph) |
| H | H | CH₃CH₂ | CH₃CH₂ | CH₃ | Q-1 |
| H | H | CH₃CH₂ | CH₃CH₂ | CH₃ | Q-3 |
| H | H | CH₃CH₂ | CH₃CH₂ | CH₃ | Q-6 |
| H | H | CH₃CH₂ | CH₃CH₂ | CH₃ | Q-7 |
| H | H | CH₃CH₂ | CH₃CH₂ | CH₃ | Q-15 |
| H | H | CH₃CH₂ | CH₃CH₂ | CH₃CH₂ | CH₂(2-FPh) |
| H | H | CH₃CH₂ | CH₃CH₂ | CH₃CH₂ | CH₂(2-ClPh) |
| H | H | CH₃CH₂ | CH₃CH₂ | CH₃CH₂ | CH₂(2-(CH₃)Ph) |
| H | H | CH₃CH₂ | CH₃CH₂ | CH₃CH₂ | CH₂(2,6-Cl₂Ph) |
| H | H | CH₃CH₂ | CH₃CH₂ | CH₃CH₂ | CH₂(2-CF₃Ph) |
| H | H | CH₃CH₂ | CH₃CH₂ | CH₃CH₂ | CH₂(2-tetrahydropyran) |
| H | H | CH₃CH₂ | CH₃CH₂ | CH₃CH₂ | CH₂(2-pyridyl) |
| H | H | CH₃CH₂ | CH₃CH₂ | CH₃CH₂ | CH₂(Ph) |
| H | H | CH₃CH₂ | CH₃CH₂ | CH₃CH₂ | Q-1 |
| H | H | CH₃CH₂ | CH₃CH₂ | CH₃CH₂ | Q-3 |
| H | H | CH₃CH₂ | CH₃CH₂ | CH₃CH₂ | Q-6 |
| H | H | CH₃CH₂ | CH₃CH₂ | CH₃CH₂ | Q-7 |
| H | H | CH₃CH₂ | CH₃CH₂ | CH₃CH₂ | Q-15 |
| H | H | CH₂CH₃ | CH₂CH₃ | CH₂CH=CH₂ | CH₂(2-FPh) |
| H | H | CH₂CH₃ | CH₂CH₃ | CH₂CH=CH₂ | CH₂(2-ClPh) |
| H | H | CH₂CH₃ | CH₂CH₃ | CH₂CH=CH₂ | CH₂(2-(CH₃)Ph) |
| H | H | CH₂CH₃ | CH₂CH₃ | CH₂CH=CH₂ | CH₂(2,6-Cl₂Ph) |
| H | H | CH₂CH₃ | CH₂CH₃ | CH₂CH=CH₂ | CH₂(2-CF₃Ph) |
| H | H | CH₂CH₃ | CH₂CH₃ | CH₂CH=CH₂ | CH₂(2-tetrahydropyran) |
| H | H | CH₂CH₃ | CH₂CH₃ | CH₂CH=CH₂ | CH₂(2-pyridyl) |
| H | H | CH₂CH₃ | CH₂CH₃ | CH₂CH=CH₂ | CH₂(Ph) |
| H | H | CH₂CH₃ | CH₂CH₃ | CH₂CH=CH₂ | Q-1 |
| H | H | CH₂CH₃ | CH₂CH₃ | CH₂CH=CH₂ | Q-3 |
| H | H | CH₂CH₃ | CH₂CH₃ | CH₂CH=CH₂ | Q-6 |
| H | H | CH₂CH₃ | CH₂CH₃ | CH₂CH=CH₂ | Q-7 |
| H | H | CH₂CH₃ | CH₂CH₃ | CH₂CH=CH₂ | Q-15 |
| H | H | H | H | CH₃ | CH₂(2-FPh) |
| H | H | H | H | CH₃ | CH₂(2-ClPh) |
| H | H | H | H | CH₃ | CH₂(2-(CH₃)Ph) |
| H | H | H | H | CH₃ | CH₂(2,6-Cl₂Ph) |
| H | H | H | H | CH₃ | CH₂(2-CF₃Ph) |
| H | H | H | H | CH₃ | CH₂(2-tetrahydropyran) |
| H | H | H | H | CH₃ | CH₂(2-pyridyl) |
| H | H | H | H | CH₃ | CH₂(Ph) |
| H | H | H | H | CH₃ | Q-1 |
| H | H | H | H | CH₃ | Q-3 |
| H | H | H | H | CH₃ | Q-6 |
| H | H | H | H | CH₃ | Q-7 |
| H | H | H | H | CH₃ | Q-15 |
| H | H | CH₃ | CH₃ | CH₃ | CH₂(2-FPh) |
| H | H | CH₃ | CH₃ | CH₃ | CH₂(2-ClPh) |
| H | H | CH₃ | CH₃ | CH₃ | CH₂(2-(CH₃)Ph) |
| H | H | CH₃ | CH₃ | CH₃ | CH₂(2,6-Cl₂Ph) |
| H | H | CH₃ | CH₃ | CH₃ | CH₂(2-CF₃Ph) |
| H | H | CH₃ | CH₃ | CH₃ | CH₂(2-tetrahydropyran) |
| H | H | CH₃ | CH₃ | CH₃ | CH₂(2-pyridyl) |
| H | H | CH₃ | CH₃ | CH₃ | CH₂(Ph) |
| H | H | CH₃ | CH₃ | CH₃ | Q-1 |
| H | H | CH₃ | CH₃ | CH₃ | Q-3 |
| H | H | CH₃ | CH₃ | CH₃ | Q-6 |
| H | H | CH₃ | CH₃ | CH₃ | Q-7 |
| H | H | CH₃ | CH₃ | CH₃ | Q-15 |
| CH₃ | CH₃ | CH₂CH₃ | CH₂CH₃ | CH₃ | CH₂(2-FPh) |
| CH₃ | CH₃ | CH₂CH₃ | CH₂CH₃ | CH₃ | CH₂(2-ClPh) |
| CH₃ | CH₃ | CH₂CH₃ | CH₂CH₃ | CH₃ | CH₂(2-(CH₃)Ph) |
| CH₃ | CH₃ | CH₂CH₃ | CH₂CH₃ | CH₃ | CH₂(2,6-Cl₂Ph) |
| CH₃ | CH₃ | CH₂CH₃ | CH₂CH₃ | CH₃ | CH₂(2-CF₃Ph) |

TABLE 4-continued

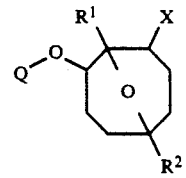

IV $X = C(R^3)(R^4)OR^5$

| $R^1$ | $R^2$ | $R^3$ | $R^4$ | $R^5$ | Q |
|---|---|---|---|---|---|
| $CH_3$ | $CH_3$ | $CH_2CH_3$ | $CH_2CH_3$ | $CH_3$ | $CH_2$(2-tetrahydropyran) |
| $CH_3$ | $CH_3$ | $CH_2CH_3$ | $CH_2CH_3$ | $CH_3$ | $CH_2$(2-pyridyl) |
| $CH_3$ | $CH_3$ | $CH_2CH_3$ | $CH_2CH_3$ | $CH_3$ | $CH_2$(Ph) |
| $CH_3$ | $CH_3$ | $CH_2CH_3$ | $CH_2CH_3$ | $CH_3$ | Q-1 |
| $CH_3$ | $CH_3$ | $CH_2CH_3$ | $CH_2CH_3$ | $CH_3$ | Q-3 |
| $CH_3$ | $CH_3$ | $CH_2CH_3$ | $CH_2CH_3$ | $CH_3$ | Q-6 |
| $CH_3$ | $CH_3$ | $CH_2CH_3$ | $CH_2CH_3$ | $CH_3$ | Q-7 |
| $CH_3$ | $CH_3$ | $CH_2CH_3$ | $CH_2CH_3$ | $CH_3$ | Q-15 |
| $CH_2CH_3$ | $CH_2CH_3$ | $CH_2CH_3$ | $CH_2CH_3$ | $CH_3$ | $CH_2$(2-FPh) |
| $CH_2CH_3$ | $CH_2CH_3$ | $CH_2CH_3$ | $CH_2CH_3$ | $CH_3$ | $CH_2$(2-ClPh) |
| $CH_2CH_3$ | $CH_2CH_3$ | $CH_2CH_3$ | $CH_2CH_3$ | $CH_3$ | $CH_2$(2-($CH_3$)Ph) |
| $CH_2CH_3$ | $CH_2CH_3$ | $CH_2CH_3$ | $CH_2CH_3$ | $CH_3$ | $CH_2$(2,6-$Cl_2$Ph) |
| $CH_2CH_3$ | $CH_2CH_3$ | $CH_2CH_3$ | $CH_2CH_3$ | $CH_3$ | $CH_2$(2-$CF_3$Ph) |
| $CH_2CH_3$ | $CH_2CH_3$ | $CH_2CH_3$ | $CH_2CH_3$ | $CH_3$ | $CH_2$(2-tetrahydropyran) |
| $CH_2CH_3$ | $CH_2CH_3$ | $CH_2CH_3$ | $CH_2CH_3$ | $CH_3$ | $CH_2$(2-pyridyl) |
| $CH_2CH_3$ | $CH_2CH_3$ | $CH_2CH_3$ | $CH_2CH_3$ | $CH_3$ | $CH_2$(Ph) |
| $CH_2CH_3$ | $CH_2CH_3$ | $CH_2CH_3$ | $CH_2CH_3$ | $CH_3$ | Q-1 |
| $CH_2CH_3$ | $CH_2CH_3$ | $CH_2CH_3$ | $CH_2CH_3$ | $CH_3$ | Q-3 |
| $CH_2CH_3$ | $CH_2CH_3$ | $CH_2CH_3$ | $CH_2CH_3$ | $CH_3$ | Q-6 |
| $CH_2CH_3$ | $CH_2CH_3$ | $CH_2CH_3$ | $CH_2CH_3$ | $CH_3$ | Q-7 |
| $CH_2CH_3$ | $CH_2CH_3$ | $CH_2CH_3$ | $CH_2CH_3$ | $CH_3$ | Q-15 |
| $CH_3$ | H | $CH_2CH_3$ | $CH_2CH_3$ | $CH_3$ | $CH_2$(2-FPh) |
| $CH_3$ | H | $CH_2CH_3$ | $CH_2CH_3$ | $CH_3$ | $CH_2$(2-ClPh) |
| $CH_3$ | H | $CH_2CH_3$ | $CH_2CH_3$ | $CH_3$ | $CH_2$(2-($CH_3$)Ph) |
| $CH_3$ | H | $CH_2CH_3$ | $CH_2CH_3$ | $CH_3$ | $CH_2$(2,6-$Cl_2$Ph) |
| $CH_3$ | H | $CH_2CH_3$ | $CH_2CH_3$ | $CH_3$ | $CH_2$(2-$CF_3$Ph) |
| $CH_3$ | H | $CH_2CH_3$ | $CH_2CH_3$ | $CH_3$ | $CH_2$(2-tetrahydropyran) |
| $CH_3$ | H | $CH_2CH_3$ | $CH_2CH_3$ | $CH_3$ | $CH_2$(2-pyridyl) |
| $CH_3$ | H | $CH_2CH_3$ | $CH_2CH_3$ | $CH_3$ | $CH_2$(Ph) |
| $CH_3$ | H | $CH_2CH_3$ | $CH_2CH_3$ | $CH_3$ | Q-1 |
| $CH_3$ | H | $CH_2CH_3$ | $CH_2CH_3$ | $CH_3$ | Q-3 |
| $CH_3$ | H | $CH_2CH_3$ | $CH_2CH_3$ | $CH_3$ | Q-6 |
| $CH_3$ | H | $CH_2CH_3$ | $CH_2CH_3$ | $CH_3$ | Q-7 |
| $CH_3$ | H | $CH_2CH_3$ | $CH_2CH_3$ | $CH_3$ | Q-15 |
| $CH_2CH_3$ | H | $CH_2CH_3$ | $CH_2CH_3$ | $CH_3$ | $CH_2$(2-FPh) |
| $CH_2CH_3$ | H | $CH_2CH_3$ | $CH_2CH_3$ | $CH_3$ | $CH_2$(2-ClPh) |
| $CH_2CH_3$ | H | $CH_2CH_3$ | $CH_2CH_3$ | $CH_3$ | $CH_2$(2-($CH_3$)Ph) |
| $CH_2CH_3$ | H | $CH_2CH_3$ | $CH_2CH_3$ | $CH_3$ | $CH_2$(2,6-$Cl_2$Ph) |
| $CH_2CH_3$ | H | $CH_2CH_3$ | $CH_2CH_3$ | $CH_3$ | $CH_2$(2-$CF_3$Ph) |
| $CH_2CH_3$ | H | $CH_2CH_3$ | $CH_2CH_3$ | $CH_3$ | $CH_2$(2-tetrahydropyran) |
| $CH_2CH_3$ | H | $CH_2CH_3$ | $CH_2CH_3$ | $CH_3$ | $CH_2$(2-pyridyl) |
| $CH_2CH_3$ | H | $CH_2CH_3$ | $CH_2CH_3$ | $CH_3$ | $CH_2$(Ph) |
| $CH_2CH_3$ | H | $CH_2CH_3$ | $CH_2CH_3$ | $CH_3$ | Q-1 |
| $CH_2CH_3$ | H | $CH_2CH_3$ | $CH_2CH_3$ | $CH_3$ | Q-3 |
| $CH_2CH_3$ | H | $CH_2CH_3$ | $CH_2CH_3$ | $CH_3$ | Q-6 |
| $CH_2CH_3$ | H | $CH_2CH_3$ | $CH_2CH_3$ | $CH_3$ | Q-7 |
| $CH_2CH_3$ | H | $CH_2CH_3$ | $CH_2CH_3$ | $CH_3$ | Q-15 |

TABLE 5

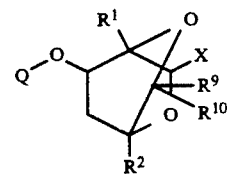

V $X = C(R^3)(R^4)OR^5$

| $R^1$ | $R^2$ | $R^3=R^4$ | $R^9=R^{10}$ | $R^5$ | Q |
|---|---|---|---|---|---|
| H | H | $CH_2CH_3$ | $CH_2CH_3$ | $CH_3$ | $CH_2$(2-FPh) |
| H | H | $CH_2CH_3$ | $CH_2CH_3$ | $CH_3$ | $CH_2$(2-ClPh) |
| H | H | $CH_2CH_3$ | $CH_2CH_3$ | $CH_3$ | $CH_2$(2-BrPh) |
| H | H | $CH_2CH_3$ | $CH_2CH_3$ | $CH_3$ | $CH_2$(2-($CH_3$)Ph) |

TABLE 5-continued

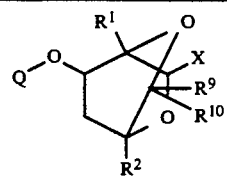

V

X = C($R^3$)($R^4$)O$R^5$

| $R^1$ | $R^2$ | $R^3$=$R^4$ | $R^9$=$R^{10}$ | $R^5$ | Q |
|---|---|---|---|---|---|
| H | H | CH$_2$CH$_3$ | CH$_2$CH$_3$ | CH$_3$ | CH$_2$(2-(OCH$_3$)Ph) |
| H | H | CH$_2$CH$_3$ | CH$_2$CH$_3$ | CH$_3$ | CH$_2$(2-(CN)Ph) |
| H | H | CH$_2$CH$_3$ | CH$_2$CH$_3$ | CH$_3$ | CH$_2$(2-(CF$_3$)Ph) |
| H | H | CH$_2$CH$_3$ | CH$_2$CH$_3$ | CH$_3$ | CH$_2$(2-(OCF$_3$)Ph) |
| H | H | CH$_2$CH$_3$ | CH$_2$CH$_3$ | CH$_3$ | CH$_2$(2-(SCH$_3$)Ph) |
| H | H | CH$_2$CH$_3$ | CH$_2$CH$_3$ | CH$_3$ | CH$_2$(2,6-(F)$_2$Ph) |
| H | H | CH$_2$CH$_3$ | CH$_2$CH$_3$ | CH$_3$ | CH$_2$(2,6-(Cl)$_2$Ph) |
| H | H | CH$_2$CH$_3$ | CH$_2$CH$_3$ | CH$_3$ | CH$_2$(2-pyridyl) |
| H | H | CH$_2$CH$_3$ | CH$_2$CH$_3$ | CH$_3$ | CH$_2$(2-furanyl) |
| H | H | CH$_2$CH$_3$ | CH$_2$CH$_3$ | CH$_3$ | CH$_2$(2-tetrahydrofuran) |
| H | H | CH$_2$CH$_3$ | CH$_2$CH$_3$ | CH$_3$ | CH$_2$(2-tetrahydrofuran) |
| H | H | CH$_2$CH$_3$ | CH$_2$CH$_3$ | CH$_3$ | CH$_2$(2-thiophenyl) |
| H | H | CH$_2$CH$_3$ | CH$_2$CH$_3$ | CH$_3$ | CH$_2$(2-isoxazolyl) |
| H | H | CH$_2$CH$_3$ | CH$_2$CH$_3$ | CH$_3$ | CH$_2$(2-pyrazinyl) |
| H | H | CH$_2$CH$_3$ | CH$_2$CH$_3$ | CH$_3$ | CH$_2$(Ph) |
| H | H | CH$_2$CH$_3$ | CH$_2$CH$_3$ | CH$_3$ | Q-1 |
| H | H | CH$_2$CH$_3$ | CH$_2$CH$_3$ | CH$_3$ | Q-3 |
| H | H | CH$_2$CH$_3$ | CH$_2$CH$_3$ | CH$_3$ | Q-6 |
| H | H | CH$_2$CH$_3$ | CH$_2$CH$_3$ | CH$_3$ | Q-7 |
| H | H | CH$_2$CH$_3$ | CH$_2$CH$_3$ | CH$_3$ | Q-15 |
| H | H | CH$_2$CH$_3$ | CH$_2$CH$_3$ | CH$_2$CH$_3$ | CH$_2$(2-FPh) |
| H | H | CH$_2$CH$_3$ | CH$_2$CH$_3$ | CH$_2$CH$_3$ | CH$_2$(2-ClPh) |
| H | H | CH$_2$CH$_3$ | CH$_2$CH$_3$ | CH$_2$CH$_3$ | CH$_2$(2-(CH$_3$)Ph) |
| H | H | CH$_2$CH$_3$ | CH$_2$CH$_3$ | CH$_2$CH$_3$ | CH$_2$(2,6-Cl$_2$Ph) |
| H | H | CH$_2$CH$_3$ | CH$_2$CH$_3$ | CH$_2$CH$_3$ | CH$_2$(2-CF$_3$Ph) |
| H | H | CH$_2$CH$_3$ | CH$_2$CH$_3$ | CH$_2$CH$_3$ | CH$_2$(2-tetrahydropyran) |
| H | H | CH$_2$CH$_3$ | CH$_2$CH$_3$ | CH$_2$CH$_3$ | CH$_2$(2-pyridyl) |
| H | H | CH$_2$CH$_3$ | CH$_2$CH$_3$ | CH$_2$CH$_3$ | CH$_2$(Ph) |
| H | H | CH$_2$CH$_3$ | CH$_2$CH$_3$ | CH$_2$CH$_3$ | Q-1 |
| H | H | CH$_2$CH$_3$ | CH$_2$CH$_3$ | CH$_2$CH$_3$ | Q-3 |
| H | H | CH$_2$CH$_3$ | CH$_2$CH$_3$ | CH$_2$CH$_3$ | Q-6 |
| H | H | CH$_2$CH$_3$ | CH$_2$CH$_3$ | CH$_2$CH$_3$ | Q-7 |
| H | H | CH$_2$CH$_3$ | CH$_2$CH$_3$ | CH$_2$CH$_3$ | Q-15 |
| H | H | CH$_2$CH$_3$ | CH$_2$CH$_3$ | CH$_2$CH=CH$_2$ | CH$_2$(2-FPh) |
| H | H | CH$_2$CH$_3$ | CH$_2$CH$_3$ | CH$_2$CH=CH$_2$ | CH$_2$(2-ClPh) |
| H | H | CH$_2$CH$_3$ | CH$_2$CH$_3$ | CH$_2$CH=CH$_2$ | CH$_2$(2-(CH$_3$)Ph) |
| H | H | CH$_2$CH$_3$ | CH$_2$CH$_3$ | CH$_2$CH=CH$_2$ | CH$_2$(2,6-Cl$_2$Ph) |
| H | H | CH$_2$CH$_3$ | CH$_2$CH$_3$ | CH$_2$CH=CH$_2$ | CH$_2$(2-CF$_3$Ph) |
| H | H | CH$_2$CH$_3$ | CH$_2$CH$_3$ | CH$_2$CH=CH$_2$ | CH$_2$(2-tetrahydropyran) |
| H | H | CH$_2$CH$_3$ | CH$_2$CH$_3$ | CH$_2$CH=CH$_2$ | CH$_2$(2-pyridyl) |
| H | H | CH$_2$CH$_3$ | CH$_2$CH$_3$ | CH$_2$CH=CH$_2$ | CH$_2$(Ph) |
| H | H | CH$_2$CH$_3$ | CH$_2$CH$_3$ | CH$_2$CH=CH$_2$ | Q-1 |
| H | H | CH$_2$CH$_3$ | CH$_2$CH$_3$ | CH$_2$CH=CH$_2$ | Q-3 |
| H | H | CH$_2$CH$_3$ | CH$_2$CH$_3$ | CH$_2$CH=CH$_2$ | Q-6 |
| H | H | CH$_2$CH$_3$ | CH$_2$CH$_3$ | CH$_2$CH=CH$_2$ | Q-7 |
| H | H | CH$_2$CH$_3$ | CH$_2$CH$_3$ | CH$_2$CH=CH$_2$ | Q-15 |
| H | H | H | H | CH$_3$ | CH$_2$(2-FPh) |
| H | H | H | H | CH$_3$ | CH$_2$(2-ClPh) |
| H | H | H | H | CH$_3$ | CH$_2$(2-(CH$_3$)Ph) |
| H | H | H | H | CH$_3$ | CH$_2$(2,6-Cl$_2$Ph) |
| H | H | H | H | CH$_3$ | CH$_2$(2-CF$_3$Ph) |
| H | H | H | H | CH$_3$ | CH$_2$(2-tetrahydropyran) |
| H | H | H | H | CH$_3$ | CH$_2$(2-pyridyl) |
| H | H | H | H | CH$_3$ | CH$_2$(Ph) |
| H | H | H | H | CH$_3$ | Q-1 |
| H | H | H | H | CH$_3$ | Q-3 |
| H | H | H | H | CH$_3$ | Q-6 |
| H | H | H | H | CH$_3$ | Q-7 |
| H | H | H | H | CH$_3$ | Q-15 |
| H | H | CH$_3$ | CH$_3$ | CH$_3$ | CH$_2$(2-FPh) |
| H | H | CH$_3$ | CH$_3$ | CH$_3$ | CH$_2$(2-ClPh) |
| H | H | CH$_3$ | CH$_3$ | CH$_3$ | CH$_2$(2-(CH$_3$)Ph) |
| H | H | CH$_3$ | CH$_3$ | CH$_3$ | CH$_2$(2,6-Cl$_2$Ph) |
| H | H | CH$_3$ | CH$_3$ | CH$_3$ | CH$_2$(2-CF$_3$Ph) |
| H | H | CH$_3$ | CH$_3$ | CH$_3$ | CH$_2$(2-tetrahydropyran) |
| H | H | CH$_3$ | CH$_3$ | CH$_3$ | CH$_2$(2-pyridyl) |
| H | H | CH$_3$ | CH$_3$ | CH$_3$ | CH$_2$(Ph) |
| H | H | CH$_3$ | CH$_3$ | CH$_3$ | Q-1 |
| H | H | CH$_3$ | CH$_3$ | CH$_3$ | Q-3 |

TABLE 5-continued

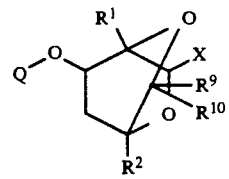

V $X = C(R^3)(R^4)OR^5$

| $R^1$ | $R^2$ | $R^3=R^4$ | $R^9=R^{10}$ | $R^5$ | Q |
|---|---|---|---|---|---|
| H | H | CH₃ | CH₃ | CH₃ | Q-6 |
| H | H | CH₃ | CH₃ | CH₃ | Q-7 |
| H | H | CH₃ | CH₃ | CH₃ | Q-15 |
| CH₃ | H | CH₂CH₃ | CH₂CH₃ | CH₃ | CH₂(2-FPh) |
| CH₃ | H | CH₂CH₃ | CH₂CH₃ | CH₃ | CH₂(2-ClPh) |
| CH₃ | H | CH₂CH₃ | CH₂CH₃ | CH₃ | CH₂(2-(CH₃)Ph) |
| CH₃ | H | CH₂CH₃ | CH₂CH₃ | CH₃ | CH₂(2,6-Cl₂Ph) |
| CH₃ | H | CH₂CH₃ | CH₂CH₃ | CH₃ | CH₂(2-CF₃Ph) |
| CH₃ | H | CH₂CH₃ | CH₂CH₃ | CH₃ | CH₂(2-tetrahydropyran) |
| CH₃ | H | CH₂CH₃ | CH₂CH₃ | CH₃ | CH₂(2-pyridyl) |
| CH₃ | H | CH₂CH₃ | CH₂CH₃ | CH₃ | CH₂(Ph) |
| CH₃ | H | CH₂CH₃ | CH₂CH₃ | CH₃ | Q-1 |
| CH₃ | H | CH₂CH₃ | CH₂CH₃ | CH₃ | Q-3 |
| CH₃ | H | CH₂CH₃ | CH₂CH₃ | CH₃ | Q-6 |
| CH₃ | H | CH₂CH₃ | CH₂CH₃ | CH₃ | Q-7 |
| CH₃ | H | CH₂CH₃ | CH₂CH₃ | CH₃ | Q-15 |
| CH₂CH₃ | H | CH₃ | CH₃ | CH₃ | CH₂(2-FPh) |
| CH₂CH₃ | H | CH₃ | CH₃ | CH₃ | CH₂(2-ClPh) |
| CH₂CH₃ | H | CH₃ | CH₃ | CH₃ | CH₂(2-(CH₃)Ph) |
| CH₂CH₃ | H | CH₃ | CH₃ | CH₃ | CH₂(2,6-Cl₂Ph) |
| CH₂CH₃ | H | CH₃ | CH₃ | CH₃ | CH₂(2-CF₃Ph) |
| CH₂CH₃ | H | CH₃ | CH₃ | CH₃ | CH₂(2-tetrahydropyran) |
| CH₂CH₃ | H | CH₃ | CH₃ | CH₃ | CH₂(2-pyridyl) |
| CH₂CH₃ | H | CH₃ | CH₃ | CH₃ | CH₂(Ph) |
| CH₂CH₃ | H | CH₃ | CH₃ | CH₃ | Q-1 |
| CH₂CH₃ | H | CH₃ | CH₃ | CH₃ | Q-3 |
| CH₂CH₃ | H | CH₃ | CH₃ | CH₃ | Q-6 |
| CH₂CH₃ | H | CH₃ | CH₃ | CH₃ | Q-7 |
| CH₂CH₃ | H | CH₃ | CH₃ | CH₃ | Q-15 |
| CH₃ | H | H | H | CH₃ | Q-1 |
| CH₃ | H | H | H | CH₃ | Q-3 |
| CH₃ | H | H | H | CH₃ | Q-6 |
| CH₃ | H | H | H | CH₃ | Q-7 |
| CH₃ | H | H | H | CH₃ | Q-15 |
| CH₃ | H | H | H | CH₃ | CH₂(2-FPh) |
| CH₃ | H | H | H | CH₃ | CH₂(2-ClPh) |
| CH₃ | H | H | H | CH₃ | CH₂(2-(CH₃)Ph) |
| CH₃ | H | H | H | CH₃ | CH₂(2,6-Cl₂Ph) |
| CH₃ | H | H | H | CH₃ | CH₂(2-CF₃Ph) |
| CH₃ | H | H | H | CH₃ | CH₂(2-tetrahydropyran) |
| CH₃ | H | H | H | CH₃ | CH₂(2-pyridyl) |
| CH₃ | H | H | H | CH₃ | CH₂(Ph) |
| CH₃ | H | CH₃ | CH₃ | CH₃ | Q-1 |
| CH₃ | H | CH₃ | CH₃ | CH₃ | Q-3 |
| CH₃ | H | CH₃ | CH₃ | CH₃ | Q-6 |
| CH₃ | H | CH₃ | CH₃ | CH₃ | Q-7 |
| CH₃ | H | CH₃ | CH₃ | CH₃ | Q-15 |
| CH₃ | H | CH₃ | CH₃ | CH₃ | CH₂(2-FPh) |
| CH₃ | H | CH₃ | CH₃ | CH₃ | CH₂(2-ClPh) |
| CH₃ | H | CH₃ | CH₃ | CH₃ | CH₂(2-(CH₃)Ph) |
| CH₃ | H | CH₃ | CH₃ | CH₃ | CH₂(2,6-Cl₂Ph) |
| CH₃ | H | CH₃ | CH₃ | CH₃ | CH₂(2-CF₃Ph) |
| CH₃ | H | CH₃ | CH₃ | CH₃ | CH₂(2-tetrahydropyran) |
| CH₃ | H | CH₃ | CH₃ | CH₃ | CH₂(2-pyridyl) |
| CH₃ | H | CH₃ | CH₃ | CH₃ | CH₂(Ph) |
| CH₃ | CH₃ | CH₃ | CH₃ | CH₃ | Q-1 |
| CH₃ | CH₃ | CH₃ | CH₃ | CH₃ | Q-3 |
| CH₃ | CH₃ | CH₃ | CH₃ | CH₃ | Q-6 |
| CH₃ | CH₃ | CH₃ | CH₃ | CH₃ | Q-7 |
| CH₃ | CH₃ | CH₃ | CH₃ | CH₃ | Q-15 |
| CH₃ | CH₃ | CH₃ | CH₃ | CH₃ | CH₂(2-FPh) |
| CH₃ | CH₃ | CH₃ | CH₃ | CH₃ | CH₂(2-ClPh) |
| CH₃ | CH₃ | CH₃ | CH₃ | CH₃ | CH₂(2-(CH₃)Ph) |
| CH₃ | CH₃ | CH₃ | CH₃ | CH₃ | CH₂(2,6-Cl₂Ph) |
| CH₃ | CH₃ | CH₃ | CH₃ | CH₃ | CH₂(2-CF₃Ph) |
| CH₃ | CH₃ | CH₃ | CH₃ | CH₃ | CH₂(2-tetrahydropyran) |
| CH₃ | CH₃ | CH₃ | CH₃ | CH₃ | CH₂(2-pyridyl) |
| CH₃ | CH₃ | CH₃ | CH₃ | CH₃ | CH₂(Ph) |
| CH₃ | H | H | CH₃ | CH₃ | Q-1 |

TABLE 5-continued

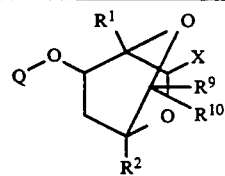

V

X = C(R³)(R⁴)OR⁵

| R¹ | R² | R³=R⁴ | R⁹=R¹⁰ | R⁵ | Q |
|---|---|---|---|---|---|
| CH₃ | H | H | CH₃ | CH₃ | Q-3 |
| CH₃ | H | H | CH₃ | CH₃ | Q-6 |
| CH₃ | H | H | CH₃ | CH₃ | Q-7 |
| CH₃ | H | H | CH₃ | CH₃ | Q-15 |
| CH₃ | H | H | CH₃ | CH₃ | CH₂(2-FPh) |
| CH₃ | H | H | CH₃ | CH₃ | CH₂(2-ClPh) |
| CH₃ | H | H | CH₃ | CH₃ | CH₂(2-(CH₃)Ph) |
| CH₃ | H | H | CH₃ | CH₃ | CH₂(2,6-Cl₂Ph) |
| CH₃ | H | H | CH₃ | CH₃ | CH₂(2-CF₃Ph) |
| CH₃ | H | H | CH₃ | CH₃ | CH₂(2-tetrahydropyran) |
| CH₃ | H | H | CH₃ | CH₃ | CH₂(2-pyridyl) |
| CH₃ | H | H | CH₃ | CH₃ | CH₂(Ph) |
| CH₃ | H | H | CH₂CH₃ | CH₃ | Q-1 |
| CH₃ | H | H | CH₂CH₃ | CH₃ | Q-3 |
| CH₃ | H | H | CH₂CH₃ | CH₃ | Q-6 |
| CH₃ | H | H | CH₂CH₃ | CH₃ | Q-7 |
| CH₃ | H | H | CH₂CH₃ | CH₃ | Q-15 |
| CH₃ | H | H | CH₂CH₃ | CH₃ | CH₂(2-FPh) |
| CH₃ | H | H | CH₂CH₃ | CH₃ | CH₂(2-ClPh) |
| CH₃ | H | H | CH₂CH₃ | CH₃ | CH₂(2-(CH₃)Ph) |
| CH₃ | H | H | CH₂CH₃ | CH₃ | CH₂(2,6-Cl₂Ph) |
| CH₃ | H | H | CH₂CH₃ | CH₃ | CH₂(2-CF₃Ph) |
| CH₃ | H | H | CH₂CH₃ | CH₃ | CH₂(2-tetrahydropyran) |
| CH₃ | H | H | CH₂CH₃ | CH₃ | CH₂(2-pyridyl) |
| CH₃ | H | H | CH₂CH₃ | CH₃ | CH₂(Ph) |
| CH₃ | H | CH₃ | H | CH₃ | Q-1 |
| CH₃ | H | CH₃ | H | CH₃ | Q-3 |
| CH₃ | H | CH₃ | H | CH₃ | Q-6 |
| CH₃ | H | CH₃ | H | CH₃ | Q-7 |
| CH₃ | H | CH₃ | H | CH₃ | Q-15 |
| CH₃ | H | CH₃ | H | CH₃ | CH₂(2-FPh) |
| CH₃ | H | CH₃ | H | CH₃ | CH₂(2-ClPh) |
| CH₃ | H | CH₃ | H | CH₃ | CH₂(2-(CH₃)Ph) |
| CH₃ | H | CH₃ | H | CH₃ | CH₂(2,6-Cl₂Ph) |
| CH₃ | H | CH₃ | H | CH₃ | CH₂(2-CF₃Ph) |
| CH₃ | H | CH₃ | H | CH₃ | CH₂(2-tetrahydropyran) |
| CH₃ | H | CH₃ | H | CH₃ | CH₂(2-pyridyl) |
| CH₃ | H | CH₃ | H | CH₃ | CH₂(Ph) |

TABLE 6

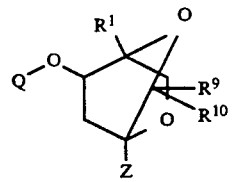

VI

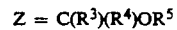

Z = C(R³)(R⁴)OR⁵

| R¹ | R³ = R⁴ | R⁹ = R¹⁰ | R⁵ | Q |
|---|---|---|---|---|
| H | CH₂CH₃ | CH₂CH₃ | CH₃ | CH₂(2-FPh) |
| H | CH₂CH₃ | CH₂CH₃ | CH₃ | CH₂(2-ClPh) |
| H | CH₂CH₃ | CH₂CH₃ | CH₃ | CH₂(2-BrPh) |
| H | CH₂CH₃ | CH₂CH₃ | CH₃ | CH₂(2-(CH₃)Ph) |
| H | CH₂CH₃ | CH₂CH₃ | CH₃ | CH₂(2-(OCH₃)Ph) |
| H | CH₂CH₃ | CH₂CH₃ | CH₃ | CH₂(2-(CN)Ph) |
| H | CH₂CH₃ | CH₂CH₃ | CH₃ | CH₂(2-(CF₃)Ph) |
| H | CH₂CH₃ | CH₂CH₃ | CH₃ | CH₂(2-(OCF₃)Ph) |
| H | CH₂CH₃ | CH₂CH₃ | CH₃ | CH₂(2-(SCH₃)Ph) |
| H | CH₂CH₃ | CH₂CH₃ | CH₃ | CH₂(2,6-(F)₂Ph) |
| H | CH₂CH₃ | CH₂CH₃ | CH₃ | CH₂(2,6-(Cl)₂Ph) |
| H | CH₂CH₃ | CH₂CH₃ | CH₃ | CH₂(2-pyridyl) |
| H | CH₂CH₃ | CH₂CH₃ | CH₃ | CH₂(2-furanyl) |
| H | CH₂CH₃ | CH₂CH₃ | CH₃ | CH₂(2-tetrahydrofuran) |

TABLE 6-continued

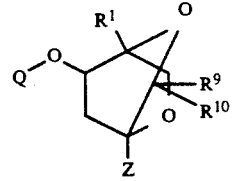

$Z = C(R^3)(R^4)OR^5$

| $R^1$ | $R^3 = R^4$ | $R^9 = R^{10}$ | $R^5$ | Q |
|---|---|---|---|---|
| H | CH$_2$CH$_3$ | CH$_2$CH$_3$ | CH$_3$ | CH$_2$(2-tetrahydropyran) |
| H | CH$_2$CH$_3$ | CH$_2$CH$_3$ | CH$_3$ | CH$_2$(2-thiophenyl) |
| H | CH$_2$CH$_3$ | CH$_2$CH$_3$ | CH$_3$ | CH$_2$(2-isoxazolyl) |
| H | CH$_2$CH$_3$ | CH$_2$CH$_3$ | CH$_3$ | CH$_2$(2-pyrazinyl) |
| H | CH$_2$CH$_3$ | CH$_2$CH$_3$ | CH$_3$ | CH$_2$(Ph) |
| H | CH$_2$CH$_3$ | CH$_2$CH$_3$ | CH$_3$ | Q-1 |
| H | CH$_2$CH$_3$ | CH$_2$CH$_3$ | CH$_3$ | Q-3 |
| H | CH$_2$CH$_3$ | CH$_2$CH$_3$ | CH$_3$ | Q-6 |
| H | CH$_2$CH$_3$ | CH$_2$CH$_3$ | CH$_3$ | Q-7 |
| H | CH$_2$CH$_3$ | CH$_2$CH$_3$ | CH$_3$ | Q-15 |
| H | CH$_2$CH$_3$ | CH$_2$CH$_3$ | CH$_2$CH$_3$ | CH$_2$(2-FPh) |
| H | CH$_2$CH$_3$ | CH$_2$CH$_3$ | CH$_2$CH$_3$ | CH$_2$(2-ClPh) |
| H | CH$_2$CH$_3$ | CH$_2$CH$_3$ | CH$_2$CH$_3$ | CH$_2$(2-(CH$_3$)Ph) |
| H | CH$_2$CH$_3$ | CH$_2$CH$_3$ | CH$_2$CH$_3$ | CH$_2$(2,6-Cl$_2$Ph) |
| H | CH$_2$CH$_3$ | CH$_2$CH$_3$ | CH$_2$CH$_3$ | CH$_2$(2-CF$_3$Ph) |
| H | CH$_2$CH$_3$ | CH$_2$CH$_3$ | CH$_2$CH$_3$ | CH$_2$(2-tetrahydropyran) |
| H | CH$_2$CH$_3$ | CH$_2$CH$_3$ | CH$_2$CH$_3$ | CH$_2$(2-pyridyl) |
| H | CH$_2$CH$_3$ | CH$_2$CH$_3$ | CH$_2$CH$_3$ | CH$_2$(Ph) |
| H | CH$_2$CH$_3$ | CH$_2$CH$_3$ | CH$_2$CH$_3$ | Q-1 |
| H | CH$_2$CH$_3$ | CH$_2$CH$_3$ | CH$_2$CH$_3$ | Q-3 |
| H | CH$_2$CH$_3$ | CH$_2$CH$_3$ | CH$_2$CH$_3$ | Q-6 |
| H | CH$_2$CH$_3$ | CH$_2$CH$_3$ | CH$_2$CH$_3$ | Q-7 |
| H | CH$_2$CH$_3$ | CH$_2$CH$_3$ | CH$_2$CH$_3$ | Q-15 |
| H | CH$_2$CH$_3$ | CH$_2$CH$_3$ | CH$_2$CH=CH$_2$ | CH$_2$(2-FPh) |
| H | CH$_2$CH$_3$ | CH$_2$CH$_3$ | CH$_2$CH=CH$_2$ | CH$_2$(2-ClPh) |
| H | CH$_2$CH$_3$ | CH$_2$CH$_3$ | CH$_2$CH=CH$_2$ | CH$_2$(2-(CH$_3$)Ph) |
| H | CH$_2$CH$_3$ | CH$_2$CH$_3$ | CH$_2$CH=CH$_2$ | CH$_2$(2,6-Cl$_2$Ph) |
| H | CH$_2$CH$_3$ | CH$_2$CH$_3$ | CH$_2$CH=CH$_2$ | CH$_2$(2-CF$_3$Ph) |
| H | CH$_2$CH$_3$ | CH$_2$CH$_3$ | CH$_2$CH=CH$_2$ | CH$_2$(2-tetrahydropyran) |
| H | CH$_2$CH$_3$ | CH$_2$CH$_3$ | CH$_2$CH=CH$_2$ | CH$_2$(2-pyridyl) |
| H | CH$_2$CH$_3$ | CH$_2$CH$_3$ | CH$_2$CH=CH$_2$ | CH$_2$(Ph) |
| H | CH$_2$CH$_3$ | CH$_2$CH$_3$ | CH$_2$CH=CH$_2$ | Q-1 |
| H | CH$_2$CH$_3$ | CH$_2$CH$_3$ | CH$_2$CH=CH$_2$ | Q-3 |
| H | CH$_2$CH$_3$ | CH$_2$CH$_3$ | CH$_2$CH=CH$_2$ | Q-6 |
| H | CH$_2$CH$_3$ | CH$_2$CH$_3$ | CH$_2$CH=CH$_2$ | Q-7 |
| H | CH$_2$CH$_3$ | CH$_2$CH$_3$ | CH$_2$CH=CH$_2$ | Q-15 |
| H | H | H | CH$_3$ | CH$_2$(2-FPh) |
| H | H | H | CH$_3$ | CH$_2$(2-ClPh) |
| H | H | H | CH$_3$ | CH$_2$(2-(CH$_3$)Ph) |
| H | H | H | CH$_3$ | CH$_2$(2,6-Cl$_2$Ph) |
| H | H | H | CH$_3$ | CH$_2$(2-CF$_3$Ph) |
| H | H | H | CH$_3$ | CH$_2$(2-tetrahydropyran) |
| H | H | H | CH$_3$ | CH$_2$(2-pyridyl) |
| H | H | H | CH$_3$ | CH$_2$(Ph) |
| H | H | H | CH$_3$ | Q-1 |
| H | H | H | CH$_3$ | Q-3 |
| H | H | H | CH$_3$ | Q-6 |
| H | H | H | CH$_3$ | Q-7 |
| H | H | H | CH$_3$ | Q-15 |
| H | CH$_3$ | CH$_3$ | CH$_3$ | CH$_2$(2-FPh) |
| H | CH$_3$ | CH$_3$ | CH$_3$ | CH$_2$(2-ClPh) |
| H | CH$_3$ | CH$_3$ | CH$_3$ | CH$_2$(2-(CH$_3$)Ph) |
| H | CH$_3$ | CH$_3$ | CH$_3$ | CH$_2$(2,6-Cl$_2$Ph) |
| H | CH$_3$ | CH$_3$ | CH$_3$ | CH$_2$(2-CF$_3$Ph) |
| H | CH$_3$ | CH$_3$ | CH$_3$ | CH$_2$(2-tetrahydropyran) |
| H | CH$_3$ | CH$_3$ | CH$_3$ | CH$_2$(2-pyridyl) |
| H | CH$_3$ | CH$_3$ | CH$_3$ | CH$_2$(Ph) |
| H | CH$_3$ | CH$_3$ | CH$_3$ | Q-1 |
| H | CH$_3$ | CH$_3$ | CH$_3$ | Q-3 |
| H | CH$_3$ | CH$_3$ | CH$_3$ | Q-6 |
| H | CH$_3$ | CH$_3$ | CH$_3$ | Q-7 |
| H | CH$_3$ | CH$_3$ | CH$_3$ | Q-15 |
| CH$_3$ | CH$_2$CH$_3$ | CH$_2$CH$_3$ | CH$_3$ | CH$_2$(2-FPh) |
| CH$_3$ | CH$_2$CH$_3$ | CH$_2$CH$_3$ | CH$_3$ | CH$_2$(2-ClPh) |
| CH$_3$ | CH$_2$CH$_3$ | CH$_2$CH$_3$ | CH$_3$ | CH$_2$(2-(CH$_3$)Ph) |
| CH$_3$ | CH$_2$CH$_3$ | CH$_2$CH$_3$ | CH$_3$ | CH$_2$(2,6-Cl$_2$Ph) |
| CH$_3$ | CH$_2$CH$_3$ | CH$_2$CH$_3$ | CH$_3$ | CH$_2$(2-CF$_3$Ph) |
| CH$_3$ | CH$_2$CH$_3$ | CH$_2$CH$_3$ | CH$_3$ | CH$_2$(2-tetrahydropyran) |
| CH$_3$ | CH$_2$CH$_3$ | CH$_2$CH$_3$ | CH$_3$ | CH$_2$(2-pyridyl) |
| CH$_3$ | CH$_2$CH$_3$ | CH$_2$CH$_3$ | CH$_3$ | CH$_2$(Ph) |

TABLE 6-continued

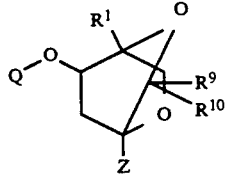

$Z = C(R^3)(R^4)OR^5$

VI

| $R^1$ | $R^3 = R^4$ | $R^9 = R^{10}$ | $R^5$ | Q |
|---|---|---|---|---|
| CH₃ | CH₂CH₃ | CH₂CH₃ | CH₃ | Q-1 |
| CH₃ | CH₂CH₃ | CH₂CH₃ | CH₃ | Q-3 |
| CH₃ | CH₂CH₃ | CH₂CH₃ | CH₃ | Q-6 |
| CH₃ | CH₂CH₃ | CH₂CH₃ | CH₃ | Q-7 |
| CH₃ | CH₂CH₃ | CH₂CH₃ | CH₃ | Q-15 |
| CH₂CH₃ | CH₃ | CH₃ | CH₃ | CH₂(2-FPh) |
| CH₂CH₃ | CH₃ | CH₃ | CH₃ | CH₂(2-ClPh) |
| CH₂CH₃ | CH₃ | CH₃ | CH₃ | CH₂(2-(CH₃)Ph) |
| CH₂CH₃ | CH₃ | CH₃ | CH₃ | CH₂(2,6-Cl₂Ph) |
| CH₂CH₃ | CH₃ | CH₃ | CH₃ | CH₂(2-CF₃Ph) |
| CH₂CH₃ | CH₃ | CH₃ | CH₃ | CH₂(2-tetrahydropyran) |
| CH₂CH₃ | CH₃ | CH₃ | CH₃ | CH₂(2-pyridyl) |
| CH₂CH₃ | CH₃ | CH₃ | CH₃ | CH₂(Ph) |
| CH₂CH₃ | CH₃ | CH₃ | CH₃ | Q-1 |
| CH₂CH₃ | CH₃ | CH₃ | CH₃ | Q-3 |
| CH₂CH₃ | CH₃ | CH₃ | CH₃ | Q-6 |
| CH₂CH₃ | CH₃ | CH₃ | CH₃ | Q-7 |
| CH₂CH₃ | CH₃ | CH₃ | CH₃ | Q-15 |
| CH₃ | H | H | CH₃ | Q-1 |
| CH₃ | H | H | CH₃ | Q-3 |
| CH₃ | H | H | CH₃ | Q-6 |
| CH₃ | H | H | CH₃ | Q-7 |
| CH₃ | H | H | CH₃ | Q-15 |
| CH₃ | H | H | CH₃ | CH₂(2-FPh) |
| CH₃ | H | H | CH₃ | CH₂(2-ClPh) |
| CH₃ | H | H | CH₃ | CH₂(2-(CH₃)Ph) |
| CH₃ | H | H | CH₃ | CH₂(2,6-Cl₂Ph) |
| CH₃ | H | H | CH₃ | CH₂(2-CF₃Ph) |
| CH₃ | H | H | CH₃ | CH₂(2-tetrahydropyran) |
| CH₃ | H | H | CH₃ | CH₂(2-pyridyl) |
| CH₃ | H | H | CH₃ | CH₂(Ph) |
| CH₃ | CH₃ | CH₃ | CH₃ | Q-1 |
| CH₃ | CH₃ | CH₃ | CH₃ | Q-3 |
| CH₃ | CH₃ | CH₃ | CH₃ | Q-6 |
| CH₃ | CH₃ | CH₃ | CH₃ | Q-7 |
| CH₃ | CH₃ | CH₃ | CH₃ | Q-15 |
| CH₃ | CH₃ | CH₃ | CH₃ | CH₂(2-FPh) |
| CH₃ | CH₃ | CH₃ | CH₃ | CH₂(2-ClPh) |
| CH₃ | CH₃ | CH₃ | CH₃ | CH₂(2-(CH₃)Ph) |
| CH₃ | CH₃ | CH₃ | CH₃ | CH₂(2,6-Cl₂Ph) |
| CH₃ | CH₃ | CH₃ | CH₃ | CH₂(2-CF₃Ph) |
| CH₃ | CH₃ | CH₃ | CH₃ | CH₂(2-tetrahydropyran) |
| CH₃ | CH₃ | CH₃ | CH₃ | CH₂(2-pyridyl) |
| CH₃ | CH₃ | CH₃ | CH₃ | CH₂(Ph) |
| CH₃ | H | CH₃ | CH₃ | Q-1 |
| CH₃ | H | CH₃ | CH₃ | Q-3 |
| CH₃ | H | CH₃ | CH₃ | Q-6 |
| CH₃ | H | CH₃ | CH₃ | Q-7 |
| CH₃ | H | CH₃ | CH₃ | Q-15 |
| CH₃ | H | CH₃ | CH₃ | CH₂(2-FPh) |
| CH₃ | H | CH₃ | CH₃ | CH₂(2-ClPh) |
| CH₃ | H | CH₃ | CH₃ | CH₂(2-(CH₃)Ph) |
| CH₃ | H | CH₃ | CH₃ | CH₂(2,6-Cl₂Ph) |
| CH₃ | H | CH₃ | CH₃ | CH₂(2-CF₃Ph) |
| CH₃ | H | CH₃ | CH₃ | CH₂(2-tetrahydropyran) |
| CH₃ | H | CH₃ | CH₃ | CH₂(2-pyridyl) |
| CH₃ | H | CH₃ | CH₃ | CH₂(Ph) |
| CH₃ | H | CH₂CH₃ | CH₃ | Q-1 |
| CH₃ | H | CH₂CH₃ | CH₃ | Q-3 |
| CH₃ | H | CH₂CH₃ | CH₃ | Q-6 |
| CH₃ | H | CH₂CH₃ | CH₃ | Q-7 |
| CH₃ | H | CH₂CH₃ | CH₃ | Q-15 |
| CH₃ | H | CH₂CH₃ | CH₃ | CH₂(2-FPh) |
| CH₃ | H | CH₂CH₃ | CH₃ | CH₂(2-ClPh) |
| CH₃ | H | CH₂CH₃ | CH₃ | CH₂(2-(CH₃)Ph) |
| CH₃ | H | CH₂CH₃ | CH₃ | CH₂(2,6-Cl₂Ph) |
| CH₃ | H | CH₂CH₃ | CH₃ | CH₂(2-CF₃Ph) |
| CH₃ | H | CH₂CH₃ | CH₃ | CH₂(2-tetrahydropyran) |
| CH₃ | H | CH₂CH₃ | CH₃ | CH₂(2-pyridyl) |
| CH₃ | H | CH₂CH₃ | CH₃ | CH₂(Ph) |

TABLE 6-continued

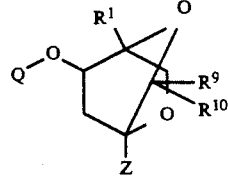

Z = C(R³)(R⁴)OR⁵

| $R^1$ | $R^3 = R^4$ | $R^9 = R^{10}$ | $R^5$ | Q |
|---|---|---|---|---|
| CH₃ | CH₃ | H | CH₃ | Q-1 |
| CH₃ | CH₃ | H | CH₃ | Q-3 |
| CH₃ | CH₃ | H | CH₃ | Q-6 |
| CH₃ | CH₃ | H | CH₃ | Q-7 |
| CH₃ | CH₃ | H | CH₃ | Q-15 |
| CH₃ | CH₃ | H | CH₃ | CH₂(2-FPh) |
| CH₃ | CH₃ | H | CH₃ | CH₂(2-ClPh) |
| CH₃ | CH₃ | H | CH₃ | CH₂(2-(CH₃)Ph) |
| CH₃ | CH₃ | H | CH₃ | CH₂(2,6-Cl₂Ph) |
| CH₃ | CH₃ | H | CH₃ | CH₂(2-CF₃Ph) |
| CH₃ | CH₃ | H | CH₃ | CH₂(2-tetrahydropyran) |
| CH₃ | CH₃ | H | CH₃ | CH₂(2-pyridyl) |
| CH₃ | CH₃ | H | CH₃ | CH₂(Ph) |

TABLE 7

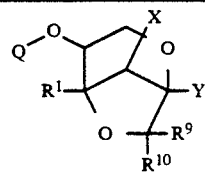

VII

X and Y are C(R³)(R⁴)OR⁵ (unless specified)

| $R^1$ | $R^3 = R^4$ | $R^9 = R^{10}$ | $R^5$ | Q | Y |
|---|---|---|---|---|---|
| H | CH₂CH₃ | CH₂CH₃ | CH₃ | CH₂(2-FPh) | H |
| H | CH₂CH₃ | CH₂CH₃ | CH₃ | CH₂(2-ClPh) | H |
| H | CH₂CH₃ | CH₂CH₃ | CH₃ | CH₂(2-BrPh) | H |
| H | CH₂CH₃ | CH₂CH₃ | CH₃ | CH₂(2-(CH₃)Ph) | H |
| H | CH₂CH₃ | CH₂CH₃ | CH₃ | CH₂(2-(OCH₃)Ph) | H |
| H | CH₂CH₃ | CH₂CH₃ | CH₃ | CH₂(2-(CN)Ph) | H |
| H | CH₂CH₃ | CH₂CH₃ | CH₃ | CH₂(2-(CF₃)Ph) | H |
| H | CH₂CH₃ | CH₂CH₃ | CH₃ | CH₂(2-(OCF₃)Ph) | H |
| H | CH₂CH₃ | CH₂CH₃ | CH₃ | CH₂(2-(SCH₃)Ph) | H |
| H | CH₂CH₃ | CH₂CH₃ | CH₃ | CH₂(2,6-(F)₂Ph) | H |
| H | CH₂CH₃ | CH₂CH₃ | CH₃ | CH₂(2,6-(Cl)₂Ph) | H |
| H | CH₂CH₃ | CH₂CH₃ | CH₃ | CH₂(2-pyridyl) | H |
| H | CH₂CH₃ | CH₂CH₃ | CH₃ | CH₂(2-furanyl) | H |
| H | CH₂CH₃ | CH₂CH₃ | CH₃ | CH₂(2-tetrahydrofuran) | H |
| H | CH₂CH₃ | CH₂CH₃ | CH₃ | CH₂(2-tetrahydropyran) | H |
| H | CH₂CH₃ | CH₂CH₃ | CH₃ | CH₂(2-thiophenyl) | H |
| H | CH₂CH₃ | CH₂CH₃ | CH₃ | CH₂(2-isoxazolyl) | H |
| H | CH₂CH₃ | CH₂CH₃ | CH₃ | CH₂(2-pyrazinyl) | H |
| H | CH₂CH₃ | CH₂CH₃ | CH₃ | CH₂(Ph) | H |
| H | CH₂CH₃ | CH₂CH₃ | CH₃ | Q-1 | H |
| H | CH₂CH₃ | CH₂CH₃ | CH₃ | Q-3 | H |
| H | CH₂CH₃ | CH₂CH₃ | CH₃ | Q-6 | H |
| H | CH₂CH₃ | CH₂CH₃ | CH₃ | Q-7 | H |
| H | CH₂CH₃ | CH₂CH₃ | CH₃ | Q-15 | H |
| H | CH₂CH₃ | CH₂CH₃ | CH₂CH₃ | CH₂(2-FPh) | H |
| H | CH₂CH₃ | CH₂CH₃ | CH₂CH₃ | CH₂(2-ClPh) | H |
| H | CH₂CH₃ | CH₂CH₃ | CH₂CH₃ | CH₂(2-(CH₃)Ph) | H |
| H | CH₂CH₃ | CH₂CH₃ | CH₂CH₃ | CH₂(2,6-Cl₂Ph) | H |
| H | CH₂CH₃ | CH₂CH₃ | CH₂CH₃ | CH₂(2-CF₃Ph) | H |
| H | CH₂CH₃ | CH₂CH₃ | CH₂CH₃ | CH₂(2-tetrahydropyran) | H |
| H | CH₂CH₃ | CH₂CH₃ | CH₂CH₃ | CH₂(2-pyridyl) | H |
| H | CH₂CH₃ | CH₂CH₃ | CH₂CH₃ | CH₂(Ph) | H |
| H | CH₂CH₃ | CH₂CH₃ | CH₂CH₃ | Q-1 | H |
| H | CH₂CH₃ | CH₂CH₃ | CH₂CH₃ | Q-3 | H |
| H | CH₂CH₃ | CH₂CH₃ | CH₂CH₃ | Q-6 | H |
| H | CH₂CH₃ | CH₂CH₃ | CH₂CH₃ | Q-7 | H |
| H | CH₂CH₃ | CH₂CH₃ | CH₂CH₃ | Q-15 | H |
| H | CH₂CH₃ | CH₂CH₃ | CH₂CH=CH₂ | CH₂(2-FPh) | H |
| H | CH₂CH₃ | CH₂CH₃ | CH₂CH=CH₂ | CH₂(2-ClPh) | H |

TABLE 7-continued

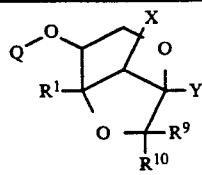

VII

X and Y are $C(R^3)(R^4)OR^5$ (unless specified)

| | | | | | |
|---|---|---|---|---|---|
| H | $CH_2CH_3$ | $CH_2CH_3$ | $CH_2CH=CH_2$ | $CH_2(2\text{-}(CH_3)Ph)$ | H |
| H | $CH_2CH_3$ | $CH_2CH_3$ | $CH_2CH=CH_2$ | $CH_2(2,6\text{-}Cl_2Ph)$ | H |
| H | $CH_2CH_3$ | $CH_2CH_3$ | $CH_2CH=CH_2$ | $CH_2(2\text{-}CF_3Ph)$ | H |
| H | $CH_2CH_3$ | $CH_2CH_3$ | $CH_2CH=CH_2$ | $CH_2(2\text{-tetrahydropyran})$ | H |
| H | $CH_2CH_3$ | $CH_2CH_3$ | $CH_2CH=CH_2$ | $CH_2(2\text{-pyridyl})$ | H |
| H | $CH_2CH_3$ | $CH_2CH_3$ | $CH_2CH=CH_2$ | $CH_2(Ph)$ | H |
| H | $CH_2CH_3$ | $CH_2CH_3$ | $CH_2CH=CH_2$ | Q-1 | H |
| H | $CH_2CH_3$ | $CH_2CH_3$ | $CH_2CH=CH_2$ | Q-3 | H |
| H | $CH_2CH_3$ | $CH_2CH_3$ | $CH_2CH=CH_2$ | Q-6 | H |
| H | $CH_2CH_3$ | $CH_2CH_3$ | $CH_2CH=CH_2$ | Q-7 | H |
| H | $CH_2CH_3$ | $CH_2CH_3$ | $CH_2CH=CH_2$ | Q-15 | H |
| H | H | H | $CH_3$ | $CH_2(2\text{-}FPh)$ | H |
| H | H | H | $CH_3$ | $CH_2(2\text{-}ClPh)$ | H |
| H | H | H | $CH_3$ | $CH_2(2\text{-}(CH_3)Ph)$ | H |
| H | H | H | $CH_3$ | $CH_2(2,6\text{-}Cl_2Ph)$ | H |
| H | H | H | $CH_3$ | $CH_2(2\text{-}CF_3Ph)$ | H |
| H | H | H | $CH_3$ | $CH_2(2\text{-tetrahydropyran})$ | H |
| H | H | H | $CH_3$ | $CH_2(2\text{-pyridyl})$ | H |
| H | H | H | $CH_3$ | $CH_2(Ph)$ | H |
| H | H | H | $CH_3$ | Q-1 | H |
| H | H | H | $CH_3$ | Q-3 | H |
| H | H | H | $CH_3$ | Q-6 | H |
| H | H | H | $CH_3$ | Q-7 | H |
| H | H | H | $CH_3$ | Q-15 | H |
| H | $CH_3$ | $CH_3$ | $CH_3$ | $CH_2(2\text{-}FPh)$ | H |
| H | $CH_3$ | $CH_3$ | $CH_3$ | $CH_2(2\text{-}ClPh)$ | H |
| H | $CH_3$ | $CH_3$ | $CH_3$ | $CH_2(2\text{-}(CH_3)Ph)$ | H |
| H | $CH_3$ | $CH_3$ | $CH_3$ | $CH_2(2,6\text{-}Cl_2Ph)$ | H |
| H | $CH_3$ | $CH_3$ | $CH_3$ | $CH_2(2\text{-}CF_3Ph)$ | H |
| H | $CH_3$ | $CH_3$ | $CH_3$ | $CH_2(2\text{-tetrahydropyran})$ | H |
| H | $CH_3$ | $CH_3$ | $CH_3$ | $CH_2(2\text{-pyridyl})$ | H |
| H | $CH_3$ | $CH_3$ | $CH_3$ | $CH_2(Ph)$ | H |
| H | $CH_3$ | $CH_3$ | $CH_3$ | Q-1 | H |
| H | $CH_3$ | $CH_3$ | $CH_3$ | Q-3 | H |
| H | $CH_3$ | $CH_3$ | $CH_3$ | Q-6 | H |
| H | $CH_3$ | $CH_3$ | $CH_3$ | Q-7 | H |
| H | $CH_3$ | $CH_3$ | $CH_3$ | Q-15 | H |
| $CH_3$ | $CH_2CH_3$ | $CH_2CH_3$ | $CH_3$ | $CH_2(2\text{-}FPh)$ | H |
| $CH_3$ | $CH_2CH_3$ | $CH_2CH_3$ | $CH_3$ | $CH_2(2\text{-}ClPh)$ | H |
| $CH_3$ | $CH_2CH_3$ | $CH_2CH_3$ | $CH_3$ | $CH_2(2\text{-}(CH_3)Ph)$ | H |
| $CH_3$ | $CH_2CH_3$ | $CH_2CH_3$ | $CH_3$ | $CH_2(2,6\text{-}Cl_2Ph)$ | H |
| $CH_3$ | $CH_2CH_3$ | $CH_2CH_3$ | $CH_3$ | $CH_2(2\text{-}CF_3Ph)$ | H |
| $CH_3$ | $CH_2CH_3$ | $CH_2CH_3$ | $CH_3$ | $CH_2(2\text{-tetrahydropyran})$ | H |
| $CH_3$ | $CH_2CH_3$ | $CH_2CH_3$ | $CH_3$ | $CH_2(2\text{-pyridyl})$ | H |
| $CH_3$ | $CH_2CH_3$ | $CH_2CH_3$ | $CH_3$ | $CH_2(Ph)$ | H |
| $CH_3$ | $CH_2CH_3$ | $CH_2CH_3$ | $CH_3$ | Q-1 | H |
| $CH_3$ | $CH_2CH_3$ | $CH_2CH_3$ | $CH_3$ | Q-3 | H |
| $CH_3$ | $CH_2CH_3$ | $CH_2CH_3$ | $CH_3$ | Q-6 | H |
| $CH_3$ | $CH_2CH_3$ | $CH_2CH_3$ | $CH_3$ | Q-7 | H |
| $CH_3$ | $CH_2CH_3$ | $CH_2CH_3$ | $CH_3$ | Q-15 | H |
| $CH_2CH_3$ | $CH_2CH_3$ | $CH_2CH_3$ | $CH_3$ | $CH_2(2\text{-}FPh)$ | H |
| $CH_2CH_3$ | $CH_2CH_3$ | $CH_2CH_3$ | $CH_3$ | $CH_2(2\text{-}ClPh)$ | H |
| $CH_2CH_3$ | $CH_2CH_3$ | $CH_2CH_3$ | $CH_3$ | $CH_2(2\text{-}(CH_3)Ph)$ | H |
| $CH_2CH_3$ | $CH_2CH_3$ | $CH_2CH_3$ | $CH_3$ | $CH_2(2,6\text{-}Cl_2Ph)$ | H |
| $CH_2CH_3$ | $CH_2CH_3$ | $CH_2CH_3$ | $CH_3$ | $CH_2(2\text{-}CF_3Ph)$ | H |
| $CH_2CH_3$ | $CH_2CH_3$ | $CH_2CH_3$ | $CH_3$ | $CH_2(2\text{-tetrahydropyran})$ | H |
| $CH_2CH_3$ | $CH_2CH_3$ | $CH_2CH_3$ | $CH_3$ | $CH_2(2\text{-pyridyl})$ | H |
| $CH_2CH_3$ | $CH_2CH_3$ | $CH_2CH_3$ | $CH_3$ | $CH_2(Ph)$ | H |
| $CH_2CH_3$ | $CH_2CH_3$ | $CH_2CH_3$ | $CH_3$ | Q-1 | H |
| $CH_2CH_3$ | $CH_2CH_3$ | $CH_2CH_3$ | $CH_3$ | Q-3 | H |
| $CH_2CH_3$ | $CH_2CH_3$ | $CH_2CH_3$ | $CH_3$ | Q-6 | H |
| $CH_2CH_3$ | $CH_2CH_3$ | $CH_2CH_3$ | $CH_3$ | Q-7 | H |
| $CH_2CH_3$ | $CH_2CH_3$ | $CH_2CH_3$ | $CH_3$ | Q-15 | H |
| H | $CH_3$ | H | $CH_3$ | $CH_2(2\text{-}FPh)$ | H |
| H | $CH_3$ | H | $CH_3$ | $CH_2(2\text{-}ClPh)$ | H |
| H | $CH_3$ | H | $CH_3$ | $CH_2(2\text{-}(CH_3)Ph)$ | H |
| H | $CH_3$ | H | $CH_3$ | $CH_2(2,6\text{-}Cl_2Ph)$ | H |
| H | $CH_3$ | H | $CH_3$ | $CH_2(2\text{-}CF_3Ph)$ | H |
| H | $CH_3$ | H | $CH_3$ | $CH_2(2\text{-tetrahydropyran})$ | H |
| H | $CH_3$ | H | $CH_3$ | $CH_2(2\text{-pyridyl})$ | H |

TABLE 7-continued

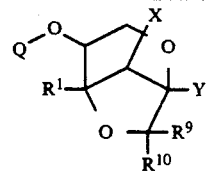

VII

X and Y are C(R³)(R⁴)OR⁵ (unless specified)

| | | | | | |
|---|---|---|---|---|---|
| H | CH₃ | H | CH₃ | CH₂(Ph) | H |
| H | CH₃ | H | CH₃ | Q-1 | H |
| H | CH₃ | H | CH₃ | Q-3 | H |
| H | CH₃ | H | CH₃ | Q-6 | H |
| H | CH₃ | H | CH₃ | Q-7 | H |
| H | CH₃ | H | CH₃ | Q-15 | H |
| CH₃ | H | CH₃ | CH₃ | CH₂(2-FPh) | H |
| CH₃ | H | CH₃ | CH₃ | CH₂(2-ClPh) | H |
| CH₃ | H | CH₃ | CH₃ | CH₂(2-(CH₃)Ph) | H |
| CH₃ | H | CH₃ | CH₃ | CH₂(2,6-Cl₂Ph) | H |
| CH₃ | H | CH₃ | CH₃ | CH₂(2-CF₃Ph) | H |
| CH₃ | H | CH₃ | CH₃ | CH₂(2-tetrahydropyran) | H |
| CH₃ | H | CH₃ | CH₃ | CH₂(2-pyridyl) | H |
| CH₃ | H | CH₃ | CH₃ | CH₂(Ph) | H |
| CH₃ | H | CH₃ | CH₃ | Q-1 | H |
| CH₃ | H | CH₃ | CH₃ | Q-3 | H |
| CH₃ | H | CH₃ | CH₃ | Q-6 | H |
| CH₃ | H | CH₃ | CH₃ | Q-7 | H |
| CH₃ | H | CH₃ | CH₃ | Q-15 | H |
| CH₃ | H | H | CH₃ | CH₂(2-FPh) | H |
| CH₃ | H | H | CH₃ | CH₂(2-ClPh) | H |
| CH₃ | H | H | CH₃ | CH₂(2-(CH₃)Ph) | H |
| CH₃ | H | H | CH₃ | CH₂(2,6-Cl₂Ph) | H |
| CH₃ | H | H | CH₃ | CH₂(2-CF₃Ph) | H |
| CH₃ | H | H | CH₃ | CH₂(2-tetrahydropyran) | H |
| CH₃ | H | H | CH₃ | CH₂(2-pyridyl) | H |
| CH₃ | H | H | CH₃ | CH₂(Ph) | H |
| CH₃ | H | H | CH₃ | Q-1 | H |
| CH₃ | H | H | CH₃ | Q-3 | H |
| CH₃ | H | H | CH₃ | Q-6 | H |
| CH₃ | H | H | CH₃ | Q-7 | H |
| CH₃ | H | H | CH₃ | Q-15 | H |
| CH₃ | CH₃ | CH₃ | CH₃ | CH₂(2-FPh) | H |
| CH₃ | CH₃ | CH₃ | CH₃ | CH₂(2-ClPh) | H |
| CH₃ | CH₃ | CH₃ | CH₃ | CH₂(2-(CH₃)Ph) | H |
| CH₃ | CH₃ | CH₃ | CH₃ | CH₂(2,6-Cl₂Ph) | H |
| CH₃ | CH₃ | CH₃ | CH₃ | CH₂(2-CF₃Ph) | H |
| CH₃ | CH₃ | CH₃ | CH₃ | CH₂(2-tetrahydropyran) | H |
| CH₃ | CH₃ | CH₃ | CH₃ | CH₂(2-pyridyl) | H |
| CH₃ | CH₃ | CH₃ | CH₃ | CH₂(Ph) | H |
| CH₃ | CH₃ | CH₃ | CH₃ | Q-1 | H |
| CH₃ | CH₃ | CH₃ | CH₃ | Q-3 | H |
| CH₃ | CH₃ | CH₃ | CH₃ | Q-6 | H |
| CH₃ | CH₃ | CH₃ | CH₃ | Q-7 | H |
| CH₃ | CH₃ | CH₃ | CH₃ | Q-15 | H |

| R¹ | R³ = R⁴ | R⁹ = R¹⁰ | R⁵ | Q | X |
|---|---|---|---|---|---|
| CH₃ | H | H | CH₃ | CH₂(2-FPh | H |
| CH₃ | H | H | CH₃ | CH₂(2-ClPh) | H |
| CH₃ | H | H | CH₃ | CH₂(2-BrPh) | H |
| CH₃ | H | H | CH₃ | CH₂(2-(CH₃)Ph) | H |
| CH₃ | H | H | CH₃ | CH₂(2-(OCH₃)Ph) | H |
| CH₃ | H | H | CH₃ | CH₂(2-(CN)Ph) | H |
| CH₃ | H | H | CH₃ | CH₂(2-(CF₃)Ph) | H |
| CH₃ | H | H | CH₃ | CH₂(2-(OCF₃)Ph) | H |
| CH₃ | H | H | CH₃ | CH₂(2-(SCH₃)Ph) | H |
| CH₃ | H | H | CH₃ | CH₂(2,6-(F)₂Ph) | H |
| CH₃ | H | H | CH₃ | CH₂(2,6-(Cl)₂Ph) | H |
| CH₃ | H | H | CH₃ | CH₂(2-pyridyl) | H |
| CH₃ | H | H | CH₃ | CH₂(2-furanyl) | H |
| CH₃ | H | H | CH₃ | CH₂(2-tetrahydrofuran) | H |
| CH₃ | H | H | CH₃ | CH₂(2-tetrahydropyran) | H |
| CH₃ | H | H | CH₃ | CH₂(2-thiophenyl) | H |
| CH₃ | H | H | CH₃ | CH₂(2-isoxazolyl) | H |
| CH₃ | H | H | CH₃ | CH₂(2-pyrazinyl) | H |
| CH₃ | H | H | CH₃ | CH₂(Ph) | H |
| CH₃ | H | H | CH₃ | Q-1 | H |
| CH₃ | H | H | CH₃ | Q-3 | H |
| CH₃ | H | H | CH₃ | Q-6 | H |
| CH₃ | H | H | CH₃ | Q-7 | H |

TABLE 7-continued

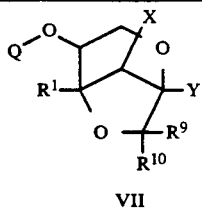

VII

X and Y are C(R³)(R⁴)OR⁵ (unless specified)

| | | | | | |
|---|---|---|---|---|---|
| CH₃ | H | H | CH₃ | Q-15 | H |
| CH₃ | H | H | CH₂CH₃ | CH₂(2-FPh) | H |
| CH₃ | H | H | CH₂CH₃ | CH₂(2-ClPh) | H |
| CH₃ | H | H | CH₂CH₃ | CH₂(2-(CH₃)Ph) | H |
| CH₃ | H | H | CH₂CH₃ | CH₂(2,6-Cl₂Ph) | H |
| CH₃ | H | H | CH₂CH₃ | CH₂(2-CF₃Ph) | H |
| CH₃ | H | H | CH₂CH₃ | CH₂(2-tetrahydropyran) | H |
| CH₃ | H | H | CH₂CH₃ | CH₂(2-pyridyl) | H |
| CH₃ | H | H | CH₂CH₃ | CH₂(Ph) | H |
| CH₃ | H | H | CH₂CH₃ | Q-1 | H |
| CH₃ | H | H | CH₂CH₃ | Q-3 | H |
| CH₃ | H | H | CH₂CH₃ | Q-6 | H |
| CH₃ | H | H | CH₂CH₃ | Q-7 | H |
| CH₃ | H | H | CH₂CH₃ | Q-15 | H |
| CH₃ | H | H | CH₂CH=CH₂ | CH₂(2-FPh) | H |
| CH₃ | H | H | CH₂CH=CH₂ | CH₂(2-ClPh) | H |
| CH₃ | H | H | CH₂CH=CH₂ | CH₂(2-(CH₃)Ph) | H |
| CH₃ | H | H | CH₂CH=CH₂ | CH₂(2,6-Cl₂Ph) | H |
| CH₃ | H | H | CH₂CH=CH₂ | CH₂(2-CF₃Ph) | H |
| CH₃ | H | H | CH₂CH=CH₂ | CH₂(2-tetrahydropyran) | H |
| CH₃ | H | H | CH₂CH=CH₂ | CH₂(2-pyridyl) | H |
| CH₃ | H | H | CH₂CH=CH₂ | CH₂(Ph) | H |
| CH₃ | H | H | CH₂CH=CH₂ | Q-1 | H |
| CH₃ | H | H | CH₂CH=CH₂ | Q-3 | H |
| CH₃ | H | H | CH₂CH=CH₂ | Q-6 | H |
| CH₃ | H | H | CH₂CH=CH₂ | Q-7 | H |
| CH₃ | H | H | CH₂CH=CH₂ | Q-15 | H |
| CH₃CH₂ | H | H | CH₃ | CH₂(2-FPh) | H |
| CH₃CH₂ | H | H | CH₃ | CH₂(2-ClPh) | H |
| CH₃CH₂ | H | H | CH₃ | CH₂(2-(CH₃)Ph) | H |
| CH₃CH₂ | H | H | CH₃ | CH₂(2,6-Cl₂Ph) | H |
| CH₃CH₂ | H | H | CH₃ | CH₂(2-CF₃Ph) | H |
| CH₃CH₂ | H | H | CH₃ | CH₂(2-tetrahydropyran) | H |
| CH₃CH₂ | H | H | CH₃ | CH₂(2-pyridyl) | H |
| CH₃CH₂ | H | H | CH₃ | CH₂(Ph) | H |
| CH₃CH₂ | H | H | CH₃ | Q-1 | H |
| CH₃CH₂ | H | H | CH₃ | Q-3 | H |
| CH₃CH₂ | H | H | CH₃ | Q-6 | H |
| CH₃CH₂ | H | H | CH₃ | Q-7 | H |
| CH₃CH₂ | H | H | CH₃ | Q-15 | H |
| CH₃ | CH₃ | CH₃ | CH₃ | CH₂(2-FPh) | H |
| CH₃ | CH₃ | CH₃ | CH₃ | CH₂(2-ClPh) | H |
| CH₃ | CH₃ | CH₃ | CH₃ | CH₂(2-(CH₃)Ph) | H |
| CH₃ | CH₃ | CH₃ | CH₃ | CH₂(2,6-Cl₂Ph) | H |
| CH₃ | CH₃ | CH₃ | CH₃ | CH₂(2-CF₃Ph) | H |
| CH₃ | CH₃ | CH₃ | CH₃ | CH₂(2-tetrahydropyran) | H |
| CH₃ | CH₃ | CH₃ | CH₃ | CH₂(2-pyridyl) | H |
| CH₃ | CH₃ | CH₃ | CH₃ | CH₂(Ph) | H |
| CH₃ | CH₃ | CH₃ | CH₃ | Q-1 | H |
| CH₃ | CH₃ | CH₃ | CH₃ | Q-3 | H |
| CH₃ | CH₃ | CH₃ | CH₃ | Q-6 | H |
| CH₃ | CH₃ | CH₃ | CH₃ | Q-7 | H |
| CH₃ | CH₃ | CH₃ | CH₃ | Q-15 | H |
| CH₃ | CH₂CH₃ | CH₂CH₃ | CH₃ | CH₂(2-FPh) | H |
| CH₃ | CH₂CH₃ | CH₂CH₃ | CH₃ | CH₂(2-ClPh) | H |
| CH₃ | CH₂CH₃ | CH₂CH₃ | CH₂CH₃ | CH₂(2-(CH₃)Ph) | H |
| CH₃ | CH₂CH₃ | CH₂CH₃ | CH₂CH₃ | CH₂(2,6-Cl₂Ph) | H |
| CH₃ | CH₃ | CH₃ | CH₃ | CH₂(2,6-(F)₂Ph) | H |
| CH₃ | CH₃ | CH₃ | CH₃ | CH₂(2,4-(F)₂Ph) | H |
| CH₃ | CH₂CH₃ | CH₂CH₃ | CH₃ | CH₂(2-tetrahydropyran) | H |
| CH₃ | CH₂CH₃ | CH₂CH₃ | CH₃ | CH₂(2-pyridyl) | H |
| CH₃ | CH₂CH₃ | CH₂CH₃ | CH₃ | CH₂(Ph) | H |
| CH₃ | CH₂CH₃ | CH₂CH₃ | CH₃ | Q-1 | H |
| CH₃ | CH₂CH₃ | CH₂CH₃ | CH₃ | Q-3 | H |
| CH₃ | CH₂CH₃ | CH₂CH₃ | CH₃ | Q-6 | H |
| CH₃ | CH₂CH₃ | CH₂CH₃ | CH₃ | Q-7 | H |
| CH₃ | CH₂CH₃ | CH₂CH₃ | CH₃ | Q-15 | H |
| CH₃ | CH₂CH₃ | CH₂CH₃ | CH₃ | CH₂(2,6-(F)₂Ph) | H |
| CH₂CH₃ | CH₂CH₃ | CH₂CH₃ | CH₃ | CH₂(2-FPh) | H |
| CH₂CH₃ | CH₂CH₃ | CH₂CH₃ | CH₃ | CH₂(2-ClPh) | H |

TABLE 7-continued

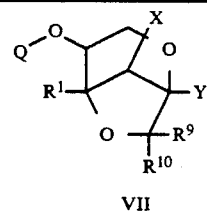

VII

X and Y are C(R³)(R⁴)OR⁵ (unless specified)

| | | | | | |
|---|---|---|---|---|---|
| CH₂CH₃ | CH₂CH₃ | CH₂CH₃ | CH₃ | CH₂(2-(CH₃)Ph) | H |
| CH₂CH₃ | CH₂CH₃ | CH₂CH₃ | CH₃ | CH₂(2,6-Cl₂Ph) | H |
| CH₂CH₃ | CH₂CH₃ | CH₂CH₃ | CH₃ | CH₂(2-CF₃Ph) | H |
| CH₂CH₃ | CH₂CH₃ | CH₂CH₃ | CH₃ | CH₂(2-tetrahydropyran) | H |
| CH₂CH₃ | CH₂CH₃ | CH₂CH₃ | CH₃ | CH₂(2-pyridyl) | H |
| CH₂CH₃ | CH₂CH₃ | CH₂CH₃ | CH₃ | CH₂(Ph) | H |
| CH₂CH₃ | CH₂CH₃ | CH₂CH₃ | CH₃ | Q-1 | H |
| CH₂CH₃ | CH₂CH₃ | CH₂CH₃ | CH₃ | Q-3 | H |
| CH₂CH₃ | CH₂CH₃ | CH₂CH₃ | CH₃ | Q-6 | H |
| CH₂CH₃ | CH₂CH₃ | CH₂CH₃ | CH₃ | Q-7 | H |
| CH₂CH₃ | CH₂CH₃ | CH₂CH₃ | CH₃ | Q-15 | H |
| CH₃ | CH₃ | H | CH₃ | CH₂(2-FPh) | H |
| CH₃ | CH₃ | H | CH₃ | CH₂(2-ClPh) | H |
| CH₃ | CH₃ | H | CH₃ | CH₂(2-(CH₃)Ph) | H |
| CH₃ | CH₃ | H | CH₃ | CH₂(2,6-Cl₂Ph) | H |
| CH₃ | CH₃ | H | CH₃ | CH₂(2-CF₃Ph) | H |
| CH₃ | CH₃ | H | CH₃ | CH₂(2-tetrahydropyran) | H |
| CH₃ | CH₃ | H | CH₃ | CH₂(2-pyridyl) | H |
| CH₃ | CH₃ | H | CH₃ | CH₂(Ph) | H |
| CH₃ | CH₃ | H | CH₃ | Q-1 | H |
| CH₃ | CH₃ | H | CH₃ | Q-3 | H |
| CH₃ | CH₃ | H | CH₃ | Q-6 | H |
| CH₃ | CH₃ | H | CH₃ | Q-7 | H |
| CH₃ | CH₃ | H | CH₃ | Q-15 | H |
| CH₃ | H | CH₃ | CH₃ | CH₂(2-FPh) | H |
| CH₃ | H | CH₃ | CH₃ | CH₂(2-ClPh) | H |
| CH₃ | H | CH₃ | CH₃ | CH₂(2-(CH₃)Ph) | H |
| CH₃ | H | CH₃ | CH₃ | CH₂(2,6-Cl₂Ph) | H |
| CH₃ | H | CH₃ | CH₃ | CH₂(2-CF₃Ph) | H |
| CH₃ | H | CH₃ | CH₃ | CH₂(2-tetrahydropyran) | H |
| CH₃ | H | CH₃ | CH₃ | CH₂(2-pyridyl) | H |
| CH₃ | H | CH₃ | CH₃ | CH₂(Ph) | H |
| CH₃ | H | CH₃ | CH₃ | Q-1 | H |
| CH₃ | H | CH₃ | CH₃ | Q-3 | H |
| CH₃ | H | CH₃ | CH₃ | Q-6 | H |
| CH₃ | H | CH₃ | CH₃ | Q-7 | H |
| CH₃ | H | CH₃ | CH₃ | Q-15 | H |
| CH₃ | H | CH₂CH₃ | CH₃ | CH₂(2-FPh) | H |
| CH₃ | H | CH₂CH₃ | CH₃ | CH₂(2-ClPh) | H |
| CH₃ | H | CH₂CH₃ | CH₃ | CH₂(2-(CH₃)Ph) | H |
| CH₃ | H | CH₂CH₃ | CH₃ | CH₂(2,6-Cl₂Ph) | H |
| CH₃ | H | CH₂CH₃ | CH₃ | CH₂(2-CF₃Ph) | H |
| CH₃ | H | CH₂CH₃ | CH₃ | CH₂(2-tetrahydropyran) | H |
| CH₃ | H | CH₂CH₃ | CH₃ | CH₂(2-pyridyl) | H |
| CH₃ | H | CH₂CH₃ | CH₃ | CH₂(Ph) | H |
| CH₃ | H | CH₂CH₃ | CH₃ | Q-1 | H |
| CH₃ | H | CH₂CH₃ | CH₃ | Q-3 | H |
| CH₃ | H | CH₂CH₃ | CH₃ | Q-6 | H |
| CH₃ | H | CH₂CH₃ | CH₃ | Q-7 | H |
| CH₃ | H | CH₂CH₃ | CH₃ | Q-15 | H |
| CH₂CH₃ | CH₃ | CH₃ | CH₃ | CH₂(2-FPh) | H |
| CH₂CH₃ | CH₃ | CH₃ | CH₃ | CH₂(2-ClPh) | H |
| CH₂CH₃ | CH₃ | CH₃ | CH₃ | CH₂(2-(CH₃)Ph) | H |
| CH₂CH₃ | CH₃ | CH₃ | CH₃ | CH₂(2,6-Cl₂Ph) | H |
| CH₂CH₃ | CH₃ | CH₃ | CH₃ | CH₂(2-CF₃Ph) | H |
| CH₂CH₃ | CH₃ | CH₃ | CH₃ | CH₂(2-tetrahydropyran) | H |
| CH₂CH₃ | CH₃ | CH₃ | CH₃ | CH₂(2-pyridyl) | H |
| CH₂CH₃ | CH₃ | CH₃ | CH₃ | CH₂(Ph) | H |
| CH₂CH₃ | CH₃ | CH₃ | CH₃ | Q-1 | H |
| CH₂CH₃ | CH₃ | CH₃ | CH₃ | Q-3 | H |
| CH₂CH₃ | CH₃ | CH₃ | CH₃ | Q-6 | H |
| CH₂CH₃ | CH₃ | CH₃ | CH₃ | Q-7 | H |
| CH₂CH₃ | CH₃ | CH₃ | CH₃ | Q-15 | H |
| H | H | H | CH₃ | CH₂(2-FPh) | H |
| H | H | H | CH₃ | CH₂(2-ClPh) | H |
| H | H | H | CH₃ | CH₂(2-(CH₃)Ph) | H |
| H | H | H | CH₃ | CH₂(2,6-Cl₂Ph) | H |
| H | H | H | CH₃ | CH₂(2-CF₃Ph) | H |
| H | H | H | CH₃ | CH₂(2-tetrahydropyran) | H |
| H | H | H | CH₃ | CH₂(2-pyridyl) | H |

TABLE 7-continued

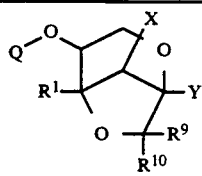

VII

X and Y are C(R³)(R⁴)OR⁵ (unless specified)

| | | | | | |
|---|---|---|---|---|---|
| H | H | H | CH₃ | CH₂(Ph) | H |
| H | H | H | CH₃ | Q-1 | H |
| H | H | H | CH₃ | Q-3 | H |
| H | H | H | CH₃ | Q-6 | H |
| H | H | H | CH₃ | Q-7 | H |
| H | H | H | CH₃ | Q-15 | H |

TABLE 8

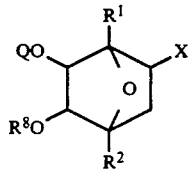

VIII $X = C(R^3)(R^4)OR^5$

| $R^1$ | $R^2$ | $R^3$ | $R^4$ | $R^5$ | Q | $R^8$ |
|---|---|---|---|---|---|---|
| H | H | CH₂CH₃ | CH₂CH₃ | CH₃ | CH₂(2-FPh) | CH₃ |
| H | H | CH₂CH₃ | CH₂CH₃ | CH₃ | CH₂(2-ClPh) | CH₃ |
| H | H | CH₂CH₃ | CH₂CH₃ | CH₃ | CH₂(2-BrPh) | CH₃ |
| H | H | CH₂CH₃ | CH₂CH₃ | CH₃ | CH₂(2-(CH₃)Ph) | CH₃ |
| H | H | CH₂CH₃ | CH₂CH₃ | CH₃ | CH₂(2-(OCH₃)Ph) | CH₃ |
| H | H | CH₂CH₃ | CH₂CH₃ | CH₃ | CH₂(2-(CN)Ph) | CH₃ |
| H | H | CH₂CH₃ | CH₂CH₃ | CH₃ | CH₂(2-CF₃)Ph) | CH₃ |
| H | H | CH₂CH₃ | CH₂CH₃ | CH₃ | CH₂(2-(OCF₃)Ph) | CH₃ |
| H | H | CH₂CH₃ | CH₂CH₃ | CH₃ | CH₂(2-(SCH₃)Ph) | CH₃ |
| H | H | CH₂CH₃ | CH₂CH₃ | CH₃ | CH₂(2,6-(F)₂Ph) | CH₃ |
| H | H | CH₂CH₃ | CH₂CH₃ | CH₃ | CH₂(2,6-(Cl)₂Ph) | CH₃ |
| H | H | CH₂CH₃ | CH₂CH₃ | CH₃ | CH₂(2-pyridyl) | CH₃ |
| H | H | CH₂CH₃ | CH₂CH₃ | CH₃ | CH₂(2-furanyl) | CH₃ |
| H | H | CH₂CH₃ | CH₂CH₃ | CH₃ | CH₂(2-tetrahydrofuran) | CH₃ |
| H | H | CH₂CH₃ | CH₂CH₃ | CH₃ | CH₂(2-tetrahydropyran) | CH₃ |
| H | H | CH₂CH₃ | CH₂CH₃ | CH₃ | CH₂(2-thiophenyl) | CH₃ |
| H | H | CH₂CH₃ | CH₂CH₃ | CH₃ | CH₂(2-isoxazolyl) | CH₃ |
| H | H | CH₂CH₃ | CH₂CH₃ | CH₃ | CH₂(2-pyrazinyl) | CH₃ |
| H | H | CH₂CH₃ | CH₂CH₃ | CH₃ | CH₂(Ph) | CH₃ |
| H | H | CH₂CH₃ | CH₂CH₃ | CH₃ | Q-1 | CH₃ |
| H | H | CH₂CH₃ | CH₂CH₃ | CH₃ | Q-3 | CH₃ |
| H | H | CH₂CH₃ | CH₂CH₃ | CH₃ | Q-6 | CH₃ |
| H | H | CH₂CH₃ | CH₂CH₃ | CH₃ | Q-7 | CH₃ |
| H | H | CH₂CH₃ | CH₂CH₃ | CH₃ | Q-15 | CH₃ |
| H | H | CH₂CH₃ | CH₂CH₃ | CH₂CH₃ | CH₂(2-FPh) | CH₂CH₃ |
| H | H | CH₂CH₃ | CH₂CH₃ | CH₂CH₃ | CH₂(2-ClPh) | CH₂CH₃ |
| H | H | CH₂CH₃ | CH₂CH₃ | CH₂CH₃ | CH₂(2-(CH₃)Ph) | CH₂CH₃ |
| H | H | CH₂CH₃ | CH₂CH₃ | CH₂CH₃ | CH₂(2,6-Cl₂Ph) | CH₂CH₃ |
| H | H | CH₂CH₃ | CH₂CH₃ | CH₂CH₃ | CH₂(2-CF₃Ph) | CH₂CH₃ |
| H | H | CH₂CH₃ | CH₂CH₃ | CH₂CH₃ | CH₂(2-tetrahydropyran) | CH₂CH₃ |
| H | H | CH₂CH₃ | CH₂CH₃ | CH₂CH₃ | CH₂(2-pyridyl) | CH₂CH₃ |
| H | H | CH₂CH₃ | CH₂CH₃ | CH₂CH₃ | CH₂(Ph) | CH₂CH₃ |
| H | H | CH₂CH₃ | CH₂CH₃ | CH₂CH₃ | Q-1 | CH₂CH₃ |
| H | H | CH₂CH₃ | CH₂CH₃ | CH₂CH₃ | Q-3 | CH₂CH₃ |
| H | H | CH₂CH₃ | CH₂CH₃ | CH₂CH₃ | Q-6 | CH₂CH₃ |
| H | H | CH₂CH₃ | CH₂CH₃ | CH₂CH₃ | Q-7 | CH₂CH₃ |
| H | H | CH₂CH₃ | CH₂CH₃ | CH₂CH₃ | Q-15 | CH₂CH₃ |
| H | H | CH₂CH₃ | CH₂CH₃ | CH₂CH=CH₂ | CH₂(2-FPh) | CH₂CH=CH₂ |
| H | H | CH₂CH₃ | CH₂CH₃ | CH₂CH=CH₂ | CH₂(2-ClPh) | CH₂CH=CH₂ |
| H | H | CH₂CH₃ | CH₂CH₃ | CH₂CH=CH₂ | CH₂(2-(CH₃)Ph) | CH₂CH=CH₂ |
| H | H | CH₂CH₃ | CH₂CH₃ | CH₂CH=CH₂ | CH₂(2,6-Cl₂Ph) | CH₂CH=CH₂ |
| H | H | CH₂CH₃ | CH₂CH₃ | CH₂CH=CH₂ | CH₂(2-CF₃Ph) | CH₂CH=CH₂ |
| H | H | CH₂CH₃ | CH₂CH₃ | CH₂CH=CH₂ | CH₂(2-tetrahydropyran) | CH₂CH=CH₂ |
| H | H | CH₂CH₃ | CH₂CH₃ | CH₂CH=CH₂ | CH₂(2-pyridyl) | CH₂CH=CH₂ |
| H | H | CH₂CH₃ | CH₂CH₃ | CH₂CH=CH₂ | CH₂(Ph) | CH₂CH=CH₂ |
| H | H | CH₂CH₃ | CH₂CH₃ | CH₂CH=CH₂ | Q-1 | CH₂CH=CH₂ |
| H | H | CH₂CH₃ | CH₂CH₃ | CH₂CH=CH₂ | Q-3 | CH₂CH=CH₂ |
| H | H | CH₂CH₃ | CH₂CH₃ | CH₂CH=CH₂ | Q-6 | CH₂CH=CH₂ |

TABLE 8-continued

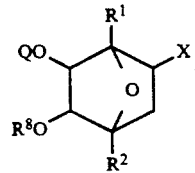

$X = C(R^3)(R^4)OR^5$

| $R^1$ | $R^2$ | $R^3$ | $R^4$ | $R^5$ | Q | $R^8$ |
|---|---|---|---|---|---|---|
| H | H | $CH_2CH_3$ | $CH_2CH_3$ | $CH_2CH=CH_2$ | Q-7 | $CH_2CH=CH_2$ |
| H | H | $CH_2CH_3$ | $CH_2CH_3$ | $CH_2CH=CH_2$ | Q-15 | $CH_2CH=CH_2$ |
| H | H | H | H | $CH_3$ | $CH_2$(2-FPh) | $CH_3$ |
| H | H | H | H | $CH_3$ | $CH_2$(2-ClPh) | $CH_3$ |
| H | H | H | H | $CH_3$ | $CH_2$(2-($CH_3$)Ph) | $CH_3$ |
| H | H | H | H | $CH_3$ | $CH_2$(2,6-$Cl_2$Ph) | $CH_3$ |
| H | H | H | H | $CH_3$ | $CH_2$(2-$CF_3$Ph) | $CH_3$ |
| H | H | H | H | $CH_3$ | $CH_2$(2-tetrahydropyran) | $CH_3$ |
| H | H | H | H | $CH_3$ | $CH_2$(2-pyridyl) | $CH_3$ |
| H | H | H | H | $CH_3$ | $CH_2$(Ph) | $CH_3$ |
| H | H | H | H | $CH_3$ | Q-1 | $CH_3$ |
| H | H | H | H | $CH_3$ | Q-3 | $CH_3$ |
| H | H | H | H | $CH_3$ | Q-6 | $CH_3$ |
| H | H | H | H | $CH_3$ | Q-7 | $CH_3$ |
| H | H | H | H | $CH_3$ | Q-15 | $CH_3$ |
| H | H | H | H | $CH_2CH_3$ | $CH_2$(2-FPh) | $CH_2CH_3$ |
| H | H | H | H | $CH_2CH_3$ | $CH_2$(2-ClPh) | $CH_2CH_3$ |
| H | H | H | H | $CH_2CH_3$ | $CH_2$(2-($CH_3$)Ph) | $CH_2CH_3$ |
| H | H | H | H | $CH_2CH_3$ | $CH_2$(2,6-$Cl_2$Ph) | $CH_2CH_3$ |
| H | H | H | H | $CH_2CH_3$ | $CH_2$(2-$CF_3$Ph) | $CH_2CH_3$ |
| H | H | H | H | $CH_2CH_3$ | $CH_2$(2-tetrahydropyran) | $CH_2CH_3$ |
| H | H | H | H | $CH_2CH_3$ | $CH_2$(2-pyridyl) | $CH_2CH_3$ |
| H | H | H | H | $CH_2CH_3$ | $CH_2$(Ph) | $CH_2CH_3$ |
| H | H | H | H | $CH_2CH_3$ | Q-1 | $CH_2CH_3$ |
| H | H | H | H | $CH_2CH_3$ | Q-3 | $CH_2CH_3$ |
| H | H | H | H | $CH_2CH_3$ | Q-6 | $CH_2CH_3$ |
| H | H | H | H | $CH_2CH_3$ | Q-7 | $CH_2CH_3$ |
| H | H | H | H | $CH_2CH_3$ | Q-15 | $CH_2CH_3$ |
| H | H | $CH_3$ | $CH_3$ | $CH_3$ | $CH_2$(2-FPh) | $CH_3$ |
| H | H | $CH_3$ | $CH_3$ | $CH_3$ | $CH_2$(2-ClPh) | $CH_3$ |
| H | H | $CH_3$ | $CH_3$ | $CH_3$ | $CH_2$(2-($CH_3$)Ph) | $CH_3$ |
| H | H | $CH_3$ | $CH_3$ | $CH_3$ | $CH_2$(2,6-$Cl_2$Ph) | $CH_3$ |
| H | H | $CH_3$ | $CH_3$ | $CH_3$ | $CH_2$(2-$CF_3$Ph) | $CH_3$ |
| H | H | $CH_3$ | $CH_3$ | $CH_3$ | $CH_2$(2-tetrahydropyran) | $CH_3$ |
| H | H | $CH_3$ | $CH_3$ | $CH_3$ | $CH_2$(2-pyridyl) | $CH_3$ |
| H | H | $CH_3$ | $CH_3$ | $CH_3$ | $CH_2$(Ph) | $CH_3$ |
| H | H | $CH_3$ | $CH_3$ | $CH_3$ | Q-1 | $CH_3$ |
| H | H | $CH_3$ | $CH_3$ | $CH_3$ | Q-3 | $CH_3$ |
| H | H | $CH_3$ | $CH_3$ | $CH_3$ | Q-6 | $CH_3$ |
| H | H | $CH_3$ | $CH_3$ | $CH_3$ | Q-7 | $CH_3$ |
| H | H | $CH_3$ | $CH_3$ | $CH_3$ | Q-15 | $CH_3$ |
| $CH_3$ | $CH_3$ | $CH_2CH_3$ | $CH_2CH_3$ | $CH_3$ | $CH_2$(2-FPh) | $CH_3$ |
| $CH_3$ | $CH_3$ | $CH_2CH_3$ | $CH_2CH_3$ | $CH_3$ | $CH_2$(2-ClPh) | $CH_3$ |
| $CH_3$ | $CH_3$ | $CH_2CH_3$ | $CH_2CH_3$ | $CH_3$ | $CH_2$(2-($CH_3$)Ph) | $CH_3$ |
| $CH_3$ | $CH_3$ | $CH_2CH_3$ | $CH_2CH_3$ | $CH_3$ | $CH_2$(2,6-$Cl_2$Ph) | $CH_3$ |
| $CH_3$ | $CH_3$ | $CH_2CH_3$ | $CH_2CH_3$ | $CH_3$ | $CH_2$(2-$CF_3$Ph) | $CH_3$ |
| $CH_3$ | $CH_3$ | $CH_2CH_3$ | $CH_2CH_3$ | $CH_3$ | $CH_2$(2-tetrahydropyran) | $CH_3$ |
| $CH_3$ | $CH_3$ | $CH_2CH_3$ | $CH_2CH_3$ | $CH_3$ | $CH_2$(2-pyridyl) | $CH_3$ |
| $CH_3$ | $CH_3$ | $CH_2CH_3$ | $CH_2CH_3$ | $CH_3$ | $CH_2$(Ph) | $CH_3$ |
| $CH_3$ | $CH_3$ | $CH_2CH_3$ | $CH_2CH_3$ | $CH_3$ | Q-1 | $CH_3$ |
| $CH_3$ | $CH_3$ | $CH_2CH_3$ | $CH_2CH_3$ | $CH_3$ | Q-3 | $CH_3$ |
| $CH_3$ | $CH_3$ | $CH_2CH_3$ | $CH_2CH_3$ | $CH_3$ | Q-6 | $CH_3$ |
| $CH_3$ | $CH_3$ | $CH_2CH_3$ | $CH_2CH_3$ | $CH_3$ | Q-7 | $CH_3$ |
| $CH_3$ | $CH_3$ | $CH_2CH_3$ | $CH_2CH_3$ | $CH_3$ | Q-15 | $CH_3$ |
| $CH_3$ | $CH_3$ | $CH_3$ | $CH_3$ | $CH_3$ | $CH_2$(2-FPh) | $CH_3$ |
| $CH_3$ | $CH_3$ | $CH_3$ | $CH_3$ | $CH_3$ | $CH_2$(2-ClPh) | $CH_3$ |
| $CH_3$ | $CH_3$ | $CH_3$ | $CH_3$ | $CH_3$ | $CH_2$(2-($CH_3$)Ph) | $CH_3$ |
| $CH_3$ | $CH_3$ | $CH_3$ | $CH_3$ | $CH_3$ | $CH_2$(2,6-$Cl_2$Ph) | $CH_3$ |
| $CH_3$ | $CH_3$ | $CH_3$ | $CH_3$ | $CH_3$ | $CH_2$(2-$CF_3$Ph) | $CH_3$ |
| $CH_3$ | $CH_3$ | $CH_3$ | $CH_3$ | $CH_3$ | $CH_2$(2-tetrahydropyran) | $CH_3$ |
| $CH_3$ | $CH_3$ | $CH_3$ | $CH_3$ | $CH_3$ | $CH_2$(2-pyridyl) | $CH_3$ |
| $CH_3$ | $CH_3$ | $CH_3$ | $CH_3$ | $CH_3$ | $CH_2$(Ph) | $CH_3$ |
| $CH_3$ | $CH_3$ | $CH_3$ | $CH_3$ | $CH_3$ | Q-1 | $CH_3$ |
| $CH_3$ | $CH_3$ | $CH_3$ | $CH_3$ | $CH_3$ | Q-3 | $CH_3$ |
| $CH_3$ | $CH_3$ | $CH_3$ | $CH_3$ | $CH_3$ | Q-6 | $CH_3$ |
| $CH_3$ | $CH_3$ | $CH_3$ | $CH_3$ | $CH_3$ | Q-7 | $CH_3$ |
| $CH_3$ | $CH_3$ | $CH_3$ | $CH_3$ | $CH_3$ | Q-15 | $CH_3$ |
| $CH_2CH_3$ | $CH_2CH_3$ | $CH_2CH_3$ | $CH_2CH_3$ | $CH_3$ | $CH_2$(2-FPh) | $CH_3$ |
| $CH_2CH_3$ | $CH_2CH_3$ | $CH_2CH_3$ | $CH_2CH_3$ | $CH_3$ | $CH_2$(2-ClPh) | $CH_3$ |
| $CH_2CH_3$ | $CH_2CH_3$ | $CH_2CH_3$ | $CH_2CH_3$ | $CH_3$ | $CH_2$(2-($CH_3$)Ph) | $CH_3$ |

TABLE 8-continued

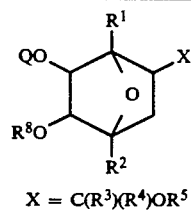

VIII $X = C(R^3)(R^4)OR^5$

| $R^1$ | $R^2$ | $R^3$ | $R^4$ | $R^5$ | Q | $R^8$ |
|---|---|---|---|---|---|---|
| CH₂CH₃ | CH₂CH₃ | CH₂CH₃ | CH₂CH₃ | CH₃ | CH₂(2,6-Cl₂Ph) | CH₃ |
| CH₂CH₃ | CH₂CH₃ | CH₂CH₃ | CH₂CH₃ | CH₃ | CH₂(2-CF₃Ph) | CH₃ |
| CH₂CH₃ | CH₂CH₃ | CH₂CH₃ | CH₂CH₃ | CH₃ | CH₂(2-tetrahydropyran) | CH₃ |
| CH₂CH₃ | CH₂CH₃ | CH₂CH₃ | CH₂CH₃ | CH₃ | CH₂(2-pyridyl) | CH₃ |
| CH₂CH₃ | CH₂CH₃ | CH₂CH₃ | CH₂CH₃ | CH₃ | CH₂(Ph) | CH₃ |
| CH₂CH₃ | CH₂CH₃ | CH₂CH₃ | CH₂CH₃ | CH₃ | Q-1 | CH₃ |
| CH₂CH₃ | CH₂CH₃ | CH₂CH₃ | CH₂CH₃ | CH₃ | Q-3 | CH₃ |
| CH₂CH₃ | CH₂CH₃ | CH₂CH₃ | CH₂CH₃ | CH₃ | Q-6 | CH₃ |
| CH₂CH₃ | CH₂CH₃ | CH₂CH₃ | CH₂CH₃ | CH₃ | Q-7 | CH₃ |
| CH₂CH₃ | CH₂CH₃ | CH₂CH₃ | CH₂CH₃ | CH₃ | Q-15 | CH₃ |
| CH₃ | CH₃ | H | H | CH₃ | CH₂(Ph) | CH₃ |
| CH₃ | CH₃ | H | H | CH₃ | CH₂(2-FPh) | CH₃ |
| CH₃ | CH₃ | H | H | CH₃ | CH₂(2-(CH₃)Ph) | CH₃ |
| CH₃ | CH₃ | H | H | CH₃ | CH₂(2,6-Cl₂Ph) | CH₃ |
| CH₃ | CH₃ | H | H | CH₃ | Q-3 | CH₃ |
| CH₃ | CH₃ | CH₃ | CH₃ | CH₃ | CH₂(Ph) | CH₃ |
| CH₃ | CH₃ | CH₃ | CH₃ | CH₃ | CH₂(2-FPh) | CH₃ |
| CH₃ | CH₃ | CH₃ | CH₃ | CH₃ | CH₂(2-(CH₃)Ph) | CH₃ |
| CH₃ | CH₃ | CH₃ | CH₃ | CH₃ | CH₂(2,6-Cl₂Ph) | CH₃ |
| CH₃ | CH₃ | CH₃ | CH₃ | CH₃ | Q-3 | CH₃ |
| CH₂CH₃ | CH₂CH₃ | H | H | CH₃ | CH₂(Ph) | CH₃ |
| CH₂CH₃ | CH₂CH₃ | H | H | CH₃ | CH₂(2-FPh) | CH₃ |
| CH₂CH₃ | CH₂CH₃ | H | H | CH₃ | CH₂(2-(CH₃)Ph) | CH₃ |
| CH₂CH₃ | CH₂CH₃ | H | H | CH₃ | CH₂(2,6-Cl₂Ph) | CH₃ |
| CH₂CH₃ | CH₂CH₃ | H | H | CH₃ | Q-3 | CH₃ |
| CH₂CH₃ | CH₂CH₃ | CH₃ | CH₃ | CH₃ | CH₂(Ph) | CH₃ |
| CH₂CH₃ | CH₂CH₃ | CH₃ | CH₃ | CH₃ | CH₂(2-FPh) | CH₃ |
| CH₂CH₃ | CH₂CH₃ | CH₃ | CH₃ | CH₃ | CH₂(2-(CH₃)Ph) | CH₃ |
| CH₂CH₃ | CH₂CH₃ | CH₃ | CH₃ | CH₃ | CH₂(2,6-Cl₂Ph) | CH₃ |
| CH₂CH₃ | CH₂CH₃ | CH₃ | CH₃ | CH₃ | Q-3 | CH₃ |
| H | CH₃ | CH₂CH₃ | CH₂CH₃ | CH₃ | CH₂(Ph) | CH₃ |
| H | CH₃ | CH₂CH₃ | CH₂CH₃ | CH₃ | CH₂(2-FPh) | CH₃ |
| H | CH₃ | CH₂CH₃ | CH₂CH₃ | CH₃ | CH₂(2-(CH₃)Ph) | CH₃ |
| H | CH₃ | CH₂CH₃ | CH₂CH₃ | CH₃ | CH₂(2,6-Cl₂Ph) | CH₃ |
| H | CH₃ | CH₂CH₃ | CH₂CH₃ | CH₃ | Q-3 | CH₃ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 9

| | Active Ingredient | Weight Percent* Diluent(s) | Surfactant(s) |
|---|---|---|---|
| Wettable Powders | 5–60 | 39–94 | 1–10 |
| Emulsifiable Concentrates | 3–80 | 20–95 | 0–20 |
| Dusts | 1–25 | 70–99 | 0–5 |
| Granules and Pellets | 0.1–50 | 50–99.9 | 0–15 |

TABLE 9-continued

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58. 132, 138–140, 152–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

| Wettable Powder | |
|---|---|
| 2-(1-ethyl-1-methoxypropyl)-6-(phenylmethoxy)-7-oxabicyclo[2.2.1]heptane | 60% |
| sodium alkylnaphthalenesulfonate | 2% |
| sodium ligninsulfonate | 2% |
| synthetic amorphous silica | 36% |

The active ingredient is first sprayed onto the amorphous silica, then the ingredients are blended, hammer-milled until all the solids are essentially under 50 microns, reblended, and packaged.

EXAMPLE B

| Wettable Powder | |
|---|---|
| 2-(1-ethyl-1-methoxypropyl)-6-(phenylmethoxy)-7-oxabicyclo[2.2.1]heptane | 50% |
| sodium alkylnaphthalenesulfonate | 2% |
| low viscosity methyl cellulose | 2% |
| diatomaceous earth | 46% |

The active ingredient is first sprayed onto the diatomaceous earth then the ingredients are blended, coarsely hammer-milled and then air-milled to produce particles essentially all below 10 microns in diameter. The product is reblended before packaging.

EXAMPLE C

| Granule | |
|---|---|
| Wettable Powder of Example B | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE D

| Emulsifiable Concentrate | |
|---|---|
| 2-(1-ethyl-1-methoxypropyl)-6-(phenylmethoxy)-7-oxabicyclo[2.2.1]heptane | 40% |
| Atlox 3403F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

| Low Strength Granule | |
|---|---|
| 2-(1-ethyl-1-methoxypropyl)-6-(phenylmethoxy)-7-oxabicyclo[2.2.1]heptane | 5% |
| attapulgite granules (U.S.S. 20–40 mesh) | 95% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE F

| Granule | |
|---|---|
| 2-(1-ethyl-1-methoxypropyl)-6-(phenylmethoxy)-7-oxabicyclo[2.2.1]heptane | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

| Concentrated Emulsion | |
|---|---|
| 2-(1-ethyl-1-methoxypropyl)-6-(phenylmethoxy)-7-oxabicyclo[2.2.1]heptane | 25% |
| xylene | 25% |
| Atlox 3404F | 5% |
| G-1284 | 5% |
| ethylene glycol | 8% |
| water | 32% |

The active ingredient, solvent and emulsifiers are blended together. This solution is added to a mixture of the ethylene glycol and water with stirring.

EXAMPLE H

| Solution | |
|---|---|
| 2-(1-ethyl-1-methoxypropyl)-6-(phenylmethoxy)-7-oxabicyclo[2.2.1]heptane | 5% |
| water | 95% |

The compound is added directly to the water with stirring to produce the solution, which may then be packaged for use.

EXAMPLE I

| Dust | |
|---|---|
| 2-(1-ethyl-1-methoxypropyl)-6-(phenylmethoxy)-7-oxabicyclo[2.2.1]heptane | 10% |
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate compounds of this invention are active postemergence and, in particular, preemergence herbicides. Many compounds in this invention are useful for the control of selected grass and broadleaf weeds with tolerance to important agronomic crops such as alfalfa (*Medicago sativa*), barley (*Hordeum vulgare*), corn (*Zea mays*), cotton (*Gossypium hirsutum*), rape (*Brassica napus*), rice (*Oryza sativa*), soybean (*Glycine max*), sugar beet (*Beta vulgaris*), and wheat (*Triticum aestivum*). Grass and broadleaf weed species controlled include, but are not limited to, barnyardgrass (*Echinochloa crus-galli*), blackgrass (*Alopecurus myosuroides*), crabgrass (*Digitaria* spp.), foxtail (*Setaria* spp.), lambsquarters (*Chenopodium* spp.), teaweed (*Sida spinosa*), umbrella sedge (*Cyperus difformis*), and waterchestnut (*Eleocharis* spp.). Several compounds in this invention are particularly useful for the control of barnyardgrass and selected broadleaf weeds such as umbrella sedge and waterchestnut in upland and paddy rice.

These compounds also have utility for weed control of selected vegetation in specified areas such as around storage tanks, parking lots, highways, and railways; in fallow crop areas; and in citrus and plantation crops such as banana, coffee, oil palm, and rubber. Alternatively, these compounds are useful to modify plant growth.

Rates of application for compounds of this invention rae determined by a number of factors. These factors include: formulation selected, method of application, amount and type of vegetation present, growing conditions, etc. In general terms, the subject compounds should be applied at rates from 0.01 to 20 kg/ha with a preferred rate range of 0.03 to 1 kg/ha. Although a small number of compounds show no herbicidal activity at the rates tested, it is anticipated these compounds have herbicidal activity at higher application rates. One skilled in the art can easily determine application rates necessary for the desired level of weed control.

Compounds of this invention may be used alone or in combination with the commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| aciflurofen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-2-ethyl-2,6-dinitro-4-(tri-fluoromethyl)benzenamine |
| bensulfuron methyl | 2-[[[[[(4,6-dimethoxy-2-pyrimi-dinyl)amino]methylcarbonyl]-amino]sulfonyl]methylcarbonyl]-acid, methyl ester |
| bensulide | O,O-bis(1-methylethyl) S-[2-[(phenylsulfonyl)amio]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoro-methyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thia-diazol-2-yl]-4-hydroxy-1-methyl-2-imidazolidinone |
| butralin | 4-(1,1-dimethylethyl)-N-(1-methyl-propyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |

-continued

| Common Name | Chemical Name |
|---|---|
| CGA 142,464 | 3-(4,6-dimethoxy-1,3,5-triazin-2-yl)-1-[2-(2-methoxyethoxy)-pehnyl-sulfonyl]-urea |
| chloroamben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]-amino]sulfonyl]benzoic acid, ethyl ester |
| chloromethoxy-nil | 2,4-dichlorophenyl 4-nitro-3-methoxyphenyl ether |
| chlornitrofen | 2,4,6-trichlorophenyl-4-nitrophenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]-phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]-propanoic acid, methyl ester |
| diethatyl | N-(chloroacetyl)-N-(2,6-diethylphenyl)-glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | $N^3,N^3$-diethyl-2,4-dinitro-6-(trifluromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DSMA | disodium salt of MAA |
| dymron | N-(4-methylphenyl)-N'-(1-methyl-1-phenylethyl)urea |

-continued

| Common Name | Chemical Name |
|---|---|
| endothall | 7-oxabicyclo[2.2.1]heptane-2,3-dicarboxylic acid |
| EPTC | S-ethyl dipropylcarbamothioate |
| esprocarb (SC2957) | S-benzyl-N-ethyl-N-(1,2-dimethyl)-propyl)thiolcarbamate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chlorethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hudrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| imazamethabenz | 1,3,5-triazine-2,4(1H,3H)-dione 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothionate |

| Common Name | Chemical Name |
|---|---|
| mecoprop | (±)-2-(4-chloro-2-methylphenoxy)-propanoic acid |
| mefenacet | 2-(2-benzothiazolyloxy-N-methyl-N-phenylacetamide |
| mefluidide | N-[2,4-dimethyl-5-[[(trifluoromethyl)-sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorofen | 2-chloro-1-(4-nitrophenoxy)-4-(trifluoromethyl)benzene |
| norea | N,N-dimethyl-N'-(octahydro-4,7-methano-1H-inden-5-yl)urea 3aα,-4α,5α,7α,7aα-isomer pyridazinone |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridine-carboxylic acid |
| PPG-1013 | 5-[2-chloro-4-(trifluoromethyl)-phenoxy]-2-nitroacetophenone oxime-O-acetic acid, methyl ester |
| pretilachlor | α-chloro-2,6-diethyl-N-(2-propoxyethyl)acetanilide |
| procyazine | 2-[[4-chloro-6-(cyclopropylamino)-1,3,5-triazin-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitro-phenyl]sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethyl-pyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxylinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(α,α-dimethylbenzyl)-3-(4-methyl-phenyl)urea |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethy)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron methyl | 3-[[[[(4-methoxy-6-methyl-1,3,5-triazin-2-yl)amino]carbonyl]amino]sulfonyl]-2-thiophenecarboxylic acid, methyl ester |
| thiobencarb | S-[(4-chlorophenyl)methyl] diethylcarbamothioate |
| triallate | S-(2,3,3-trichloro-2-propenyl) bis(1-methylethyl)carbamothioate |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| triclopyr | [3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

TABLE 10

(Structures I and 18 shown with R¹, R², O, X, Q groups)

| Cmpd | R¹ | R² | R³ | R⁴ | R⁵ | Q | Physical Properties Configuration Ratio (I:(18)) | Partial NMR(δ) |
|---|---|---|---|---|---|---|---|---|
| 1 | CH₃ | CH₃ | H | H | CH₂Ph | CH₂(Ph) | oil, exo, 1:2 | 4.58–4.36(m, 2H), 3.54(m, 2H), 3.20(m, 1H) |
| 2 | CH₃ | CH₃ | H | H | CH₂CH=CH₂ | CH₂(2-FPh) | oil, exo, 1:2 | 5.90(m, 1H), 5.32–5.06(m, 2H), 4.54(dq, 2H), 3.94(m, 2H), 3.6–3.43(m, 2H), 3.16(m, 1H) |
| 3 | CH₃ | CH₃ | H | H | CH₂CH=CH₂ | CH₂(2-(CH₃)Ph) | oil, exo, 1:2 | 5.90(m, 1H), 5.28–5.15(m, 2H), 4.44(dq, 2H), 3.84(m, 2H), 3.55–3.43(m, 2H), 3.15(m, 1H) |
| 4 | CH₃ | CH₃ | H | H | CH₂CH=CH₂ | CH₂(Ph) | oil, exo, 1:2 | 5.90(m, 1H), 5.3–5.16(m, 2H), 4.49(dq, 2H), 3.94(m, 2H), 3.58–3.42(m, 2H), 3.16(m, 1H) |
| 5 | CH₃ | CH₃ | H | H | CH₃ | CH₂(2-FPh) | oil, exo | 4.52(dd, 2H), 3.56(dd, 1H), 3.43(dd, 1H), 3.3(s, 3H), 3.12(dd, 1H) |
| 6 | CH₃ | CH₃ | H | H | CH₂CH₃ | CH₂(2,6-F₂Ph) | oil, endo | 3.3(m, 4H), 4.60(d, 1H), 4.5(d, 1H), 3.76(dd, 1H) |
| 7 | CH₃ | CH₃ | H | H | CH₂CH₃ | CH₂(2,6-Cl₂Ph) | oil, endo | 4.76(d, 1H), 4.66(d, 1H), 3.74(dd, 1H), 3.3(m, 4H) |
| 8 | CH₃ | CH₃ | H | H | CH₂CH₃ | CH₂(2-FPh) | oil, exo, 3:1 | 4.58(d, 1H), 4.45(d, 1H), 3.56(dd, 1H), 3.4–3.1(m, 4H) |
| 9 | CH₃ | CH₃ | H | H | CH₂CH₃ | CH₂(2,6-Cl₂Ph) | oil, exo, 2:1 | 4.73(dd, 1H), 4.64(dd, 1H), 3.5(m, 2H), 3.4–3.1(m, 4H) |
| 10 | CH₃ | CH₃ | H | H | CH₃ | CH₂(2,6-Cl₂Ph) | oil, exo, 1:1 | 4.73(dd, 1H), 4.64(dd, 1H), 3.5(m, 2H), 3.08(dd+dd, 1H-1:1 ratio) |
| 11 | CH₃ | CH₃ | H | H | Et | CH₂(2-BrPh) | oil, exo, 2:1 | 4.56(d, 1H), 4.43(dd, 1H), 3.60(dd, 1H), 3.5(m, 3H), 3.12(dd+dd, 1H) |
| 12 | CH₃ | CH₃ | H | H | CH₃ | CH₂(2-BrPh) | oil, exo, 1:1 | 4.58(d, 1H), 4.42(dd, 1H), 3.61(dd, 1H), 3.45(m, 1H), 3.3(s+s, 3H), 3.1(dd+dd, 1H) |
| 13 | CH₃ | CH₃ | H | H | Et | CH₂(2-ClPh) | oil, endo | 4.61(d, 1H), 4.56(d, 1H), 3.82(dd, 1H), 3.35(m, 4H) |
| 14 | CH₃ | CH₃ | H | H | Et | CH₂(2-BrPh) | oil, endo | 4.59(d, 1H), 4.43(d, 1H), 3.84(dd, 1H), 3.25(m, 4H) |
| 15 | CH₃ | CH₃ | H | H | CH₂CH=CH(CH₃) | CH₂(2-FPh) | oil, exo | 5.61(m, 2H), |

TABLE 10-continued

| Cmpd | R¹ | R² | R³ | R⁴ | R⁵ | Q | Physical Properties Configuration Ratio (I:(18)) | Partial NMR(δ) |
|---|---|---|---|---|---|---|---|---|
| 16 | $CH_3$ | $CH_3$ | H | H | $CH_2OCH_3$ | $CH_2$(2-FPh) | oil, endo | 4.56(d, 1H), 4.50(d, 1H), 3.9(d+d, 2H) 3.5(dd+dd, 2H), 3.14(dd, 1H) 4.56(dd+s, 4H), 3.81(dd, 1H), 3.45(dd, 2H), 3.29(s, 3H) |
| 17 | $CH_3$ | $CH_3$ | H | H | $CH_2CH_3$ | $CH_2$(2-($CH_3$)Ph) | oil, exo | 4.53(d, 1H), 4.35(d, 1H), 3.45(m, 4H), 3.13(dd, 1H) |
| 18 | H | H | $CH_3$ | $CH_3$ | $CH_3$ | $CH_2$(2-($CH_3$)Ph) | oil, exo | 4.6(br, 1H), 4.50(m, 3H), 3.65(dd, 1H), 3.18(s, 3H) |
| 21 | H | H | $CH_3$ | $CH_3$ | $CH_3$ | $CH_2$(Ph) | oil, exo | 4.55(t, 1H), 4.49(m, 3H), 3.64(dd, 1H), 3.16(s, 3H) |
| 22 | $CH_3$ | $CH_3$ | $CH_3$ | $CH_3$ | $CH_2CH_3$ | $CH_2$(2-FPh) | oil, exo | 4.59(d, 1H), 4.45(d, 1H), 3.55(dd, 1H), 3.38(dq, 2H) |
| 23 | $CH_3$ | $CH_3$ | $CH_3$ | $CH_3$ | $CH_2CH_3$ | $CH_2$(Ph) | oil, exo | 4.52(dd, 1H), 4.40(dd, 1H), 3.52(dd, 1H), 3.37(dq, 2H) |
| 25 | H | H | Et | Et | $CH_3$ | $CH_2$(Ph) | oil, exo | 4.65(m, 4H), 3.72(dd, 1H), 3.22(s, 3H) |
| 26 | H | H | Et | Et | $CH_3$ | $CH_2$(2,6-$Cl_2$Ph) | oil, exo | 4.75(dd, 2H), 4.59(m, 2H), 3.75(dd, 1H), 3.18(s, 3H) |
| 27 | H | H | Et | Et | $CH_3$ | $CH_2$(2-($CH_3$)-Ph) | oil, exo | 4.7(m, 4H), 3.7(dd, 1H), 3.2(s, 3H) |
| 28 | H | H | Et | Et | $CH_3$ | $CH_2$(2-FPh) | oil, exo | 4.7(m, 4H), 3.73(dd, 1H), 3.2(s, 3H) |
| 29 | H | H | Et | Et | $CH_3$ | $CH_2$(2-ClPh) | oil, exo | 4.7(m, 4H), 3.72(dd, 1H), 3.2(s, 3H) |
| 30 | H | H | Et | Et | $CH_3$ | $CH_2$(2-BrPh) | oil, exo | 4.59(brd, 4H), 3.71(dd, 1H), 3.18(s, 3H) |
| 31 | H | H | Et | Et | $CH_3$ | $CH_2$(2,6-$F_2$Ph) | oil, exo | 4.56(m, 4H), 3.68(dd, 1H), 3.17(s, 3H) |
| 32 | H | H | n-Pr | n-Pr | $CH_3$ | $CH_2$(Ph) | oil, exo | 4.52(m, 4H), 3.62(dd, 1H), 3.15(s, 3H), |
| 33 | H | H | n-Pr | n-Pr | $CH_3$ | $CH_2$(2-($CH_3$)Ph) | oil, exo | 4.50(t, 1H), 4.48(s, 1H), 4.45(dd, 2H), 3.62(dd, 1H), 3.19(s, 3H) |
| 34 | H | H | n-Pr | n-Pr | $CH_3$ | $CH_2$(2-FPh) | oil, exo | 4.50(m, 4H), 3.65(dd, 1H), 3.16(s, 3H) |
| 35 | H | H | n-Pr | n-Pr | $CH_3$ | $CH_2$(2-ClPh) | oil, exo | 4.59(m, 4H), 3.68(dd, 1H), 3.17(s, 3H) |
| 36 | H | H | n-Pr | n-Pr | $CH_3$ | $CH_2$(2-BrPh) | oil, exo | 4.50(m, 4H), 3.69(dd, 1H), |

TABLE 10-continued

| Cmpd | R[1] | R[2] | R[3] | R[4] | R[5] | Q | Physical Properties Configuration Ratio (I:(18)) | Partial NMR($\delta$) |
|---|---|---|---|---|---|---|---|---|
| 37 | H | H | n-Pr | n-Pr | $CH_3$ | $CH_2$(2,6-$F_2$Ph) | oil, exo | 3.17(s, 3H) 4.50(m, 4H), 3.67(dd, 1H), 3.16(s, 3H) |
| 40 | H | H | Pr | Pr | $CH_2$Ph | $CH_2$(Ph) | oil, exo | 4.9–4.6(m, 6H), 3.8(dd, 1H) |
| 41 | H | H | n-Pr | n-Pr | $CH_2$(2-$CH_3$(Ph)) | $CH_2$(2-($CH_3$)Ph) | oil, exo | 4.6–4.4(m, 6H), 3.6(dd, 1H) |
| 42 | H | H | n-Pr | n-Pr | $CH_2$(2-F(Ph)) | $CH_2$(2-FPh) | oil, exo | 4.6(m, 6H), 3.72(dd, 1H) |
| 48 | H | H | $CH=CH_2$ | $CH=CH_2$ | $CH_2CH_3$ | $CH_2$(Ph) | oil, exo | 5.95–5.7(m, 2H), 5.4–5.1(m, 4H), 4.6–4.45(m, 4H), 3.68(dd, 1H), 3.35(q, 2H) |
| 49 | H | H | $CH=CH_2$ | $CH=CH_2$ | $CH_2CH_3$ | $CH_2$(2-$CH_3$)Ph) | oil, exo | 5.95–5.7(m, 2H), 5.4–5.15(m, 4H), 4.65–4.4(m, 2H), 3.68(dd, 1H), 3.33(q, 1H) |
| 50 | H | H | $CH=CH_2$ | $CH=CH_2$ | $CH_2CH_3$ | $CH_2$(2-FPh) | oil, exo | 5.95–5.6(m, 2H), 5.36–5.16(m, 4H), 4.57(m, 4H), 3.72(dd, 1H), 3.33(q, 2H) |
| 51 | H | H | $CH_2CH=CH_2$ | $CH_2CH=CH_2$ | $CH_2CH_3$ | $CH_2$(Ph) | oil, exo | 6.0–5.8(m, 2H), 5.15–5.0(m, 4H), 4.61=4.4(m, 4H), 3.62(dd, 1H), 3.45(q, 2h) |
| 52 | H | H | $CH_2CH=CH_2$ | $CH_2CH=CH_2$ | CH2$CH_3$ | $CH_2$(2-($CH_3$)Ph) | oil, exo | 5.8–6.0(m, 2H), 5.15–5.0(m, 4H), 4.6–4.4(m, 4H), 3.62(dd, 1H), 3.46(q, 2H) |
| 53 | H | H | $CH_2CH=CH_2$ | $CH_2CH=CH_2$ | $CH_2CH_3$ | $CH_2$(2-FPh) | oil, exo | 6.0–5.72(m, 2H), 5.2–4.95(m, 4H), 4.58(m, 4H), 3.65(dd, 1H), 3.45(q, 2H) |
| 54 | H | H | $CH_2CH=CH_2$ | $CH_2CH=CH_2$ | $CH_3$ | $CH_2$(Ph) | oil, exo | 6.0–5.75(m, 2H), 5.15–5.0(m, 4H), 4.62–4.4(m, 4H), 3.62(dd, 1H), 3.25(s, 3H) |
| 55 | H | H | $CH_2CH=CH_2$ | $CH_2CH=CH_2$ | $CH_3$ | $CH_2$(2-($CH_3$)Ph) | oil, exo | 5.9(m, 2H), 5.15–5.0(m, 4H), 4.6–4.4(m, 4H), 3.62(dd, 1H), 3.26(s, 3H) |
| 56 | H | H | $CH_2CH=CH_2$ | $CH_2CH=CH_2$ | $CH_3$ | $CH_2$(2-FPh) | oil, exo | 6.0–5.75(m, 2H), 5.1–5.0(m, 4H), 4.5(m, 4H), 3.65(dd, 1H), 3.26(s, 3H) |
| 57 | H | H | $CH_2CH=CH_2$ | $CH_2CH=CH_2$ | $CH_3$ | $CH_2$(2,6-($F)_2$Ph) | oil, exo | 6.95–6.8 (dd, 2H), 6.04–5.75(m, 2H), 5.15–5.00(m, 2H), 4.55(m, 4H), 3.66(dd, 1H), 3.26(s, 3H) |
| 58 | H | H | $CH_2CH=CH_2$ | $CH_2CH=CH_2$ | $CH_3$ | $CH_2$(2,6-($Cl)_2$Ph) | oil, exo | 6.02–5.75(m, 2H), 5.15–5.04(m, 4H), 4.8–4.55(m, 4H), 3.70(dd, 1H), 3.27(q, 3H) |
| 59 | H | H | $CH_2CH_2CH_3$ | $CH_2CH_2CH_3$ | $CH_2CH=CH_2$ | $CH_2$(Ph) | oil, exo | 6.0–5.8(dd+1H), |

TABLE 10-continued

| Cmpd | R¹ | R² | R³ | R⁴ | R⁵ | Q | Physical Properties Configuration Ratio (I:(18)) | Partial NMR($\delta$) |
|---|---|---|---|---|---|---|---|---|
| 60 | H | H | $CH_2CH_2CH_3$ | $CH_2CH_2CH_3$ | $CH_2CH=CH_2$ | $CH_2$(2-FPh) | oil, exo | 5.28(dd, 1H), 5.10(dd, 1H), 4.58(brs, 2H), 4.51(d, 2H), 3.82(d, 2H), 3.62(dd, 1H) 6.0–5.8(m, 1H), |
| 61 | H | H | $CH_2CH_2CH_3$ | $CH_2CH_2CH_3$ | $CH_2CH=CH_2$ | $CH_2$(2,6-$(F)_2$Ph) | oil, exo | 5.26(dd, 1H), 5.10(dd, 1H), 4.58(br, 4H), 3.85(d, 2H), 3.65(dd, 1H) 6.88(t, 2H), 6.0–5.79(m, 1H), |
| 62 | H | H | $CH_2CH_2CH_3$ | $CH_2CH_2CH_3$ | $CH_2CH_2=CH_2$ | $CH_2$(2-$(CH_3)$Ph) | oil, exo | 5.28(dd, 1H), 5.10(dd, 1H), 4.56(m, 4H), 3.87(m, 2H), 3.65 (dd, 1H) 6.0–5.78(m, 1H), 5.27(dd, 1H), 5.09(dd, 1H), 4.59(br, 2H), 4.50(dd, 2H) |
| 63 | H | H | $CH_2CH(CH)_3$ | $CH_2CH(CH)_3$ | $CH_3$ | $CH_2$(Ph) | oil, exo | 4.66(m, 2H), 4.58(m, 2H), 3.73(dd, 1H), 3.27(s, 3H) |
| 64 | H | H | $CH_2CH(CH)_3$ | $CH_2CH(CH)_3$ | $CH_3$ | $CH_2$(2-FPh) | oil, exo | 4.62(m, 1H), 3.72(dd, 1H), 3.28(s, 3H) |
| 65 | H | H | $CH_2CH(CH)_3$ | $CH_2CH(CH)_3$ | $CH_3$ | $CH_2$(2-ClPh) | oil, exo | 4.66(m, 4H), 3.75(dd, 1H), 3.26(s, 3H) |
| 66 | H | H | $CH_2CH(CH)_3$ | $CH_2CH(CH)_3$ | $CH_3$ | $CH_2$(2-$(CH_3)$Ph) | oil, exo | 4.65(m, 2H), 4.52(m, 2H), 3.7(dd, 1H), 3.26(s, 3H) |
| 67 | H | H | $CH_2CH(CH)_3$ | $CH_2CH(CH)_3$ | $CH_3$ | $CH_2$(2-BrPh) | oil, exo | 4.59(m, 4H), 3.72(m, 1H), 3.24(s, 3H) |
| 68 | H | H | $CH_2CH(CH)_3$ | $CH_2CH(CH)_3$ | $CH_3$ | $CH_2$(2,6-$(F)_2$Ph) | oil, exo | 4.58(m, 4H), 3.7(dd, 1H), 3.26(s, 3H) |
| 69 | H | H | $CH_2CH(CH)_3$ | $CH_2CH(CH)_3$ | $CH_3$ | $CH_2$(2,6-$(Cl)_2$Ph) | oil, exo | 4.78(m, 3H), 4.5(t, 1H), 3.83(dd, 1H), 3.22(s, 3H) |
| 70 | H | H | $CH_2CH_3$ | $CH_2CH_3$ | $CH_2CH=CH_2$ | $CH_2$(Ph) | oil, exo | 6.0–5.8(m, 1H), 5.4–5.05(m, 2H), 4.55(m, 4H), 3.9(dd, 2H), 3.65(dd, 2H) |
| 71 | H | H | $CH_2CH_2CH_2CH_3$ | $CH_2CH_2CH_2CH_3$ | $CH_3$ | $CH_2$(Ph) | oil, exo | 4.55(m, 4H), 3.63(dd, 1H), 3.15(s, 3H) |
| 72 | H | H | $CH_2CH_2CH_2CH_3$ | $CH_2CH_2CH_2CH_3$ | $CH_3$ | $CH_2$(2-FPh) | oil, exo | 4.58(m, 4H), 3.63(dd, 1H), 3.17(s, 3H) |
| 73 | H | H | $CH_2CH_2CH_2CH_3$ | $CH_2CH_2CH_2CH_3$ | $CH_3$ | $CH_2$(2-ClPh) | oil, exo | 4.6(m, 4H), 3.69(dd, 1H), 3.17(s, 3H) |
| 74 | H | H | $CH_2CH_2CH_2CH_3$ | $CH_2CH_2CH_2CH_3$ | $CH_3$ | $CH_2$(2-$(CH_3)$Ph) | oil, exo | 4.6–4.42(m, 4H), 3.62(dd, 1H), 3.17(s, 3H) |
| 75 | H | H | $CH_2CH_2CH_2CH_3$ | $CH_2CH_2CH_2CH_3$ | $CH_3$ | $CH_2$(2-BrPh) | oil, exo | 4.58(m, 4H), 3.7(dd, 1H), |

TABLE 10-continued

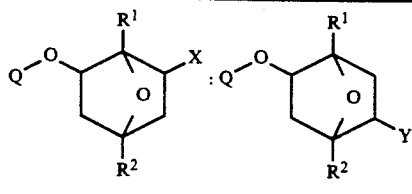

(I)      (18)

| Cmpd | R¹ | R² | R³ | R⁴ | R⁵ | Q | Physical Properties Configuration Ratio (I:(18)) | Partial NMR(δ) |
|---|---|---|---|---|---|---|---|---|
| 76 | H | H | $CH_2CH_2CH_2CH_3$ | $CH_2CH_2CH_2CH_3$ | $CH_3$ | $CH_2(2,6\text{-}(F)_2Ph)$ | oil, exo | 3.17(s, 3H) 4.57(m, 4H), 3.63(dd, 1H) |
| 77 | H | H | $CH_2CH_2CH_2CH_3$ | $CH_2CH_2CH_2CH_3$ | $CH_3$ | $CH_2(2,6\text{-}(Cl)_2Ph)$ | oil, exo | 3.16(s, 3H) 4.74(brm, 2H), 4.58(br, 2H), 3.70(dd, 1H) |
| 78 | H | H | $CH_2CH_2CH_3$ | $CH_2CH_2CH_3$ | $CH_3$ | $CH_2(2,4\text{-}(F)_2Ph)$ | oil, exo | 3.17(s, 3H) 6.8(m, 2H), 4.59(t, 1H), 4.51(m, 3H), 3.64(dd, 1H) |
| 79 | H | H | $CH_2CH_2CH_3$ | $CH_2CH_2CH_3$ | $CH_3$ | $CH_2(4\text{-}FPh)$ | oil, exo | 3.17(s, 3H) 4.61(t, 1H), 4.54(d, 1H), 4.48(d+s, 2H) |
| 80 | H | H | $CH_2CH_2CH_3$ | $CH_2CH_2CH_3$ | $CH_3$ | $CH_2(3\text{-}FPh)$ | oil, exo | 3.16(s, 3H) 4.55(t+d+d+s, 4H), 4.64(d+d, 1H), 3.18(s, 3H) |
| 81 | H | H | $CH_2CH_2CH_3$ | $CH_2CH_2CH_3$ | $CH_3$ | $CH_2(2,5\text{-}(F)_2Ph)$ | oil, exo | 4.5(m, 4H), 3.64(dd, 1H), 3.17(s, 3H) |
| 82 | H | H | $CH_2CH_2CH_3$ | $CH_2CH_2CH_3$ | $CH_3$ | $CH_2(3\text{-}ClPh)$ | oil, exo | 4.6(t, 1H), 4.55(s, 1H), 4.48(d+d, 2H), 3.62(dd, 1H) |
| 83 | H | H | $CH_2CH(CH_3)_2$ | $CH_2CH(CH_3)_2$ | $CH_3$ | $CH_2(2,4\text{-}(F)_2Ph)$ | oil, exo | 3.16(s, 3H) 6.8(m, 2H), 4.53(m, 4H), 3.68(dd, 1H) |
| 84 | H | H | $CH_2CH(CH_3)_2$ | $CH_2CH(CH_3)_2$ | $CH_3$ | $CH_2(4\text{-}FPh)$ | oil, exo | 3.28(s, 3H) 4.6–4.5(m, 4H), 3.62(dd, 1H) |
| 85 | H | H | $CH_2CH(CH_3)_2$ | $CH_2CH(CH_3)_2$ | $CH_3$ | $CH_2(3\text{-}FPh)$ | oil, exo | 3.22(s, 3H) 4.6–4.5(m, 4H), 3.63(dd, 1H) |
| 86 | H | H | $CH_2CH(CH_3)_2$ | $CH_2CH(CH_3)_2$ | $CH_3$ | $CH_2(2,5\text{-}(F)_2Ph)$ | oil, exo | 3.23(s, 3H) 4.6(m, 4H), 3.66(dd, 1H) |
| 87 | H | H | $CH_2CH(CH_3)_2$ | $CH_2CH(CH_3)_2$ | $CH_3$ | $CH_2(3\text{-}ClPh)$ | oil, exo | 3.23(s, 3H) 4.62(m, 2H), 4.5(m, 2H), 3.62(dd, 1H) |
| 88 | H | H | $CH_2CH_3$ | $CH_2CH_3$ | $CH_3$ | $CH_2(4\text{-}(F)_2Ph)$ | oil, exo | 3.28(s, 3H) 4.6–4.5(m, 4H), 3.64(dd, 1H) |
| 89 | H | H | $CH_2CH_3$ | $CH_2CH_3$ | $CH_3$ | $CH_2(4\text{-}FPh)$ | oil, exo | 3.17(s, 3H) 4.6–4.5(m, 4H), 3.61(dd, 1H) |
| 90 | H | H | $CH_2CH_3$ | $CH_2CH_3$ | $CH_3$ | $CH_2(3\text{-}FPh)$ | oil, exo | 3.16(s, 3H) 4.7–4.4(m, 4H), 3.64(dd, 1H) |
| 91 | H | H | $CH_2CH_3$ | $CH_2CH_3$ | $CH_3$ | $CH_2(2,5\text{-}(F)_2Ph)$ | oil, exo | 3.16(s, 3H) 4.8–4.5(m, 4H), 3.70(dd, 1H) |
| 92 | H | H | $CH_2CH_3$ | $CH_2CH_3$ | $CH_3$ | $CH_2(3\text{-}ClPh)$ | oil, exo | 3.18(s, 3H) 4.7–4.4(m, 4H), 3.63(dd, 1H) |
| 93 | H | H | $CH_3$ | $CH_2CH_2CH_3$ | $CH_3$ | $CH_2(Ph)$ | oil, exo | 3.17(s, 3H) 4.6–4.5(m, 4H), 3.65(dd, 1H) |
| 94 | H | H | $CH_3$ | $CH_2CH_2CH_3$ | $CH_3$ | $CH_3(2\text{-}FPh)$ | oil, exo | 3.15(s, 3H) 4.58(m, 4H), 3.7(dd, 1H) |
| 95 | H | H | $CH=CH_2$ | $CH=CH_2$ | $CH_3$ | $CH_2(Ph)$ | oil, exo | 3.16(s, 3H) 5.8(m, 2H), |

TABLE 10-continued

| Cmpd | R¹ | R² | R³ | R⁴ | R⁵ | Q | Physical Properties Configuration Ratio (I:(18)) | Partial NMR(δ) |
|---|---|---|---|---|---|---|---|---|
| 96 | H | H | CH=CH$_2$ | CH=CH$_2$ | CH$_3$ | CH$_2$(2-FPh) | oil, exo | 5.3(m, 4H), 4.54(m, 4H), 3.69(dd, 1H), 3.15(s, 3H) |
| 97 | H | H | CH=CH$_2$ | CH=CH$_2$ | CH$_3$ | CH$_2$(2,6-(F)$_2$Ph) | oil, exo | 5.8(m, 2H), 5.27(m, 4H), 4.57(m, 4H), 3.70(dd, 1H), 3.16(s, 3H) |
| 98 | H | H | CH=CH$_2$ | CH=CH$_2$ | CH$_3$ | CH$_2$(4-FPh) | oil, exo | 5.8(m, 2H), 5.3(m, 4H), 4.53(m, 4H), 3.70(dd, 1H), 3.16(s, 3H) |
| 99 | H | H | CH=CH$_2$ | CH=CH$_2$ | CH$_3$ | CH$_2$(2,4-(F)$_2$Ph) | oil, exo | 5.8(m, 2H), 5.3(m, 4H), 4.5(m, 4H), 3.65(dd, 1H), 3.16(s, 3H) |
| 100 | H | H | CH=CH$_2$ | CH=CH$_2$ | CH$_3$ | CH$_2$(2,5-(F)$_2$Ph) | oil, exo | 5.8(m, 2H), 5.3(m, 4H), 4.51(m, 4H), 3.70(dd, 1H), 3.16(s, 3H) |
| 101 | H | H | CH$_3$ | CH$_2$CH$_2$CH$_3$ | CH$_3$ | CH$_2$(2-ClPh) | oil, exo | 5.8(m, 2H), 5.3(m, 4H), 4.55(m, 4H), 3.70(dd, 1H), 3.17(s, 3H) |
| 102 | H | H | CH$_3$ | CH$_2$CH$_2$CH$_3$ | CH$_3$ | CH$_2$(2,6-(F)$_2$Ph) | oil, exo | 4.61(br, 4H), 3.71(dd, 1H), 3.17(s, 3H) |
| 103 | H | H | CH$_3$ | CH$_2$CH$_2$CH$_3$ | CH$_3$ | CH$_2$(2-(CH$_3$)Ph) | oil, exo | 4.57(m, 4H), 3.7(dd, 1H), 3.17(s, 3H) |
| 104 | H | H | CH$_3$ | CH$_2$CH$_2$CH$_3$ | CH$_3$ | CH$_2$(2,4-(F)$_2$Ph) | oil, exo | 4.6(m, 2H), 4.5(d+d, 2H) 3.64(dd, 1H), 3.16(s, 3H) |
| 105 | H | H | CH$_2$CH$_3$ | CH$_2$CH$_3$ | CH$_3$ | CH$_2$(2-tetra-hydropyran) | oil, exo | 4.58(br, 2H), 4.52(br, 2H) 3.7(dd, 1H), 3.16(s, 3H) |
| 106 | H | H | CH$_2$CH$_2$CH$_3$ | CH$_2$CH$_2$CH$_3$ | CH$_3$ | CH$_2$(2-tetra-hydropyran) | oil, exo | 4.59(t, 1H), 4.5(s, 1H) 3.5(dd, 1H), 3.4(m, 2H), 3.31(m, 4H), 3.18(s, 3H) |
| 107 | H | H | CH$_3$ | CH$_2$CH$_3$ | CH$_3$ | CH$_2$(Ph) | oil, exo | 4.5(t+s, 1H), 3.5–3.3(m, 6H) 3.17(s, 3H) |
| 108 | H | H | CH$_3$ | CH$_2$CH$_3$ | CH$_3$ | CH$_2$(2-FPh) | oil, exo | 4.5(m, 4H), 3.7(dd, 1H) 3.15(s, 3H) |
| 109 | H | H | CH$_3$ | CH$_2$CH$_3$ | CH$_3$ | CH$_2$(2,6-(F)$_2$Ph) | oil, exo | 4.59(brs, 4H), 3.7(dd, 1H) 3.16(s, 3H) |
| 110 | H | H | CH$_3$ | CH$_2$CH$_3$ | CH$_3$ | CH$_2$(2-(CH$_3$)Ph) | oil, exo | 4.58(brs, 4H), 3.71(dd, 1H) 3.17(s, 3H) |
| 111 | H | H | CH$_3$ | CH$_2$CH$_2$CH$_2$CH$_3$ | CH$_3$ | CH$_2$(Ph) | oil, exo | 4.5(m, 4H), 3.69(dd, 1H) 3.16(s, 3H) |
|  |  |  |  |  |  |  |  | 4.5(m, 4H), 3.69(dd, 1H) 3.15(s, 3H) |

TABLE 10-continued structures (I) and (18) with substituents $R^1$, $R^2$, Q, X, Y on bicyclic ether framework

| Cmpd | $R^1$ | $R^2$ | $R^3$ | $R^4$ | $R^5$ | Q | Physical Properties Configuration Ratio (I:(18)) | Partial NMR($\delta$) |
|---|---|---|---|---|---|---|---|---|
| 112 | H | H | $CH_3$ | $CH_2CH_2CH_2CH_3$ | $CH_3$ | $CH_2$(2-FPh) | oil, exo | 4.58(m, 4H), 3.7(dd, 1H) 3.16(s, 3H) |
| 113 | H | H | $CH_3$ | $CH_2CH_2CH_2CH_3$ | $CH_3$ | $CH_2$(2-ClPh) | oil, exo | 4.6(m, 4H), 3.71(dd, 1H) 3.17(s, 3H) |
| 114 | H | H | $CH_3$ | $CH_2CH_2CH_2CH_3$ | $CH_3$ | $CH_2$(2-($CH_3$)Ph) | oil, exo | 4.5(m, 4H), 3.69(dd, 1H) 3.16(s, 3H) |
| 115 | H | H | $CH_3$ | $CH_2CH_2CH_2CH_3$ | $CH_3$ | $CH_2$(2,6-(F)$_2$Ph) | oil, exo | 4.57(m, 4H), 3.7(dd, 1H) 3.17(s, 3H) |
| 116 | H | H | $CH_3$ | $CH_2CH_2CH_2CH_3$ | $CH_3$ | $CH_2$(2,6-(Cl)$_2$Ph) | oil, exo | 4.61(s, 1H), 4.59(t, 1H), 3.71(dd, 1H) 3.17(s, 3H) |
| 117 | H | H | $CH_3$ | $CH_2CH_2CH_2CH_3$ | $CH_3$ | $CH_2$(2,4-(F)$_2$Ph) | oil, exo | 4.5(m, 1H), 3.7(dd, 1H) 3.16(s, 3H) |

TABLE 11 structure (I) with $WCH_2O$-, $R^1$, $R^2$, $C(R^3)(R^4)OR^5$ substituents

| Cmpd | $R^1$ | $R^2$ | $R^3$ | $R^4$ | $R^5$ | W | Physical Properties Configuration | Partial NMR ($\delta$) |
|---|---|---|---|---|---|---|---|---|
| 43 | H | H | H | H | $CH_2CH_3$ | 2-FPh | exo, oil, exo | 4.5 (d, d, 4H), 3.78 (dd, 1H), 3.45–3.28 (m, 8H) |
| 44 | H | H | H | H | $CH_3$ | Ph | exo, oil, exo | 4.52 (d, d, 4H), 3.63 (m, 5H), 3.5–3.3 (s + s, 6H), |
| 45 | H | H | H | H | $CH_3$ | 2-FPh | exo, oil, exo | 4.62 (d, 1H), 4.51 (d, 1H), 3.6–3.3 (m, 13H) |
| 46 | H | H | H | H | $CH_2CH_3$ | 2-($CH_3$)Ph | exo, oil, exo | 4.48 (d, d, 4H), 3.75 (dd, 1H), 3.4 (m, 8H) |
| 47 | H | H | H | H | $CH_2CH_3$ | Ph | exo, oil, exo | 4.5 (m, 4H), 3.75 (dd, 1H), 3.4 (m, 8H) |

TABLE 12

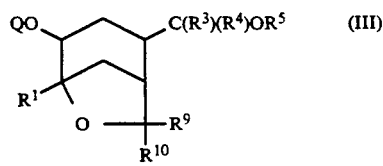

| Cmpd | R¹ | R³ | R4 | R⁵ | R⁹ | R¹⁰ | Q | Physical Properties Configuration | Partial NMR ($\delta$) |
|---|---|---|---|---|---|---|---|---|---|
| 118 | $CH_3$ | H | H | $CH_3$ | H | H | $CH_2(Ph)$ | oil, endo | 4.64 (d, 1H) 4.44 (d, 1H), 3.82 (m, 2H), 3.32 (s, 3H), 3.21 (m, 3H) |
| 119 | $CH_3$ | H | H | $CH_3$ | H | H | $CH_2(2\text{-FPh})$ | oil, endo | 4.6 (m, 1H) 3.8 (m, 2H), 3.31 (s, 3H), 3.2 (m, 3H), |
| 120 | $CH_3$ | H | H | $CH_3$ | H | H | $CH_2(2,6\text{-}(F)_2Ph)$ | oil, endo | 4.65 (d, 1H) 4.48 (d, 1H), 3.78 (m, 2H), 3.32 (s, 3H), 3.2 (m, 3H) |
| 121 | H | H | H | $CH_2CH_3$ | H | H | $CH_2(Ph)$ | oil, endo | 4.36 (d + d, 1H), 4.40 (d, 1H), 3.91 (d, 1H), 3.75 (dd, 1H), 3.45 (m, 3H), 3.25 (d, 2H) |
| 122 | H | H | H | $CH_3$ | H | H | $CH_2(Ph)$ | oil, endo | 4.40 (d, 1H), 3.90 (d, 1H), 3.7 (dd, 2H), 3.31 (s, 3H), 3.3 (m, 1H) 3.1 (m, 2H) |
| 123 | H | H | H | $CH_3$ | H | H | $CH_2(2\text{-FPh})$ | oil, endo | 4.62 (s, 2H), 4.40 (d, 1H), 3.90 (d, 1H), 3.71 (dd, 1H), 3.32 (s, 3H), 3.21 (m, 2H) |
| 124 | H | H | H | $CH_3$ | H | H | $CH_2(2\text{-}(CH_3)Ph)$ | oil, endo | 4.53 (dd, 2H), 4.39 (d, 1H), 3.90 (d, 1H), 3.7 (dd, 1H), 3.31 (s, 3H), 3.31 (m, 1H), 3.10 (m, 2H) |
| 125 | H | H | H | $CH_3$ | H | H | $CH_2(2\text{-ClPh})$ | oil, endo | 4.64 (s, 2H), 4.40 (d, 1H), 3.9 (d, 1H), 3.72 (dd, 1H), 3.4 (dd, 1H), 3.32 (s, 3H), 3.2 (m, 2H) |
| 126 | H | H | H | $CH_3$ | H | H | $CH_2(2,6\text{-}(F)_2Ph)$ | oil, endo | 4.61 (s, 2H), 4.4 (d, 1H), 3.9 (d, 1H), 3.7 (dd, 1H), 3.38 (dt, 1H), 3.32 (s, 3H), 3.2 (d + d, 2H) |
| 127 | H | H | H | $CH_3$ | H | H | $CH_2(2,4\text{-}(F)_2Ph)$ | oil, endo | 4.56 (s, 2H), 4.38 (d, 1H), 3.89 (d, 1H), 3.72 (dd, 1H), 3.38 (m, 1H), 3.31 (s, 3H), 3.20 (d + d, 2H) |
| 128 | H | H | H | $CH_3$ | H | H | $CH_2(2,5\text{-}(F)_2Ph)$ | oil, endo | 4.59 (s, 2H), 4.40 (d, 1H), 3.90 (d, 1H), 3.75 (dd, 1H), 3.38 (m, 1H), 3.33 (s, 3H), 3.2 (m, 2H) |
| 129 | H | H | H | $CH_3$ | H | H | $CH_2(2,6\text{-}(Cl)_2Ph)$ | oil, endo | 4.78 (dd, 2H), 4.43 (d, 1H), 3.9 (d, 1H), |

TABLE 12-continued

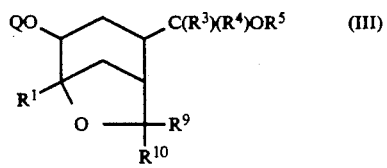

(III)

| Cmpd | R[1] | R[3] | R4 | R[5] | R[9] | R[10] | Q | Physical Properties Configuration | Partial NMR (δ) |
|---|---|---|---|---|---|---|---|---|---|
| 130 | CH₃ | H | H | CH₃ | H | H | CH₂(2-(CH₃)Ph) | oil, endo | 3.7 (dd, 1H), 3.4 (m, 1H), 3.32 (s, 3H), 3.2 (dd, 2H) 4.63 (d, 1H), 4.41 (d, 1H), 3.84 (m, 1H), 3.4–3.2, (m, 6H) |
| 131 | CH₃ | H | H | CH₂CH₃ | H | H | CH₂(Ph) | oil, endo | 4.65 (d, 1H), 4.45 (d, 1H), 3.85 (d + dd, 1H), 3.44 (dq, 6H), 3.26 (m, 3H) |
| 132 | CH₃ | H | H | CH₂CH₃ | H | H | CH₂(2-FPh) | oil, endo | 4.7 (d, 1H), 4.5 (d, 1H), 3.87 (d + dd, 2H), 3.43 (dq, 2H), 3.28 (d + m, 3H) |
| 133 | CH₃ | H | H | CH₂CH₃ | H | H | CH₂(2-(CH₃)Ph) | oil, endo | 4.63 (d, 1H), 4.40 (d, 1H), 3.83 (d + dd, 2H), 3.42 (dq, 2H), 3.27 (d + m, 3H) |
| 134 | CH₃ | H | H | CH₂CH₃ | H | H | CH₂(2,6-(F)₂Ph) | oil, endo | 4.71 (d, 1H), 4.50 (d, 1H), 3.8 (d + dd, 2H), 3.42 (dq, 2H), 3.27 (d + m, 3H) |
| 135 | CH₃ | H | H | CH₂CH₃ | H | H | CH₂(2-ClPh) | oil, endo | 4.72 (d, 1H), 4.5 (d, 1H), 3.82 (d + dd, 2H), 3.45 (dq, 2H), 3.3 (m, 3H) |
| 136 | CH₃ | H | H | CH₃ | H | H | CH₂(2-ClPh) | oil, endo | 4.71 (d, 1H), 4.54 (d, 1H), 3.88 (m, 2H), 3.3 (m, 6H) |
| 137 | CH₃ | H | H | CH₃ | H | H | CH₂(2,6-(Cl)₂Ph) | oil, endo | 4.83 (d, 1H), 4.72 (d, 1H), 3.9 (m, 2H), 3.33 (s, 3H), 3.33 (m, 1H), 3.23 (m, 2H) |
| 138 | H | CH₃ | CH₃ | CH₃ | CH₃ | CH₃ | CH₂(Ph) | endo m.p. 78–80° C. | 4.65 (d + d, 2H), 4.40 (d, 1H), 3.3 (t, 1H), 3.15 (s, 3H) |
| 139 | H | CH₃ | CH₃ | CH₃ | CH₃ | CH₃ | CH₂(2-FPh) | endo m.p. 84–86° C. | 4.65 (d + d, 2H), 4.39 (d, 1H), 3.31 (t, 1H), 3.15 (s, 3H) |
| 140 | H | CH₃ | CH₃ | CH₃ | CH₃ | CH₃ | CH₂(2-ClPh) | endo m.p. 50–52° C. | 4.65 (d + d, 2H), 4.42 (d, 1H), 3.38 (t, 1H), 3.16 (s, 3H) |
| 141 | H | CH₃ | CH₃ | CH₃ | CH₃ | CH₃ | CH₂(2,6-(F)₂Ph) | endo m.p. 102–104° C. | 4.66 (d + d, 2H), 4.39 (d, 1H), 3.31 (t, 1H), 3.14 (s, 3H) |
| 142 | H | CH₃ | CH₃ | CH₃ | CH₃ | CH₃ | CH₂(2-(CH₃)Ph) | endo m.p. 49–50° C. | 4.6 (d + d, 2H), 4.4 (d, 1H), 3.29 (t, 1H), 3.15 (s, 3H) |
| 143 | H | CH₃ | CH₃ | CH₃ | CH₃ | CH₃ | CH₂(2,6-(Cl)₂Ph) | endo m.p. 100–101° C. | 4.82 (s, 2H), 4.4 (d, 1H), 3.3 (t, 1H), 3.14 (s, 3H) |
| 144 | H | CH₃ | CH₃ | CH₃ | CH₃ | CH₃ | CH₂(2,4-(F)₂Ph) | endo m.p. 102–103° C. | 4.6 (d + d, 2H), 4.39 (d, 1H), 3.11 (t, 1H), |

TABLE 12-continued $$\text{(III)}$$

structure with QO, C(R³)(R⁴)OR⁵, R¹, O, R⁹, R¹⁰ substituents on cyclohexane ring

| Cmpd | R¹ | R³ | R4 | R⁵ | R⁹ | R¹⁰ | Q | Physical Properties Configuration | Partial NMR (δ) |
|---|---|---|---|---|---|---|---|---|---|
| 145 | CH₃ | H | H | CH₃ | CH₃ | CH₃ | CH₂(Ph) | oil, endo | 3.15 (s, 3H) 4.64 (d, 1H), 4.46 (d, 1H), 3.50 (dd, 1H), 3.34 (s, 3H), 3.21 (dd, 1H) |
| 146 | CH₃ | H | H | CH₃ | CH₃ | CH₃ | CH₂(2-F(Ph) | oil, endo | 4.69 (d, 1H), 4.50 (d, 1H), 3.5 (dd, 1H), 3.4 (dd, 1H), 3.35 (s, 3H) 3.25 (dd, 1H) |
| 147 | CH₃ | H | H | CH₃ | CH₃ | CH₃ | CH₂(2,6-(F)₂Ph) | oil, endo | 4.70 (d, 1H), 4.50 (d, 1H), 3.50 (dd, 1H), 3.40 (dd, 1H), 3.35 (s, 3H) 3.21 (d + d, 1H) |
| 148 | CH₃ | H | H | CH₃ | CH₃ | CH₃ | CH₂(2-ClPh) | oil, endo | 4.72 (d, 1H), 4.52 (d, 1H), 3.52 (dd, 1H), 3.39 (dd, 1H), 3.35 (s, 3H) 3.30 (dd, 1H) |
| 149 | CH₃ | H | H | CH₃ | CH₂CH₃ | CH₂CH₃ | CH₂(Ph) | oil, endo | 4.64 (d, 1H), 4.48 (d, 1H), 3.45 (dd, 1H), 3.34 (s, 3H) 3.34 (dd, 1H) 3.20 (dd, 1H) |
| 150 | CH₃ | H | H | CH₃ | CH₂CH₃ | CH₂CH₃ | CH₂(2-FPh) | oil, endo | 4.68 (d, 1H), 4.52 (d, 1H), 3.45 (dd, 1H), 3.34 (s + dd, 4H) 3.24 (dd, 1H) |
| 151 | CH₃ | H | H | CH₃ | CH₂CH₃ | CH₂CH₃ | CH₂(2,6-(F)₂Ph) | oil, endo | 4.7 (d, 1H), 4.5 (d, 1H), 3.45 (s + dd, 1H), 3.24 (dd, 1H) |
| 152 | CH₂CH₃ | H | H | CH₃ | H | H | CH₂(Ph) | oil, endo | 4.65 (d, 1H), 4.40 (d, 1H), 3.9 (d, 1H), 3.78 (dd, 1H), 3.36 (dd, 2H), 3.33 (s, 3H), 3.24 (dd + dd, 2H) |
| 153 | CH₂CH₃ | H | H | CH₃ | H | H | CH₂(2-FPh) | oil, endo | 4.7 (d, 1H), 4.45 (d, 1H), 3.9 (d, 1H), 3.79 (dd, 1H), 3.4 (dd, 2H), 3.33 (s, 3H), 3.24 (dd + dd, 2H) |
| 154 | CH₂CH₃ | H | H | CH₃ | H | H | CH₂(2,6-(F)₂Ph) | oil, endo | 4.7 (d, 1H), 4.47 (d, 1H), 3.89 (d, 1H), 3.78 (dd, 1H), 3.39 (dd, 2H), 3.36 (s, 3H), 3.26 (dd + dd, 2H) |
| 155 | CH₂CH₃ | H | H | CH₃ | H | H | CH₂(2-ClPh) | oil, endo | 4.75 (d, 1H), 4.46 (d, 1H), 3.91 (d, 1H), 3.8 (dd, 1H), 3.44 (dd, 2H), 3.34 (s, 3H), 3.25 (dd + dd, 2H) |
| 156 | CH₂CH₃ | H | H | CH₃ | H | H | CH₂(2,6-(Cl)₂Ph) | endo m.p. 77–77.5° C. | 4.82 (d, 1H), 4.69 (d, 1H), 3.89 (d, 1H), |

TABLE 12-continued

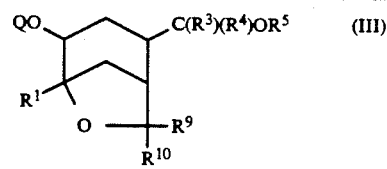

| Cmpd | R¹ | R³ | R4 | R⁵ | R⁹ | R¹⁰ | Q | Physical Properties Configuration | Partial NMR (δ) |
|---|---|---|---|---|---|---|---|---|---|
| 157 | CH₂CH₃ | H | H | CH₃ | H | H | CH₂(2-(CH₃)Ph) | oil, endo | 3.79 (dd, 1H), 3.4 (dd, 2H), 3.34 (s, 3H), 3.24 (s + s, 2H) |
| 158 | CH₂CH₃ | H | H | CH₃ | H | H | CH₂(2-BrPh) | oil, endo | 4.85 (d, 1H), 4.38 (d, 1H), 3.9 (d, 1H), 3.8 (dd, 1H), 3.39 (dd, 2H), 3.34 (s, 3H), 3.22 (m, 2H) 4.71 (d, 1H), 4.41 (d, 1H), 3.92 (d, 1H), 3.80 (dd, 1H), 3.46 (dd, 2H), 3.33 (s, 3H), 3.24 (m, 2H) |

TABLE 13

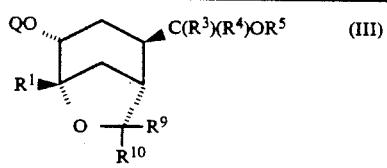

| Cmpd | R¹ | R³ | R⁴ | R⁵ | R⁹ | R¹⁰ | Q | Physical Properties Configuration Ratio (I:(18)) | Partial NMR (δ) |
|---|---|---|---|---|---|---|---|---|---|
| 159 | CH₃ | H | H | CH₃ | H | H | CH₂(Ph) | oil, endo | 4.64 (d, 1H), 4.44 (d, 1H), 3.88 (d, 1H), 3.82 (dd, 1H), 3.32 (s, 3H), 3.2 (m, 3H) |
| 160 | CH₃ | H | H | CH₃ | H | H | CH₂P(2-FPh) | oil, endo | 4.7 (d, 1H), 4.52 (d, 1H), 4.88 (d, 1H), 4.81 (dd, 1H), 3.33 (s, 3H), 3.3–3.2 (m, 3H) |
| 161 | CH₃ | H | H | CH₃ | H | H | CH₂P(2,6-(F)₂Ph) | oil, endo | 4.7 (d, 1H), 4.5 (d, 1H), 3.85 (d, 1H), 3.8 (dd, 1H), 3.33 (s, 3H), 3.22 (m, 3H) |

TABLE 14

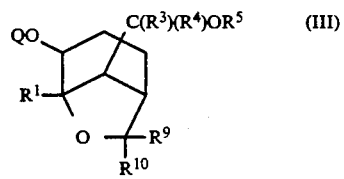

(III)

| Cmpd | $R^1$ | $R^3$ | $R^4$ | $R^5$ | $R^9$ | $R^{10}$ | Q | Physical Properties Configuration | Partial NMR ($\delta$) |
|---|---|---|---|---|---|---|---|---|---|
| 162 | H | H | H | $CH_3$ | $CH_3$ | H | $CH_2(Ph)$ | oil, endo | 4.62 (d, 1H), 4.52 (d, 1H), 4.35 (s, 1H), 4.09 (q, 1H), 3.5 (t, 1H), 3.4 (dd, 1H), 3.32 (dd, 1H), 3.36 (s, 3H) |
| 163 | H | H | H | $CH_3$ | $CH_3$ | H | $CH_2(2\text{-FPh})$ | oil, endo | 4.62 (d + d, 2H), 4.36 (s, 1H), 4.06 (q, 1H), 3.5 (t, 1H), 3.4 (dd, 1H), 3.36 (s, 3H), 3.35 (m, 1H) |
| 164 | H | H | H | $CH_3$ | $CH_3$ | H | $CH_2(Ph)$ | oil, endo | 4.62 (d, 2H), 4.54 (d, 1H), 4.23 (s + m, 2H), 3.4 (d, 2H), 3.35 (s, 3H), 3.34 (m, 1H) |
| 165 | H | H | H | $CH_3$ | $CH_3$ | H | $CH_2(2\text{-FPh})$ | oil, endo | 4.63 (d + d, 2H), 4.24 (m + s, 2H), 3.41 (d, 2H), 3.35 (s, 3H), 3.34 (m, 1H) |

TABLE 15

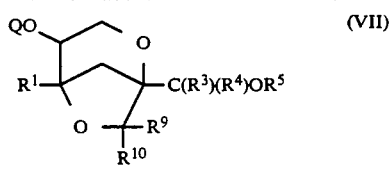

(VII)

| Cmpd | $R^1$ | $R^3$ | $R^4$ | $R^5$ | $R^9$ | $R^{10}$ | Q | Physical Properties Configuration | Partial NMR ($\delta$) |
|---|---|---|---|---|---|---|---|---|---|
| 166 | $CH_3$ | H | H | $CH_2CH_3$ | H | H | $CH_2(Ph)$ | oil, endo | 4.55 (s, 2H), 4.0 (d + d + dd, 3H), 3.68 (t, 1H), 3.4 (m, 4H), 3.38 (dd, 1H) |
| 167 | $CH_3$ | H | H | $CH_2CH_3$ | H | H | $CH_2(2\text{-FPh})$ | oil, endo | 4.6 (d + d, 2H), 4.07 (t + d, 2H), 3.9 (d, 1H), 3.69 (dd, 1H), 3.4 (m, 4H), 3.4 (dd, 1H) |
| 168 | $CH_3$ | H | H | $CH_2CH_3$ | H | H | $CH_2(2\text{-}(CH_3)Ph)$ | oil, endo | 4.55 (d + d, 2H), 4.05 (d, 1H), 4.04 (dd, 1H), 3.9 (d, 1H), 3.69 (t, 1H), 3.49 (m, 4H), 3.35 (dd, 1H) |

TABLE 16

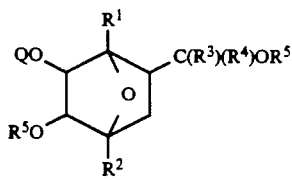

(VIII)

| Cmpd | R¹ | R² | R³ | R⁴ | R⁵ | Q | Physical Properties Configuration | Partial NMR (δ) |
|---|---|---|---|---|---|---|---|---|
| 169 | H | H | $CH_2CH_3$ | $CH_2CH_3$ | $CH_2(Ph)$ | $CH_2(Ph)$ | oil, endo | 4.67 (m, 4H), 4.51 (s + d, 2H), 3.65 (d + d, 2H), 3.13 (s, 3H) |
| 170 | H | H | $CH_2CH_3$ | $CH_2CH_3$ | $CH_2(2\text{-}FPh)$ | $CH_2(2\text{-}FPh)$ | oil, endo | 4.70 (d, 4H), 4.52 (s + d, 2H), 3.7 (d + d, 2H), 3.15 (s, 3H) |
| 171 | H | H | $CH_2CH_3$ | $CH_2CH_3$ | $CH_3$ | $CH_2(2\text{-}FPh)$ | oil, endo | 4.71 (brs, 2H), 4.45 (s + d, 2H), 3.66 (d, 1H), 3.52 (d, 1H), 3.42 (s, 3H), 3.15 (s, 3H) |

TEST A

Seeds of barley (*Hordeum vulgare*), barnyardgrass (*Echinochloa crus-galli*), cheatgrass (*Bromus secalinum*), cocklebur (*Xanthium pensylvanicum*), corn (*Zea mays*), cotton (*Gossypium hirsutum*), crabgrass (Digitaria spp.), giant foxtail (*Setaria faberi*), morningglory (Ipomoea spp.), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crops and weed species were also treated with postemergence applications of test chemicals. Plats ranged in height from two to eighteen cm (two to three leaf stage) for postemergence treatments. Treated plants and untreated controls were maintained in a greenhouse for approximately sixteen days, after which all species were compared to untreated controls and visually evaluated. Plant response ratings, summarized in Table A, are based on a scale of 0 to 10 where 0 is no effect and 10 is complete control. A dash (-) response means no test result.

TABLE A

POSTEMERGENCE

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 43 | (2000 g/ha) | 0 | 0 | 0 | 3 | 0 | 0 | 3 | 0 | 0 | 0 | 0 | 0 | 0 | 0 | 0 | 0 | 0 |
| 44 |  | 0 | 0 | 0 | 0 | 0 | 0 | 0 | 0 | 0 | 0 | 0 | 0 | 0 | 0 | 0 | 0 | 0 |
| 45 |  | 0 | 0 | 0 | 0 | 0 | 0 | 0 | 0 | 0 | — | 0 | 0 | 0 | 0 | 0 | 0 | 0 |
| 46 |  | 0 | 0 | 0 | 0 | 0 | 0 | — | 0 | 0 | 0 | 0 | 0 | 0 | 0 | 0 | 0 | 0 |
| 47 |  | 0 | 6 | 0 | 2 | 0 | 8 | 3 | 0 | 0 | 0 | 0 | 0 | 3 | 0 | 1 | 0 | 0 |
| 1 | (400 g/ha) | 0 | 0 | 0 | 0 | 0 | 0 | 0 | 0 | 0 | 0 | 0 | 0 | 0 | 0 | 0 | 0 | 0 |
| 2 |  | 0 | 0 | 0 | 2 | 0 | 0 | 0 | 0 | 0 | 9 | 0 | 0 | 0 | 0 | 0 | 0 | 0 |
| 3 |  | 0 | 0 | 0 | 1 | 5 | 0 | 0 | 0 | 0 | 0 | 1 | 0 | 3 | 0 | 0 | 0 | 0 |
| 4 |  | 0 | 9 | 0 | 2 | 1 | 0 | 8 | 8 | 0 | 0 | 1 | 0 | 0 | 0 | 0 | 0 | 0 |
| 5 |  | 0 | 9 | 0 | 4 | 0 | 0 | 2 | 4 | 0 | 0 | 0 | 0 | 3 | 0 | 0 | 0 | 0 |
| 6 |  | 0 | 9 | 0 | 0 | 5 | 2 | 9 | 0 | 0 | 0 | 6 | 0 | 0 | 2 | 6 | 0 | 0 |
| 7 |  | 2 | 3 | 0 | 3 | 0 | 0 | 3 | 9 | 0 | 0 | 0 | 0 | 0 | 0 | 0 | 0 | 0 |
| 8 |  | 0 | 2 | 0 | 3 | 5 | 0 | 3 | 2 | 0 | 0 | 0 | 0 | 2 | 2 | 2 | 0 | 0 |
| 9 |  | 0 | 3 | 0 | 2 | 0 | 0 | 3 | 0 | 0 | 0 | 0 | 0 | 0 | 0 | 0 | 0 | 0 |
| 10 |  | 0 | 2 | 0 | 1 | 0 | 0 | 3 | 0 | 0 | 0 | 0 | 0 | 0 | 0 | 0 | 0 | 0 |
| 11 |  | 0 | 6 | 0 | 2 | 2 | 0 | 2 | 4 | 0 | 0 | 0 | 0 | 2 | 0 | 0 | 0 | 0 |
| 12 |  | 0 | 0 | 3 | 2 | 0 | 0 | 0 | 2 | 0 | — | 0 | 0 | 0 | 0 | 0 | 0 | 0 |
| 13 |  | 0 | 0 | 0 | 0 | 0 | 0 | 1 | 0 | 0 | 0 | 0 | 0 | 0 | 0 | 0 | 0 | 0 |
| 14 |  | 0 | 0 | 0 | 1 | 0 | 0 | 0 | 0 | 0 | 0 | 0 | 0 | 0 | 0 | 0 | 0 | 0 |
| 16 |  | 0 | 0 | 0 | 1 | 0 | 0 | 0 | 0 | 0 | 0 | 0 | 0 | 0 | 0 | 0 | 0 | 0 |
| 18 | (200 g/ha) | 0 | 2 | 0 | 1 | 0 | 0 | 3 | 2 | 0 | 0 | 0 | 0 | 0 | 0 | 0 | 0 | 0 |
| 21 |  | 6 | 9 | 0 | 1 | 7 | 0 | 6 | 0 | 0 | 0 | 0 | 0 | 0 | 0 | 0 | 0 | 0 |
| 22 |  | 0 | 0 | 0 | 2 | 0 | 2 | 4 | 0 | 0 | 0 | 0 | 0 | 0 | 0 | 0 | 0 | 0 |
| 23 |  | 0 | 0 | 0 | 3 | 0 | 4 | 0 | 2 | 0 | 0 | 0 | 0 | 1 | 0 | 1 | 0 | 0 |
| 25 |  | 0 | 3 | 0 | 4 | 4 | 0 | 3 | 0 | 0 | 0 | 0 | 0 | 0 | 0 | 8 | 0 | 0 |
| 26 |  | 0 | 0 | 0 | 1 | 0 | 0 | 0 | 0 | 0 | 7 | 0 | 0 | 2 | 0 | 8 | 0 | 0 |
| 27 |  | 0 | 0 | 0 | 1 | 2 | 0 | 3 | 2 | 0 | 0 | 0 | 0 | 0 | 0 | 0 | 0 | 0 |
| 28 |  | 0 | 6 | 2 | 1 | 5 | 0 | 8 | 9 | 1 | 8 | 0 | 0 | 1 | 2 | 3 | 0 | 0 |
| 29 |  | 0 | 9 | 3 | 1 | 0 | 0 | 0 | 9 | 0 | 9 | 0 | 0 | 0 | 4 | 7 | 0 | 0 |
| 30 |  | 0 | 0 | 0 | 6 | 0 | 0 | 0 | 0 | 0 | 0 | 0 | 0 | 1 | 0 | 0 | 0 | 0 |
| 31 |  | 0 | 0 | 0 | 4 | 0 | 0 | 3 | 0 | 0 | 0 | 0 | 0 | 0 | 0 | 0 | 0 | 0 |
| 32 |  | 0 | 5 | 0 | 2 | 0 | 0 | 0 | 8 | 0 | 0 | 0 | 0 | 0 | 0 | 2 | 0 | 0 |
| 33 |  | 0 | 0 | 0 | 1 | 0 | 0 | 0 | 0 | 0 | 0 | 0 | 0 | 0 | 0 | 0 | 0 | 0 |
| 35 |  | 0 | 0 | 0 | 1 | 0 | 0 | 0 | 0 | 0 | 9 | 0 | 0 | 0 | 0 | 3 | 0 | 0 |
| 36 |  | 0 | 0 | 0 | 0 | 0 | 0 | 0 | 0 | 0 | 0 | 0 | 0 | 0 | 0 | 0 | 0 | 0 |
| 37 |  | 0 | 0 | 0 | 0 | 0 | 0 | 0 | 0 | 0 | 0 | 0 | 0 | 0 | 0 | 0 | 0 | 0 |
| 40 |  | 0 | 0 | 0 | 0 | 0 | 0 | 0 | 0 | 0 | — | 0 | 0 | 0 | 0 | 0 | 0 | 0 |
| 41 |  | 0 | 0 | 0 | 0 | 0 | 0 | 0 | 0 | 0 | 0 | 0 | 0 | 0 | 0 | 0 | 0 | 0 |
| 42 |  | 0 | 0 | 0 | 0 | 0 | 0 | 0 | 0 | 0 | 0 | 0 | 0 | 0 | 0 | 0 | 0 | 0 |
| 43 |  | 0 | 0 | 0 | 0 | 0 | 0 | 0 | 0 | 0 | 0 | 0 | 0 | 0 | 0 | 0 | 0 | 0 |
| 44 |  | 0 | 0 | 0 | 0 | 0 | 0 | 0 | 0 | 0 | 0 | 0 | 0 | 0 | 0 | 0 | 0 | 0 |
| 45 |  | 0 | 0 | 0 | 0 | 3 | 0 | 0 | 0 | 0 | 0 | 0 | 0 | 0 | 0 | 0 | 0 | 0 |
| 46 |  | 0 | 0 | 0 | 1 | 0 | 1 | 0 | 2 | 0 | 0 | 0 | 0 | 0 | 0 | 1 | 0 | 0 |
| 47 |  | 0 | 2 | 4 | 2 | 0 | 0 | 0 | 2 | 0 | 0 | 0 | 0 | 2 | 0 | 5 | 0 | 0 |
| 48 |  | 0 | 0 | 0 | 1 | 0 | 0 | 0 | 0 | 0 | 0 | 0 | 0 | 0 | 0 | 0 | 0 | 0 |
| 49 |  | 0 | 0 | 0 | 1 | 0 | 0 | 7 | 1 | 0 | — | 0 | 0 | 0 | 0 | 1 | 0 | 0 |
| 50 |  | 0 | 0 | 0 | 2 | 0 | 0 | — | 0 | 0 | — | 0 | 0 | 0 | 0 | 5 | 0 | 0 |
| 51 |  | 0 | 0 | 0 | 1 | 0 | 0 | — | 1 | 0 | — | 0 | 0 | 0 | 4 | 5 | 0 | 0 |
| 52 |  | 0 | 0 | 0 | 1 | 0 | 0 | — | 0 | 0 | — | 0 | 0 | 2 | 0 | 1 | 0 | 0 |
| 53 |  | 0 | 3 | 0 | 0 | 2 | 0 | 0 | 0 | 0 | 6 | 0 | 0 | 0 | 3 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 54 | | 0 | 0 | 0 | — | 0 | 0 | 0 | 0 | 0 | — | 0 | 0 | 0 | 0 | — | 0 | 0 |
| 55 | | 0 | 0 | 0 | — | 0 | 0 | 0 | 2 | 0 | — | 0 | 0 | 0 | 0 | 0 | 0 | 0 |
| 56 | | 0 | 6 | 2 | — | 0 | — | 3 | 0 | 0 | 0 | 0 | 0 | 0 | 5 | 5 | 0 | 0 |
| 57 | | 0 | 0 | 0 | 2 | 0 | 3 | 3 | 0 | 0 | 0 | 0 | 5 | — | 3 | — | 0 | 0 |
| 58 | | 0 | 2 | 0 | — | 0 | 0 | 8 | 0 | 0 | 4 | 0 | 3 | 0 | 3 | — | 0 | 0 |
| 59 | | 0 | 0 | 0 | — | 0 | 0 | 4 | 0 | 0 | 0 | 0 | 0 | 0 | 4 | 6 | 0 | 0 |
| 60 | | 0 | 0 | 0 | 3 | 0 | 0 | 0 | 2 | 0 | 0 | 0 | 3 | — | 2 | — | 0 | 0 |
| 61 | | 0 | 3 | 0 | 2 | 0 | 3 | 0 | 0 | 0 | 0 | 0 | 0 | 0 | 2 | 3 | 0 | 0 |
| 62 | | 0 | — | 0 | — | 0 | 3 | 0 | 2 | 0 | 0 | 0 | 3 | — | — | 3 | 0 | 0 |
| 63 | | 0 | 0 | 0 | 3 | 0 | 2 | 0 | 0 | 0 | 0 | 0 | 0 | 0 | 0 | 2 | 0 | 0 |
| 64 | | 0 | 0 | 0 | — | 0 | 6 | 0 | 0 | 0 | 0 | 0 | 0 | 0 | 0 | 2 | 0 | 0 |
| 65 | | 0 | 0 | 0 | — | 0 | 5 | 0 | 0 | 0 | 0 | 0 | 0 | 0 | 0 | — | 0 | 0 |
| 66 | | 0 | 0 | 0 | 2 | 0 | 0 | 0 | 0 | 0 | 0 | 0 | 0 | 0 | 0 | — | 0 | 0 |
| 67 | | 0 | 2 | 0 | — | 0 | 0 | 0 | 0 | 0 | 0 | 0 | 0 | 0 | 0 | 0 | 0 | 0 |
| 68 | | 0 | 2 | 0 | — | 0 | 0 | 0 | 0 | 0 | 0 | 0 | 0 | 0 | 0 | — | 0 | 0 |
| 69 | | 0 | 3 | 0 | 0 | 0 | 0 | 0 | 5 | 0 | 0 | 0 | 0 | 0 | 0 | 0 | 0 | 0 |
| 70 | | 0 | 3 | 6 | — | 0 | 0 | 0 | 0 | 0 | 0 | 0 | 0 | 0 | 0 | 0 | 0 | 3 |
| 71 | | 0 | 3 | 0 | — | 0 | 0 | 0 | 0 | 0 | 0 | 0 | 0 | 0 | 0 | 0 | 0 | 0 |
| 72 | | 0 | 0 | 0 | 2 | 0 | 0 | 0 | 0 | 0 | 0 | 0 | 0 | 0 | 0 | 0 | 0 | 0 |
| 73 | | 0 | 0 | 0 | — | 0 | 0 | 0 | 0 | 0 | 0 | 0 | 0 | 0 | 0 | 0 | 0 | 0 |
| 74 | | 0 | 2 | 0 | — | 0 | 0 | 0 | 0 | 0 | 0 | 0 | 0 | 0 | 0 | 0 | 0 | 0 |
| 75 | | 0 | 0 | 0 | — | 0 | 0 | 0 | 0 | 0 | 0 | 0 | 0 | 0 | 0 | 0 | 0 | 0 |
| 76 | | 0 | 0 | 0 | 0 | 0 | 0 | 0 | 0 | 0 | 0 | 0 | 0 | 0 | 0 | 0 | 0 | 0 |
| 77 | | 0 | 0 | 0 | 5 | 0 | 0 | 0 | 0 | 0 | 0 | 0 | 0 | 0 | 0 | 0 | 0 | 0 |
| 78 | | 0 | 8 | 0 | 0 | 0 | 0 | 0 | 0 | 0 | 0 | 0 | 0 | 2 | 0 | 0 | 0 | 0 |
| 79 | | 0 | 8 | 0 | 0 | 0 | 0 | 0 | 0 | 0 | 0 | 0 | 0 | 0 | 0 | 0 | 0 | 0 |
| 80 | | 0 | 0 | 0 | 0 | 2 | 0 | 2 | 0 | 0 | 0 | 0 | 0 | — | 0 | 0 | 0 | 0 |
| 81 | | 0 | 0 | 0 | — | 2 | 0 | 2 | 0 | 0 | 0 | 0 | 0 | — | — | — | 0 | 0 |
| 82 | | 0 | 0 | 0 | — | 2 | 0 | 0 | 0 | 0 | 0 | 0 | 0 | 0 | 0 | 0 | 0 | 0 |
| 83 | | 0 | 0 | 0 | 2 | 2 | 0 | 2 | 0 | 0 | 0 | 4 | 0 | 0 | 0 | 0 | 0 | 0 |
| 84 | | 0 | 0 | 0 | — | 0 | 0 | 2 | 0 | 0 | 0 | 0 | 0 | 0 | 0 | 0 | 0 | 0 |
| 85 | | 0 | 0 | 0 | — | 0 | 0 | 2 | 4 | 0 | 0 | 0 | 0 | 0 | 0 | 0 | 0 | 0 |
| 86 | | 0 | 0 | 0 | 0 | 0 | 0 | 2 | 2 | 0 | 0 | 0 | 0 | 0 | 0 | 0 | 0 | 0 |
| 87 | | 0 | 0 | 0 | 0 | 0 | 0 | 0 | 0 | — | 0 | 0 | 0 | 2 | 0 | 2 | 0 | 0 |
| 88 | | 0 | 0 | 0 | 2 | 0 | 0 | 2 | 0 | 0 | 0 | 2 | 0 | 0 | — | 0 | 0 | 0 |
| 89 | | 0 | 0 | 0 | — | 0 | 0 | 0 | 0 | 0 | 0 | 0 | 0 | 0 | 0 | 0 | 0 | 0 |
| 90 | | 0 | 0 | 0 | — | 2 | 0 | — | 2 | 0 | 0 | 0 | 0 | 0 | 0 | 0 | 0 | 0 |
| 92 | | 0 | 7 | 0 | 2 | 2 | 7 | 2 | 4 | 0 | 0 | 0 | 0 | 0 | — | 0 | 0 | 0 |
| 93 | | 0 | 0 | 0 | 2 | 0 | 0 | 0 | 2 | — | 0 | 2 | 0 | 2 | 0 | — | 0 | 0 |
| 94 | | 0 | 0 | 0 | 4 | 0 | 0 | — | 0 | 0 | 0 | 0 | 0 | 0 | 0 | 0 | 0 | 0 |
| 95 | | 0 | 0 | 0 | 2 | 0 | 0 | 0 | 0 | — | 0 | 0 | 0 | — | 0 | 3 | 0 | 0 |
| 96 | | 0 | 0 | 0 | 3 | 0 | 0 | 0 | 0 | 0 | 0 | 0 | 0 | 3 | 0 | 0 | 0 | 0 |
| 97 | | 0 | 3 | 0 | — | 0 | 0 | 2 | 0 | 0 | 0 | 0 | 0 | — | 0 | — | 0 | 0 |
| 98 | | 0 | 0 | 0 | — | 0 | 0 | 3 | 0 | 0 | 4 | 2 | 0 | 0 | 0 | 2 | 0 | 0 |
| 99 | | 0 | 4 | 0 | — | 0 | 0 | 0 | 5 | 0 | 0 | 0 | 0 | — | 0 | 0 | 0 | 0 |
| 100 | | 0 | 4 | 0 | — | 0 | 0 | 0 | 3 | 0 | 0 | 0 | 0 | — | 2 | 2 | 0 | 0 |
| 101 | | 0 | 0 | 0 | — | 0 | 0 | 3 | 3 | 0 | 0 | 0 | 0 | 3 | 0 | 0 | 0 | 0 |
| 102 | | 0 | 3 | 0 | — | 0 | 0 | 0 | 3 | 0 | 0 | 0 | 0 | 0 | 0 | 0 | 0 | 0 |
| 103 | | 0 | 0 | 0 | — | 0 | 0 | 0 | 0 | 0 | 0 | 5 | 0 | 0 | 0 | 0 | 0 | 0 |
| 104 | | 0 | 5 | 0 | — | 0 | 0 | 0 | 0 | 0 | 0 | 0 | 0 | 0 | 0 | 0 | 0 | 0 |
| 107 | | 0 | 5 | 0 | — | 6 | 0 | 0 | 4 | 0 | 0 | 0 | 0 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 111 | | 0 | 0 | 0 | — | 0 | 0 | 0 | 0 | 0 | 0 | 0 | 0 | 0 | 0 | 0 | 0 | 0 |
| 112 | | 0 | 7 | 0 | — | — | 0 | 0 | 0 | 0 | 0 | 0 | 0 | 0 | 0 | 0 | 0 | 0 |
| 113 | | 0 | 0 | 0 | — | 0 | 0 | 0 | 0 | 0 | 0 | 0 | 0 | 0 | 0 | 0 | 0 | 0 |
| 114 | | 0 | 0 | 0 | — | 0 | 0 | 0 | 0 | 0 | 0 | 0 | 0 | 0 | 0 | 0 | 0 | 0 |
| 115 | | 0 | 0 | 0 | — | 0 | 0 | 0 | 0 | 0 | 0 | 0 | 0 | 0 | 0 | 0 | 0 | 0 |
| 116 | | 0 | 0 | 0 | — | 0 | 0 | 0 | 0 | 0 | 0 | 0 | 0 | 0 | 0 | 0 | 6 | 5 |
| 117 | | 8 | 9 | 9 | 0 | 9 | 2 | 9 | 9 | 2 | 9 | 9 | 7 | 3 | 6 | 7 | 2 | 2 |
| 118 | | 6 | 9 | 9 | — | 8 | 0 | 9 | 9 | 1 | 8 | 8 | 0 | 9 | 3 | 7 | 9 | 8 |
| 119 | | 9 | 9 | 9 | — | 9 | 3 | 9 | 9 | 0 | — | 9 | 7 | 2 | 0 | 7 | 0 | 0 |
| 120 | | 0 | 0 | 0 | — | 0 | 2 | 0 | 0 | 0 | 0 | 0 | 0 | 6 | 0 | 0 | 0 | 0 |
| 121 | | 0 | 0 | 0 | — | 0 | 0 | 0 | 0 | 0 | — | 0 | 0 | 0 | 0 | 0 | 0 | 0 |
| 122 | | 0 | 0 | 0 | — | 0 | 0 | 0 | 0 | 0 | — | 0 | 0 | 0 | 0 | 0 | 0 | 0 |
| 123 | | 0 | 0 | 0 | 0 | 0 | 0 | 0 | 0 | 0 | — | 0 | 0 | 0 | 0 | 0 | 0 | 0 |
| 124 | | 0 | 0 | 0 | — | 0 | 0 | 0 | 0 | 0 | — | 0 | 0 | 0 | 0 | 3 | 0 | 0 |
| 125 | | 0 | 1 | 0 | — | 0 | 0 | 0 | 0 | 0 | — | 0 | 0 | 1 | 0 | 0 | 0 | 0 |
| 126 | | 0 | 0 | 0 | 0 | 0 | 0 | 0 | 0 | 0 | — | 0 | 0 | 0 | 0 | 0 | 0 | 0 |
| 127 | | 0 | 0 | 0 | — | 0 | 0 | 0 | 0 | 0 | — | 0 | 0 | 0 | 0 | 0 | 0 | 0 |
| 128 | | 0 | 0 | 0 | 0 | 0 | 0 | 0 | 0 | 0 | 0 | 0 | 0 | 0 | 0 | 0 | 0 | 0 |
| 129 | | 9 | 9 | 9 | 2 | 9 | 0 | 9 | 9 | 2 | 9 | 9 | 4 | 4 | 2 | 7 | 0 | 0 |
| 130 | | 0 | 3 | 0 | 1 | 7 | 1 | 0 | 2 | 0 | 0 | 8 | 0 | 2 | 0 | 5 | 0 | 0 |
| 131 | | 0 | 9 | 3 | — | 7 | 2 | 7 | 9 | 1 | 0 | 6 | 7 | 3 | 2 | 4 | 0 | 0 |
| 132 | | 0 | 9 | 0 | — | 4 | 1 | 8 | 9 | 0 | 0 | 8 | 0 | 4 | 0 | 3 | 9 | 0 |
| 133 | | 3 | 10 | 3 | — | 8 | 2 | 3 | 9 | 1 | 0 | 9 | 7 | 5 | 2 | 6 | 0 | 0 |
| 134 | | 0 | — | 0 | — | 2 | — | 2 | 4 | — | 0 | 2 | 0 | 3 | 0 | 3 | 0 | 0 |
| 135 | | 0 | 9 | 0 | 2 | 7 | — | 2 | 9 | 0 | 0 | 9 | 1 | 4 | 2 | 5 | 0 | 0 |
| 136 | | 0 | 9 | 0 | 2 | 2 | 0 | 3 | 0 | 1 | 0 | 2 | 0 | 3 | 0 | 5 | 0 | 0 |
| 137 | | 0 | 0 | 0 | 0 | 0 | 0 | 0 | 0 | 0 | 0 | 0 | 0 | 0 | 0 | 0 | 0 | 0 |
| 138 | | 0 | 0 | 0 | 0 | 0 | 0 | 0 | 0 | 0 | 0 | 0 | 0 | 0 | 0 | 0 | 0 | 0 |
| 139 | | 0 | 0 | 0 | 0 | 0 | 0 | 0 | 0 | 0 | 0 | 0 | 0 | 0 | 0 | 0 | 0 | 0 |
| 140 | | 0 | 0 | 0 | 0 | 0 | 0 | 0 | 0 | 0 | 0 | 0 | 0 | 0 | 0 | 0 | 0 | 0 |
| 141 | | 0 | 0 | 0 | 1 | 3 | 0 | 6 | 2 | 2 | 0 | 4 | 0 | 0 | 0 | 3 | 2 | 0 |
| 142 | | 0 | 9 | 0 | — | 6 | 0 | 1 | 9 | 0 | 3 | 9 | 6 | 1 | 0 | 2 | 0 | 0 |
| 145 | | 3 | 8 | 3 | — | 5 | 0 | 0 | 2 | 1 | 6 | 0 | 5 | 0 | 0 | 1 | 0 | 0 |
| 146 | | 7 | 8 | 0 | — | 0 | 0 | 0 | 0 | 0 | 9 | 0 | 0 | 0 | 0 | 1 | 0 | 0 |
| 147 | | 0 | 1 | 0 | — | 1 | 0 | 0 | 2 | 1 | 7 | 0 | 0 | 0 | 0 | — | 2 | 0 |
| 148 | | 0 | 0 | 0 | — | 0 | 0 | 0 | 0 | 1 | 0 | 0 | 0 | 0 | 0 | — | 0 | 0 |
| 149 | | 0 | 2 | 3 | 2 | 2 | 0 | 9 | 3 | 0 | 0 | 4 | 0 | 0 | 0 | 3 | 2 | 3 |
| 150 | | 3 | 2 | 0 | 2 | 8 | 8 | 9 | 9 | 0 | 0 | 9 | 0 | 8 | 0 | 2 | 7 | 0 |
| 151 | | 2 | 9 | 8 | 7 | 8 | 2 | 9 | 9 | 0 | 0 | 9 | 6 | 5 | 0 | 7 | 6 | 3 |
| 152 | | 6 | 9 | 6 | 0 | 9 | 6 | 9 | 9 | 0 | 0 | 9 | 5 | 2 | 0 | 3 | 0 | 0 |
| 153 | | 6 | 9 | 9 | 2 | 2 | 5 | 8 | 4 | 0 | 3 | 3 | 3 | 3 | 0 | 8 | 0 | 0 |
| 154 | | 0 | 9 | 0 | 2 | 0 | 4 | 4 | 3 | 0 | 6 | 0 | 0 | 2 | 0 | 6 | 7 | 3 |
| 155 | | 0 | 3 | 0 | — | 8 | 3 | 9 | 8 | 0 | 9 | 2 | 0 | 2 | 3 | 6 | 0 | 0 |
| 156 | | 3 | 9 | 0 | — | 0 | 3 | 2 | 7 | 0 | 7 | 0 | 0 | 0 | 0 | 8 | 0 | 0 |
| 157 | | 0 | 8 | 0 | — | 0 | 0 | 0 | 0 | 0 | 0 | 0 | 0 | 0 | 0 | 4 | 7 | 0 |
| 158 | | 0 | 0 | 0 | — | 0 | 0 | 0 | 2 | 0 | 0 | 2 | 0 | 0 | 0 | 0 | 0 | 0 |
| 166 | | 0 | 1 | 0 | — | 0 | 0 | 0 | 0 | 0 | 0 | 0 | 0 | 0 | 0 | 2 | 0 | 0 |
| 167 | | 0 | 2 | 0 | 1 | 0 | 0 | 0 | 0 | 0 | 0 | 0 | 0 | 0 | 0 | 0 | 0 | 0 |
| 168 | | 0 | 0 | 0 | — | 0 | 0 | 0 | 0 | 0 | 0 | 0 | 0 | 0 | 0 | 0 | 0 | 0 |
| 1 | (100 g/ha) | 0 | 0 | 0 | — | 0 | 0 | 0 | 0 | 0 | 0 | 0 | 0 | 0 | 0 | 0 | 0 | 0 |
| 2 | | 0 | 0 | 0 | 1 | 0 | 0 | 0 | 0 | 0 | 0 | 0 | 0 | 1 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 3 | | 0 | 0 | 0 | — | 0 | 0 | 0 | 0 | 0 | 0 | 0 | 0 | 0 | 0 | 0 | 0 | 0 |
| 4 | | 0 | 0 | 0 | 0 | 0 | 0 | 0 | 0 | 0 | 0 | 0 | 0 | 0 | 0 | 0 | 0 | 0 |
| 5 | | 0 | 3 | 0 | 3 | 0 | 0 | 0 | 0 | 0 | 0 | 0 | 0 | 0 | 0 | 0 | 0 | 0 |
| 6 | | 0 | 0 | 0 | 0 | 0 | 0 | 2 | 0 | 0 | 0 | 0 | 0 | 0 | 0 | 0 | 0 | 0 |
| 7 | | 0 | 5 | 0 | 2 | 0 | 0 | 2 | 4 | 0 | 0 | 0 | 0 | 0 | 0 | 0 | 0 | 0 |
| 8 | | 0 | 0 | 0 | — | 0 | 0 | 0 | 0 | 0 | 0 | 0 | 0 | 0 | 0 | 0 | 0 | 0 |
| 9 | | 0 | 0 | 0 | 2 | 0 | 0 | 0 | 0 | 0 | 0 | 0 | 0 | 0 | 0 | 0 | 0 | 0 |
| 10 | | 0 | 0 | 0 | 2 | 0 | 0 | 0 | 0 | 0 | 0 | 0 | 0 | 0 | 0 | 0 | 0 | 0 |
| 11 | | 0 | 0 | 0 | 1 | 0 | 0 | 0 | 0 | 0 | 0 | 0 | 0 | 0 | 0 | 0 | 0 | 0 |
| 12 | | 0 | 0 | 0 | 0 | 0 | 0 | 0 | 0 | 0 | 0 | 0 | 0 | 0 | 0 | 0 | 0 | 0 |
| 13 | | 0 | 0 | 0 | 0 | 0 | 0 | 0 | 2 | 0 | 0 | 0 | 0 | 0 | 0 | 0 | 0 | 0 |
| 14 | | 0 | 0 | 0 | 1 | 0 | 0 | 0 | 2 | 0 | — | 0 | 0 | 0 | 0 | 0 | 0 | 0 |
| 15 | | 0 | 0 | 0 | 3 | 0 | 0 | 3 | 0 | 0 | 0 | 0 | 0 | 0 | 0 | 0 | 0 | 0 |
| 16 | | 0 | — | 0 | 0 | 0 | 0 | 0 | 2 | 0 | 0 | 0 | 0 | 0 | 0 | 0 | 0 | 0 |
| 17 | | 0 | 0 | 0 | 0 | 0 | 0 | 0 | 0 | 0 | — | 0 | 0 | 0 | 0 | 1 | 0 | 0 |
| 34 | | 0 | 0 | 0 | 0 | 0 | 0 | 0 | 0 | 0 | 0 | 0 | 0 | 0 | 0 | 0 | 0 | 0 |
| 40 | | 0 | 0 | 0 | 0 | 0 | 0 | 0 | 0 | 0 | 0 | 0 | 0 | 0 | 0 | 0 | 0 | 0 |
| 41 | | 0 | 0 | 0 | 1 | 0 | 0 | 0 | 0 | 0 | 0 | 0 | 0 | 0 | 0 | 0 | 0 | 0 |
| 42 | | 0 | 0 | 0 | 0 | 0 | 0 | 0 | 0 | 0 | 0 | 0 | 0 | 0 | 0 | 0 | 0 | 0 |
| 105 | | 0 | 0 | 0 | 0 | 0 | 0 | 0 | 0 | 0 | — | 0 | 0 | 0 | 0 | 0 | 0 | 0 |
| 106 | | 0 | 0 | 0 | 0 | 0 | 0 | 0 | 0 | 0 | — | 0 | 0 | 0 | 0 | 0 | 0 | 0 |
| 18 | (50 g/ha) | 0 | 0 | 0 | 0 | 0 | 0 | 0 | 0 | 0 | 0 | 0 | 0 | 0 | 0 | 0 | 0 | 0 |
| 21 | | 0 | 0 | 0 | 0 | 0 | 0 | 0 | 0 | 0 | 0 | 0 | 0 | 0 | 0 | 0 | 0 | 0 |
| 22 | | 0 | 0 | 0 | 0 | 0 | 0 | 0 | 0 | 0 | 0 | 0 | 0 | 0 | 0 | 1 | 0 | 0 |
| 23 | | 0 | 2 | 0 | 0 | 0 | 0 | 0 | 0 | 0 | 0 | 0 | 0 | 0 | 0 | 0 | 0 | 0 |
| 25 | | 0 | 0 | 0 | 2 | 0 | 0 | 0 | 0 | 0 | 0 | 0 | 0 | 0 | 0 | 0 | 0 | 0 |
| 26 | | 0 | 0 | 0 | 0 | 0 | 0 | 0 | 0 | 0 | 0 | 0 | 0 | 0 | 0 | 0 | 0 | 0 |
| 27 | | 0 | 0 | 0 | 2 | 0 | 0 | 0 | 0 | 0 | 0 | 0 | 0 | 0 | 0 | 0 | 0 | 0 |
| 28 | | 0 | 0 | 0 | 0 | 0 | 0 | 0 | 0 | 0 | 8 | 0 | 0 | 0 | 0 | 0 | 0 | 0 |
| 29 | | 0 | 0 | 0 | 2 | 0 | 0 | 0 | 0 | 0 | 0 | 0 | 0 | 0 | 0 | 0 | 0 | 0 |
| 30 | | 0 | 0 | 0 | 0 | 0 | 0 | 0 | 0 | 0 | 0 | 0 | 0 | 0 | 0 | 0 | 0 | 0 |
| 31 | | 0 | 0 | 0 | — | 0 | 0 | 0 | 0 | 0 | 0 | 0 | 0 | 0 | 0 | 0 | 0 | 0 |
| 32 | | 0 | 0 | 0 | — | 0 | 0 | 0 | 0 | 0 | — | 0 | 0 | 0 | 0 | 0 | 0 | 0 |
| 33 | | 0 | 0 | 0 | — | 0 | 0 | 0 | 0 | 0 | — | 0 | 0 | 0 | 0 | 0 | 0 | 0 |
| 35 | | 0 | 0 | 0 | — | 0 | 0 | 0 | 0 | 0 | 0 | 0 | 0 | 0 | 0 | 0 | 0 | 0 |
| 36 | | 0 | 0 | 0 | 0 | 0 | 0 | 0 | 0 | 0 | 0 | 0 | 0 | 0 | 0 | 0 | 0 | 0 |
| 37 | | 0 | 0 | 0 | 0 | 0 | 0 | 0 | 0 | 0 | 0 | 0 | 0 | 0 | 0 | 0 | 0 | 0 |
| 40 | | 0 | 0 | 0 | 0 | 0 | 0 | 0 | 0 | 0 | 0 | 0 | 0 | 0 | 0 | 0 | 0 | 0 |
| 41 | | 0 | 0 | 0 | 0 | 0 | 0 | 0 | 0 | 0 | 0 | 0 | 0 | 0 | 0 | 0 | 0 | 0 |
| 42 | | 0 | 0 | 0 | 0 | 0 | 0 | 0 | 0 | 0 | 0 | 0 | 0 | 0 | 0 | 0 | 0 | 0 |
| 43 | | 0 | 0 | 0 | 0 | 0 | 0 | 0 | 0 | 0 | 0 | 0 | 0 | 0 | 0 | 0 | 0 | 0 |
| 44 | | 0 | 0 | 0 | 0 | 0 | 0 | 0 | 0 | 0 | 0 | 0 | 0 | 0 | 0 | 0 | 0 | 0 |
| 45 | | 0 | 0 | 0 | 0 | 0 | 0 | 0 | 0 | 0 | 0 | 0 | 0 | 0 | 0 | 0 | 0 | 0 |
| 46 | | 0 | 0 | 0 | 0 | 0 | 0 | 0 | 0 | 0 | 0 | 0 | 0 | 0 | 0 | 0 | 0 | 0 |
| 47 | | 0 | 0 | 0 | 0 | 0 | 0 | 0 | 0 | 0 | 0 | 0 | 0 | 0 | 0 | 0 | 0 | 0 |
| 48 | | 0 | 0 | 0 | 0 | 0 | 0 | 0 | 0 | 0 | 0 | 0 | 0 | 0 | 0 | 0 | 0 | 0 |
| 49 | | 0 | 0 | 0 | 1 | 0 | 0 | 0 | 0 | 0 | 0 | 0 | 0 | 0 | 0 | 1 | 0 | 0 |
| 50 | | 0 | 0 | 0 | 0 | 0 | 0 | 2 | 0 | 0 | 0 | 0 | 0 | 0 | 0 | 0 | 0 | 0 |
| 51 | | 0 | 0 | 0 | 0 | 0 | 0 | — | 0 | 0 | — | 0 | 0 | 0 | — | 0 | 0 | 0 |
| 52 | | 0 | 0 | 0 | 0 | 0 | 0 | 0 | 0 | 0 | 0 | 0 | 0 | 0 | 0 | 0 | 0 | 0 |
| 53 | | 0 | 0 | 0 | 0 | 0 | 0 | 0 | 0 | 0 | 0 | 0 | 0 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 54 | | 0 | 0 | 0 | 0 | 0 | 0 | 0 | 0 | 0 | 0 | 0 | 0 | 0 | 0 | 0 | 0 | 0 |
| 55 | | 0 | 0 | 0 | 0 | 0 | 0 | 0 | 0 | 0 | — | 0 | 0 | 0 | 0 | 0 | 0 | 0 |
| 56 | | 0 | 2 | 0 | — | 0 | — | 0 | 0 | 0 | 0 | 0 | 0 | 0 | 0 | — | 0 | 0 |
| 57 | | 0 | 0 | 0 | 2 | 0 | 2 | — | 0 | 0 | — | 0 | 0 | 0 | 0 | — | 0 | 0 |
| 58 | | 0 | 0 | 0 | — | 0 | 0 | 0 | 6 | 0 | — | 0 | 0 | 0 | 2 | 0 | 0 | 0 |
| 59 | | 0 | 0 | 0 | 0 | 0 | 0 | 2 | 0 | 0 | 0 | 0 | 0 | 0 | 0 | 0 | 0 | 0 |
| 60 | | 0 | 0 | 0 | 2 | 0 | 0 | 0 | 0 | 0 | 0 | 0 | 0 | 0 | 0 | — | 0 | 0 |
| 61 | | 0 | 0 | 0 | — | 0 | 0 | 0 | 0 | 0 | 0 | 0 | 0 | 0 | 0 | 0 | 0 | 0 |
| 62 | | 0 | 0 | 0 | 0 | 0 | 0 | 0 | 0 | 0 | 0 | 0 | 0 | 0 | 0 | — | 0 | 0 |
| 63 | | 0 | 0 | 0 | 0 | 0 | 0 | 0 | 0 | 0 | 0 | 0 | 0 | 0 | 0 | 0 | 0 | 0 |
| 64 | | 0 | 0 | 0 | 0 | 0 | 0 | 0 | 0 | 0 | 0 | 0 | 0 | 0 | 0 | — | 0 | 0 |
| 65 | | 0 | 0 | 0 | 0 | 0 | 0 | 0 | 0 | 0 | 0 | 0 | 0 | 0 | 0 | — | 0 | 0 |
| 66 | | 0 | 0 | 0 | 0 | 0 | 0 | 0 | 0 | 0 | 0 | 0 | 0 | 0 | 0 | — | 0 | 0 |
| 67 | | 0 | 0 | 0 | 0 | 0 | 0 | 0 | 0 | 0 | 0 | 0 | 0 | 0 | 0 | — | 0 | 0 |
| 68 | | 0 | 0 | 0 | 0 | 0 | 0 | 0 | 0 | 0 | 0 | 0 | 0 | 0 | 0 | — | 0 | 0 |
| 69 | | 0 | 0 | 0 | 0 | 0 | 0 | 0 | 0 | 0 | 0 | 0 | 0 | 0 | 0 | — | 0 | 0 |
| 70 | | 0 | 0 | 0 | 0 | 0 | 0 | 0 | 0 | 0 | 0 | 0 | 0 | 0 | 0 | — | 0 | 0 |
| 71 | | 0 | 0 | 0 | 0 | 0 | 0 | 0 | 0 | 0 | 0 | 0 | 0 | 0 | 0 | 0 | 0 | 0 |
| 72 | | 0 | 0 | 0 | 0 | 0 | 0 | 0 | 0 | 0 | 0 | 0 | 0 | 0 | 0 | 0 | 0 | 0 |
| 73 | | 0 | 0 | 0 | 0 | 0 | 0 | 0 | 0 | 0 | 0 | 0 | 0 | 0 | 0 | 0 | 0 | 0 |
| 74 | | 0 | 0 | 0 | — | 0 | 0 | 0 | 0 | 0 | 0 | 0 | 0 | 0 | 0 | 0 | 0 | 0 |
| 75 | | 0 | 0 | 0 | — | 0 | 0 | 0 | 0 | 0 | 0 | 0 | 0 | 0 | 0 | 0 | 0 | 0 |
| 76 | | 0 | 0 | 0 | — | 0 | 0 | 0 | 0 | 0 | 0 | 0 | 0 | 0 | 0 | 0 | 0 | 0 |
| 77 | | 0 | 0 | 0 | — | 0 | 0 | 0 | 0 | 0 | 0 | 0 | 0 | 0 | 0 | 0 | 0 | 0 |
| 78 | | 0 | 0 | 0 | — | 0 | 0 | 0 | 0 | 0 | 0 | 0 | 0 | 0 | 0 | 0 | 0 | 0 |
| 79 | | 0 | 0 | 0 | — | 0 | 0 | 0 | 0 | 0 | 0 | 0 | 0 | 0 | 0 | 0 | 0 | 0 |
| 80 | | 0 | 0 | 0 | 0 | 0 | 0 | 0 | 0 | 0 | 0 | 0 | 0 | 0 | 0 | 0 | 0 | 0 |
| 81 | | 0 | 0 | 0 | — | 0 | 0 | 0 | 0 | 0 | 0 | 0 | 0 | 0 | 0 | 0 | 0 | 0 |
| 82 | | 0 | 0 | 0 | 0 | 0 | 0 | 0 | 0 | 0 | 0 | 0 | 0 | 0 | 0 | 0 | 0 | 0 |
| 83 | | 0 | 0 | 0 | 0 | 0 | 0 | 0 | 0 | 0 | 0 | 0 | 0 | 0 | 0 | 0 | 0 | 0 |
| 84 | | 0 | 0 | 0 | 0 | 0 | 0 | 0 | 0 | 0 | 0 | 0 | 0 | 0 | 0 | 0 | 0 | 0 |
| 85 | | 0 | 0 | 0 | 0 | 0 | 0 | 0 | 0 | 0 | 0 | 0 | 0 | 0 | 0 | 0 | 0 | 0 |
| 86 | | 0 | 0 | 0 | 0 | 0 | 0 | 0 | 0 | 0 | 0 | 0 | 0 | 0 | 0 | 0 | 0 | 0 |
| 87 | | 0 | 0 | 0 | 0 | 0 | 0 | 0 | 0 | 0 | 0 | 0 | 0 | 0 | 0 | 0 | 0 | 0 |
| 88 | | 0 | 0 | 0 | 0 | 0 | 0 | 0 | 0 | 0 | 0 | 0 | 0 | 0 | 0 | 2 | 0 | 0 |
| 89 | | 0 | 2 | 0 | — | 0 | 0 | 2 | 0 | 0 | 4 | 0 | 0 | 0 | 0 | 0 | 0 | 0 |
| 90 | | 0 | 0 | 0 | — | 0 | 0 | 0 | 0 | 0 | 0 | 0 | 0 | 0 | 0 | — | 0 | 0 |
| 92 | | 0 | 0 | 0 | 0 | 0 | 0 | 0 | 0 | 0 | 0 | 0 | 0 | 0 | 0 | 0 | 0 | 0 |
| 93 | | 0 | 0 | 0 | — | 0 | 0 | 0 | 0 | 0 | 0 | 0 | 0 | 0 | 0 | — | 0 | 0 |
| 94 | | 0 | 0 | 0 | | 0 | 0 | 0 | 0 | 0 | 0 | 0 | 0 | 0 | 0 | | 0 | 0 |
| 95 | | 0 | 0 | 0 | 3 | 0 | 0 | 0 | 0 | 0 | 0 | 0 | 0 | 0 | 0 | 0 | 0 | 0 |
| 96 | | 0 | 0 | 0 | 2 | 0 | 0 | 0 | 0 | 0 | 0 | 0 | 0 | 0 | 0 | 0 | 0 | 0 |
| 97 | | 0 | 0 | 0 | | 0 | 0 | 0 | 0 | 0 | 0 | 0 | 0 | 0 | 0 | 0 | 0 | 0 |
| 98 | | 0 | 0 | 0 | — | 0 | 0 | 0 | 0 | 0 | 0 | 0 | 0 | 0 | 0 | 0 | 0 | 0 |
| 99 | | 0 | 0 | 0 | — | 0 | 0 | 0 | 0 | 0 | 0 | 0 | 0 | 0 | 0 | 0 | 0 | 0 |
| 100 | | 0 | 0 | 0 | — | 0 | 0 | 0 | 0 | 0 | 0 | 0 | 0 | 0 | 0 | 0 | 0 | 0 |
| 101 | | 0 | 0 | 0 | — | 0 | 0 | 0 | 0 | 0 | 0 | 0 | 0 | 0 | 0 | 0 | 0 | 0 |
| 102 | | 0 | 0 | 0 | 0 | 0 | 0 | 0 | 0 | 0 | 0 | 0 | 0 | 0 | 0 | 0 | 0 | 0 |
| 103 | | 0 | 0 | 0 | — | 0 | 0 | 0 | 0 | 0 | 0 | 0 | 0 | 0 | 0 | 0 | 0 | 0 |
| 104 | | 0 | 0 | 0 | 0 | 0 | 0 | 0 | 0 | 0 | 0 | 0 | 0 | 0 | 0 | 0 | 0 | 0 |
| 107 | | 0 | 0 | 0 | — | 2 | 0 | 0 | 0 | 0 | 0 | 0 | 0 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 108 | | 0 | 0 | 0 | 2 | 0 | 0 | 0 | 2 | 0 | 0 | 0 | 0 | 0 | 0 | 0 | 0 | 0 |
| 109 | | 0 | 0 | 0 | 1 | 0 | 0 | 0 | 0 | 0 | 0 | 0 | 0 | 0 | 0 | 0 | 0 | 0 |
| 110 | | 0 | 0 | 0 | 1 | 0 | 0 | 0 | 0 | 0 | 0 | 0 | 0 | 0 | 0 | 0 | 0 | 0 |
| 111 | | 0 | 0 | 0 | 0 | 0 | 0 | 0 | 0 | 0 | 0 | 0 | 0 | 0 | 0 | 0 | 0 | 0 |
| 112 | | 0 | 0 | 0 | 0 | 0 | 0 | 0 | 0 | 0 | 0 | 0 | 0 | 0 | 0 | 0 | 0 | 0 |
| 113 | | 0 | 0 | 0 | 1 | 0 | 0 | 0 | 0 | 0 | 0 | 0 | 0 | 0 | 0 | 0 | 0 | 0 |
| 114 | | 0 | 0 | 0 | 0 | 0 | 0 | 0 | 0 | 0 | 0 | 0 | 0 | 0 | 0 | 0 | 0 | 0 |
| 115 | | 0 | 0 | 0 | 1 | 0 | 0 | 0 | 0 | 0 | 0 | 0 | 0 | 0 | 0 | 0 | 0 | 0 |
| 116 | | 0 | 0 | 0 | 0 | 0 | 0 | 0 | 0 | 0 | 5 | 0 | 0 | 0 | 0 | 0 | 0 | 0 |
| 117 | | 0 | 0 | 0 | 1 | 7 | 0 | 7 | 9 | 0 | 0 | 2 | 3 | 2 | 4 | 3 | 2 | 2 |
| 118 | | 0 | 9 | 2 | 1 | 0 | 0 | 9 | 9 | 0 | 0 | 8 | 0 | 2 | 0 | 1 | 7 | 0 |
| 119 | | 5 | 3 | 3 | 2 | 7 | 0 | 7 | 9 | 0 | 0 | 0 | 7 | 0 | 0 | 0 | 0 | 0 |
| 120 | | 0 | 8 | 8 | 1 | 9 | 0 | 9 | 9 | 0 | 0 | 0 | 0 | 0 | 0 | 6 | 0 | 0 |
| 121 | | 0 | 0 | 0 | 0 | 0 | 0 | 0 | 0 | 0 | — | 0 | 0 | 0 | 0 | 0 | 0 | 0 |
| 122 | | 0 | 0 | 0 | 0 | 0 | 0 | 0 | 0 | 0 | — | 0 | 0 | 0 | 0 | 0 | 0 | 0 |
| 123 | | 0 | 0 | 0 | 0 | 0 | 0 | 0 | 0 | 0 | — | 0 | 0 | 0 | 0 | 0 | 0 | 0 |
| 124 | | 0 | 0 | 0 | 0 | 0 | 0 | 0 | 0 | 0 | — | 0 | 0 | 0 | 0 | 0 | 0 | 0 |
| 125 | | 0 | 0 | 0 | 0 | 0 | 2 | 0 | 0 | 0 | — | 2 | 0 | 2 | 0 | 0 | 0 | 0 |
| 126 | | 0 | 0 | 0 | 0 | 0 | 0 | 0 | 0 | 0 | — | 0 | 0 | 0 | 0 | 0 | 0 | 0 |
| 127 | | 0 | 0 | 0 | 0 | 0 | 0 | 0 | 0 | 0 | — | 0 | 0 | 1 | 0 | 0 | 0 | 0 |
| 128 | | 0 | 6 | 0 | 0 | 0 | 0 | 2 | 4 | 0 | 0 | 0 | 0 | 0 | 0 | 0 | 0 | 0 |
| 129 | | 0 | 0 | 0 | 1 | 0 | 0 | 0 | 3 | 0 | 0 | 0 | 0 | 2 | 0 | 1 | 0 | 0 |
| 130 | | 0 | 1 | 0 | 0 | 0 | 0 | 0 | 6 | 0 | 0 | 0 | 0 | 1 | 0 | 0 | 0 | 0 |
| 131 | | 0 | 1 | 0 | 1 | 0 | 0 | 0 | 5 | 0 | 0 | 0 | 0 | 0 | 0 | 0 | 0 | 0 |
| 132 | | 0 | 0 | 0 | 1 | 0 | 0 | 0 | 3 | 0 | 0 | 2 | 0 | 2 | 0 | 1 | 0 | 0 |
| 133 | | 0 | 3 | 0 | 1 | 0 | 0 | 0 | 5 | 0 | 0 | 0 | 0 | 0 | 0 | 0 | 0 | 0 |
| 134 | | 0 | 0 | 0 | 1 | 0 | 0 | 0 | 2 | 0 | 0 | 0 | 0 | 0 | 0 | 0 | 0 | 0 |
| 135 | | 0 | 0 | 0 | 0 | 0 | 0 | 0 | 0 | 0 | 0 | 0 | 0 | 0 | 0 | 1 | 0 | 0 |
| 136 | | 0 | 3 | 0 | 0 | 0 | 0 | 0 | 0 | 0 | 0 | 0 | 0 | 0 | 0 | 0 | 0 | 0 |
| 137 | | 0 | 0 | 0 | 0 | 0 | 0 | 0 | 0 | 0 | 0 | 0 | 0 | 0 | 0 | 1 | 0 | 0 |
| 138 | | 0 | 0 | 0 | 0 | 0 | 0 | 0 | 0 | 0 | 0 | 0 | 0 | 0 | 0 | 0 | 0 | 0 |
| 139 | | 0 | 0 | 1 | 0 | 0 | 0 | 0 | 0 | 0 | 0 | 0 | 0 | 0 | 0 | 0 | 0 | 0 |
| 140 | | 0 | 0 | 0 | 0 | 0 | 0 | 0 | 2 | 0 | 0 | 0 | 0 | 0 | 0 | 0 | 0 | 0 |
| 141 | | 0 | 0 | 0 | 0 | 0 | 0 | 0 | 0 | 0 | 0 | 0 | 0 | 0 | 0 | 0 | 0 | 0 |
| 142 | | 0 | 0 | 0 | 0 | 0 | 0 | 0 | 0 | 0 | — | 0 | 0 | 0 | 0 | 0 | 0 | 0 |
| 143 | | 0 | 0 | 0 | 0 | 0 | 0 | 0 | 0 | 0 | 0 | 0 | 0 | 0 | 0 | 0 | 0 | 0 |
| 144 | | 0 | 0 | 0 | 1 | 0 | 0 | 0 | 0 | 0 | 0 | 0 | 0 | 0 | 0 | 0 | 0 | 0 |
| 145 | | 0 | 0 | 0 | 1 | 0 | 0 | 0 | 0 | 0 | 0 | 0 | 0 | 0 | 0 | 0 | 0 | 0 |
| 146 | | 0 | 0 | 0 | 1 | 0 | 0 | 0 | 0 | 0 | 0 | 0 | 0 | 0 | — | 0 | 0 | 0 |
| 147 | | 0 | 0 | 0 | 0 | 0 | 0 | 0 | 0 | 0 | 0 | 0 | 0 | 0 | 0 | 0 | 0 | 0 |
| 148 | | 0 | 2 | 0 | 0 | 0 | 0 | 2 | 9 | 0 | 0 | 0 | 0 | 0 | 0 | 0 | 0 | 0 |
| 149 | | 0 | 0 | 0 | 1 | 0 | 0 | 0 | 0 | 0 | 0 | 0 | 0 | 0 | 0 | 0 | 0 | 0 |
| 150 | | 0 | 2 | 0 | 0 | 2 | 0 | 0 | 9 | 0 | 0 | 0 | 3 | 3 | 0 | 0 | 0 | 0 |
| 151 | | 0 | 9 | 4 | 1 | 6 | 3 | 3 | 9 | 0 | 3 | 3 | 3 | 3 | 0 | 2 | 0 | 0 |
| 152 | | 0 | 8 | 0 | 1 | 4 | 0 | 3 | 9 | 0 | 3 | 8 | 2 | 2 | 0 | 2 | 0 | 0 |
| 153 | | 0 | 9 | 0 | 1 | 0 | 0 | 7 | 2 | 0 | 0 | 8 | 0 | 1 | 0 | 3 | 0 | 0 |
| 154 | | 0 | 4 | 4 | 1 | 0 | 0 | 2 | 0 | 0 | 0 | 0 | 0 | 0 | 0 | 2 | 0 | 0 |
| 155 | | 0 | 0 | 0 | 1 | 0 | 0 | 0 | 2 | 0 | 0 | 0 | 0 | 0 | 0 | 2 | 0 | 0 |
| 156 | | 0 | 6 | 0 | 2 | 0 | 3 | 2 | 8 | 0 | 0 | 0 | 2 | 0 | 0 | 2 | 0 | 0 |
| 157 | | 0 | 2 | 0 | 1 | 0 | 0 | 0 | 0 | 0 | 0 | 0 | 0 | 0 | 0 | 2 | 0 | 0 |
| 158 | | 0 | 0 | 0 | 0 | 0 | 0 | 0 | 0 | 0 | — | 0 | 0 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|
| 166 | | 0 | 0 | 0 | 0 | 0 | 0 | 0 | 0 | 0 | 0 | 0 | 0 | 0 | 0 | 0 | 0 | 0 |
| 167 | | 0 | 0 | 0 | — | 0 | 0 | 0 | 0 | 0 | 0 | 0 | 0 | 0 | 0 | 0 | 0 | 0 |
| 168 | | 0 | 0 | 0 | — | 0 | 0 | 0 | 0 | 0 | 0 | 0 | 0 | 0 | 0 | 0 | 0 | 0 |

PREEMERGENCE

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|
| 43 | (2000 g/ha) | 0 | 0 | 0 | 0 | 0 | 0 | 4 | 5 | 0 | — | 0 | 0 | 0 | 0 | 0 | 0 | 0 |
| 44 | | 0 | 2 | 0 | 0 | 0 | 0 | 0 | 2 | 0 | 0 | 0 | 0 | 0 | 0 | — | 0 | 0 |
| 45 | | 0 | 2 | 0 | 0 | 0 | 0 | 0 | 3 | 0 | 0 | 0 | 0 | 0 | 0 | — | 0 | 0 |
| 46 | | 0 | 0 | 0 | 0 | 0 | 0 | 2 | 5 | 0 | 0 | 0 | 0 | 0 | 1 | — | 0 | 0 |
| 47 | | 0 | 0 | 0 | 0 | 0 | 0 | 3 | 3 | 0 | 0 | 0 | 0 | 0 | 0 | — | 0 | 0 |
| 1 | (400 g/ha) | 3 | 10 | 0 | 0 | 3 | 0 | 9 | 9 | 0 | 0 | 0 | 9 | 0 | 0 | 7 | 0 | 0 |
| 2 | | 0 | 10 | 0 | 0 | 0 | 0 | 9 | 8 | 0 | 0 | 0 | 0 | 0 | 1 | 0 | 0 | 0 |
| 3 | | 2 | 9 | 0 | 0 | 3 | 0 | 7 | 9 | 0 | 0 | 0 | 8 | 6 | 0 | 6 | 2 | 3 |
| 4 | | 5 | 10 | 6 | 3 | 6 | 2 | 9 | 9 | 0 | 4 | 0 | 7 | 0 | 2 | 6 | 0 | 2 |
| 5 | | 0 | 10 | 3 | 4 | 4 | 0 | 9 | 9 | 0 | 0 | 0 | 0 | 0 | 4 | 2 | 3 | 0 |
| 6 | | 2 | 9 | 0 | 0 | 4 | 3 | 6 | 6 | 0 | 2 | 0 | 5 | 3 | 3 | 5 | 0 | 0 |
| 7 | | 0 | 0 | 4 | 5 | 0 | 0 | 0 | 0 | 5 | 0 | 0 | 0 | 2 | 0 | 2 | 0 | 0 |
| 8 | | 2 | 10 | 0 | 0 | 4 | 0 | 9 | 9 | 0 | 2 | 0 | 5 | 0 | 0 | 6 | 0 | 2 |
| 9 | | 0 | 7 | 2 | 0 | 0 | 0 | 7 | 7 | 0 | 0 | 0 | 0 | 0 | 0 | 0 | 0 | 0 |
| 10 | | 0 | 8 | 3 | 0 | 0 | 0 | 8 | 8 | 0 | 0 | 0 | 0 | 0 | 0 | 0 | 0 | 0 |
| 11 | | 0 | 9 | 0 | 5 | 0 | 0 | 7 | 7 | 0 | 0 | 0 | 6 | 0 | 0 | 1 | 0 | 0 |
| 12 | | 0 | 8 | 2 | 0 | 0 | 0 | 7 | 8 | 0 | 2 | 0 | 0 | 0 | 0 | 2 | 0 | 0 |
| 13 | | 0 | 8 | 3 | 0 | 0 | 0 | 0 | 2 | 0 | 0 | 0 | 0 | 0 | 0 | 2 | 0 | 0 |
| 14 | | 0 | 0 | 0 | 0 | 0 | 0 | 3 | 0 | 0 | 0 | 0 | 0 | 0 | 0 | 0 | 0 | 0 |
| 16 | | 0 | 7 | 2 | 0 | 2 | 0 | 0 | 5 | 0 | 2 | 0 | 6 | 0 | 0 | — | 0 | 0 |
| 18 | (200 g/ha) | 0 | 2 | 0 | 0 | 0 | 0 | 3 | 2 | 0 | 0 | 0 | 0 | 0 | 0 | — | 0 | 0 |
| 21 | | 2 | 9 | 2 | 0 | 0 | 0 | 2 | 9 | 0 | 0 | 0 | 0 | 0 | 0 | 2 | 0 | 2 |
| 22 | | 0 | 9 | 3 | 0 | 0 | 0 | 5 | 8 | 0 | 0 | 0 | 0 | 0 | 0 | — | 0 | 0 |
| 23 | | 2 | 9 | 2 | 0 | 0 | 0 | 5 | 9 | 0 | 0 | 0 | 6 | 0 | 0 | — | 0 | 0 |
| 25 | | 3 | 9 | 7 | 0 | 3 | 5 | 6 | 6 | 0 | 0 | 0 | 0 | 0 | 0 | 1 | 0 | 0 |
| 26 | | 0 | 9 | 0 | 0 | 0 | 0 | 8 | 9 | 0 | 0 | 0 | 8 | 0 | 3 | — | 0 | 0 |
| 27 | | 0 | 0 | 0 | 3 | 0 | 0 | 7 | 6 | 0 | 0 | 0 | 0 | 0 | 0 | — | 0 | 0 |
| 28 | | 0 | 9 | 3 | — | 0 | 0 | 0 | 8 | 0 | 0 | 4 | 0 | 0 | 0 | 2 | 0 | 0 |
| 29 | | 0 | 10 | 0 | 7 | 1 | 0 | 8 | 9 | 2 | 0 | 0 | 8 | 2 | 3 | 4 | 0 | 0 |
| 30 | | 0 | 9 | 6 | 8 | 2 | 0 | 8 | 5 | 0 | 3 | 0 | 0 | 0 | 3 | 8 | 0 | 2 |
| 31 | | 0 | 6 | 0 | — | 0 | 0 | 2 | 6 | 0 | 0 | 0 | 8 | 0 | 2 | 0 | 0 | 0 |
| 32 | | 0 | 9 | 0 | 0 | 0 | 0 | 0 | 9 | 0 | 0 | 0 | 0 | 0 | 0 | 0 | 0 | 0 |
| 33 | | 0 | 9 | 0 | 0 | 0 | 0 | 4 | 9 | 0 | 0 | 0 | 2 | 0 | 0 | 0 | 0 | 0 |
| 35 | | 0 | 9 | 2 | 0 | 0 | 0 | 2 | 8 | 0 | 0 | 0 | 9 | 0 | 0 | 0 | 0 | 0 |
| 36 | | 0 | 9 | 0 | 0 | 0 | 0 | 1 | 9 | 0 | 0 | 0 | 0 | 0 | 0 | 0 | 0 | 0 |
| 37 | | 0 | 8 | 0 | 0 | 2 | 0 | 5 | 7 | 0 | 0 | 0 | 2 | 0 | 0 | 5 | 0 | 0 |
| 40 | | 0 | 9 | 2 | 0 | 0 | 0 | 8 | 9 | 0 | 0 | 0 | 9 | 0 | 0 | 0 | 0 | 0 |
| 41 | | 0 | 0 | 0 | 0 | 0 | 0 | 2 | 0 | 0 | 0 | 0 | 0 | 0 | 0 | 2 | 0 | 0 |
| 42 | | 0 | 0 | 0 | 0 | 0 | 0 | 0 | 0 | 0 | 0 | 0 | 0 | 0 | 0 | 4 | 0 | 0 |
| 43 | | 0 | 0 | 0 | 4 | 0 | 0 | 0 | 0 | 0 | 4 | 0 | 0 | 0 | 0 | 8 | 0 | 0 |
| 44 | | 0 | 0 | 0 | — | 0 | 0 | 0 | 0 | 0 | 0 | 0 | 0 | 0 | 0 | 0 | 0 | 0 |
| 45 | | 0 | 0 | 0 | 0 | 0 | 0 | 0 | 0 | 0 | 0 | 0 | 0 | 0 | 0 | 0 | 0 | 0 |
| 46 | | 0 | 0 | 0 | 0 | 0 | 0 | 0 | 0 | 0 | 0 | 0 | 0 | 0 | 0 | 0 | 0 | 0 |
| 47 | | 0 | 0 | 0 | 0 | 0 | 0 | 0 | 0 | 0 | 0 | 0 | 0 | 0 | 0 | 1 | 0 | 0 |
| 48 | | 0 | 0 | 0 | 0 | 0 | 0 | 0 | 0 | 0 | 0 | 0 | 0 | 0 | 0 | 0 | 0 | 0 |
| 49 | | 0 | 10 | 3 | 0 | 0 | 0 | 3 | 9 | 0 | 0 | 0 | 3 | 0 | 0 | 0 | 0 | 0 |
| 50 | | 0 | 10 | 2 | 7 | 0 | 0 | 7 | 9 | 0 | 0 | 0 | 7 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 51 | | 0 | 3 | 0 | 0 | 0 | 0 | 0 | 2 | 0 | 0 | 0 | 0 | 0 | 0 | 0 | 0 | 0 |
| 52 | | 0 | 0 | 0 | 0 | 0 | 0 | 3 | 3 | 0 | 0 | 0 | 0 | 0 | 0 | 0 | 0 | 0 |
| 53 | | 0 | 3 | 0 | 0 | 0 | 0 | 0 | 4 | 0 | — | 0 | 4 | 0 | 0 | 0 | 0 | 0 |
| 54 | | 0 | 9 | 0 | 0 | 0 | 0 | 4 | 7 | 0 | 0 | 0 | 0 | 0 | 0 | — | 0 | 0 |
| 55 | | 0 | 0 | 2 | 3 | 2 | 2 | 6 | 4 | — | 0 | 2 | 5 | 0 | 0 | 3 | 0 | 0 |
| 56 | | 0 | 10 | 0 | 0 | 2 | 0 | 0 | 4 | 0 | 10 | 0 | 3 | 0 | 0 | 2 | 0 | 0 |
| 57 | | 0 | 2 | 0 | 0 | 0 | — | 4 | 6 | — | 0 | 0 | 0 | 0 | 0 | 0 | 0 | 0 |
| 58 | | 0 | 10 | 0 | 0 | 0 | 0 | 0 | 2 | 0 | 0 | 0 | 0 | 0 | 0 | 2 | 0 | 0 |
| 59 | | 0 | 0 | 0 | 0 | 0 | 0 | 0 | 9 | 0 | 0 | 0 | 0 | 0 | 0 | 0 | 0 | 0 |
| 60 | | 0 | 2 | 0 | — | 0 | 0 | 0 | 8 | 0 | 0 | 0 | 0 | 0 | 0 | 0 | 0 | 0 |
| 61 | | 0 | 9 | 0 | — | 0 | 0 | 6 | 8 | 0 | 0 | 0 | 0 | 0 | 0 | — | 0 | 0 |
| 62 | | 0 | 5 | 0 | — | 0 | 0 | 2 | 8 | 0 | 0 | 0 | 0 | 0 | 0 | 0 | 0 | 0 |
| 63 | | 0 | 0 | 0 | 0 | 0 | 0 | 0 | — | 0 | 0 | 0 | 0 | 0 | 0 | — | 0 | 0 |
| 64 | | 0 | 0 | 0 | 2 | 0 | 0 | 0 | 4 | 0 | 0 | 0 | 0 | 0 | 0 | 0 | 0 | 0 |
| 65 | | 0 | 0 | 0 | 0 | 0 | 0 | 0 | — | 0 | 0 | 0 | 0 | 0 | 0 | 0 | 0 | 0 |
| 66 | | 0 | 7 | 0 | 0 | 0 | 0 | 0 | 4 | 0 | 0 | 0 | 0 | 0 | 0 | 0 | 0 | 0 |
| 67 | | 0 | 7 | 0 | 0 | 0 | 0 | 0 | 0 | 0 | 0 | 0 | 0 | 0 | 0 | 0 | 0 | 0 |
| 68 | | 0 | 8 | 0 | 0 | 0 | 0 | 0 | 7 | 0 | 0 | 0 | 0 | 0 | 0 | 0 | 0 | 0 |
| 69 | | 0 | 0 | 0 | 0 | 0 | 0 | 0 | 6 | 0 | 0 | 0 | 0 | 0 | 0 | 0 | 0 | 0 |
| 70 | | 0 | 0 | 0 | 0 | 0 | 0 | 0 | 5 | 0 | 0 | 0 | 0 | 0 | 0 | 0 | 0 | 0 |
| 71 | | 0 | 0 | 0 | 0 | 0 | 0 | 0 | 2 | 0 | 0 | 0 | 0 | 0 | 0 | 0 | 0 | 0 |
| 72 | | 0 | 0 | 0 | 0 | 0 | 0 | 0 | 0 | 0 | 0 | 0 | 0 | 0 | 0 | 0 | 0 | 0 |
| 73 | | 0 | 4 | 0 | 0 | 0 | 0 | 0 | — | 0 | 0 | 0 | 0 | 0 | 0 | 0 | 0 | 0 |
| 74 | | 0 | 0 | 0 | 0 | 0 | 0 | 0 | — | 0 | 0 | 0 | 0 | 0 | 0 | 0 | 0 | 0 |
| 75 | | 0 | 9 | 0 | 0 | 0 | 0 | 2 | 7 | 0 | — | 0 | 0 | 0 | 0 | 0 | 0 | 0 |
| 76 | | 0 | 9 | 0 | 0 | 0 | 0 | 0 | 3 | 0 | 0 | 0 | 0 | 0 | 0 | 0 | 0 | 0 |
| 77 | | 0 | 9 | 0 | 0 | 0 | 0 | 4 | 9 | 0 | 0 | 0 | 2 | 0 | 0 | 0 | 0 | 0 |
| 78 | | 0 | 9 | 0 | 0 | 0 | 0 | 2 | 8 | 0 | 0 | 0 | 0 | 0 | 0 | 0 | 0 | 0 |
| 79 | | 0 | 9 | 3 | 2 | 0 | 0 | 0 | 8 | 0 | 0 | 0 | 0 | 0 | 0 | 0 | 0 | 0 |
| 80 | | 0 | 0 | 0 | 0 | 0 | 0 | 0 | 8 | 0 | 0 | 0 | 0 | 0 | 0 | 0 | 0 | 0 |
| 81 | | 0 | 0 | 0 | 0 | 0 | 0 | 0 | 0 | 0 | 0 | 0 | 0 | 0 | 0 | 0 | 0 | 0 |
| 82 | | 0 | 3 | 0 | 0 | 0 | 0 | 0 | 5 | 0 | 0 | 0 | 0 | 0 | 0 | 0 | 0 | 0 |
| 83 | | 0 | 0 | 0 | 4 | 0 | 0 | 0 | 7 | 0 | 0 | 0 | 0 | 0 | 0 | 0 | 0 | 0 |
| 84 | | 0 | 0 | 0 | 0 | 0 | 0 | 0 | 4 | 0 | 0 | 0 | 0 | 0 | 0 | 0 | 0 | 0 |
| 85 | | 0 | 0 | 0 | 0 | 0 | 0 | 0 | 0 | 0 | 0 | 0 | 0 | 0 | 0 | 0 | 0 | 0 |
| 86 | | 0 | 0 | 0 | — | 3 | 0 | 8 | 9 | 0 | 0 | 0 | 2 | 0 | 0 | 0 | 0 | 0 |
| 87 | | 0 | 9 | 0 | 3 | 3 | 2 | 2 | 9 | 0 | 0 | 0 | 2 | 0 | 0 | 7 | 0 | 2 |
| 88 | | 0 | 9 | 0 | 3 | 0 | 0 | 0 | 8 | 0 | 3 | 0 | 2 | 0 | 0 | 7 | 0 | 3 |
| 89 | | 0 | 9 | 0 | 0 | 6 | 2 | 9 | 8 | 0 | 6 | 0 | 7 | 0 | 0 | 5 | 0 | 0 |
| 90 | | 0 | 0 | 0 | 8 | 3 | 0 | 9 | 9 | 0 | 0 | 0 | 0 | 0 | 3 | 0 | 0 | 2 |
| 92 | | 0 | 10 | 2 | 0 | 0 | 0 | 3 | 4 | 0 | 0 | 0 | 0 | 0 | — | 2 | 0 | 0 |
| 93 | | 2 | 10 | 4 | 3 | 3 | 2 | 8 | 10 | 0 | 0 | 0 | 2 | 0 | 0 | 0 | 2 | 3 |
| 94 | | 0 | 10 | 2 | 0 | 2 | 0 | 9 | 10 | — | 0 | 0 | 2 | 0 | 0 | 0 | 0 | 0 |
| 95 | | 0 | 10 | 4 | 0 | 0 | 0 | 3 | 9 | 0 | 0 | 0 | 7 | 0 | 0 | 0 | 0 | 2 |
| 96 | | 0 | 10 | 2 | 0 | 2 | 0 | 8 | 9 | 0 | 0 | 0 | 0 | 0 | 0 | 0 | 0 | 0 |
| 97 | | 0 | 10 | 0 | 3 | 3 | 0 | 5 | 7 | 0 | 0 | 0 | 0 | 0 | 0 | 0 | 0 | 0 |
| 98 | | 0 | 10 | 2 | 0 | 0 | 0 | 2 | 8 | — | 0 | 0 | 0 | 0 | 0 | 0 | 0 | 0 |
| 99 | | 0 | 0 | 0 | 0 | 0 | 0 | 0 | 5 | 0 | 0 | 0 | 0 | 0 | 0 | 2 | 0 | 0 |
| 100 | | 0 | 7 | 0 | 0 | 0 | 0 | 9 | 9 | 0 | 0 | 2 | 2 | 0 | 0 | 2 | 0 | 0 |
| 101 | | 0 | 9 | 0 | 4 | 0 | 0 | 9 | 9 | 0 | 0 | 2 | 2 | 0 | 0 | 2 | 0 | 0 |
| 102 | | 2 | 10 | 0 | — | 8 | 0 | 7 | 9 | 0 | 0 | 2 | 8 | 0 | 0 | 2 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 103 | | 0 | 9 | 0 | — | 2 | 0 | 3 | 9 | 0 | 0 | 0 | 0 | 0 | 0 | 0 | 0 | 0 |
| 104 | | 5 | 10 | — | 0 | 3 | 0 | 9 | 9 | 0 | — | 2 | 0 | 0 | 7 | 1 | 0 | 0 |
| 107 | | 0 | 10 | 6 | 0 | 2 | 0 | 7 | 9 | 0 | 0 | 0 | 0 | 1 | 7 | 2 | 2 | 0 |
| 111 | | 0 | 10 | 0 | — | 0 | 0 | 0 | 9 | 0 | 0 | 0 | 7 | 0 | 0 | 0 | 0 | 0 |
| 112 | | 0 | 10 | 0 | 0 | 0 | 0 | 1 | 8 | 0 | 0 | 0 | 2 | 0 | 0 | 0 | 0 | 0 |
| 113 | | 0 | 9 | 0 | — | 0 | 0 | 0 | 9 | 0 | 0 | 0 | 0 | 0 | 0 | 0 | 0 | 0 |
| 114 | | 0 | 7 | 0 | 0 | 0 | 0 | 0 | 8 | 0 | 0 | 0 | 0 | 0 | 0 | 0 | 0 | 0 |
| 115 | | 0 | 10 | 0 | — | 0 | 0 | 8 | 8 | 0 | 0 | 9 | 3 | 9 | 0 | 7 | 7 | 4 |
| 116 | | 0 | 2 | 0 | 0 | 0 | 0 | 0 | 9 | 0 | 0 | 9 | 0 | 8 | 4 | 7 | 8 | 6 |
| 117 | | 0 | 7 | 0 | 0 | 0 | 4 | 1 | 3 | 2 | — | 9 | 0 | 9 | 3 | 8 | 9 | 8 |
| 118 | | 9 | 10 | 9 | 6 | 5 | 7 | 10 | 10 | 3 | 4 | 10 | 3 | 0 | 5 | 8 | 0 | 0 |
| 119 | | 9 | 10 | 7 | 3 | 9 | 0 | 10 | 10 | 0 | 9 | 0 | 0 | 0 | 0 | 3 | 0 | 0 |
| 120 | | 9 | 10 | 10 | 2 | 8 | 0 | 10 | 10 | 0 | 0 | 0 | 0 | 0 | 0 | 0 | 0 | 0 |
| 121 | | 0 | 10 | 2 | 0 | 0 | 0 | 8 | 9 | 0 | 0 | 0 | 0 | 0 | 0 | 3 | 0 | 0 |
| 122 | | 0 | 7 | 0 | 0 | 0 | 0 | 9 | 8 | 0 | 0 | 7 | 0 | 0 | 0 | — | 0 | 0 |
| 123 | | 0 | 0 | 0 | 0 | 2 | 0 | 8 | 7 | 0 | 0 | 2 | 2 | 0 | 0 | 1 | 0 | 0 |
| 124 | | 0 | 9 | 0 | 0 | 2 | 0 | 7 | 8 | 0 | 0 | 0 | 0 | 0 | 0 | 3 | 0 | 2 |
| 125 | | 0 | 9 | 0 | 0 | 0 | 0 | 0 | 9 | 0 | 4 | 9 | 0 | 0 | 0 | 2 | 0 | 3 |
| 126 | | 0 | 0 | 0 | — | 0 | 0 | 0 | 2 | 0 | 0 | 0 | 2 | 0 | 0 | 4 | 0 | 0 |
| 127 | | 0 | 0 | 0 | 0 | 0 | 0 | 0 | 0 | 0 | 0 | 0 | 0 | 0 | 0 | 1 | 0 | 0 |
| 128 | | 0 | 0 | 0 | 0 | 0 | 0 | 2 | 8 | 0 | 0 | 0 | 0 | 0 | 0 | 4 | 0 | 0 |
| 129 | | 5 | 10 | 3 | 0 | 7 | 0 | 10 | 10 | 0 | 10 | 0 | 9 | 8 | 2 | 7 | 5 | 2 |
| 130 | | 6 | 10 | 9 | 0 | 9 | 2 | 10 | 10 | 0 | 10 | 2 | 10 | 8 | 8 | 6 | 0 | 0 |
| 131 | | 9 | 10 | 7 | 0 | 9 | 3 | 10 | 10 | 0 | 0 | 7 | 10 | 9 | 3 | 7 | 0 | 3 |
| 132 | | 9 | 10 | 8 | 0 | 3 | 3 | 10 | 10 | 0 | 0 | 9 | 9 | 5 | 2 | 7 | 0 | 0 |
| 133 | | 9 | 10 | 10 | 0 | 9 | 0 | 10 | 10 | 0 | 5 | 0 | 10 | 9 | 5 | 7 | 8 | 7 |
| 134 | | 0 | 10 | 0 | 0 | 3 | 2 | 10 | 10 | 1 | 0 | 1 | 9 | — | 5 | 2 | 0 | 0 |
| 135 | | — | 10 | 5 | 0 | 3 | 0 | 10 | 10 | 0 | 0 | 0 | 2 | 6 | 7 | 7 | 1 | 3 |
| 136 | | 0 | 9 | 2 | 0 | 9 | 0 | 10 | 3 | — | 5 | 0 | 10 | 0 | 7 | 7 | 0 | 0 |
| 137 | | 0 | 0 | 0 | — | 0 | 0 | 9 | 0 | 0 | 0 | 0 | 2 | 0 | 7 | 7 | 0 | 3 |
| 138 | | 0 | 0 | 0 | 0 | 0 | 0 | 0 | 0 | 0 | 0 | 0 | 0 | 0 | 2 | 0 | 0 | 0 |
| 139 | | 0 | 0 | 0 | 0 | 0 | 0 | 2 | 2 | 0 | 0 | 0 | 0 | 0 | 0 | 0 | 0 | 0 |
| 140 | | 0 | 0 | 0 | 0 | 0 | 0 | 0 | 0 | 0 | 0 | 0 | 0 | 0 | 0 | 0 | 0 | 0 |
| 141 | | 0 | 0 | 0 | 0 | 0 | 0 | 0 | 0 | 0 | 0 | 0 | 0 | 0 | 0 | 0 | 0 | 0 |
| 142 | | 0 | 10 | 5 | 0 | 5 | 0 | 0 | 10 | 0 | 10 | 0 | 0 | 0 | 0 | 5 | 2 | 0 |
| 145 | | 0 | 10 | 0 | 0 | 6 | 0 | 9 | 10 | 0 | 5 | 0 | 9 | 0 | 2 | 4 | 3 | 5 |
| 146 | | 1 | 10 | 4 | 0 | 8 | 0 | 10 | 10 | 3 | 0 | 0 | 8 | 0 | 8 | 4 | 4 | 2 |
| 147 | | 7 | 10 | 4 | 3 | 8 | 0 | 10 | 10 | 2 | 0 | 0 | 8 | 1 | 3 | 0 | 3 | 3 |
| 148 | | 0 | 9 | 0 | 3 | 0 | 0 | 2 | 3 | 0 | 5 | 0 | 0 | 1 | 7 | 0 | 0 | 0 |
| 149 | | 0 | 10 | 0 | — | 0 | 0 | 3 | 6 | 0 | 0 | 0 | 0 | 0 | 0 | 0 | 0 | 0 |
| 150 | | 0 | 10 | 7 | 0 | 0 | 0 | 10 | 5 | 0 | 0 | 0 | 0 | 0 | 0 | 0 | 0 | 0 |
| 151 | | 0 | 10 | 7 | 3 | 0 | 1 | 10 | 10 | 0 | 10 | 0 | 10 | 0 | 0 | 5 | 2 | 6 |
| 152 | | 7 | 10 | 9 | 2 | 10 | 2 | 10 | 10 | 2 | 10 | 9 | 9 | 9 | 4 | 9 | 3 | 2 |
| 153 | | 8 | 10 | 9 | 3 | 10 | 6 | 10 | 10 | 3 | 10 | 8 | 4 | 9 | 5 | 9 | 8 | 2 |
| 154 | | 8 | 10 | 5 | — | 3 | — | 9 | 10 | 2 | 0 | 2 | 0 | 8 | 7 | 9 | 6 | 3 |
| 155 | | 0 | 0 | 2 | 0 | 0 | 0 | 9 | 0 | 0 | 5 | 0 | 2 | 2 | 6 | 6 | 8 | 2 |
| 156 | | 0 | 10 | 6 | 0 | 5 | 2 | 9 | 10 | 0 | 0 | 0 | 3 | 0 | 3 | 7 | 2 | 2 |
| 157 | | 3 | 9 | 2 | 0 | 0 | 0 | 9 | 9 | 0 | 0 | 2 | 2 | 3 | 7 | 7 | 0 | 0 |
| 158 | | 0 | 0 | 0 | 0 | — | 0 | 9 | 9 | 0 | 0 | 2 | 2 | 0 | 2 | 6 | 2 | 0 |
| 166 | | 0 | 9 | 2 | 0 | — | 0 | 9 | 9 | 0 | 0 | 2 | 2 | 1 | 2 | 0 | 0 | 0 |
| 167 | | 0 | 10 | 2 | 0 | 1 | 0 | 9 | 10 | 0 | 0 | 5 | 2 | 1 | 4 | 1 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 168 | | 0 | 7 | 0 | 0 | 0 | 0 | 5 | 7 | 0 | 0 | 0 | 0 | 0 | 0 | 2 | 0 | 0 |
| 1 | (100 g/ha) | 0 | 6 | 0 | — | 0 | 0 | 2 | 6 | 0 | 0 | 0 | 0 | 0 | 0 | 2 | 0 | 0 |
| 2 | | 0 | 9 | 0 | 0 | 0 | 0 | 5 | 9 | 0 | 0 | 0 | 0 | 0 | 0 | 0 | 0 | 0 |
| 3 | | 0 | 0 | 0 | — | 0 | 0 | 0 | 0 | 0 | 0 | 0 | 0 | 0 | 0 | 0 | 0 | 0 |
| 4 | | 0 | 9 | 0 | 3 | 0 | 0 | 9 | 9 | 0 | 0 | 0 | 0 | 0 | 0 | 5 | 0 | 0 |
| 5 | | 0 | 9 | 2 | 3 | 0 | 0 | 8 | 8 | 0 | 0 | 0 | 0 | 0 | 0 | 0 | 0 | 0 |
| 6 | | 0 | 8 | 0 | 0 | 0 | 0 | 5 | 6 | 0 | 0 | 0 | 0 | 0 | 0 | 2 | 0 | 0 |
| 7 | | 0 | 0 | 3 | 1 | 2 | 0 | 6 | 0 | 0 | 0 | 0 | 0 | 0 | 0 | 0 | 0 | 0 |
| 8 | | 0 | 9 | 0 | 0 | 0 | 0 | 6 | 8 | 0 | 0 | 0 | 0 | 0 | 0 | 0 | 0 | 0 |
| 9 | | 0 | 0 | 0 | 0 | 0 | 0 | 0 | 0 | 0 | 0 | 0 | 0 | 0 | 0 | 0 | 0 | 0 |
| 10 | | 0 | 2 | 0 | 0 | 0 | 0 | 5 | 2 | 0 | 0 | 0 | 0 | 0 | 0 | 0 | 0 | 0 |
| 11 | | 0 | 2 | 0 | 5 | 0 | 0 | 2 | 2 | 0 | 0 | 0 | 0 | 0 | 0 | 1 | 0 | 0 |
| 12 | | 0 | 2 | 2 | 0 | 0 | 0 | 4 | 4 | 0 | 0 | 0 | 0 | 0 | 0 | 1 | 0 | 0 |
| 13 | | 0 | 0 | 0 | 0 | 0 | 0 | 0 | 0 | 0 | 0 | 0 | 0 | 0 | 0 | 0 | 0 | 0 |
| 14 | | 0 | 2 | 0 | 0 | 0 | 0 | 5 | 0 | 0 | 0 | 0 | 0 | 0 | 0 | 0 | 0 | 0 |
| 15 | | 0 | 0 | 0 | 0 | 0 | 0 | 0 | 0 | 0 | 0 | 0 | 0 | 0 | 0 | 2 | 0 | 0 |
| 16 | | 0 | 5 | 0 | 0 | 0 | 0 | 0 | 5 | 0 | 0 | 0 | 0 | 0 | 0 | 0 | 0 | 0 |
| 17 | | 0 | 8 | 0 | 0 | 0 | 0 | 8 | 8 | 0 | 0 | 0 | 0 | 0 | 0 | 0 | 0 | 0 |
| 34 | | 0 | 0 | 0 | 0 | 0 | 0 | 0 | 0 | 0 | 0 | 0 | 0 | 0 | 0 | 0 | 0 | 0 |
| 40 | | 0 | 0 | 0 | 0 | 0 | 0 | 0 | 0 | 0 | 0 | 0 | 0 | 0 | 0 | 0 | 0 | 0 |
| 41 | | 0 | 0 | 2 | 0 | 0 | 0 | 0 | 0 | 0 | 0 | 0 | 0 | 0 | 0 | 0 | 0 | 0 |
| 42 | | 0 | 0 | 0 | 0 | 0 | 0 | 0 | 0 | 0 | 0 | 0 | 0 | 0 | 0 | 0 | 0 | 0 |
| 105 | | 0 | 0 | 0 | 0 | 0 | 0 | 0 | 0 | 0 | 0 | 0 | 0 | 0 | 0 | 0 | 0 | 0 |
| 106 | | 0 | 0 | 0 | 0 | 0 | 0 | 0 | 0 | 0 | 0 | 0 | 0 | 0 | 0 | 0 | 0 | 0 |
| 18 | (50 g/ha) | 0 | 0 | 0 | 0 | 0 | 0 | 0 | 0 | 0 | 0 | 0 | 0 | 0 | 0 | 0 | 0 | 0 |
| 21 | | 0 | 0 | 0 | 3 | 0 | 0 | 3 | 2 | 0 | 0 | 0 | 0 | 0 | 0 | 0 | 0 | 0 |
| 22 | | 0 | 9 | 0 | — | 0 | 0 | 0 | 0 | 0 | 0 | 0 | 0 | 0 | 0 | 2 | 0 | 0 |
| 23 | | 0 | 9 | 0 | 7 | 0 | 0 | 7 | 6 | 0 | 0 | 0 | 0 | 0 | 0 | 0 | 0 | 0 |
| 25 | | 0 | 0 | 0 | — | 0 | 0 | 7 | 2 | 0 | 0 | 0 | 0 | 0 | 0 | 0 | 0 | 0 |
| 26 | | 0 | 0 | 0 | — | 0 | 0 | 4 | 0 | 0 | 0 | 0 | 0 | 0 | 0 | 0 | 0 | 0 |
| 27 | | 0 | 9 | 0 | — | 0 | 0 | 7 | 8 | 0 | 0 | 0 | 0 | 0 | 0 | 0 | 0 | 0 |
| 28 | | 0 | 2 | 0 | 0 | 0 | 0 | 0 | 4 | 0 | 0 | 0 | 0 | 0 | 0 | 4 | 0 | 0 |
| 29 | | 0 | 8 | 0 | 0 | 0 | 0 | 3 | 2 | 0 | 0 | 0 | 2 | 0 | 0 | 0 | 0 | 0 |
| 30 | | 0 | 0 | 0 | 0 | 0 | 0 | 0 | 6 | 0 | 2 | 0 | 0 | 0 | 0 | 0 | 0 | 0 |
| 31 | | 0 | 0 | 0 | 0 | 0 | 0 | 3 | 2 | 0 | 0 | 0 | 0 | 0 | 0 | 0 | 0 | 0 |
| 32 | | 0 | 8 | 0 | 0 | 0 | 0 | 2 | 6 | 0 | 0 | 0 | 0 | 0 | 0 | 0 | 0 | 0 |
| 33 | | 0 | 9 | 0 | 0 | 0 | 0 | 2 | 8 | 0 | 0 | 0 | 0 | 0 | 0 | 0 | 0 | 0 |
| 35 | | 0 | 0 | 0 | 0 | 0 | 0 | 0 | 5 | 0 | 0 | 0 | 0 | 0 | 0 | 0 | 0 | 0 |
| 36 | | 0 | 0 | 0 | 0 | 0 | 0 | 2 | 5 | 0 | 0 | 0 | 0 | 0 | 0 | 0 | 0 | 0 |
| 37 | | 0 | 1 | 0 | 0 | 0 | 0 | 2 | 7 | 0 | 0 | 0 | 0 | 0 | 0 | 0 | 0 | 0 |
| 40 | | 0 | 0 | 0 | 0 | 0 | 0 | 0 | 0 | 0 | 0 | 0 | 0 | 0 | 0 | 0 | 0 | 0 |
| 41 | | 0 | 0 | 0 | 0 | 0 | 0 | 0 | 0 | 0 | 0 | 0 | 0 | 0 | 0 | 0 | 0 | 0 |
| 42 | | 0 | 0 | 0 | 0 | 0 | 0 | 0 | 0 | 0 | 0 | 0 | 0 | 0 | 0 | 0 | 0 | 0 |
| 43 | | 0 | 0 | 0 | 0 | 0 | 0 | 0 | 0 | 0 | 0 | 0 | 0 | 0 | 0 | 0 | 0 | 0 |
| 44 | | 0 | 0 | 0 | 0 | 0 | 0 | 0 | 0 | 0 | 0 | 0 | 0 | 0 | 0 | 0 | 0 | 0 |
| 45 | | 0 | 0 | 0 | 0 | 0 | 0 | 0 | 0 | 0 | 0 | 0 | 0 | 0 | 0 | 0 | 0 | 0 |
| 46 | | 0 | 0 | 0 | 0 | 0 | 0 | 0 | 0 | 0 | 0 | 0 | 0 | 0 | 0 | 0 | 0 | 0 |
| 47 | | 0 | 0 | 0 | 0 | 0 | 0 | 0 | 0 | 0 | 0 | 0 | 0 | 0 | 0 | 0 | 0 | 0 |
| 48 | | 0 | 2 | 0 | — | 0 | 0 | 0 | 2 | 0 | 0 | 0 | 0 | 0 | 0 | 0 | 0 | 0 |
| 49 | | 0 | 0 | 0 | — | 0 | 0 | 0 | 0 | 0 | 0 | 0 | 0 | 0 | 0 | 0 | 0 | 0 |
| 50 | | 0 | 3 | 0 | 0 | 0 | 0 | 0 | 2 | 0 | 0 | 0 | 0 | 0 | 0 | 0 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 51 | | 0 | 0 | 0 | 0 | 0 | 0 | 0 | 0 | 0 | 0 | 0 | 0 | 0 | 0 | 0 | 0 | 0 |
| 52 | | 0 | 0 | 0 | 0 | 0 | 0 | 2 | 1 | 0 | 0 | 0 | 0 | 0 | 0 | 0 | 0 | 0 |
| 53 | | 0 | 0 | 0 | 0 | 0 | 0 | 0 | 0 | 0 | 0 | 0 | 0 | 0 | 0 | 0 | 0 | 0 |
| 54 | | 0 | 1 | 0 | 0 | 0 | 0 | 4 | 0 | 0 | 0 | 0 | 0 | 0 | 0 | 0 | 0 | 0 |
| 55 | | 0 | 0 | 0 | 0 | 0 | 0 | 0 | 0 | 0 | 0 | 0 | 0 | 0 | 0 | 0 | 0 | 0 |
| 56 | | 0 | 6 | 0 | 2 | 0 | 0 | 4 | 0 | 0 | 0 | 0 | 0 | 0 | 0 | 0 | 0 | 0 |
| 57 | | 0 | 2 | 0 | 2 | 0 | 0 | 0 | 2 | 0 | 0 | 0 | 0 | 0 | 0 | 1 | 0 | 0 |
| 58 | | 0 | 0 | 0 | 0 | 0 | 0 | 2 | 2 | 0 | 0 | 0 | 0 | 0 | 0 | 0 | 0 | 0 |
| 59 | | 0 | 0 | 0 | — | 0 | 0 | 3 | 2 | 0 | 0 | 0 | 0 | 0 | 0 | 0 | 0 | 0 |
| 60 | | 0 | 0 | 0 | 0 | 0 | 0 | 0 | 0 | 0 | 0 | 0 | 0 | 0 | 0 | 0 | 0 | 0 |
| 61 | | 0 | 0 | 0 | 0 | 0 | 0 | 0 | 0 | 0 | 0 | 0 | 0 | 0 | 0 | 0 | 0 | 0 |
| 62 | | 0 | 2 | 0 | 0 | 0 | 0 | 0 | 2 | 0 | 0 | 0 | 0 | 0 | 0 | 0 | 0 | 0 |
| 63 | | 0 | 0 | 0 | 0 | 0 | 0 | 0 | 5 | 0 | 0 | 0 | 0 | 0 | 0 | 0 | 0 | 0 |
| 64 | | 0 | 0 | 0 | 0 | 0 | 0 | 0 | 2 | 0 | 0 | 0 | 0 | 0 | 0 | 0 | 0 | 0 |
| 65 | | 0 | 0 | 0 | 0 | 0 | 0 | 0 | 0 | 0 | 0 | 0 | 0 | 0 | 0 | 0 | 0 | 0 |
| 66 | | 0 | 0 | 0 | 0 | 0 | 0 | 0 | 0 | 0 | 0 | 0 | 0 | 0 | 0 | 0 | 0 | 0 |
| 67 | | 0 | 0 | 0 | 0 | 0 | 0 | 0 | 0 | 0 | 0 | 0 | 0 | 0 | 0 | 0 | 0 | 0 |
| 68 | | 0 | 5 | 0 | 0 | 0 | 0 | 0 | 0 | 0 | 0 | 0 | 0 | 0 | 0 | 0 | 0 | 0 |
| 69 | | 0 | 0 | 0 | 0 | 0 | 0 | 0 | 0 | 0 | 0 | 0 | 0 | 0 | 0 | 0 | 0 | 0 |
| 70 | | 0 | 0 | 0 | 0 | 0 | 0 | 0 | 0 | 0 | — | 0 | 0 | 0 | 0 | 0 | 0 | 0 |
| 71 | | 0 | 0 | 0 | 0 | 0 | 0 | 0 | 0 | 0 | 0 | 0 | 0 | 0 | 0 | 0 | 0 | 0 |
| 72 | | 0 | 0 | 0 | 0 | 0 | 0 | 0 | 0 | 0 | 0 | 0 | 0 | 0 | 0 | 0 | 0 | 0 |
| 73 | | 0 | 0 | 0 | 0 | 0 | 0 | 0 | 0 | 0 | 0 | 0 | 0 | 0 | 0 | 0 | 0 | 0 |
| 74 | | 0 | 0 | 0 | 0 | 0 | 0 | 0 | 0 | 0 | 0 | 0 | 0 | 0 | 0 | 0 | 0 | 0 |
| 75 | | 0 | 0 | 0 | 0 | 0 | 0 | 0 | 0 | 0 | 0 | 0 | 0 | 0 | 0 | 0 | 0 | 0 |
| 76 | | 0 | 0 | 0 | 0 | 0 | 0 | 0 | 3 | 0 | 0 | 0 | 0 | 0 | 0 | 0 | 0 | 0 |
| 77 | | 0 | 3 | 0 | 0 | 0 | 0 | 0 | 4 | 0 | 0 | 0 | 0 | 0 | 0 | 0 | 0 | 0 |
| 78 | | 0 | 2 | 0 | 0 | 0 | 0 | 0 | 0 | 0 | 0 | 0 | 0 | 0 | 0 | 0 | 0 | 0 |
| 79 | | 0 | 2 | 0 | 0 | 2 | 0 | 0 | 0 | 0 | 0 | 0 | 0 | 0 | 0 | 0 | 0 | 0 |
| 80 | | 0 | 9 | 0 | 0 | 0 | 0 | 0 | 4 | 0 | 0 | 0 | 0 | 0 | 0 | 0 | 0 | 0 |
| 81 | | 0 | 9 | 0 | 0 | 0 | 0 | 0 | 5 | 0 | 0 | 0 | 0 | 0 | 0 | 0 | 0 | 0 |
| 82 | | 0 | 9 | 2 | 0 | 1 | 0 | 0 | 6 | 0 | 0 | 0 | 0 | 0 | 0 | 0 | 0 | 0 |
| 83 | | 0 | 6 | 0 | — | 0 | 0 | 0 | 0 | 0 | 0 | 0 | 0 | 0 | 0 | 0 | 0 | 0 |
| 84 | | 0 | 7 | 0 | 0 | 0 | 0 | 0 | 9 | 0 | 0 | 0 | 0 | 0 | 0 | 0 | 0 | 0 |
| 85 | | 0 | 1 | 0 | 0 | 0 | 0 | 0 | 9 | 0 | 0 | 0 | 0 | 0 | 0 | 0 | 0 | 0 |
| 86 | | 0 | 0 | 0 | 0 | 0 | 0 | 0 | 8 | 0 | 0 | 0 | 0 | 0 | 0 | 0 | 0 | 0 |
| 87 | | 0 | 0 | 0 | — | 0 | 0 | 0 | 7 | 0 | 0 | 0 | 0 | 0 | 0 | 0 | 0 | 0 |
| 88 | | 0 | 0 | 0 | 0 | 0 | 0 | 3 | 5 | 0 | 0 | 0 | 0 | 0 | 0 | 0 | 0 | 0 |
| 89 | | 0 | 0 | 0 | 0 | 0 | 0 | 2 | 2 | 0 | 0 | 0 | 0 | 0 | 0 | 0 | 0 | 0 |
| 90 | | 0 | 0 | 0 | 0 | 0 | 0 | 3 | 0 | 0 | 0 | 0 | 0 | 0 | 0 | 2 | 0 | 0 |
| 91 | | 0 | 0 | 0 | — | 0 | 0 | 2 | 0 | 0 | 2 | 0 | 0 | 0 | 0 | 0 | 0 | 0 |
| 92 | | 0 | 0 | 0 | 0 | 0 | 0 | 0 | 0 | 0 | 0 | 0 | 0 | 0 | 0 | 0 | 0 | 0 |
| 93 | | 0 | 0 | 0 | 0 | 0 | 0 | 0 | 0 | 0 | 0 | 0 | 0 | 0 | 0 | 0 | 0 | 0 |
| 94 | | 0 | 0 | 0 | 0 | 0 | 0 | 0 | 0 | 0 | 0 | 0 | 0 | 0 | 0 | 0 | 0 | 0 |
| 95 | | 0 | 0 | 0 | 0 | 0 | 0 | 0 | 0 | 0 | 0 | 0 | 0 | 0 | 0 | 0 | 0 | 0 |
| 96 | | 0 | 0 | 0 | 0 | 0 | 0 | 0 | 0 | 0 | 0 | 0 | 0 | 0 | 0 | 0 | 0 | 0 |
| 97 | | 0 | 0 | 0 | 0 | 0 | 0 | 0 | 0 | 0 | 0 | 0 | 0 | 0 | 0 | 0 | 0 | 0 |
| 98 | | 0 | 0 | 0 | 0 | 0 | 0 | 0 | 0 | 0 | 0 | 0 | 0 | 0 | 0 | 0 | 0 | 0 |
| 99 | | 0 | 0 | 0 | 0 | 0 | 0 | 0 | 0 | 0 | 0 | 0 | 0 | 0 | 0 | 0 | 0 | 0 |
| 100 | | 0 | 0 | 0 | 0 | 0 | 0 | 0 | 3 | 0 | 0 | 0 | 0 | 0 | 0 | 0 | 0 | 0 |
| 101 | | 0 | 9 | 0 | 0 | 0 | 0 | 4 | 9 | 0 | — | 0 | 0 | 0 | 0 | 1 | 0 | 0 |
| 102 | | 0 | 9 | 0 | 0 | 0 | 0 | 4 | 9 | 0 | — | 0 | 0 | 0 | 0 | 1 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 103 | | 0 | 5 | 0 | 0 | 0 | 0 | 0 | 6 | 0 | 0 | 0 | 0 | 0 | 0 | 0 | 0 | 0 |
| 104 | | 0 | 2 | 0 | — | 0 | 0 | 0 | 9 | 0 | 0 | 0 | 0 | 0 | 0 | 0 | 0 | 0 |
| 107 | | 0 | 7 | 0 | 0 | 0 | 0 | 5 | 9 | 0 | 0 | 4 | 0 | 0 | 0 | 0 | 0 | 0 |
| 108 | | 0 | 10 | 0 | 0 | 0 | 0 | 3 | 8 | 0 | 0 | 0 | 0 | 0 | 0 | 0 | 0 | 0 |
| 109 | | 0 | 3 | 0 | 0 | 0 | 0 | 1 | 7 | 0 | 0 | 0 | 0 | 0 | 0 | — | 0 | 0 |
| 110 | | 0 | 5 | 0 | 0 | 0 | 0 | 2 | 6 | 0 | 0 | 0 | 0 | 0 | 0 | 0 | 0 | 0 |
| 111 | | 0 | 8 | 0 | 0 | 0 | 0 | 0 | 5 | 0 | 0 | 0 | 0 | 2 | 0 | 0 | 0 | 0 |
| 112 | | 0 | 6 | 0 | 0 | 0 | 0 | 0 | 3 | 0 | 0 | 0 | 0 | 3 | 0 | 3 | 0 | 0 |
| 113 | | 0 | 0 | 0 | 0 | 0 | 0 | 0 | 2 | 0 | 0 | 0 | 0 | 7 | 0 | 3 | 0 | 0 |
| 114 | | 0 | 3 | 0 | 0 | 0 | 0 | — | 7 | — | 0 | 2 | 0 | 0 | 2 | 6 | 0 | 0 |
| 115 | | 0 | 0 | 0 | 0 | 0 | 0 | 0 | 0 | 0 | 0 | 0 | 0 | 0 | 0 | — | 0 | 0 |
| 116 | | 2 | 0 | 0 | 0 | 0 | 0 | 0 | 2 | 0 | 0 | 0 | 0 | 0 | 7 | 0 | 0 | 0 |
| 117 | | 3 | 10 | 8 | 0 | 2 | 0 | 10 | 9 | 0 | 0 | 2 | 9 | 2 | 0 | 3 | 2 | 2 |
| 118 | | 7 | 10 | 3 | 0 | 3 | 4 | 9 | 10 | 0 | 0 | 3 | 9 | 3 | 0 | 3 | 3 | 3 |
| 119 | | 0 | 10 | 2 | 8 | 7 | 5 | 9 | 10 | 0 | 5 | 7 | 9 | 7 | 7 | 6 | 0 | 0 |
| 120 | | 0 | 5 | 0 | 0 | 0 | 0 | 0 | 3 | 0 | 8 | 0 | 0 | 0 | 0 | 0 | 0 | 0 |
| 121 | | 0 | 0 | 0 | 0 | 0 | 0 | 0 | 5 | 0 | 0 | 0 | 0 | 0 | 0 | — | 0 | 0 |
| 122 | | 0 | 0 | 0 | 0 | 0 | 0 | 0 | 4 | 0 | 0 | 0 | 0 | 0 | 0 | 0 | 0 | 0 |
| 123 | | 0 | 0 | 0 | 0 | 0 | 0 | 0 | 0 | 0 | 0 | 0 | 0 | 0 | 0 | 0 | 0 | 0 |
| 124 | | 0 | 0 | 0 | 0 | 0 | 0 | 0 | 6 | 0 | 0 | 0 | 0 | 0 | 0 | 0 | 0 | 0 |
| 125 | | 0 | 0 | 0 | 0 | 0 | 0 | 2 | 2 | 0 | 0 | 0 | 0 | 0 | 0 | 0 | 0 | 0 |
| 126 | | 0 | 0 | 0 | 0 | 0 | 0 | 0 | 0 | 0 | 0 | 0 | 0 | 0 | 0 | 0 | 0 | 0 |
| 127 | | 0 | 0 | 0 | 0 | 0 | 0 | 0 | 0 | 0 | 0 | 0 | 0 | 0 | 0 | 0 | 0 | 0 |
| 128 | | 0 | 0 | 0 | 0 | 0 | 0 | 0 | 9 | 0 | 0 | 0 | 0 | 0 | 0 | 3 | 0 | 0 |
| 129 | | 0 | 9 | 3 | 8 | 3 | 0 | 9 | 10 | 0 | 0 | 2 | 7 | 5 | 3 | 2 | 0 | 0 |
| 130 | | 0 | 10 | 0 | 0 | 3 | 0 | 10 | 9 | 0 | 0 | 3 | 7 | — | 2 | 3 | 0 | 0 |
| 131 | | 0 | 10 | 4 | 0 | 0 | 0 | 9 | 10 | 0 | 0 | 0 | 9 | 0 | 0 | — | — | 0 |
| 132 | | 0 | 9 | 2 | 9 | 4 | — | 9 | 9 | 0 | 5 | 2 | 9 | 5 | 3 | 2 | 0 | 0 |
| 133 | | 0 | 10 | — | 0 | 0 | 0 | 10 | 10 | 0 | 8 | 3 | 0 | 0 | 2 | 0 | 0 | 0 |
| 134 | | 0 | 10 | 0 | 0 | 4 | 0 | 9 | 10 | 0 | 0 | 0 | 0 | 5 | 3 | 3 | 0 | 0 |
| 135 | | 0 | 9 | 0 | 0 | 0 | 0 | 9 | 9 | 0 | 0 | 0 | 0 | 0 | 2 | 0 | 0 | 0 |
| 136 | | 0 | 10 | 0 | 0 | 0 | 0 | 0 | 0 | 0 | 4 | 0 | 0 | 0 | 0 | 0 | 0 | 0 |
| 137 | | 0 | 0 | 0 | 0 | 0 | 0 | 0 | 0 | 0 | 0 | 0 | 0 | 0 | 0 | 0 | 0 | 0 |
| 138 | | 0 | 0 | 0 | 0 | 0 | 0 | 0 | 0 | 0 | 0 | 0 | 0 | 0 | 0 | 0 | 0 | 0 |
| 139 | | 0 | 0 | 0 | 0 | 0 | 0 | 0 | 0 | 0 | 0 | 0 | 0 | 0 | 0 | 0 | 0 | 0 |
| 140 | | 0 | 0 | 0 | 0 | 0 | 0 | 0 | 0 | 0 | 0 | 0 | 0 | 0 | 0 | 0 | 0 | 0 |
| 141 | | 0 | 0 | 0 | 0 | 0 | 0 | 0 | 0 | 0 | 0 | 0 | 0 | 0 | 0 | 0 | 0 | 0 |
| 142 | | 0 | 0 | 0 | 0 | 0 | 0 | 0 | 0 | 0 | 0 | 0 | 0 | 0 | 0 | 0 | 0 | 0 |
| 143 | | 0 | 0 | 2 | 0 | 2 | 0 | 0 | 2 | 0 | 0 | 0 | 2 | 0 | 0 | 0 | 0 | 0 |
| 144 | | 0 | 8 | 0 | — | 0 | 0 | 9 | 9 | 0 | 0 | 0 | 0 | 0 | 0 | — | 0 | 0 |
| 145 | | 0 | 9 | 0 | 0 | 0 | 0 | 9 | 9 | 0 | — | 4 | 0 | 0 | 0 | 6 | 0 | 0 |
| 146 | | 0 | 9 | 2 | 0 | 0 | 0 | 5 | 10 | 0 | 0 | 6 | 5 | 9 | 3 | 7 | 2 | 3 |
| 147 | | 0 | — | 0 | 2 | 0 | 2 | 2 | 5 | 0 | 2 | 6 | 3 | 5 | 2 | 7 | 3 | 2 |
| 148 | | 0 | 0 | 0 | 3 | 0 | 2 | 0 | 0 | 0 | 0 | 0 | 0 | — | 2 | 5 | 2 | 0 |
| 149 | | 0 | 2 | 2 | 0 | 8 | 0 | 0 | 3 | 0 | 0 | 0 | 0 | 0 | 0 | 0 | 0 | 0 |
| 150 | | 0 | 10 | 0 | 2 | 3 | 2 | 0 | 10 | 0 | 2 | 4 | 5 | 9 | 3 | 6 | 2 | 3 |
| 151 | | 0 | 10 | 2 | 3 | 3 | 2 | 9 | 10 | 0 | 0 | 6 | 3 | 5 | 2 | 7 | 3 | 2 |
| 152 | | 3 | 10 | 6 | 0 | 0 | 0 | 9 | 10 | 0 | 0 | 6 | 0 | 5 | 2 | 5 | 2 | 0 |
| 153 | | 0 | 10 | 2 | 0 | 0 | 0 | 10 | 10 | 0 | 0 | 0 | 0 | 0 | 3 | 0 | 0 | 0 |
| 154 | | 0 | 10 | 0 | 0 | 0 | 0 | 0 | 0 | 0 | 0 | 0 | 0 | 0 | 0 | 0 | 0 | 0 |
| 155 | | 0 | 10 | 0 | 0 | 0 | 0 | 10 | 9 | 0 | 0 | 0 | 0 | — | 3 | 5 | 0 | 0 |

TABLE A-continued

| COMPOUND | Rate | Barley | Barnyard-grass | Cheat-grass | Cocklebur | Corn | Cotton | Crab-grass | Giant foxtail | Morning-glory | Nutsedge | Rice | Sorghum | Soybean | Sugar beet | Velvet-leaf | Wheat | Wild Oat |
|---|---|---|---|---|---|---|---|---|---|---|---|---|---|---|---|---|---|---|
| 156 | | 0 | 9 | 0 | 0 | 0 | 0 | 0 | 9 | 0 | 0 | 0 | 0 | 0 | 2 | 1 | 0 | 0 |
| 157 | | 0 | 10 | 2 | 0 | 0 | 0 | 5 | 9 | 0 | 0 | 0 | 0 | 0 | 0 | 3 | 0 | 0 |
| 158 | | 0 | 10 | 0 | 0 | 0 | 0 | 9 | 5 | 0 | 0 | 0 | 0 | 0 | 0 | 2 | 0 | 0 |
| 166 | | 0 | 5 | 0 | 0 | 0 | 0 | 3 | 5 | 0 | — | 0 | 0 | 0 | 0 | 0 | 0 | 0 |
| 167 | | 0 | 0 | 0 | — | 0 | 0 | 0 | 2 | 0 | 0 | 0 | 0 | 0 | 0 | 0 | 0 | 0 |
| 168 | | 0 | 1 | 0 | 0 | 0 | 0 | 0 | 2 | 0 | 0 | 0 | 0 | 0 | 0 | 0 | 0 | 0 |

TEST B

Seeds of barley (*Hordeum vulgare*), barnyardgrass (*Echinochloa crus-galli*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria* spp.), Galium (*Galium aparine*), giant foxtail (*Setaria faberii*), lambsquarters (*Chenopodium album*), morningglory (*Ipomea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and untreated controls were maintained in a greenhouse for approximately fifteen to twenty days, after which all treated plants were compared to untreated controls and visually evaluated. Plant response ratings, summarized in Table B, are based on a scale of 0 to 10 where 0 is no effect and 10 is complete control. A dash (-) response means no test result.

TABLE B

| Rate | COMPOUND | Barley | Barnyardgrass | Blackgrass | Cheatgrass | Chickweed | Cocklebur | Corn | Cotton | Crabgrass | Galium | Giant foxtail | Lambsquarters | Morningglory | Nutsedge | Rape | Rice | Sorghum | Soybean | Sugar beet | Velvetleaf | Wheat | Wildbuckwheat | Wild oat |
|---|---|---|---|---|---|---|---|---|---|---|---|---|---|---|---|---|---|---|---|---|---|---|---|---|
| | POSTEMERGENCE |
| (400 g/ha) | 169 | 0 | 0 | 0 | 0 | 0 | 1 | 1 | 1 | 0 | 0 | 0 | 3 | 1 | 0 | 0 | 1 | 1 | 2 | 0 | 1 | 0 | 0 | 0 |
| | 170 | 0 | 0 | 0 | 0 | 0 | 1 | 0 | 0 | 0 | 0 | 0 | 0 | 0 | 0 | 0 | 0 | 2 | 0 | 4 | 0 | 0 | 0 | 0 |
| (200 g/ha) | 162 | 0 | 0 | 0 | 0 | 2 | 2 | 0 | 0 | 0 | 0 | 0 | 0 | 0 | 0 | 0 | 0 | 0 | 0 | 2 | 0 | 0 | 0 | 0 |
| | 163 | 0 | 0 | 0 | 0 | 2 | 0 | 0 | 0 | 0 | 0 | 0 | 0 | 0 | 0 | 0 | 0 | 0 | 0 | 2 | 0 | 0 | 0 | 0 |
| | 164 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| | 165 | 7 | 0 | 0 | 5 | 5 | 8 | 2 | 0 | 0 | 2 | 9 | 2 | 2 | 9 | 5 | 9 | 5 | 7 | 5 | 7 | 8 | 4 | 4 |
| | 171 | 7 | 10 | 5 | 0 | 0 | 1 | 0 | 0 | 0 | 0 | 0 | 0 | 0 | 0 | 0 | 0 | 0 | 0 | 0 | 0 | 0 | 0 | 0 |
| (100 g/ha) | 169 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 170 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| (50 g/ha) | 162 | 0 | 0 | 0 | 0 | 0 | 0 | 0 | 0 | 0 | 0 | 0 | 0 | 0 | 0 | 0 | 0 | 0 | 0 | 3 | 0 | 0 | 0 | 0 |
| | 163 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| | 164 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| | 165 | 0 | 0 | 0 | 0 | 0 | 0 | 0 | 0 | 0 | 0 | 0 | 0 | 0 | 0 | 0 | 0 | 0 | 4 | 0 | 5 | 0 | 0 | 0 |
| | 171 | 0 | 9 | 0 | 1 | 0 | 4 | 2 | 5 | 0 | 5 | 0 | 2 | 0 | 2 | 0 | 9 | 2 | 0 | 0 | 0 | 0 | 0 | 0 |
| | PREEMERGENCE |
| (400 g/ha) | 169 | 0 | 0 | 0 | 0 | 0 | 0 | 0 | 2 | 0 | 0 | 1 | 0 | 0 | 0 | 0 | 0 | 0 | 0 | 0 | 0 | 0 | 0 | 2 |
| | 170 | 2 | 0 | 3 | 2 | 2 | 0 | 0 | 2 | 0 | 0 | 0 | 0 | 0 | 0 | 2 | 0 | 0 | 0 | 0 | 0 | 0 | 0 | 2 |
| (200 g/ha) | 162 | 2 | 1 | 2 | 2 | 2 | 1 | 0 | 2 | 0 | 0 | 3 | 0 | 0 | 0 | 0 | 0 | 0 | 0 | 3 | 0 | 0 | 0 | 9 |
| | 163 | 0 | 0 | 2 | 2 | 6 | 0 | 0 | 0 | 0 | 0 | 3 | 2 | 0 | 0 | 0 | 0 | 0 | 0 | 2 | 0 | 2 | 2 | 0 |
| | 164 | 3 | 0 | 2 | 2 | 0 | 0 | 0 | 0 | 0 | 0 | 2 | — | 0 | 0 | 7 | 5 | 0 | 0 | 9 | 8 | 0 | 10 | 0 |
| | 165 | 0 | 10 | 10 | 10 | 10 | 5 | 0 | 9 | 10 | 9 | 9 | 10 | 4 | 0 | 0 | 0 | 0 | 0 | 0 | 0 | 0 | 0 | 0 |
| | 171 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| (100 g/ha) | 169 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 170 | 0 | 0 | 2 | 2 | 0 | — | 0 | 0 | 0 | 0 | 0 | 0 | 0 | 0 | 0 | 0 | 0 | 0 | 2 | 0 | 0 | 0 | 0 |
| (50 g/ha) | 162 | 0 | 0 | 2 | 2 | 0 | — | 0 | 0 | 0 | 0 | 0 | 0 | 0 | 0 | 0 | 0 | 0 | 0 | 2 | 0 | 0 | 0 | 0 |
| | 163 | 0 | 0 | 2 | 0 | 5 | 0 | 0 | 0 | 0 | 0 | 0 | 0 | 0 | 0 | 0 | 0 | 0 | 0 | 2 | 0 | 0 | 0 | 0 |
| | 164 | 0 | 0 | 2 | 0 | 0 | — | 0 | 0 | 0 | 0 | 0 | — | 0 | 0 | 0 | 0 | 0 | 0 | 2 | 0 | 0 | 0 | 0 |
| | 165 | 0 | 9 | 5 | 2 | 5 | 3 | 2 | 10 | 2 | 0 | 9 | 1 | 2 | 1 | 1 | 2 | 0 | 2 | 0 | 4 | 0 | 0 | 0 |

TEST C

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (Digitaria spp.), downy brome (*Bromus tectorum*), giant foxtail (*Setaria faberii*), green foxtail (*Setaria viridis*), jimsonweed (*Datura stramonium*), johnsongrass (*Sorghum halepense*), lambsquarters (*Chenopodium album*), morningglory (Ipomea spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and untreated controls were maintained in a greenhouse for approximately 24 days, after which all treated plants were compared to untreated controls and visually evaluated. Plant response ratings, summarized in Table C, are reported on a 0 to 10 scale where 0 is no effect and 10 is complete control. A dash (-) response means no test result.

TABLE C

| Rate | COMPOUND | Barley | Barnyard-grass | Blackgrass | Chickweed | Cocklebur | Corn | Cotton | Crabgrass | Downy brome |
|---|---|---|---|---|---|---|---|---|---|---|
| | | | | POSTMERGENCE | | | | | | |
| (500 g/ha) | 32 | 0 | 10 | 0 | 0 | 0 | 0 | 0 | 5 | 0 |
| | 34 | 0 | 7 | 0 | 0 | 0 | 0 | 0 | — | 0 |
| | 93 | 0 | 7 | 4 | 0 | 3 | 3 | 0 | 0 | 4 |
| (250 g/ha) | 2 | 0 | 6 | 0 | 0 | 0 | 0 | 0 | 5 | 0 |
| | 25 | 0 | 8 | 3 | 0 | 6 | 0 | 0 | 0 | 0 |
| | 32 | 0 | 10 | 0 | 0 | 0 | 0 | 0 | 0 | 0 |
| | 34 | 0 | 7 | 0 | 0 | 0 | 0 | 0 | 0 | 0 |
| | 93 | 0 | 5 | 3 | 0 | 0 | 0 | 0 | 0 | 3 |
| | 94 | 0 | 2 | 3 | 0 | 5 | 0 | 0 | 0 | 0 |
| | 102 | 0 | 8 | 7 | 0 | 0 | 0 | 0 | 4 | 0 |
| | 118 | 0 | 10 | 8 | 7 | 0 | 0 | 0 | 2 | 1 |
| | 120 | — | 10 | 10 | 6 | 2 | 1 | 0 | 9 | 4 |
| | 130 | 5 | 10 | 9 | 7 | 0 | 0 | 0 | 9 | 8 |
| | 131 | 0 | 10 | 6 | 4 | — | 2 | 0 | 3 | 3 |
| | 132 | 3 | 8 | 6 | 4 | — | 0 | 2 | 6 | 4 |
| | 133 | 0 | 7 | 4 | 4 | 0 | 0 | 4 | 0 | 3 |
| | 134 | 2 | 10 | 6 | 5 | 4 | 0 | 0 | 3 | 3 |
| | 135 | 0 | 8 | 4 | 3 | — | 0 | 0 | 4 | 0 |
| (125 g/ha) | 2 | 0 | 2 | 0 | 0 | 0 | 0 | 0 | 0 | 0 |
| | 25 | 0 | 4 | 0 | 0 | 5 | 0 | — | 0 | 0 |
| | 32 | 0 | 4 | 0 | 0 | 0 | 0 | 0 | 0 | 0 |
| | 34 | 0 | 7 | 0 | 0 | 0 | 0 | 0 | 0 | 0 |
| | 94 | 0 | 0 | 0 | 0 | 0 | 0 | 0 | 0 | 0 |
| | 102 | 0 | 6 | 3 | 0 | — | 0 | 0 | | |
| | 118 | 0 | 10 | 0 | 5 | 0 | 0 | 0 | 2 | 0 |
| | 119 | 5 | 9 | 9 | 6 | 0 | 0 | 1 | 5 | 7 |
| | 120 | 9 | 10 | 9 | 6 | 1 | 0 | 0 | 9 | 4 |
| | 130 | 0 | 9 | 9 | 7 | — | 0 | 0 | 0 | 3 |
| | 131 | 0 | 5 | 4 | 4 | — | 0 | 0 | 0 | 0 |
| | 132 | 0 | 7 | 3 | 3 | 0 | 0 | 2 | 3 | 0 |
| | 133 | 0 | 4 | 3 | 4 | 0 | 0 | 3 | 0 | 0 |
| | 134 | 0 | 8 | 4 | 4 | 0 | 0 | 0 | 0 | 0 |
| | 135 | 0 | 7 | 3 | 0 | — | 0 | 0 | 3 | 0 |
| (62 g/ha) | 32 | 0 | 0 | 0 | 0 | 0 | 0 | 0 | 0 | 0 |
| | 34 | 0 | 3 | 0 | 0 | 0 | 0 | 0 | 0 | 0 |
| | 94 | 0 | 0 | 0 | 0 | 0 | 0 | 0 | 0 | 0 |
| | 102 | 0 | 0 | 0 | 0 | — | — | 0 | 0 | 0 |
| | 118 | 0 | 9 | 0 | 0 | 0 | 0 | 0 | 0 | 0 |
| | 120 | 1 | 10 | 4 | 3 | 0 | 0 | 0 | 7 | 0 |
| | 130 | 0 | 0 | 0 | 3 | 0 | 0 | 0 | 0 | 0 |
| | 131 | 0 | 5 | 0 | 3 | — | 0 | 0 | 0 | 0 |
| | 132 | 0 | 5 | 2 | 0 | 0 | 0 | 0 | 0 | 0 |
| | 133 | 0 | 3 | 0 | 0 | 0 | 0 | 2 | 0 | 0 |
| | 134 | 0 | 7 | 3 | 3 | 0 | 0 | 0 | 0 | 0 |
| | 135 | 0 | 6 | 0 | 0 | — | 0 | 0 | 3 | 0 |
| (31 g/ha) | 94 | 0 | 0 | 0 | 0 | 0 | 0 | 0 | 0 | 0 |
| | 102 | 0 | 0 | 0 | 0 | — | 0 | 0 | 0 | 0 |
| | 118 | 0 | 4 | 0 | 0 | 0 | 0 | 0 | 0 | 0 |
| | 120 | 0 | 10 | 0 | 0 | 0 | 0 | 0 | 0 | 0 |
| | 130 | 0 | 0 | 0 | 0 | 0 | 0 | 0 | 0 | 0 |
| | 131 | 0 | 3 | 0 | 0 | — | 0 | 0 | 0 | 0 |
| | 132 | 0 | 3 | 0 | 0 | 0 | 0 | 0 | 0 | 0 |
| | 133 | 0 | 0 | 0 | 0 | 0 | 0 | 0 | 0 | 0 |
| | 134 | 0 | 6 | 0 | 0 | 0 | 0 | 0 | 0 | 0 |
| | 135 | 0 | 4 | 0 | 0 | — | 0 | 0 | 0 | 0 |

| Rate | COMPOUND | Giant foxtail | Green foxtail | Jimsonweed | Johnsongrass | Lambsquarters | Morningglory | Nutsedge |
|---|---|---|---|---|---|---|---|---|
| (500 g/ha) | 32 | 7 | 5 | 0 | 3 | 5 | 0 | 0 |
| | 34 | 5 | 0 | 7 | 0 | — | 0 | 3 |
| | 93 | 7 | 0 | 0 | 0 | — | 0 | 3 |

TABLE C-continued

| Rate | Compound | | | | | | | |
|---|---|---|---|---|---|---|---|---|
| | 2 | 0 | 0 | 0 | 0 | 7 | 0 | 0 |
| | 25 | 3 | 0 | 0 | 0 | 5 | 0 | 0 |
| | 32 | 3 | 0 | 0 | 0 | 3 | 0 | 0 |
| | 34 | 3 | 0 | 3 | 0 | 0 | 0 | 0 |
| | 93 | 4 | 0 | 0 | 0 | — | 0 | 0 |
| | 94 | 5 | 2 | 0 | 0 | — | 0 | 0 |
| | 102 | 5 | 0 | 0 | 3 | 0 | 3 | 0 |
| | 118 | 10 | 10 | 5 | 4 | 10 | 4 | 0 |
| | 120 | 10 | 10 | 0 | 6 | — | 0 | 0 |
| | 130 | 9 | 8 | 0 | 6 | 3 | 4 | 0 |
| | 131 | 6 | 0 | 0 | 0 | 8 | 0 | 0 |
| | 132 | 7 | 6 | 3 | 3 | 6 | 0 | 6 |
| | 133 | 6 | 0 | 0 | 0 | 8 | 3 | 0 |
| | 134 | 7 | 6 | 4 | 6 | 6 | 4 | 7 |
| | 135 | 6 | 3 | 2 | 6 | 6 | 2 | 5 |
| (125 g/ha) | 2 | 0 | 0 | 0 | 0 | 5 | 0 | 0 |
| | 25 | 0 | 0 | 0 | 0 | 4 | 0 | 0 |
| | 32 | 0 | 0 | 0 | 0 | 0 | 0 | 0 |
| | 34 | 0 | 0 | 0 | 0 | 0 | 0 | 0 |
| | 94 | 2 | 0 | 0 | 0 | — | 0 | 0 |
| | 102 | 3 | 0 | 0 | 0 | 0 | 2 | 0 |
| | 118 | 7 | 9 | 0 | 4 | 5 | 0 | — |
| | 119 | 9 | 4 | 0 | 0 | 9 | 1 | 0 |
| | 120 | 10 | 10 | 0 | — | 8 | 0 | 0 |
| | 130 | 9 | 0 | 0 | 0 | 3 | 3 | 0 |
| | 131 | 6 | 0 | 0 | 0 | 5 | 0 | 0 |
| | 132 | 5 | 2 | 2 | 0 | 4 | 0 | 0 |
| | 133 | 4 | 0 | 0 | 0 | 6 | 0 | 0 |
| | 134 | 6 | 3 | 3 | 3 | 3 | 3 | 5 |
| | 135 | 5 | 0 | 0 | 3 | 5 | 0 | 5 |
| (62 g/ha) | 32 | 0 | 0 | 0 | 0 | 0 | 0 | 0 |
| | 34 | 0 | 0 | 0 | 0 | 0 | 0 | 0 |
| | 94 | 0 | 0 | — | 0 | 0 | 0 | 0 |
| | 102 | 0 | 0 | 0 | 0 | 0 | 0 | 0 |
| | 118 | 5 | 8 | 0 | 0 | 0 | 0 | 0 |
| | 120 | 10 | 5 | 0 | 5 | 8 | 0 | 0 |
| | 130 | 0 | 0 | 0 | 0 | 2 | 0 | 0 |
| | 131 | 3 | 0 | 0 | 0 | 4 | 0 | 0 |
| | 132 | 3 | 0 | 0 | 0 | 0 | 0 | 0 |
| | 133 | 3 | 0 | 0 | 0 | 0 | 0 | 0 |
| | 134 | 5 | 0 | 3 | 2 | 0 | 3 | 3 |
| | 135 | 4 | 0 | 0 | 0 | 4 | 0 | 3 |
| (31 g/ha) | 94 | 0 | 0 | 0 | 0 | — | 0 | 0 |
| | 102 | 0 | 0 | 0 | 0 | 0 | 0 | 0 |
| | 118 | 2 | 0 | 0 | 0 | — | 0 | 0 |
| | 120 | 8 | 3 | 0 | 0 | 2 | 0 | 0 |
| | 130 | 0 | 0 | 0 | 0 | — | 0 | 0 |
| | 131 | 0 | 0 | 0 | 0 | 3 | 0 | 0 |
| | 132 | 0 | 0 | 0 | 0 | 0 | 0 | 0 |
| | 133 | 0 | 0 | 0 | 0 | 0 | 0 | 0 |
| | 134 | 4 | 0 | 2 | 0 | 0 | 3 | 0 |
| | 135 | 3 | 0 | 0 | 0 | 0 | 0 | 0 |

| Rate | COMPOUND | Rape | Rice | Sicklepod | Soybean | Sugar beet | Teaweed | Velvetleaf | Wheat | Wild buckwheat | Wild oat |
|---|---|---|---|---|---|---|---|---|---|---|---|
| (500 g/ha) | 32 | 0 | 5 | 0 | 0 | 0 | 0 | 7 | 0 | 8 | 0 |
| | 34 | 7 | 0 | — | 0 | 5 | 0 | 6 | 0 | 6 | 3 |
| | 93 | 0 | 3 | 0 | 0 | 3 | 7 | 4 | 5 | 0 | 0 |
| (250 g/ha) | 2 | 4 | 0 | 0 | 0 | 0 | 0 | — | 0 | — | 0 |
| | 25 | 0 | 0 | 2 | 2 | — | 0 | 0 | 0 | 3 | 0 |
| | 32 | 0 | 2 | 0 | 0 | 0 | 0 | 5 | 0 | 3 | 0 |
| | 34 | 3 | 0 | 0 | 0 | 3 | 0 | 5 | 0 | 5 | 0 |
| | 93 | 0 | 0 | 0 | 0 | 3 | 5 | 2 | 3 | 0 | 0 |
| | 94 | 0 | 0 | 0 | 0 | 4 | 0 | — | 0 | 0 | 0 |
| | 102 | 0 | 3 | 0 | 0 | 6 | 0 | 0 | 3 | 3 | 0 |
| | 118 | 0 | 9 | 0 | 3 | 2 | 6 | 3 | 0 | 10 | 3 |
| | 120 | 0 | 6 | 3 | 3 | 6 | 4 | — | 6 | 10 | — |
| | 130 | 0 | 2 | 0 | 0 | 0 | 0 | 0 | 5 | 9 | 7 |
| | 131 | 0 | 6 | 0 | 0 | 7 | 0 | 0 | 4 | 7 | 0 |
| | 132 | 2 | 6 | 0 | 0 | 6 | 5 | 5 | 0 | 9 | 0 |
| | 133 | 2 | 5 | 0 | 0 | 3 | 3 | 6 | 3 | 7 | 0 |
| | 134 | 0 | 7 | 0 | 2 | 6 | 0 | 4 | 4 | 7 | 0 |
| | 135 | 4 | 3 | 0 | 0 | 6 | 5 | 6 | 0 | 7 | 0 |
| (125 g/ha) | 2 | 0 | 0 | 0 | 0 | 0 | 0 | — | 0 | — | 0 |
| | 25 | 0 | 0 | 2 | 0 | 5 | 0 | 5 | 0 | 0 | 0 |
| | 32 | 0 | 0 | 0 | 0 | 0 | 0 | 4 | 0 | 0 | 0 |
| | 34 | 0 | 0 | 0 | 0 | 0 | 0 | 0 | 0 | 0 | 0 |
| | 94 | 0 | 0 | 0 | 0 | 3 | — | 0 | 0 | 0 | 0 |
| | 102 | 0 | 0 | 0 | 0 | 4 | 0 | 0 | 2 | 0 | 0 |
| | 118 | 0 | 0 | 0 | 0 | 0 | 0 | 0 | 0 | 9 | 0 |
| | 119 | 0 | 3 | 3 | 0 | 6 | 2 | 6 | 7 | 9 | 7 |
| | 120 | 0 | 6 | 0 | 3 | 4 | 2 | 6 | 6 | 10 | 5 |

TABLE C-continued

|  | | | | | | | | | | | |
|---|---|---|---|---|---|---|---|---|---|---|---|
| | 130 | 0 | 0 | 0 | 0 | 0 | 0 | 0 | 3 | 7 | 3 |
| | 131 | 0 | 3 | 0 | 0 | 6 | 0 | 0 | 3 | 6 | 0 |
| | 132 | 0 | 5 | 0 | 0 | 3 | 3 | 2 | 0 | 6 | 0 |
| | 133 | 0 | 2 | 0 | 0 | 3 | 0 | 3 | 0 | 5 | 0 |
| | 134 | 0 | 6 | 0 | 2 | 3 | 0 | 3 | 3 | 7 | 0 |
| | 135 | 3 | 0 | 0 | 0 | 3 | 3 | 4 | 0 | 5 | 0 |
| (62 g/ha) | 32 | 0 | 0 | 0 | 0 | 0 | 0 | 3 | 0 | 0 | 0 |
| | 34 | 0 | 0 | 0 | 0 | 0 | 0 | 0 | 0 | 0 | 0 |
| | 94 | 0 | 0 | — | 0 | 0 | 0 | 0 | 0 | 0 | 0 |
| | 102 | 0 | 0 | 0 | 0 | 3 | 0 | 0 | 0 | 0 | 0 |
| | 118 | 0 | 0 | 0 | 0 | 0 | 0 | 0 | 0 | 9 | 0 |
| | 120 | 0 | 6 | 0 | 2 | 0 | 2 | 5 | 0 | 2 | 0 |
| | 130 | 0 | 0 | 0 | 0 | 0 | 0 | 0 | 0 | 6 | 0 |
| | 131 | 0 | 0 | 0 | 0 | 3 | 0 | 0 | 0 | 3 | 0 |
| | 132 | 0 | 0 | 0 | 0 | 0 | 0 | 0 | 0 | 5 | 0 |
| | 133 | 0 | 0 | 0 | 0 | 3 | 0 | 0 | 0 | 3 | 0 |
| | 134 | 0 | 4 | 0 | 0 | 3 | 0 | 3 | 0 | 4 | 0 |
| | 135 | 0 | 0 | 0 | 0 | 3 | 0 | 3 | 0 | 0 | 0 |
| (31 g/ha) | 94 | 0 | 0 | 0 | 0 | 0 | 0 | 0 | 0 | 0 | 0 |
| | 102 | 0 | 0 | 0 | 0 | 0 | 0 | 0 | 0 | 0 | 0 |
| | 118 | 0 | 0 | 0 | 0 | 0 | 0 | 0 | 0 | 6 | 0 |
| | 120 | 0 | 0 | 0 | 0 | 0 | 2 | 0 | 0 | 0 | 0 |
| | 130 | 0 | 0 | 0 | 0 | 0 | 0 | 0 | 0 | 3 | 0 |
| | 131 | 0 | 0 | 0 | 0 | 0 | 0 | 0 | 0 | 0 | 0 |
| | 132 | 0 | 0 | 0 | 0 | 0 | 0 | 0 | 0 | 4 | 0 |
| | 133 | 0 | 0 | 0 | 0 | 0 | 0 | 0 | 0 | 0 | 0 |
| | 134 | 0 | 3 | 0 | 0 | 3 | 0 | 3 | 0 | 4 | 0 |
| | 135 | 0 | 0 | 0 | 0 | 0 | 0 | 3 | 0 | 0 | 0 |

PREEMERGENCE

| Rate | COMPOUND | Barley | Barnyard-grass | Blackgrass | Chickweed | Cocklebur | Corn | Cotton | Crabgrass | Downy brome |
|---|---|---|---|---|---|---|---|---|---|---|
| (500 g/ha) | 32 | 0 | 10 | 9 | 4 | 0 | 10 | 0 | 9 | 4 |
| | 34 | 0 | 10 | 5 | 0 | — | 8 | 0 | 9 | 0 |
| | 93 | 8 | 10 | 10 | 6 | 9 | 10 | 0 | 9 | 0 |
| (250 g/ha) | 2 | 0 | 10 | 7 | 0 | 0 | 2 | 0 | 8 | 0 |
| | 25 | 0 | 10 | 10 | 6 | 7 | 3 | 0 | 9 | 2 |
| | 32 | 0 | 10 | 8 | 2 | 0 | 3 | 0 | 2 | 2 |
| | 34 | 0 | 10 | 5 | 0 | 0 | 0 | 0 | 8 | 0 |
| | 93 | 7 | 10 | 9 | 6 | 7 | 8 | 0 | 9 | 0 |
| | 94 | 3 | 10 | 7 | 4 | 10 | 0 | 3 | 10 | 4 |
| | 102 | 4 | 20 | 6 | 9 | 3 | 2 | 0 | 10 | 3 |
| | 118 | 7 | 10 | 7 | 7 | 4 | 10 | 3 | 10 | 5 |
| | 120 | 10 | 10 | 10 | 7 | 3 | 10 | 9 | 10 | 5 |
| | 130 | 5 | 10 | 7 | 8 | 6 | 4 | 5 | 10 | 4 |
| | 131 | 7 | 10 | 8 | 8 | 0 | 6 | 0 | 10 | 5 |
| | 132 | 6 | 10 | 7 | 7 | 10 | 5 | 2 | 10 | 6 |
| | 133 | 3 | 10 | 6 | 8 | 7 | 3 | 3 | 10 | 4 |
| | 134 | 7 | 10 | 10 | 9 | 3 | 8 | 4 | 10 | 8 |
| | 135 | 0 | 10 | 6 | 9 | 0 | 0 | 0 | 10 | 3 |
| (125 g/ha) | 2 | 0 | 10 | 0 | 0 | 0 | 0 | 2 | 0 | |
| | 25 | 0 | 10 | 10 | 3 | 0 | 2 | 0 | 7 | 0 |
| | 32 | 0 | 10 | 6 | 0 | 0 | 3 | 0 | 2 | 0 |
| | 34 | 0 | 10 | 3 | 0 | 0 | 0 | 0 | 3 | 0 |
| | 93 | 3 | 10 | 7 | 4 | 0 | 2 | 0 | 8 | 0 |
| | 94 | 0 | 10 | 3 | 3 | 5 | 0 | 2 | 9 | 3 |
| | 102 | 0 | 10 | 3 | 3 | 0 | 0 | 0 | 7 | 2 |
| | 118 | 2 | 10 | 6 | 7 | 4 | 5 | 3 | 10 | 5 |
| | 119 | 7 | 10 | 6 | 7 | 3 | 3 | 3 | 10 | 7 |
| | 120 | 5 | 10 | 10 | 7 | 0 | 10 | 5 | 10 | 4 |
| | 130 | 0 | 10 | 4 | 7 | 5 | 3 | 5 | 10 | 3 |
| | 131 | 4 | 10 | 7 | 8 | 0 | 2 | 0 | 10 | 3 |
| | 132 | 4 | 10 | 7 | 7 | 10 | 4 | 0 | 10 | 4 |
| | 133 | 3 | 10 | 3 | 8 | 7 | 0 | 0 | 10 | 3 |
| | 134 | 7 | 10 | 7 | 9 | — | 3 | 3 | 10 | 5 |
| | 135 | 0 | 10 | 3 | 7 | 0 | 0 | 0 | 10 | 0 |
| (62 g/ha) | 2 | 0 | 8 | 0 | 0 | 0 | 0 | 0 | 0 | 0 |
| | 25 | 0 | 10 | 7 | 0 | 0 | 0 | 0 | 6 | 0 |
| | 32 | 0 | 10 | 2 | 0 | 0 | 0 | 0 | 0 | 0 |
| | 34 | 0 | 10 | 3 | 0 | 0 | 0 | 0 | 0 | 0 |
| | 93 | 0 | 10 | 0 | 0 | — | 0 | 0 | 0 | 0 |
| | 94 | 0 | 7 | 0 | 0 | 3 | 0 | 0 | 6 | 0 |
| | 102 | 0 | 9 | 3 | 0 | 0 | 0 | 0 | 4 | 0 |
| | 118 | 0 | 10 | 5 | 2 | 4 | 0 | 3 | 10 | 0 |
| | 119 | 6 | 10 | 5 | 7 | 0 | 0 | 0 | 10 | 5 |
| | 120 | 2 | 10 | 7 | 6 | 0 | 2 | 5 | 10 | 3 |
| | 130 | 0 | 10 | 3 | 7 | — | 0 | 0 | 10 | 2 |
| | 131 | 3 | 10 | 5 | 8 | 0 | 0 | 0 | 9 | 0 |
| | 132 | 3 | 10 | 7 | 7 | 5 | 2 | 0 | 10 | 2 |
| | 133 | 3 | 7 | 0 | 7 | 6 | 0 | 0 | 9 | 2 |
| | 134 | 6 | 10 | 5 | 9 | — | 3 | 3 | 9 | 3 |
| | 135 | 0 | 10 | 0 | 6 | 0 | 0 | 0 | 8 | 0 |

TABLE C-continued

| (31 g/ha) | 2 | 0 | 3 | 0 | 0 | 0 | 0 | 0 | 0 | 0 |
|---|---|---|---|---|---|---|---|---|---|---|
| | 25 | 0 | 10 | 0 | 0 | — | 0 | 0 | 6 | 0 |
| | 94 | 0 | 5 | 0 | 0 | 0 | 0 | 0 | 5 | 0 |
| | 102 | 0 | 4 | 0 | 0 | 0 | 0 | 0 | 0 | 0 |
| | 118 | 0 | 10 | 4 | 0 | 0 | 0 | 0 | 8 | 0 |
| | 119 | 2 | 10 | 3 | 7 | 0 | 0 | 0 | 9 | 3 |
| | 120 | 0 | 10 | 4 | 6 | 0 | 0 | 4 | 9 | 0 |
| | 130 | 0 | 4 | 0 | 6 | — | 0 | 0 | 7 | 0 |
| | 131 | 0 | 10 | 4 | 7 | 0 | 0 | 0 | 8 | 0 |
| | 132 | 0 | 10 | 3 | 7 | 3 | 0 | 0 | 9 | 0 |
| | 133 | 2 | 5 | 0 | 6 | 3 | 0 | 0 | 7 | 0 |
| | 134 | 3 | 10 | 4 | 9 | — | 0 | 0 | 8 | 3 |
| | 135 | 0 | 7 | 0 | 5 | 0 | 0 | 6 | 0 | |

| Rate | COMPOUND | Giant foxtail | Green foxtail | Jimsonweed | Johnsongrass | Lambsquarters | Morningglory | Nutsedge |
|---|---|---|---|---|---|---|---|---|
| (500 g/ha) | 32 | 10 | 10 | 0 | 10 | — | 0 | 0 |
| | 34 | 10 | 10 | 0 | 10 | — | 0 | 0 |
| | 93 | 10 | 10 | 0 | 9 | — | 0 | 3 |
| (250 g/ha) | 2 | 10 | 10 | 0 | 8 | 3 | 0 | 0 |
| | 25 | 10 | 9 | 6 | 10 | 10 | 10 | 0 |
| | 32 | 10 | 10 | 0 | 8 | — | 0 | 0 |
| | 34 | 10 | 10 | 0 | 7 | — | 0 | 0 |
| | 93 | 10 | 10 | 0 | 8 | — | 0 | 0 |
| | 94 | 10 | 9 | 3 | 6 | — | 4 | 5 |
| | 102 | 10 | 7 | 3 | 4 | 6 | 3 | 0 |
| | 118 | 10 | 10 | 0 | 10 | 10 | — | 4 |
| | 120 | 10 | 10 | 4 | 10 | 9 | — | 5 |
| | 130 | 10 | 10 | 5 | 9 | 9 | — | 4 |
| | 131 | 10 | 10 | 5 | 10 | 9 | 5 | 4 |
| | 132 | 10 | 10 | 5 | 10 | 9 | 3 | 4 |
| | 133 | 10 | 10 | 5 | 7 | 8 | 5 | 8 |
| | 134 | 10 | 10 | 6 | 8 | 10 | 5 | 5 |
| | 135 | 10 | 10 | 0 | 8 | 9 | 0 | 0 |
| (125 g/ha) | 2 | 9 | 7 | 0 | 5 | 2 | 0 | 0 |
| | 25 | 10 | 6 | 3 | 7 | 3 | 6 | 0 |
| | 32 | 8 | 7 | 0 | 8 | — | 0 | 0 |
| | 34 | 10 | 10 | 0 | 7 | — | 0 | 0 |
| | 93 | 10 | 10 | 0 | 5 | — | 0 | 0 |
| | 94 | 10 | 6 | 0 | 5 | — | 4 | 3 |
| | 102 | 8 | 5 | 0 | 2 | 5 | 0 | 0 |
| | 118 | 10 | 10 | 0 | 10 | 3 | — | 3 |
| | 119 | 10 | 10 | 0 | 8 | 9 | 4 | 3 |
| | 120 | 10 | 10 | 3 | 10 | 9 | — | 5 |
| | 130 | 10 | 10 | 2 | 8 | 0 | — | 0 |
| | 131 | 10 | 10 | 5 | 10 | 8 | 3 | 4 |
| | 132 | 10 | 10 | 5 | 9 | 8 | 3 | 3 |
| | 133 | 10 | 9 | 4 | 5 | 8 | 3 | 3 |
| | 134 | 10 | 10 | 6 | 7 | 7 | 4 | 0 |
| | 135 | 10 | 10 | 0 | 7 | 7 | 0 | 0 |
| (62 g/ha) | 2 | 7 | 5 | 0 | 2 | 0 | 0 | — |
| | 25 | 10 | 6 | 3 | 5 | 0 | 0 | 0 |
| | 32 | 7 | 7 | 0 | 2 | 8 | 0 | 0 |
| | 34 | 7 | 7 | 0 | 4 | — | 0 | 0 |
| | 93 | 2 | 2 | 0 | 0 | — | 0 | 0 |
| | 94 | 4 | 4 | 0 | 0 | — | 4 | 0 |
| | 102 | 7 | 5 | 0 | 0 | 3 | 0 | 0 |
| | 118 | 10 | 10 | 0 | 7 | 0 | — | 3 |
| | 119 | 9 | 10 | 0 | 7 | 9 | 4 | 3 |
| | 120 | 10 | 10 | 2 | 6 | 8 | — | 0 |
| | 130 | 10 | 10 | 2 | 3 | 0 | — | 0 |
| | 131 | 8 | 10 | 4 | 7 | 7 | 3 | 4 |
| | 132 | 10 | 10 | 5 | 7 | 7 | 3 | 0 |
| | 133 | 7 | 5 | 3 | 4 | 7 | 0 | 0 |
| | 134 | 9 | 10 | 5 | 7 | 7 | 3 | 0 |
| | 135 | 9 | 9 | 0 | 4 | 7 | 0 | 0 |
| (31 g/ha) | 2 | 2 | 3 | 0 | 0 | 0 | 0 | 0 |
| | 25 | 9 | 6 | 3 | 5 | 0 | 0 | 0 |
| | 94 | 3 | 3 | 0 | 0 | — | 4 | 0 |
| | 102 | 5 | 4 | 0 | 0 | 3 | 0 | 0 |
| | 118 | 6 | 9 | 0 | 5 | 0 | — | 0 |
| | 119 | 8 | 9 | 0 | 4 | 9 | 3 | 0 |
| | 120 | 10 | 6 | 0 | 4 | 0 | — | 0 |
| | 130 | 2 | 2 | 0 | 0 | 0 | — | 0 |
| | 131 | 6 | 5 | 4 | 4 | 5 | 0 | 4 |
| | 132 | 7 | 8 | 5 | 7 | 7 | 3 | 0 |
| | 133 | 5 | 4 | 0 | 3 | 7 | 0 | 0 |
| | 134 | 8 | 5 | 4 | 5 | 5 | 0 | 0 |
| | 135 | 7 | 7 | 0 | 3 | 6 | 0 | 0 |

| Rate | COMPOUND | Rape | Rice | Sicklepod | Soybean | Sugar beet | Teaweed | Velvetleaf | Wheat | Wild buckwheat | Wild oat |
|---|---|---|---|---|---|---|---|---|---|---|---|
| (500 g/ha) | 32 | 3 | 0 | 0 | 0 | 0 | 3 | 6 | 0 | 0 | 4 |

TABLE C-continued

| | Cmpd | | | | | | | | | | |
|---|---|---|---|---|---|---|---|---|---|---|---|
| | 34 | 0 | 0 | — | 0 | 0 | 5 | 3 | 0 | 0 | 0 |
| | 93 | 0 | 3 | — | 0 | 5 | 6 | 4 | 8 | 8 | 6 |
| (250 g/ha) | 2 | 2 | 0 | 0 | 0 | 0 | 0 | 3 | 0 | 0 | 0 |
| | 25 | 3 | 0 | 3 | 0 | 4 | 9 | 0 | 0 | 5 | 3 |
| | 32 | 2 | 0 | 0 | 0 | 0 | 2 | 5 | 0 | 0 | 2 |
| | 34 | 0 | 0 | 3 | 0 | 0 | 5 | 3 | 0 | 0 | 0 |
| | 93 | 0 | — | 7 | 0 | 0 | 2 | 2 | 5 | 6 | 2 |
| | 94 | 0 | 6 | 3 | 0 | 0 | 7 | 8 | 3 | 0 | 4 |
| | 102 | 0 | 3 | 3 | 0 | 6 | 3 | 0 | 4 | 7 | 3 |
| | 118 | 2 | 3 | 9 | 7 | 9 | 6 | 9 | 2 | 9 | 6 |
| | 120 | 0 | 9 | 7 | 6 | 6 | 9 | 9 | — | 9 | 4 |
| | 130 | 0 | 0 | 5 | 3 | 5 | 8 | 9 | 4 | 10 | 2 |
| | 131 | 0 | 7 | 8 | 4 | 7 | 6 | 7 | 2 | 8 | 3 |
| | 132 | 0 | 6 | 7 | 3 | 8 | 7 | 7 | 4 | 10 | 4 |
| | 133 | 0 | 3 | 7 | 6 | 7 | 7 | 5 | 4 | 7 | 0 |
| | 134 | 2 | 3 | 7 | 6 | 9 | 5 | 7 | 6 | 7 | 6 |
| | 135 | 3 | 0 | 8 | 5 | 6 | 10 | 7 | 0 | 8 | 0 |
| (125 g/ha) | 2 | 0 | 0 | 0 | 0 | 0 | 0 | 2 | 0 | 0 | 0 |
| | 25 | 0 | 0 | 0 | 0 | 3 | 5 | 0 | 0 | 0 | 0 |
| | 32 | 0 | 0 | 0 | 0 | 0 | 0 | 1 | 0 | 0 | 0 |
| | 34 | 0 | 0 | 0 | 0 | 0 | 2 | 0 | 0 | 0 | 0 |
| | 93 | 0 | 3 | — | 0 | 0 | 0 | 0 | 3 | 3 | 0 |
| | 94 | 0 | 0 | 0 | 0 | 0 | 6 | 3 | 2 | 0 | 3 |
| | 102 | 0 | 0 | 0 | 0 | 3 | 0 | 0 | 3 | 5 | 0 |
| | 118 | 0 | 2 | 5 | 5 | 7 | — | 8 | 0 | 9 | 0 |
| | 119 | 0 | 7 | 8 | 3 | 6 | 3 | 6 | 7 | 8 | 6 |
| | 120 | 0 | — | 5 | 5 | 5 | 9 | 8 | 5 | 8 | 2 |
| | 130 | 0 | 0 | 5 | 0 | 4 | 6 | 5 | 4 | 9 | 0 |
| | 131 | 0 | 6 | 6 | 4 | 6 | 5 | 6 | 0 | 7 | 3 |
| | 132 | 0 | 5 | 6 | 0 | 6 | 7 | 7 | 3 | 8 | 3 |
| | 133 | 0 | 3 | 5 | 4 | 6 | 6 | 4 | 2 | 7 | 0 |
| | 134 | 0 | 0 | 7 | 5 | 7 | 3 | 6 | 4 | 7 | 4 |
| | 135 | 2 | 0 | 3 | 0 | 6 | 3 | 6 | 0 | 7 | 0 |
| (62 g/ha) | 2 | 0 | 0 | 0 | 0 | 0 | 0 | — | 0 | 0 | 0 |
| | 25 | 0 | 0 | 0 | 0 | 0 | 5 | 0 | 0 | 0 | 0 |
| | 32 | 0 | 0 | 0 | 0 | 0 | 0 | 0 | 0 | 0 | 0 |
| | 34 | 0 | 0 | 0 | 0 | 0 | 2 | 0 | 0 | 0 | 0 |
| | 93 | 0 | 0 | 6 | 0 | 0 | — | 0 | 0 | 0 | 0 |
| | 94 | 0 | 0 | 0 | 0 | 0 | 6 | 0 | 0 | 0 | 0 |
| | 102 | 0 | 0 | 0 | 0 | 0 | 0 | 0 | 0 | 3 | 0 |
| | 118 | 0 | 0 | 2 | 0 | 4 | — | 8 | 0 | 5 | 0 |
| | 119 | 0 | 5 | 6 | 3 | 5 | 3 | 6 | 4 | 7 | 4 |
| | 120 | 0 | 8 | 3 | 3 | 5 | 8 | 7 | 3 | 8 | 0 |
| | 130 | 0 | 0 | 2 | 0 | 4 | 3 | 4 | 0 | 4 | 0 |
| | 131 | 0 | 0 | 5 | 3 | 5 | 4 | 0 | 0 | 7 | 0 |
| | 132 | 0 | 3 | 6 | 0 | 6 | 6 | 3 | 2 | 7 | 2 |
| | 133 | 0 | 2 | 5 | 3 | 5 | 4 | 3 | 0 | 5 | 0 |
| | 134 | 0 | 0 | 7 | 3 | 6 | 3 | 5 | 3 | 7 | 3 |
| | 135 | 0 | 0 | 0 | 0 | 4 | 3 | 4 | 0 | 5 | 0 |
| (31 g/ha) | 2 | 0 | 0 | 0 | 0 | 0 | 0 | 0 | 0 | 0 | 0 |
| | 25 | 0 | 0 | 0 | 0 | 0 | 5 | 0 | 0 | 0 | 0 |
| | 94 | 0 | 0 | 0 | 0 | 0 | 6 | 0 | 0 | 0 | 0 |
| | 102 | 0 | 0 | 0 | 0 | 0 | 0 | 0 | 0 | 2 | 0 |
| | 118 | 0 | 0 | 2 | 0 | 2 | 5 | 2 | 0 | — | 0 |
| | 119 | 0 | 2 | 4 | 0 | 3 | 3 | 5 | 3 | 6 | 3 |
| | 120 | 0 | 0 | 3 | 0 | 4 | 6 | 3 | 0 | 6 | 0 |
| | 130 | 0 | 0 | 0 | 0 | 0 | 2 | 0 | 0 | 3 | 0 |
| | 131 | 0 | 0 | 5 | 0 | 4 | 3 | 0 | 0 | 6 | 0 |
| | 132 | 0 | 3 | 5 | 0 | 5 | 6 | 0 | 0 | 6 | 0 |
| | 133 | 0 | 0 | 0 | 2 | 4 | 0 | 2 | 0 | 5 | 0 |
| | 134 | 0 | 0 | 5 | 0 | 6 | 0 | 4 | 3 | 7 | 0 |
| | 135 | 0 | 0 | 0 | 0 | 4 | 0 | 3 | 0 | 3 | 0 |

TEST D

Compounds evaluated in this test were formulated in a non-phytotoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgate*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), galium (*Galium aparine*), giant foxtail (*Setaria faberii*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta fulgaris*), velvetleaf (*Abutilon theophrasti*), wheat (*Triticum aestivum*), wild buckwheat (*Polygonum convolvulus*), and wild oat (*Avena fatua*). All plant species were planted one day before application of compounds for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), and umbrella sedge (*Cyperus difformis*).

All plant species were grown using normal greenhouse practices. Visual evaluations of injury expressed on treated plants, when compared to untreated controls, were recorded approximately fourteen to twenty-one days after application of test compounds. Plant response ratings, summarized in Table D, were recorded on a 1 to 10 scale where 0 is no injury and 10 is plant death. A dash (-) response means no test result.

TABLE D

POSTEMERGENCE

| COMPOUND | Rate (250 g/ha) | Barley | Blackgrass | Chickweed | Corn | Cotton | Crabgrass | Downy brome | Galium | Giant foxtail | Lambsquarters | Morningglory | Pigweed | Rape | Ryegrass | Sorghum | Soybean |
|---|---|---|---|---|---|---|---|---|---|---|---|---|---|---|---|---|---|
| 136 | | 2 | 5 | 9 | 2 | 0 | 8 | 0 | 7 | 7 | 9 | 0 | 2 | 5 | 4 | 3 | 0 |
| 145 | | 2 | 0 | 0 | 2 | 0 | 3 | 0 | 5 | 5 | 0 | 3 | 0 | 0 | 3 | 0 | 0 |
| 146 | | 5 | 9 | 4 | 2 | 0 | 7 | 0 | 2 | 6 | 0 | 0 | 0 | 0 | 7 | 3 | 0 |
| 147 | | 6 | 4 | 0 | 3 | 3 | 8 | 2 | 0 | 8 | 8 | 3 | 0 | 0 | 6 | 4 | 6 |
| 152 | | 8 | 9 | 9 | 8 | 3 | 8 | 8 | 8 | 7 | 9 | 2 | 7 | 0 | 8 | 6 | 6 |
| 153 | | 9 | 9 | 8 | 7 | 0 | 7 | 7 | 6 | 8 | 6 | 0 | 7 | 0 | 9 | 8 | 2 |
| 154 | | 7 | 8 | 8 | 7 | 3 | 9 | 6 | 7 | 8 | 5 | 2 | 6 | 3 | 8 | 6 | 2 |
| 155 | | 0 | 5 | 8 | 3 | 0 | 3 | 0 | 2 | 7 | 6 | 0 | 0 | 0 | 0 | 0 | 2 |
| 157 | | 4 | 8 | 9 | 6 | 3 | 6 | 5 | 4 | 8 | 8 | 0 | 0 | 0 | 7 | 6 | 4 |
| 158 | | 0 | 5 | 6 | 0 | 3 | 6 | 0 | 4 | 7 | 6 | 0 | 5 | 2 | 0 | 0 | 7 |

POSTEMERGENCE

| COMPOUND | Rate (250 g/ha) | Speedwell | Sugar beet | Velvetleaf | Wheat | Wild buckwheat | Wild oat |
|---|---|---|---|---|---|---|---|
| 136 | | 9 | 8 | 5 | 3 | 9 | 0 |
| 145 | | 0 | 8 | 5 | 3 | 9 | 0 |
| 146 | | 0 | 0 | 2 | 4 | 6 | 0 |
| 147 | | 0 | 0 | 4 | 6 | 0 | 3 |
| 152 | | 9 | 10 | 6 | 8 | 10 | 8 |
| 153 | | 10 | 10 | 7 | — | 10 | 6 |
| 154 | | 9 | 8 | 6 | 7 | 9 | 6 |
| 155 | | 7 | 9 | 6 | 0 | 9 | 4 |
| 157 | | 9 | 9 | 4 | 4 | 9 | 5 |
| 158 | | 6 | 10 | 5 | 0 | 7 | 0 |

PADDY

| COMPOUND | Rate (250 g/ha) | Barnyardgrass | Rice | Umbrella sedge |
|---|---|---|---|---|
| 136 | | 9 | 8 | 9 |
| 145 | | 9 | 7 | 4 |
| 146 | | 8 | 7 | 8 |
| 147 | | 8 | 7 | 8 |
| 152 | | 10 | 9 | 10 |
| 153 | | 10 | 9 | 9 |
| 154 | | 10 | 9 | 10 |
| 155 | | 10 | 8 | 9 |
| 157 | | 10 | 9 | 9 |
| 158 | | 10 | 7 | 9 |

PREEMERGENCE

| COMPOUND | Rate (250 g/ha) | Galium | Giant foxtail | Blackgrass | Chickweed | Corn | Cotton | Crabgrass | Morningglory | Pigweed | Rape | Ryegrass | Sorghum | Soybean |
|---|---|---|---|---|---|---|---|---|---|---|---|---|---|---|
| 136 | | — | 10 | 4 | 9 | 0 | 0 | 6 | 0 | 7 | 5 | 4 | 5 | 3 |
| 145 | | 3 | 10 | 0 | 0 | 0 | 0 | 0 | 2 | 3 | 0 | 0 | 3 | 1 |
| 146 | | 0 | 10 | 2 | 0 | 0 | 0 | 3 | 0 | 0 | 0 | 0 | 4 | 0 |
| 147 | | 0 | 10 | — | — | 2 | 2 | 7 | 2 | 2 | 0 | 0 | 8 | 2 |
| 152 | | — | 10 | 8 | 9 | 6 | 0 | 0 | 0 | 8 | 6 | 10 | 10 | 7 |
| 153 | | — | 10 | 6 | 9 | 2 | 0 | 8 | 0 | 8 | 0 | 10 | 10 | 8 |
| 154 | | — | 10 | 7 | 8 | 6 | 0 | 7 | 0 | 7 | 4 | 3 | 6 | 0 |
| 155 | | — | 10 | 5 | 9 | 6 | 0 | 7 | 0 | 7 | 0 | 10 | 4 | 0 |
| 157 | | — | 10 | 4 | 8 | 0 | 0 | 4 | 0 | 0 | 3 | 6 | 6 | 0 |
| 158 | | 6 | 10 | 6 | 7 | 6 | 2 | 5 | 0 | 5 | 3 | 5 | 3 | 0 |

PREEMERGENCE

| COMPOUND | Rate (250 g/ha) | Speedwell | Sugar beet | Velvetleaf | Wheat | Wild buckwheat | Wild oat |
|---|---|---|---|---|---|---|---|
| 136 | | 8 | 9 | 8 | 4 | 9 | 4 |
| 145 | | — | 0 | 5 | 3 | 5 | 0 |
| 146 | | — | 0 | 5 | 3 | 5 | 0 |
| 147 | | — | 0 | 7 | 4 | 4 | 3 |
| 152 | | 9 | 9 | 8 | 5 | 9 | 10 |
| 153 | | 8 | 8 | 8 | 5 | 9 | 10 |
| 154 | | 10 | 8 | 8 | 5 | 8 | 6 |
| 155 | | 7 | 8 | 8 | 0 | 7 | — |
| 157 | | 8 | 8 | 7 | 4 | 8 | 0 |
| 158 | | 7 | 7 | 8 | 0 | 6 | 0 |

POSTEMERGENCE

| COMPOUND | Rate (125 g/ha) | Barley | Blackgrass | Chickweed | Corn | Cotton | Crabgrass | Downy brome | Galium | Giant foxtail | Lambsquarters | Morningglory | Pigweed | Rape | Ryegrass | Sorghum | Soybean |
|---|---|---|---|---|---|---|---|---|---|---|---|---|---|---|---|---|---|
| 136 | | 0 | 4 | 9 | 0 | 0 | 6 | 0 | 4 | 5 | 6 | 0 | 2 | 5 | 0 | 2 | 0 |
| 145 | | 0 | 0 | 0 | 0 | 0 | 0 | 0 | 0 | 5 | 0 | 0 | 0 | 0 | 5 | 0 | 0 |
| 146 | | 2 | 2 | 0 | 0 | 0 | 3 | 0 | 0 | 4 | 0 | 2 | 0 | 0 | 6 | 3 | 0 |
| 147 | | — | — | 0 | 2 | 2 | 7 | 5 | 3 | 7 | 0 | 0 | 0 | 0 | 4 | 3 | 4 |
| 152 | | 5 | 8 | 7 | 6 | 6 | 4 | 5 | 3 | 7 | 7 | 0 | 3 | 0 | 7 | 3 | 3 |
| 153 | | 4 | 6 | 7 | 6 | 2 | 5 | 5 | 3 | 7 | 6 | 0 | 5 | 0 | 7 | 3 | 3 |

TABLE D-continued

| COMPOUND | Speedwell | Giant foxtail | Sugar beet | Velvet-leaf | Wheat | Wild buckwheat | Wild oat | Barnyardgrass | Rice | Sorghum | Umbrella sedge | Soybean | Barley | Blackgrass | Chickweed | Sugar beet | Velvet-leaf | Wheat | Cotton | Crabgrass | Downy brome |
|---|---|---|---|---|---|---|---|---|---|---|---|---|---|---|---|---|---|---|---|---|---|
| 154 | 6 | 6 | 2 | 8 | 6 | 0 | 7 | 5 | — | 6 | 6 | — | — | — | 3 | — | — | 7 | 2 | — | 0 |
| 155 | 0 | 3 | 0 | 5 | 0 | 0 | 0 | 0 | 3 | 2 | — | — | — | — | 0 | — | — | 0 | 0 | 0 | 0 |
| 157 | 4 | 7 | 0 | 7 | 6 | 0 | 3 | 4 | 4 | 3 | 7 | — | — | — | 0 | — | — | 4 | 4 | 0 | 0 |
| 158 | 0 | 0 | 8 | 2 | 0 | 2 | 4 | 0 | 0 | 0 | 5 | — | — | — | 5 | — | — | 0 | 0 | 0 | 3 |

POSTEMERGENCE / PADDY / PREEMERGENCE

| COMPOUND | Rate (125 g/ha) | Barley | Galium | Speedwell | Giant foxtail | Blackgrass | Chickweed | Lambsquarters | Morningglory | Pigweed | Rape | Ryegrass | Sorghum | Rice | Soybean | Barley | Blackgrass | Chickweed | Sugar beet | Velvet-leaf | Wheat | Cotton | Crabgrass | Wild buckwheat | Wild oat |
|---|---|---|---|---|---|---|---|---|---|---|---|---|---|---|---|---|---|---|---|---|---|---|---|---|---|
| 136 |  | 7 | — | 2 | 10 | 4 | 8 | 0 | 0 | 2 | 5 | 7 | 4 | 1 | 0 | 2 | 8 | 7 | 9 | 7 | 3 | 0 | 10 | 9 | 2 |
| 145 |  | 0 | 0 | 0 | 9 | 0 | 10 | 0 | 0 | 2 | 0 | 7 | 1 | 3 | 0 | 0 | 7 | 7 | 5 | 3 | 0 | 2 | 9 | 3 | 0 |
| 146 |  | 0 | 0 | 0 | 10 | 0 | 10 | 0 | 2 | 0 | 0 | 5 | 2 | 4 | 0 | 0 | 7 | 6 | 0 | 5 | 3 | 1 | 10 | 3 | 2 |
| 147 |  | 4 | 0 | 6 | 9 | 5 | — | 0 | 0 | 7 | 3 | 10 | 10 | 7 | 4 | 3 | 8 | 7 | 8 | 5 | 3 | 2 | 10 | 3 | 2 |
| 152 |  | 4 | — | 9 | 10 | 4 | 9 | 0 | 2 | 7 | 0 | 5 | 10 | 8 | 6 | 5 | — | 9 | 0 | 7 | 3 | 2 | 10 | 8 | 3 |
| 153 |  | 2 | — | 9 | 10 | 6 | 9 | 2 | 0 | 7 | 3 | 6 | 3 | 8 | 0 | 4 | 8 | 8 | 8 | 8 | 2 | 3 | 10 | 8 | 10 |
| 154 |  | 3 | 7 | 8 | 10 | 0 | 8 | 6 | 0 | 6 | 0 | 8 | 5 | 9 | 0 | 3 | 10 | 8 | 7 | 8 | 3 | 3 | 10 | 7 | 3 |
| 155 |  | 0 | — | 7 | 10 | 0 | 9 | 4 | 0 | 6 | 3 | 0 | 7 | 5 | 0 | 0 | 7 | 6 | 6 | 8 | 0 | 0 | 10 | 7 | 0 |
| 157 |  | 2 | 0 | 9 | 10 | 2 | 8 | 5 | 0 | 3 | 0 | 5 | 0 | 8 | 0 | 2 | 8 | 8 | 6 | 6 | 2 | 2 | 10 | 4 | 0 |
| 158 |  | 0 | 0 | 4 | 10 | 0 | 8 | 0 | 0 | 6 | 2 | 0 | 3 | 2 | 0 | 0 | 4 | 8 | 6 | 6 | 0 | 0 | 10 | 4 | 0 |

POSTEMERGENCE / PADDY / PREEMERGENCE

| COMPOUND | Rate (62 g/ha) | Barley | Blackgrass | Chickweed | Sugar beet | Velvet-leaf | Wheat | Wild buckwheat | Wild oat | Downy brome | Galium | Giant foxtail | Lambsquarters | Morningglory | Pigweed | Rape | Ryegrass | Sorghum | Rice | Umbrella sedge | Soybean | Barley | Blackgrass | Chickweed | Corn | Cotton | Crabgrass | Sorghum | Soybean |
|---|---|---|---|---|---|---|---|---|---|---|---|---|---|---|---|---|---|---|---|---|---|---|---|---|---|---|---|---|---|
| 136 |  | 0 | 0 | 2 | 0 | 7 | 3 | 0 | 3 | 0 | 0 | 2 | 3 | 0 | 0 | 0 | 0 | 2 | 4 | 9 | 0 | 0 | 0 | 0 | 0 | 0 | 0 | 0 | 0 |
| 145 |  | 0 | 0 | 0 | 0 | 3 | 0 | 0 | 0 | 0 | 0 | 5 | 0 | 0 | 0 | 0 | 0 | 5 | — | — | — | — | — | — | — | — | — | — | — |
| 146 |  | 0 | 0 | 0 | 0 | 5 | 3 | 0 | 2 | 0 | 0 | 3 | 0 | 0 | 0 | 0 | 0 | 3 | — | — | — | — | — | — | — | — | — | — | — |
| 147 |  | 4 | 0 | 0 | 8 | 5 | 3 | 2 | 2 | 4 | 0 | 2 | 5 | 0 | 4 | 0 | 4 | 2 | — | — | — | — | — | — | — | — | — | — | — |
| 152 |  | 2 | 0 | 7 | 7 | 7 | 4 | 0 | 8 | 0 | 0 | 4 | 4 | 0 | 0 | 0 | 3 | 4 | — | — | — | — | — | — | — | — | — | — | — |
| 153 |  | 4 | 0 | 6 | 8 | 8 | 4 | 2 | 8 | 0 | 0 | 6 | 0 | 0 | 4 | 0 | 0 | 6 | — | — | — | — | — | — | — | — | — | — | — |
| 154 |  | 4 | 0 | 6 | 8 | 8 | 3 | 5 | 7 | 0 | 5 | 5 | 4 | 0 | 0 | 0 | 0 | 0 | — | — | — | — | — | — | — | — | — | — | — |
| 155 |  | 0 | 0 | 0 | 6 | 6 | 0 | 0 | 3 | 0 | 0 | 0 | 0 | 0 | 0 | 0 | 0 | 4 | — | — | — | — | — | — | — | — | — | — | — |
| 157 |  | 2 | 0 | 5 | 6 | 6 | 4 | 3 | 0 | 0 | 0 | 4 | — | 0 | 0 | 0 | 4 | 3 | — | — | — | — | — | — | — | — | — | — | — |
| 158 |  | 0 | 0 | 0 | 6 | 6 | 0 | 2 | 0 | 2 | 0 | 3 | 4 | 0 | 3 | 0 | 0 | 0 | — | — | — | — | — | — | — | — | — | — | — |

PADDY / PREEMERGENCE

| COMPOUND | Rate (62 g/ha) | Speedwell | Barnyardgrass | Rice | Umbrella sedge | Barley | Blackgrass | Chickweed | Corn | Cotton | Crabgrass | Downy brome |
|---|---|---|---|---|---|---|---|---|---|---|---|---|
| 136 |  | 0 | 0 | 2 | 4 | 9 | 0 | 7 | 5 | 0 | 0 | 10 | 0 |

TABLE D-continued

PREEMERGENCE

| COMPOUND | Rate (62 g/ha) | Galium | Blackgrass | Giant foxtail | Lambsquarters | Morningglory | Pigweed | Rape | Ryegrass | Sorghum | Soybean | Speedwell | Sugar beet | Velvet-leaf | Wheat | Wild buckwheat | Wild oat |
|---|---|---|---|---|---|---|---|---|---|---|---|---|---|---|---|---|---|
| 145 | | 0 | 0 | 10 | 5 | 0 | 6 | 2 | 4 | 2 | 2 | 2 | 8 | 5 | 0 | 8 | 2 |
| 146 | | 0 | 0 | 8 | 10 | 0 | 0 | 3 | 0 | 0 | 2 | 3 | 2 | 0 | 3 | 0 | 0 |
| 147 | | 6 | 0 | 8 | 10 | 3 | 0 | 0 | 0 | 0 | 2 | — | 0 | 2 | 0 | 3 | 0 |
| 152 | | 6 | — | 8 | — | 3 | — | 0 | 7 | 0 | 9 | — | 7 | 5 | 3 | 0 | 3 |
| 153 | | 8 | 5 | 10 | 7 | 4 | 6 | 0 | 4 | 6 | 9 | 8 | 6 | 6 | 3 | 7 | 3 |
| 154 | | 4 | 2 | 10 | 9 | 5 | 6 | 0 | 6 | 3 | 9 | 8 | 6 | 7 | 3 | 7 | 3 |
| 155 | | 8 | 3 | 10 | 8 | 0 | 5 | 0 | 5 | 2 | 7 | 7 | 6 | 3 | 0 | 6 | 3 |
| 157 | | 0 | 0 | 10 | 7 | 1 | 3 | 0 | 3 | 0 | 9 | 6 | 6 | 4 | 0 | 4 | 3 |
| 158 | | 0 | 0 | 10 | 8 | 0 | 4 | 0 | 0 | 0 | 8 | 5 | 5 | 3 | 0 | 3 | 0 |

POSTEMERGENCE

| COMPOUND | Rate (31 g/ha) | Barley | Blackgrass | Chickweed | Corn | Cotton | Crabgrass | Downy brome | Galium | Giant foxtail | Lambsquarters | Morningglory | Pigweed | Rape | Ryegrass | Sorghum | Soybean |
|---|---|---|---|---|---|---|---|---|---|---|---|---|---|---|---|---|---|
| 136 | | 0 | 3 | 0 | 0 | 0 | 0 | 0 | 0 | 0 | 0 | 0 | 0 | 0 | 0 | 0 | 0 |
| 145 | | 0 | 0 | 0 | 0 | 0 | 0 | 0 | 0 | 0 | 0 | 0 | 0 | 0 | 0 | 0 | 0 |
| 146 | | 0 | 0 | 0 | 0 | 0 | 0 | 0 | 0 | 0 | 0 | 0 | 0 | 0 | 0 | 0 | 0 |
| 147 | | 0 | 0 | 2 | 0 | 0 | 2 | 2 | 0 | 0 | 0 | 0 | 3 | 0 | 0 | 0 | 0 |
| 152 | | 0 | 0 | 0 | 2 | 0 | 2 | 0 | 0 | 0 | 0 | 0 | 0 | 0 | 0 | 0 | 0 |
| 153 | | 3 | 0 | 3 | 0 | 0 | 3 | 0 | 0 | 4 | 0 | 0 | 3 | 0 | 0 | 0 | 0 |
| 154 | | 0 | 0 | 0 | 2 | 0 | 0 | 2 | 0 | 4 | 0 | 0 | 4 | 0 | 0 | 0 | 0 |
| 155 | | 0 | 0 | 0 | 0 | 2 | 3 | 0 | 0 | 0 | 0 | 0 | 0 | 0 | 0 | 0 | 0 |
| 157 | | — | 0 | — | 0 | 0 | 0 | 0 | 0 | 3 | 0 | 0 | 0 | 0 | 0 | 0 | 0 |
| 158 | | 0 | 0 | 0 | 0 | 0 | 0 | 0 | 0 | 0 | 0 | 0 | 0 | 0 | 0 | 0 | 0 |

PADDY

| COMPOUND | Rate (31 g/ha) | Barnyardgrass | Rice | sedge | Umbrella |
|---|---|---|---|---|---|
| 136 | | 6 | 2 | 7 | |
| 145 | | 3 | 0 | 0 | |
| 146 | | 4 | 1 | 0 | |
| 147 | | 3 | 4 | 9 | |
| 152 | | 9 | 4 | 9 | |
| 153 | | 9 | 2 | — | |
| 154 | | 10 | 4 | — | |
| 155 | | 10 | 2 | — | |
| 157 | | 9 | 2 | — | |
| 158 | | 9 | 0 | 2 | |

PREEMERGENCE

| COMPOUND | Rate (31 g/ha) | Blackgrass | Chickweed | Corn | Cotton | Crabgrass | Downy brome |
|---|---|---|---|---|---|---|---|
| 136 | | 5 | 4 | 0 | 0 | 8 | 0 |
| 145 | | 0 | 3 | 0 | 0 | 7 | 0 |
| 146 | | 3 | 5 | 0 | 0 | 9 | 0 |
| 147 | | 5 | 7 | 0 | 0 | 9 | 0 |
| 152 | | 6 | 7 | 0 | 0 | 10 | 0 |
| 153 | | 3 | 8 | 0 | 0 | 10 | 0 |
| 154 | | 3 | 7 | 0 | 0 | 10 | 0 |
| 155 | | 3 | 5 | 0 | 0 | 7 | 0 |
| 157 | | 3 | 7 | 0 | 0 | 8 | 0 |
| 158 | | 0 | 3 | 0 | 0 | 5 | 0 |

TABLE D-continued

PREEMERGENCE

| COMPOUND | Rate | Galium | Giant foxtail | Lambsquarters | Morningglory | Cotton | Wild buckwheat | Crabgrass | Pigweed | Rape | Ryegrass | Sorghum | Soybean | Speedwell | Sugar beet | Velvet-leaf | Wheat | Wild buckwheat | Wild oat |
|---|---|---|---|---|---|---|---|---|---|---|---|---|---|---|---|---|---|---|---|
| 136 | (31 g/ha) | 8 | 8 | 0 | 0 | 0 | 0 | 0 | 4 | 0 | 0 | 0 | 0 | 2 | 7 | 3 | 0 | 5 | 0 |
| 145 | | 0 | 4 | 10 | 0 | 0 | 0 | 0 | 0 | 0 | 0 | 0 | 0 | — | 0 | 2 | 0 | 0 | 0 |
| 146 | | 0 | 6 | 10 | 0 | 0 | 0 | 0 | 0 | 0 | 0 | 0 | 0 | — | 0 | 2 | 0 | 0 | 0 |
| 147 | | 0 | 7 | — | 0 | 0 | 0 | 0 | 0 | 0 | 0 | 0 | 0 | — | 0 | 0 | 0 | 6 | 0 |
| 152 | | — | 10 | — | 0 | 0 | 0 | 2 | 5 | 0 | 3 | 3 | 2 | 6 | 6 | 6 | 0 | 6 | 0 |
| 153 | | 0 | 10 | 3 | 0 | 0 | 0 | 0 | 3 | 0 | 3 | 2 | 0 | 6 | 5 | 3 | 0 | 6 | 0 |
| 154 | | 0 | 10 | 5 | 0 | 0 | 0 | 0 | 0 | 0 | 3 | 0 | 0 | 6 | 4 | 0 | 0 | 6 | 0 |
| 155 | | 0 | 9 | 5 | 0 | 0 | 0 | 0 | 0 | 0 | 0 | 0 | 0 | 4 | 4 | 4 | 0 | 4 | 0 |
| 157 | | 0 | 10 | 8 | 0 | 0 | 0 | 3 | 0 | 0 | 0 | 0 | 0 | 6 | 2 | 3 | 0 | 3 | 0 |
| 158 | | 0 | 8 | 3 | 0 | 0 | 0 | 0 | 0 | 0 | 0 | 0 | 0 | 3 | 4 | 0 | 0 | 0 | 0 |

POSTEMERGENCE

| COMPOUND | Rate | Barley | Blackgrass | Chickweed | Corn | Wheat | Wild buckwheat | Wild oat | Downy brome | Galium | Giant foxtail | Lambsquarters | Morningglory | Pigweed | Rape | Ryegrass | Sorghum | Soybean |
|---|---|---|---|---|---|---|---|---|---|---|---|---|---|---|---|---|---|---|
| 145 | (16 g/ha) | 0 | 0 | 0 | 0 | 0 | 0 | 0 | 0 | 0 | 0 | 0 | 0 | 0 | 0 | 0 | 0 | 0 |
| 146 | | 0 | 0 | 0 | 0 | 0 | 0 | 0 | 0 | 0 | 0 | 0 | 0 | 0 | 0 | 0 | 0 | 0 |
| 147 | | 0 | 0 | 0 | 0 | 0 | 0 | 0 | 0 | 0 | 0 | 0 | 0 | 0 | 0 | 0 | 0 | 0 |
| 152 | | 0 | 0 | 0 | 0 | 0 | 0 | 0 | 0 | 0 | 3 | 0 | 0 | 0 | 0 | 0 | 0 | 0 |
| 153 | | 0 | 0 | 0 | 0 | 0 | 5 | 0 | 0 | 2 | 0 | 0 | 0 | 0 | 0 | 0 | 0 | 0 |
| 154 | | 2 | 0 | 0 | 0 | 0 | 0 | 0 | 0 | 0 | 0 | 0 | 0 | 0 | 0 | 0 | 0 | 4 |
| 155 | | 0 | 0 | 0 | 0 | 0 | 0 | 0 | 0 | 0 | 0 | 0 | 0 | 0 | 0 | 0 | 0 | 0 |
| 157 | | 0 | 0 | — | 0 | 0 | — | 3 | 0 | 0 | 0 | 0 | 0 | 0 | 0 | 0 | 0 | 0 |
| 158 | | 0 | 0 | 0 | 0 | 0 | 0 | 0 | 0 | 0 | 0 | 0 | 0 | 0 | 0 | 0 | 0 | 0 |

PADDY

| COMPOUND | Rate | Speedwell | Sugar beet | Velvet-leaf | Barley | Blackgrass | Barnyardgrass | Rice | Umbrella sedge |
|---|---|---|---|---|---|---|---|---|---|
| 145 | (16 g/ha) | 0 | 0 | 0 | 0 | 0 | 0 | 0 | 0 |
| 146 | | 0 | 0 | 0 | 0 | 0 | 2 | 0 | 0 |
| 147 | | 0 | 0 | 0 | 0 | 0 | 3 | 1 | 0 |
| 152 | | 0 | 0 | 0 | 0 | 3 | 9 | 2 | — |
| 153 | | 2 | 0 | 0 | 0 | 3 | 8 | 1 | — |
| 154 | | 0 | 0 | 0 | 0 | 3 | 8 | 2 | — |
| 155 | | 0 | 0 | 0 | 0 | 0 | 9 | 0 | — |
| 157 | | 0 | 0 | 0 | 0 | 0 | 8 | 0 | — |
| 158 | | 0 | 0 | 0 | 0 | 0 | 9 | 0 | — |

PREEMERGENCE

| COMPOUND | Rate | Galium | Giant foxtail | Lambsquarters | Morningglory | Pigweed | Rape | Ryegrass | Sorghum | Soybean | Speedwell | Sugar beet | Velvet-leaf | Wheat | Wild buckwheat | Wild oat |
|---|---|---|---|---|---|---|---|---|---|---|---|---|---|---|---|---|
| 145 | (16 g/ha) | 0 | 2 | 10 | 0 | 0 | 0 | 0 | 0 | 0 | — | 0 | 0 | 0 | 0 | 0 |
| 146 | | 0 | 2 | 10 | 0 | 0 | 0 | 0 | 0 | 0 | — | 0 | 2 | 0 | 0 | 0 |
| 147 | | — | 2 | — | 0 | 0 | 0 | 0 | 0 | 0 | — | 0 | 0 | 0 | 0 | 0 |
| 152 | | 0 | 8 | 0 | 0 | 0 | 4 | 0 | 0 | 0 | 5 | 3 | 0 | 0 | 4 | 0 |
| 153 | | 10 | 10 | 0 | 0 | 0 | 0 | 0 | 0 | 0 | 5 | 3 | 0 | 0 | 3 | 0 |
| 154 | | 0 | 3 | 0 | 0 | 0 | 0 | 0 | 0 | 0 | 4 | 0 | 0 | 0 | 3 | 0 |
| 155 | | 0 | 6 | 3 | 0 | 0 | 0 | 0 | 0 | 0 | 3 | 0 | 0 | 0 | 0 | 0 |
| 157 | | 0 | 10 | 3 | 0 | 0 | 0 | 0 | 0 | 0 | 3 | 0 | 0 | 0 | 0 | 0 |
| 158 | | 0 | 5 | 0 | 0 | 0 | 0 | 0 | 0 | 0 | 3 | 0 | 0 | 0 | 0 | 0 |

TEST E

Plastic pots were partially filled with silt loam soil. The soil was then saturated with water. Indica and/or Japonica rice (*Oryza sativa*) seedlings at the 2.0 to 2.5 lead stage; seeds of barnyardgrass (*Echinochloa crusgalli*), bulrush (*Scirpus mucronatus*), duck salad (*Heteranthera limosa*), and umbrella sedge (*Cyperus difformis*); and tubers of arrowhead (Sagittaria spp.) and waterchestnut (Eleocharis spp.) were planted into this soil. Several days after planting, water levels were raised to 3 cm above the soil surface and maintained at this level throughout the test. Chemical treatments were formulated in a non-phytotoxic solvent and applied directly tot he paddy water. Treated plants and untreated controls were maintained in a greenhouse for 21 days, after which all treated plants were compared to untreated controls and visually evaluated. Plant response ratings, summarized in Table E, are reported on a 0 to 10 scale where 0 is no effect and 10 is complete control. A dash (-) response means no test result.

TABLE E

PADDY

| COMPOUND | Rate | Arrowhead | Barnyardgrass | Bulrush | Duck salad | Indica rice | Japonica rice | Umbrella sedge | Waterchestnut |
|---|---|---|---|---|---|---|---|---|---|
| 5 | (500 g/ha) | 7 | 10 | 7 | — | 4 | 7 | 10 | 10 |
| 8 | | 8 | 10 | 9 | — | 3 | 7 | 10 | 9 |
| 25 | | 0 | 10 | 0 | 10 | 7 | 5 | 10 | 6 |
| 26 | | — | 8 | 7 | 9 | 0 | 0 | 10 | 0 |
| 27 | | — | 9 | 8 | 10 | 0 | 4 | 10 | 0 |
| 28 | | — | 10 | 7 | 10 | 4 | 7 | 10 | 0 |
| 29 | | — | 10 | 0 | 10 | 0 | 0 | 10 | 0 |
| 30 | | — | 9 | 0 | 10 | 0 | 0 | 10 | 0 |
| 31 | | — | 10 | 7 | 10 | 3 | 5 | 10 | 0 |
| 32 | | — | 10 | 8 | 10 | — | 5 | 10 | 5 |
| 50 | | — | 10 | 8 | 10 | 0 | 3 | 10 | 5 |
| 51 | | — | 10 | 4 | 10 | — | 0 | 8 | 0 |
| 53 | | — | 10 | 0 | 10 | 0 | 0 | 0 | 0 |
| 54 | | — | 10 | 6 | 10 | 5 | 4 | 7 | 0 |
| 56 | | — | 10 | 6 | 10 | 0 | 0 | 10 | 0 |
| 58 | | — | 6 | 0 | 0 | 0 | 0 | 0 | 0 |
| 59 | | — | 10 | 0 | 0 | 2 | 3 | 0 | 9 |
| 107 | | 5 | 10 | — | 10 | — | 5 | 10 | 7 |
| 110 | | 0 | 8 | — | 10 | — | 1 | 10 | 0 |
| 118 | | 8 | 10 | — | 10 | — | 9 | 10 | 6 |
| 119 | | 9 | 10 | — | 10 | — | 7 | 10 | 8 |
| 130 | | 9 | 9 | — | 10 | — | 8 | 10 | 8 |
| 149 | | 0 | 7 | — | 4 | — | 1 | 2 | 0 |
| 150 | | 0 | 6 | — | 7 | — | 3 | 8 | 3 |
| 151 | | 0 | 8 | — | 4 | — | 2 | 6 | 3 |

| COMPOUND | Rate | Arrowhead | Barnyardgrass | Bulrush | Duck salad | Indica rice | Japonica rice | Umbrella sedge | Waterchestnut |
|---|---|---|---|---|---|---|---|---|---|
| 5 | (250 g/ha) | 10 | 8 | 7 | — | 0 | 2 | 10 | 8 |
| 8 | | 0 | 9 | 9 | — | 0 | 0 | 10 | 9 |
| 25 | | 0 | 10 | 0 | 10 | 6 | 0 | 10 | 0 |
| 26 | | — | 6 | 0 | 7 | 0 | 0 | 10 | 0 |
| 27 | | — | 9 | 4 | 10 | 0 | 2 | 10 | 0 |
| 28 | | — | 10 | 0 | 10 | 0 | 4 | 9 | 0 |
| 29 | | — | 7 | 0 | 10 | 0 | 0 | 10 | 0 |
| 30 | | — | 8 | 0 | 10 | 0 | 0 | 8 | 0 |
| 31 | | — | 10 | 6 | 10 | 3 | 4 | 10 | 0 |
| 32 | | — | 10 | 6 | 8 | — | 4 | 10 | 0 |
| 50 | | — | 10 | 5 | 10 | 0 | 0 | 10 | 0 |
| 51 | | — | 9 | 0 | 10 | — | 0 | 7 | 0 |
| 53 | | — | 9 | 0 | 5 | 0 | 0 | 0 | 0 |
| 54 | | — | 10 | 4 | 10 | 3 | 3 | 7 | 0 |
| 56 | | — | 10 | 9 | 10 | 0 | 0 | 10 | 0 |
| 58 | | — | 6 | 0 | 0 | 0 | 0 | 0 | 0 |
| 59 | | — | 8 | 0 | 0 | 0 | 2 | 0 | 9 |
| 93 | | — | 10 | 5 | — | 5 | 5 | — | 6 |
| 107 | | 3 | 9 | — | 10 | — | 3 | 10 | 4 |
| 110 | | 0 | 7 | — | 10 | — | 0 | 8 | 0 |
| 118 | | 8 | 10 | — | 10 | — | 6 | 10 | 5 |
| 119 | | 8 | 9 | — | 10 | — | 6 | 10 | 7 |
| 130 | | 9 | 10 | — | 10 | — | 5 | 10 | 8 |
| 149 | | 0 | 3 | — | 1 | — | 1 | 1 | 0 |
| 150 | | 0 | 0 | — | 0 | — | 1 | 1 | 1 |
| 151 | | 0 | 4 | — | 0 | — | 1 | 0 | 3 |

| COMPOUND | Rate | Arrowhead | Barnyardgrass | Bulrush | Duck salad | Indica rice | Japonica rice | Umbrella sedge | Waterchestnut |
|---|---|---|---|---|---|---|---|---|---|
| 5 | (125 g/ha) | 0 | 6 | 6 | — | 0 | 0 | 10 | 0 |
| 8 | | 0 | 8 | 0 | — | 0 | 0 | 10 | 9 |
| 25 | | 0 | 10 | 0 | 10 | 2 | 0 | 10 | 0 |
| 26 | | — | 0 | 0 | 0 | 0 | 0 | 0 | 0 |
| 27 | | — | 6 | 0 | 7 | 0 | 0 | 9 | 0 |
| 28 | | — | 9 | 0 | 10 | 0 | 4 | 8 | 0 |
| 29 | | — | 7 | 0 | 10 | 0 | 0 | 10 | 0 |
| 30 | | — | 4 | 0 | 0 | 0 | 0 | 0 | 0 |

TABLE E-continued

| COMPOUND | Rate | Arrowhead | Barnyardgrass | Bulrush | Duck salad | Indica rice | Japonica rice | Umbrella sedge | Waterchestnut |
|---|---|---|---|---|---|---|---|---|---|
| 31 | | — | 8 | 0 | 10 | 0 | 0 | 10 | 0 |
| 32 | | — | 10 | 4 | 6 | — | 0 | 10 | 0 |
| 50 | | — | 9 | 0 | 10 | 0 | 0 | 6 | 0 |
| 51 | | — | 8 | 0 | 6 | — | 0 | 5 | 0 |
| 53 | | — | 8 | 0 | 0 | 0 | 0 | 0 | 0 |
| 54 | | — | 10 | 4 | 10 | 3 | 0 | 5 | 0 |
| 56 | | — | 8 | 0 | 6 | 0 | 0 | 0 | 0 |
| 58 | | — | 4 | 0 | 0 | 0 | 0 | 0 | 0 |
| 59 | | — | 7 | 0 | 0 | 0 | 0 | 0 | 0 |
| 93 | | — | 10 | 2 | — | 0 | 0 | — | 2 |
| 107 | | 0 | 5 | — | 10 | — | 2 | 8 | 2 |
| 110 | | 0 | 4 | — | 10 | — | 0 | 8 | 0 |
| 118 | | 7 | 10 | — | 10 | — | 4 | 10 | 2 |
| 119 | | 5 | 10 | — | 10 | — | 4 | 10 | 5 |
| 130 | | 4 | 8 | — | 10 | — | 4 | 10 | 5 |
| 149 | | 0 | 0 | — | 0 | — | 1 | 0 | 0 |
| 150 | | 0 | 0 | — | 0 | — | 0 | 0 | 0 |
| 151 | | 0 | 0 | — | 0 | — | 1 | 0 | 0 |
| 5 | (64 g/ha) | 0 | 4 | 0 | — | 0 | 0 | 9 | 0 |
| 8 | | 0 | 5 | 0 | — | 0 | 0 | 10 | 0 |
| 25 | | 0 | 10 | 0 | 8 | 0 | 0 | 10 | 0 |
| 26 | | — | 0 | 0 | 0 | 0 | 0 | 0 | 0 |
| 27 | | — | 5 | 0 | 8 | 0 | 0 | 9 | 0 |
| 28 | | — | 9 | 0 | 10 | 0 | 0 | 0 | 0 |
| 29 | | — | 6 | 0 | 10 | 0 | 0 | 10 | 0 |
| 30 | | — | 4 | 0 | 0 | 0 | 0 | 0 | 0 |
| 31 | | — | 7 | 0 | 10 | 0 | 0 | 10 | 0 |
| 32 | | — | 10 | 0 | 6 | — | 0 | 4 | 0 |
| 50 | | — | 8 | 0 | 5 | 0 | 0 | 6 | 0 |
| 51 | | — | 8 | 0 | 0 | — | 0 | 0 | 0 |
| 53 | | — | 7 | 0 | 0 | 0 | 0 | 0 | 0 |
| 54 | | — | 9 | 0 | 10 | 0 | 0 | 4 | 0 |
| 56 | | — | 7 | 0 | 0 | 0 | 0 | 0 | 0 |
| 58 | | — | 0 | 0 | 0 | 0 | 0 | 0 | 0 |
| 59 | | — | 7 | 0 | 0 | 0 | 0 | 0 | 0 |
| 93 | | — | 10 | 2 | — | 0 | 0 | — | 2 |
| 107 | | 0 | 4 | — | 10 | — | 0 | 4 | 2 |
| 110 | | 0 | 2 | — | 9 | — | 0 | 6 | 0 |
| 118 | | 6 | 7 | — | 10 | — | 3 | 10 | 0 |
| 119 | | 2 | 7 | — | 10 | — | 3 | 10 | 5 |
| 130 | | 2 | 7 | — | 10 | — | 1 | 10 | 2 |
| 149 | | 0 | 0 | — | 0 | — | 0 | 0 | 0 |
| 150 | | 0 | 0 | — | 0 | — | 0 | 0 | 0 |
| 151 | | 0 | 0 | — | 0 | — | 0 | 0 | 0 |
| 5 | (32 g/ha) | 0 | 0 | 0 | — | 0 | 0 | 5 | 0 |
| 8 | | 0 | 0 | 0 | — | 0 | 0 | 5 | 0 |
| 25 | | 0 | 10 | 0 | 5 | 0 | 0 | 8 | 0 |
| 26 | | — | 0 | 0 | 0 | 0 | 0 | 0 | 0 |
| 27 | | — | 4 | 0 | 0 | 0 | 0 | 0 | 0 |
| 28 | | — | 8 | 0 | 8 | 0 | 0 | 0 | 0 |
| 29 | | — | 3 | 0 | 10 | 0 | 0 | 10 | 0 |
| 30 | | — | 0 | 0 | 0 | 0 | 0 | 0 | 0 |
| 31 | | — | 6 | 0 | 9 | 0 | 0 | 8 | 0 |
| 32 | | — | 10 | 0 | 0 | — | 0 | 0 | 0 |
| 50 | | — | 7 | 0 | 0 | 0 | 0 | 0 | 0 |
| 51 | | — | 6 | 0 | 0 | — | 0 | 0 | 0 |
| 53 | | — | 7 | 0 | 0 | 0 | 0 | 0 | 0 |
| 54 | | — | 9 | 0 | 0 | 0 | 0 | 0 | 0 |
| 56 | | — | 6 | 0 | 0 | 0 | 0 | 0 | 0 |
| 58 | | — | 0 | 0 | 0 | 0 | 0 | 0 | 0 |
| 59 | | — | 5 | 0 | 0 | 0 | 0 | 0 | 0 |
| 93 | | — | 7 | 2 | — | 0 | 0 | — | 2 |
| 107 | | 0 | 0 | — | 10 | — | 0 | 0 | 2 |
| 110 | | 0 | 0 | — | 9 | — | 0 | 2 | 0 |
| 118 | | 2 | 6 | — | 10 | — | 2 | 10 | 0 |
| 119 | | 0 | 4 | — | 9 | — | 2 | 9 | 4 |
| 130 | | 0 | 5 | — | 10 | — | 0 | 10 | 2 |
| 149 | | 0 | 0 | — | 0 | — | 0 | 0 | 0 |
| 150 | | 0 | 0 | — | 0 | — | 0 | 0 | 0 |
| 151 | | 0 | 0 | — | 0 | — | 0 | 0 | 0 |

| COMPOUND | Rate | Barnyardgrass | Bulrush | Indica rice | Japonica rice | Waterchestnut |
|---|---|---|---|---|---|---|
| 93 | (16 g/ha) | 4 | 2 | 0 | 0 | 0 |

TEST F

Seeds of spring and winter barley (*Hordeum vulgare*), blackgrass (*Alopecurus myosuroides*), black nightshade (*Solanum nigrum*), bluegrass (*Poa annua*), cheatgrass (*Bromus secalinus*), downy brome (*Bromus tectorum*), field pennycress (*Thlaspi arvense*), field violet (*Viola arvensis*), galium (*Galium aparine*), green foxtail (*Setaria viridis*), ivyleaf speedwell (*Veronica hederaefolia*), jointed goatgrass (*Aegilops cylindrica*), kochia (*Kochia scoparia*), lambsquarters (*Chenopodium album*), persian speedwell (*Veronica persica*), rape (*Brassica napus*), Russian thistle (*Salsola kali*), ryegrass (*Lolium multiflorum*), scentless chamomile (*Matricaria inodora*), sugar beet (*Beta vulgaris*), spring and winter wheat (*Triticum aestivum*), wild buckwheat (*Polygonum convolvulus*) and wild oat (*Avena fatua*) were planted and treated preemergence with the test chemical dissolved in a nonphytotoxic solvent. At the same time, these crop and weed species were also treated with postemergence applications of the test chemical. Plants ranged in height from two to twenty-four cm for postemergence treatments. Blackgrass and wild oat were treated postemergence at two growth stages. The first growth stage (1) was at the 1-2 leaf stage while the second stage (2) was at the four leaf stage. Treated plants and untreated controls were maintained in a greenhouse for approximately 21 days. All treated plants were then compared to untreated controls and visually evaluated for injury. Plant response ratings, summarized in Table F, are based on a zero to ten scale where 0 is no effect and 10 is complete control.

TABLE F

POSTEMERGENCE

| COMPOUND 25 | Rate (500 g/ha) | Rate (250 g/ha) | Rate (125 g/ha) | Rate (64 g/ha) | Rate (32 g/ha) |
|---|---|---|---|---|---|
| Barley (Spring) | 5 | 4 | 4 | 2 | 1 |
| Barley (Winter) | 5 | 4 | 2 | 1 | 0 |
| Blackgrass (1) | 3 | 1 | 0 | 0 | 0 |
| Blackgrass (2) | 2 | 0 | 0 | 0 | 0 |
| Blk. nightshade | 0 | 0 | 0 | 0 | 0 |
| Bluegrass | 2 | 1 | 0 | 0 | 0 |
| Cheatgrass | 0 | 0 | 0 | 0 | 0 |
| Downy brome | 0 | 0 | 0 | 0 | 0 |
| Fld. pennycress | 0 | 0 | 0 | 0 | 0 |
| Fld. violet | 2 | 0 | 0 | 0 | 0 |
| Galium | 0 | 0 | 0 | 0 | 0 |
| Green foxtail | 4 | 2 | 1 | 0 | 0 |
| Ivylf speedwell | 0 | 0 | 0 | 0 | 0 |
| Jntd. goatgrass | 1 | 0 | 0 | 0 | 0 |
| Kochia | 2 | 0 | 0 | 0 | 0 |
| Lambsquarters | 4 | 3 | 0 | 0 | 0 |
| Prsn. speedwell | 0 | 0 | 0 | 0 | 0 |
| Rape | 4 | 2 | 1 | 0 | 0 |
| Russian thistle | 1 | 0 | 0 | 0 | 0 |
| Ryegrass | 3 | 1 | 0 | 0 | 0 |
| Snls. chamomile | 0 | 0 | 0 | 0 | 0 |
| Sugar beet | 2 | 1 | 1 | 0 | 0 |
| Wheat (Spring) | 7 | 4 | 2 | 1 | 0 |
| Wheat (Winter) | 2 | 2 | 1 | 0 | 0 |
| Wild buckwheat | 0 | 0 | 0 | 0 | 0 |
| Wild oat (1) | 1 | 0 | 0 | 0 | 0 |
| Wild oat (2) | 1 | 0 | 0 | 0 | 0 |

PREEMERGENCE

| COMPOUND 25 | Rate (500 g/ha) | Rate (250 g/ha) | Rate (125 g/ha) | Rate (64 g/ha) | Rate (32 g/ha) |
|---|---|---|---|---|---|
| Barley (Spring) | 6 | 3 | 2 | 1 | 1 |
| Barley (Winter) | 4 | 2 | 1 | 0 | 0 |
| Blackgrass | 6 | 3 | 2 | 0 | 0 |
| Blk. nightshade | 0 | 0 | 0 | 0 | 0 |
| Bluegrass | 8 | 8 | 7 | 5 | 2 |
| Cheatgrass | 6 | 6 | 5 | 3 | 0 |
| Downy brome | 3 | 1 | 0 | 0 | 0 |
| Fld. pennycress | 10 | 7 | 4 | 0 | 0 |
| Fld. violet | 2 | 0 | 0 | 0 | 0 |
| Galium | 5 | 0 | 0 | 0 | 0 |
| Green foxtail | 10 | 10 | 10 | 8 | 3 |
| Ivylf speedwell | 2 | 0 | 0 | 0 | 0 |
| Jntd. goatgrass | 3 | 1 | 0 | 0 | 0 |
| Kochia | 3 | 1 | 0 | 0 | 0 |
| Lambsquarters | 2 | 1 | 1 | 0 | 0 |
| Prsn. speedwell | 7 | 7 | 2 | 0 | 0 |
| Rape | 3 | 3 | 2 | 0 | 0 |
| Russian thistle | 3 | 1 | 0 | 0 | 0 |
| Ryegrass | 9 | 9 | 9 | 7 | 4 |
| Snls. chamomile | 7 | 2 | 0 | 0 | 0 |
| Sugar beet | 5 | 3 | 3 | 2 | 2 |
| Wheat (Spring) | 3 | 1 | 1 | 0 | 0 |
| Wheat (Winter) | 2 | 1 | 0 | 0 | 0 |
| Wild buckwheat | 2 | 0 | 0 | 0 | 0 |
| Wild oat | 2 | 1 | 0 | 0 | 0 |

TEST G

Seeds, rhizomes, or tubers of alfalfa (*Medicago sativa*), barnyardgrass (*Echinochloa crus-galli*), bermudagrass (Cynodon dactylon), broadleaf signalgrass (Brachiaria plantaginea), field bindweed (Convolvulus arvensis), guineagrass (Panicum maximum), johnsongrass (Sorghum halepense), large crabgrass (Digitaria sanguinalis), pitted morningglory (Ipomoea lacunosa), purple nutsedge (Cyperus rotundus), purslane (Portulaca oleracea), ragweed (Ambrosia artemisiifolia), sandbar (Cenchrus echinatus), smooth crabgrass (Digitaria ischaemum), Texas panicum (Panicum texanum), tropical kudzu (Pueraria javanica), and yellow nutsedge (Cyperus esculentus) were planted into greenhouse pots containing greenhouse planting medium. Each pot contained only one plant species. Test compounds were dissolved in a non-phytotoxic solvent and applied to the soil surface (preemergence). These applications were made within one day of planting. Control pots receiving not test treatments and treated pots were maintained under greenhouse conditions for 13 to 21 days after herbicide application. Growth of treated plants was compared to that of untreated controls and visually evaluated. Plant response ratings, summarized in Table G, are based on a zero to 10 scale where zero is no injury, and 10 is plant death. A dash (-) response means no test result.

TABLE G

| PREEMERGENCE | | | | | | | |
|---|---|---|---|---|---|---|---|
| | COMPOUND | | | | | | |
| | 118 | 132 | 136 | 147 | 153 | 154 | 157 |
| Rate (250 g/ha) | | | | | | | |
| Alfalfa | 2 | 5 | 3 | 0 | 2 | 4 | 3 |
| Barnyardgrass | 10 | 10 | 10 | 10 | 10 | 10 | 10 |
| Bermudagrass | 10 | 10 | 10 | 10 | 10 | 10 | 10 |
| Brdlf sgnlgrass | 10 | 10 | 10 | 10 | 10 | 10 | 10 |
| Field bindweed | 0 | 5 | 1 | 0 | 1 | 1 | 0 |
| Guineagrass | 10 | 10 | 9 | 10 | 10 | 10 | 10 |
| Johnsongrass | 8 | 10 | 2 | 2 | 10 | 10 | 10 |
| Large crabgrass | 9 | 10 | 10 | 10 | 10 | 10 | 10 |
| Pitted mrnglory | 0 | 3 | 2 | 1 | 0 | 3 | 2 |
| Purple nutsedge | 10 | 10 | 10 | 7 | 10 | 3 | 8 |
| Purslane | 7 | 10 | 8 | 1 | 9 | 9 | 7 |
| Ragweed | 1 | 6 | 2 | 0 | 5 | 10 | 9 |
| Sandbur | — | 10 | — | — | — | — | — |
| Smooth crbgrass | 10 | 10 | 10 | 10 | 10 | 10 | 10 |
| Texas panicum | 6 | 10 | 5 | 9 | 10 | 10 | 9 |
| Trop. kudzu | 6 | 10 | 9 | 7 | 9 | 9 | 9 |
| Yellow nutsedge | 6 | 10 | 2 | 0 | 8 | 2 | 1 |
| Rate (125 g/ha) | | | | | | | |
| Alfalfa | 0 | 3 | 1 | 0 | 1 | 4 | 5 |
| Barnyardgrass | 10 | 10 | 10 | 10 | 10 | 10 | 10 |
| Bermudagrass | 10 | 10 | 10 | 10 | 10 | 10 | 10 |
| Brdlf sgnlgrass | 10 | 10 | 10 | 7 | 10 | 10 | 9 |
| Field bindweed | 0 | 0 | 1 | 0 | 1 | 1 | 0 |
| Guineagrass | 10 | 8 | 9 | 8 | 10 | 10 | 10 |
| Johnsongrass | 4 | 10 | 2 | 0 | 9 | 9 | 10 |
| Large crabgrass | 9 | 10 | 10 | 10 | 10 | 10 | 9 |
| Pitted mrnglory | 1 | 0 | 1 | 0 | 1 | 3 | 2 |
| Purple nutsedge | 10 | 8 | 10 | 0 | 7 | 1 | 3 |
| Purslane | 5 | 7 | 3 | 0 | 10 | 6 | 2 |
| Ragweed | 0 | 3 | 0 | 0 | 1 | 9 | 9 |
| Sandbur | — | 10 | — | — | — | — | — |
| Smooth crbgrass | 10 | 10 | 10 | 10 | 10 | 10 | 10 |
| Texas panicum | 1 | 9 | 2 | 8 | 10 | 9 | 8 |
| Trop. kudzu | 5 | 6 | 10 | 0 | 9 | 9 | 9 |
| Yellow nutsedge | 1 | 4 | 0 | 0 | 1 | 1 | 0 |
| Rate (64 g/ha) | | | | | | | |
| Alfalfa | 0 | 3 | 1 | 0 | 0 | 2 | 1 |
| Barnyardgrass | 10 | 10 | 8 | 0 | 10 | 10 | 10 |
| Bermudagrass | 9 | 10 | 1 | 10 | 10 | 10 | 10 |
| Brdlf sgnlgrass | 2 | 10 | 4 | 2 | 9 | 10 | 9 |
| Field bindweed | 0 | 2 | 0 | 0 | 2 | 1 | 0 |
| Guineagrass | 9 | 9 | 10 | 1 | 9 | 9 | 10 |
| Johnsongrass | 1 | 3 | 0 | 0 | 10 | 6 | 8 |
| Large crabgrass | 3 | 10 | 4 | 3 | 10 | 10 | 9 |
| Pitted mrnglory | 0 | 0 | 0 | 0 | 1 | 1 | 2 |
| Purple nutsedge | 10 | 10 | 10 | 0 | 1 | 0 | 1 |
| Purslane | 3 | 2 | 2 | 0 | 2 | 6 | 1 |
| Ragweed | 0 | 0 | 0 | 0 | — | 8 | 6 |
| Sandbur | — | 10 | — | — | — | — | — |
| Smooth crbgrass | 10 | 10 | 10 | 9 | 10 | 10 | 9 |
| Texas panicum | 0 | 3 | 1 | 1 | 8 | 8 | 6 |
| Trop. kudzu | 0 | 4 | 0 | 0 | 9 | 9 | 9 |
| Yellow nutsedge | 0 | 3 | 0 | 0 | 1 | 0 | 0 |
| Rate (32 g/ha) | | | | | | | |
| Alfalfa | 0 | 2 | 0 | 0 | 1 | 0 | 1 |
| Barnyardgrass | 0 | 10 | 7 | 0 | 10 | 10 | 10 |
| Bermudagrass | 2 | 9 | 9 | 10 | 10 | 10 | 9 |
| Brdlf sgnlgrass | 0 | 10 | 0 | 0 | 9 | 9 | 7 |
| Field bindweed | 0 | 0 | 0 | 0 | 1 | 0 | 0 |
| Guineagrass | 0 | 9 | 1 | 0 | 9 | 9 | 4 |
| Johnsongrass | 0 | 2 | 0 | 0 | 3 | 2 | 1 |
| Large crabgrass | 1 | 6 | 0 | 0 | 9 | 8 | 7 |
| Pitted mrnglory | 0 | 0 | 0 | 0 | 0 | 1 | 2 |
| Purple nutsedge | 1 | 0 | 0 | — | 1 | 0 | 0 |
| Purslane | 0 | 0 | 0 | 0 | 1 | 2 | 0 |
| Ragweed | 0 | — | 0 | 0 | 7 | 2 | 6 |
| Sandbur | — | 10 | — | — | — | — | — |
| Smooth crbgrass | 3 | 10 | 7 | 2 | 9 | 8 | 7 |
| Texas panicum | 0 | 3 | 1 | 0 | 6 | 7 | 7 |
| Trop. kudzu | 0 | 0 | 0 | 0 | 6 | 8 | 9 |
| Yellow nutsedge | 0 | 2 | 0 | 0 | 1 | 0 | 0 |

What is claimed is:

1. The compounds of the formula

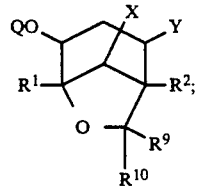

III and stereoisomers thereof,
wherein
X and Y are independently H or $C(R^3)(R^4) OR^5$;
$R^1$ is H or a straight-chain $C_1$-$C_3$ alkyl;
$R^2$ is H, $C_1$-$C_6$ alkyl, $C_2$-$C_4$ alkenyl, $C_2$-$C_4$ alkynyl, phenyl or $C_1$-$C_4$ alkyl substituted by Ph, OH, CN, $OR^8$, $SO_2R^8$, $PhSO_2$, $N_3$, $CO_2R^8$ or $CO_2H$;
$R^3$, $R^4$, $R^9$ and $R^{10}$ are independently H, $C_1$-$C_4$ alkyl, $C_2$-$C_4$ alkenyl, $C_2$-$C_4$ alkynyl or $C_1$-$C_3$ alkyl substituted with $OCH_3$ or $OCH_2CH_3$;
$R^5$ is $C_1$-$C_3$ alkyl, $C_2$-$C_4$ alkenyl, $C_3$-$C_4$ alkynyl, benzyl or $C_1$-$C_4$ alkyl substituted with $OR^8$, $OCF_3$;
$R^8$ is $C_1$-$C_3$ alkyl;
Q is $WCH_2$ or

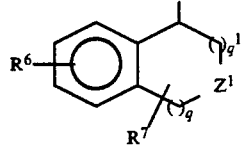

W is phenyl optionally substituted with 1-3 substituents selected from F, Cl, Br, $C_1$-$C_3$ alkyl, $C_1$-$C_3$ alkoxy, OH, CN, $C_1$-$C_3$ haloalkyl, $C_1$-$C_3$ haloalkoxy, $C_1$-$C_3$ alkylthio, $C_2$-$C_4$ alkenyl and $C_2$-$C_4$ alkynyl, or W is a 5 or 6-membered heterocyclic ring containing 0-2 nitrogens, 0-2 oxygens of 0-2 sulfurs, each ring optionally substituted with 1-2 substituents selected from F, Cl, Br, CH₃ and OCH₃;

$Z^1$ is $CH_2$, $NR_a$, O, S or may be taken to form a double bond with an adjacent carbon;

$R_a$ is H or $C_1$-$C_3$ alkyl;

$R^6$ is H, halogen, $R^8$, $OR^8$, $SR^8$ or CN;

$R^7$ is H, F, Cl, $CH_3$, $OCH_3$, OH or $OR^8$;

$q^1$ is 0, 1 or 2; and q is 0, 1 or 2, provided that 1) at least one of X and Y is $C(R^3)(R^4)OR^5$;
2) $R^3$, $R^4$, $R^9$ and $R^{10}$ each contains no more than four carbon atoms;
3) the sum of q and $q^1$ is 0, 1 or 2; and
4) if the sum of q and $q^1$ is 0 then $Z^1$ is $CH_2$.

2. The compounds of Formula III according to claim 1 wherein:

W is phenyl optionally substituted by 1-2 substituents selected from F, Cl, Br, CH₃ and OCH₃; or W is tetrahydropyran, tetrahydrofuran, thiophene, isoxazole, pyridine or pyrazine, each ring optionally substituted with 1-2 substituents selected from F, Cl, Br, CH₃ or OCH₃;

Q is

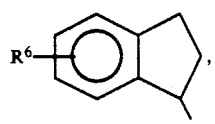 Q-1

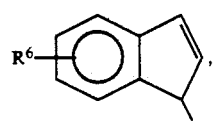 Q-2

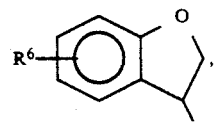 Q-3

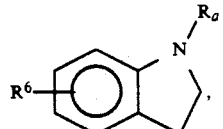 Q-4

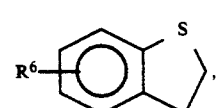 Q-5

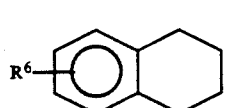 Q-6

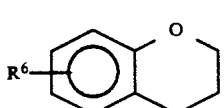 Q-7

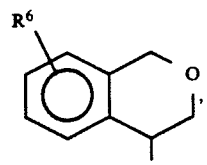 Q-8

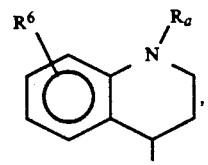 Q-9

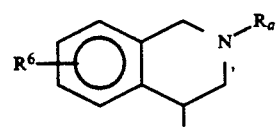 Q-10

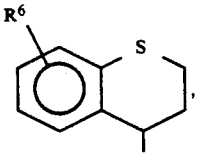 Q-11

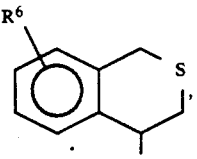 Q-12

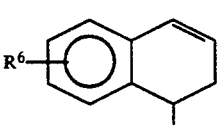 Q-13

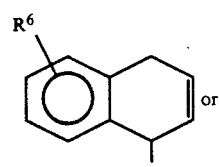 Q-14 or

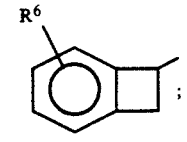 Q-15 ;

$R_a$ is H or $C_1$-$C_3$ alkyl; and $R^5$ is other than benzyl.

3. The compounds of claim 2 wherein $R^3$ is H, $C_1$-$C_3$ alkyl, $C_3$-$C_4$ alkenyl or $C_3$-$C_4$ alkynyl;

4. The compounds of claim 3 wherein $R^3$ is H, $C_1$-$C_3$ alkyl, $C_3$-$C_4$ alkenyl or $C_3$-$C_4$ alkynyl;

$R^4$ is H, $C_1$-$C_3$ alkyl, $C_3$-$C_4$ alkenyl or $C_3$-$C_4$ alkynyl;

$R^5$ is H, $C_1$-$C_3$ alkyl, $C_3$-$C_4$ alkenyl or $C_3$-$C_4$ alkynyl;

$R^9$ is H, $C_1$-$C_3$ alkyl, $C_3$-$C_4$ alkenyl or $C_3$-$C_4$ alkynyl;

$R^{10}$ is H, $C_1$-$C_3$ alkyl, $C_3$-$C_4$ alkenyl or $C_3$-$C_4$ alkynyl;

5. The compounds of claim 4 wherein Q is Q-1, Q-3, Q-6, Q-7 or Q-15.

6. The compound of claim 4 which is: 2-(ethoxymethyl)-5-methyl-4-(phenylmethoxy)-6-oxabicyclo[3.2.1]octane, (2-endo, 4-endo).

7. The compound of claim 4 which is 5-ethyl-4-(2,6-difluorophenylmethoxy)-2-methoxymethyl-6-oxabicyclo[3.2.1]octane, (2-endo, 4-endo).

8. An agriculturally suitable composition for controlling the growth of undesired vegetation comprising an effective amount of the compound of claim 1 and at least one of the following: surfactant, solid or liquid diluent.

9. An agriculturally suitable composition for controlling the growth of undesired vegetation comprising an effective amount of the compound of claim 2 and at least one of the following: surfactant, solid or liquid diluent.

10. An agriculturally suitable composition for controlling the growth of undesired vegetation comprising an effective amount of the compound of claim 3 and at least one of the following: surfactant, solid or liquid diluent.

11. An agriculturally suitable composition for controlling the growth of undesired vegetation comprising an effective amount of the compound of claim 4 and at least one of the following: surfactant, solid or liquid diluent.

12. An agriculturally suitable composition for controlling the growth of undesired vegetation comprising an effective amount of the compound of claim 5 and at least one of the following: surfactant, solid or liquid diluent.

13. An agriculturally suitable composition for controlling the growth of undesired vegetation comprising an effective amount of the compound of claim 6 and at least one of the following: surfactant, solid or liquid diluent.

14. An agriculturally suitable composition for controlling the growth of undesired vegetation comprising an effective amount of the compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound of claim 5.

20. A method for controlling the growth of undesired vegetation which comprises applying to the locus to be protected an effective amount of a compound of claim 15.

21. A method for controlling the growth of undesired vegetation which comprises applying to the locus to be protected an effective amount of the compound of claim 7.

* * * * *

UNITED STATES PATENT AND TRADEMARK OFFICE
CERTIFICATE OF CORRECTION

PATENT NO.  : 5,234,900

DATED       : August 10, 1993

INVENTOR(S) : James E. POWELL, JR: WENDY S. TAYLOR

It is certified that error appears in the above-indentified patent and that said Letters Patent is hereby corrected as shown below:

Col. 2, lines 41-48, delete formula VI and substitute therefor the following:

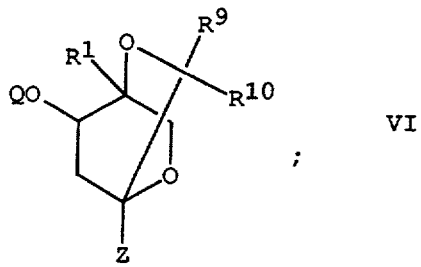

VI ;

Col. 10, delete the formula appearing between lines 1 and 9 and substitute therefor the following:

a) 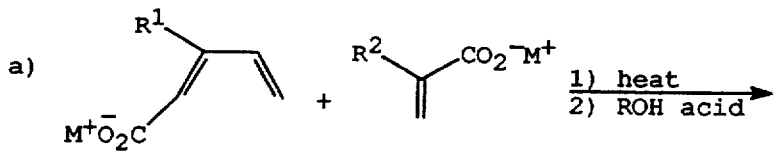

UNITED STATES PATENT AND TRADEMARK OFFICE
CERTIFICATE OF CORRECTION

PATENT NO. : 5,234,900                                         Page 2 of 2
DATED      : August 10, 1993
INVENTOR(S) : James E. POWELL, JR: WENDY S. TAYLOR It is certified that error appears in the above-indentified patent and that said Letters Patent is hereby corrected as shown below:

Col. 194, line 58, delete "$R^3$" and insert -- $R^2$ --.

Signed and Sealed this

Sixth Day of September, 1994

Attest:

BRUCE LEHMAN

Attesting Officer        Commissioner of Patents and Trademarks